United States Patent [19]

Sinclair et al.

[11] Patent Number: 5,349,061
[45] Date of Patent: Sep. 20, 1994

[54] O-HETEROARYL, O-ALKYLHETEROARYL, O-ALKENYLHETEROARYL AND O-ALKYNYLHETEROARYLMACROLIDES HAVING IMMUNOSUPPRESSIVE ACTIVITY

[75] Inventors: Peter J. Sinclair, Highland Park; Joung Goulet, Westfield; Frederick Wong, Glen Ridge; Mark Goulet, Westfield; William H. Parsons, Rahway; Matthew J. Wyvratt, Mountainside, all of N.J.

[73] Assignee: Merck & Co., Inc., Rahway, N.J.

[21] Appl. No.: 135,200

[22] Filed: Oct. 12, 1993

Related U.S. Application Data

[63] Continuation-in-part of Ser. No. 921,851, Aug. 5, 1992, Pat. No. 5,252,732, which is a continuation-in-part of Ser. No. 756,946, Sep. 9, 1991, abandoned.

[51] Int. Cl.⁵ .................. A61K 31/345; C07D 491/16
[52] U.S. Cl. ..................................................... 540/45.6
[58] Field of Search ......................................... 540/45.6

[56] References Cited

U.S. PATENT DOCUMENTS

| | | | |
|---|---|---|---|
| 3,244,592 | 4/1966 | Arai | 167/65 |
| 5,162,334 | 11/1992 | Goulet et al. | 514/291 |
| 5,189,042 | 2/1993 | Goulet et al. | 514/291 |
| 5,190,950 | 3/1993 | Beattie et al. | 514/291 |
| 5,208,228 | 5/1993 | Ok et al. | 514/183 |
| 5,208,241 | 5/1993 | Ok et al. | 514/291 |
| 5,247,076 | 9/1993 | Goulet et al. | 540/456 |
| 5,250,678 | 10/1993 | Goulet et al. | 540/456 |
| 5,252,732 | 10/1993 | Sinclair et al. | 540/456 |
| 5,262,533 | 11/1993 | Sinclair et al. | 540/456 |

Primary Examiner—Robert T. Bond
Attorney, Agent, or Firm—J. Eric Thies; David L. Rose; Joseph F. DiPrima

[57] ABSTRACT

O-Heteroaryl, O-alkylheteroaryl, O-alkenylheteroaryl and O-alkynylheteroaryl-macrolides of the general structural Formula I:

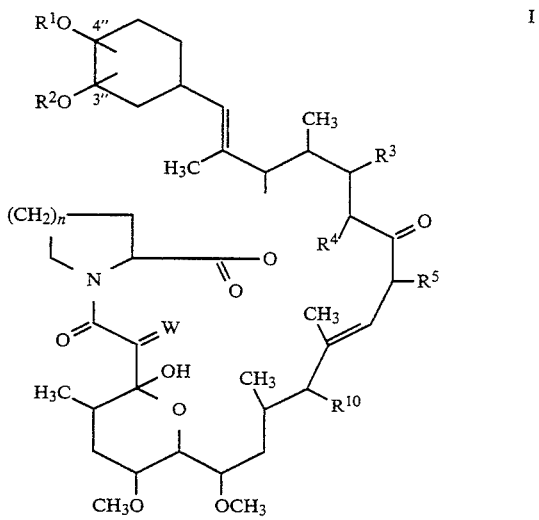

have been prepared from suitable precursors by alkylation and/or arylation at C-3" and/or C-4" of the cyclohexyl ring. These macrolide immunosuppressants are useful in a mammalian host for the treatment of autoimmune diseases, infectious diseases, the prevention of rejection of foreign organ transplants and/or related afflictions, diseases and illnesses.

1 Claim, No Drawings

O-HETEROARYL, O-ALKYLHETEROARYL, O-ALKENYLHETEROARYL AND O-ALKYNYLHETEROARYLMACROLIDES HAVING IMMUNOSUPPRESSIVE ACTIVITY

SUMMARY OF THE INVENTION

This application is a continuation-in-part of copending application Ser. No. 07/921,851, filed Aug. 5, 1992, now issued as U.S. Pat. No. 5,252,732 issued which in turn is a continuation-in-part of copending application Ser. No. 07/756,946, filed Sep. 9, 1991, now abandoned.

The present invention is related to O-heteroaryl, O-alkylheteroaryl, O-alkenylheteroaryl and O-alkynylheteroarylmacrolides which are useful in a mammalian host for the treatment of autoimmune diseases <such as juvenile-onset diabetes mellitus, multiple sclerosis and rheumatoid arthritis), immunodepression, infectious diseases, the prevention of rejection of foreign organ transplants (e.g. bone marrow and heart transplants and xeno transplants), the topical treatment of inflammatory and hyperproliferative skin diseases and cutaneous manifestations of immunologically-mediated illnesses (such as: psoriasis, *atopical dermatitis*, contact dermatitis and further eczematous dermatitises, *seborrhoeic dermatitis*, *Lichen* planus, Pemphigus, bullous Pemphigoid, *Epidermolysis* bullosa, urticaria, angioedemas, vasculitides, erythemas, cutaneous eosinophilias, *Lupus erythematosus, Alopecia areata*), male pattern alopecia, *alopecia senilis*, reversible obstructive airways disease, particularly asthma, alopecia, inflammation of mucosa and blood vessels, cytomegalovirus infection, multidrug resistance, idiopathic thrombocytopenic purpura, Behcet's syndrome, conjunctivitis, Crohn's disease, Mooren's ulcer, uveitis, severe intraocular inflammation, and-/or hepatic injury associated with ischemia. The present compounds are further useful in combination with a 5α-reductase inhibitor, a cyclosporin, a potassium channel opener or a phospholipid in a mammalian host for the treatment of baldness, especially male pattern alopecia, female pattern alopecia, alopecia senills, or alopecia areata. In addition, some of the compounds of this invention may have antagonistic properties and so have utility in the reversal of immunosuppressive activity and/or diminishing the toxicity of other immunosuppressive agents.

More particularly, this invention relates to compounds of the general structural formula I:

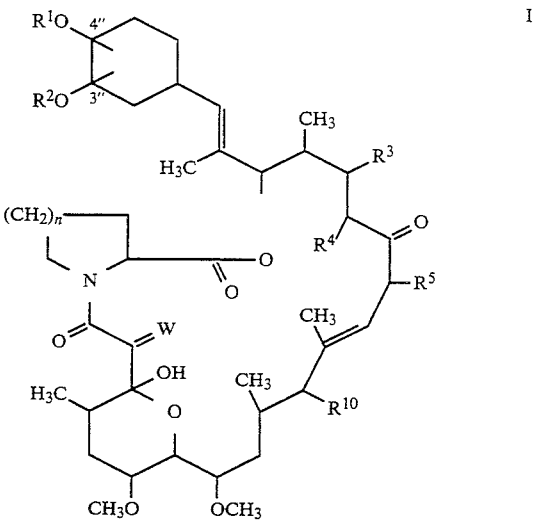

wherein $R^1$, $R^2$, $R^3$, R4, $R^5$, $R^{10}$, W and n are hereinafter defined.

This invention also relates to pharmaceutical compositions containing the compounds and to a method of use of the present compounds and other agents for the treatment of and prevention of certain afflictions, diseases and illnesses.

BRIEF DESCRIPTION OF DISCLOSURES IN THE ART

Fujisawa United States, European and Japanese patents and applications (U.S. Pat. No. 4,894,366, issued Jan. 16, 1990, EPO Publication No. 0,184,162 and PBJ Disclosure 63-17884) and publications (J. Am. Chem. Soc., 1987, 109, 5031 and J. Antibiotics 1987, 40, 1249) disclose 17-allyl-1,14-dihydroxy-12-[2'-<4"-hydroxy-3"-methoxycyclohexyl)1'-methylvinyl]-23,25-dimethoxy-13,19,21,27-tetramethyl-11,28-dioxa-4-azatricyclo -22.3.1.0$^{4,9}$]octacos-18-ene -2,3,10, 16-tetraone (FR-900506), (FK-506), (L-679,934), 17-ethyl-1,14-dihydroxy-12-[2'-(4"-hydroxy-3"-methoxycyclohexyl)-1'-methylvinyl]-23,25-dimethoxy-13,19,21,27-tetramethyl -11,28-dioxa-4azatricyclo [22 .3.1.0$^{4,9}$]octacos-18-ene-2,3,10,16-tetraone (FR-900520) and related compounds which are the starting materials for the preparation of the compounds described. The synthetic preparation of the aforementioned starting material (FR-900506) has recently been reported (*J. Am. Chem. Soc.,* 1989, 111, 1157). A Sandoz European patent application (*EPO Publication No.* 0,356,399) discloses stereoisomers of FR-900506 and derivatives at the 17-position. Fisons European and WIPO patent applications (*EPO Publication No.* 0,323,042 and *PCT Publication No. WO* 89/05304) discloses various derivatives of FR-900506, FR-900520 and related compounds. A Sandoz European Patent application (*EPO Publication No.* 0,437,680) discloses chloro, bromo, iodo and azido derivatives of FR-900506, FR-900520 and related compounds. A Merck European Patent application (*EPO Publication No.* 0,428,365) discloses various amino derivatives of FR-900506, FR-900520 and related compounds. A Fujisawa patent application (*UK Publication No. GB 2,245,891-A*) discloses various derivatives of FR-900506 bearing a heterocyclic group. Merck WIPO patent applications (*PCT Publication Nos. WO* 93/05058 & *WO*

93/05059) disclose various heteroaryl derivatives of FR-900506, FR-900520 and related compounds.

Fujisawa United States patents (U.S. Pat. No. 4,929,611, issued May 29, 1990, U.S. Pat. No. 4,956.352, issued Sep. 11, 1990 and U.S. Pat. No. 5,110,811, issued May 5, 1992) discloses the use of FK-506-type compounds in treating resistance to transplantation. A Sandoz European patent application (*EPO Publication No.* 0,315,978) discloses the use of FR-900506 and related compounds in the topical treatment of inflammatory and hyperproliferative skin diseases and of cutaneous manifestations of immunologically-mediated illness. A Fisons WIPO patent application (*PCT Publication No. WO* 91/04025) discloses the use of various derivatives of FR-900506 in the treatment of immunodepression. A Fisons WIPO patent application (*PCT Publication WO* 90/14826) discloses the use of FR-900506 and related compounds in the treatment of reversible obstructive airways disease, particularly asthma. A Fujisawa European patent application (*EPO Publication No.* 0,423,714) discloses the use of FK-506 and derivatives as hair revitalizing agents. Various studies have suggested the efficacy of FK-506 in the treatment of a number of ailments, including rheumatoid arthitis (C. Arita, et al., *Clincial exp. Immunol.*, 1990, 82, 456–461; N. Inamura, et al., *Clin. Immunol. Immunopathol*, 1988, 46, 82–90), recent-onset diabetes (N. Murase, et al., Diabetes, 1990, 39, 1584–86; N. Murase, et al., Lancet., 1990, 336, 373–74), posterior uveitis (H. Kawashima, *Invest. Ophthalmol, Vis. Sci.,* 1988, 29, 1265–71), hepatic injury associated with ischemia (M. Sakr, et al., Life Sci., 1990, 47, 687–91) allergic encephalomyelitis (K, Deguchi, et al., Brain Nerve, 1990, 42, 391–97), glomerulonephritis (J: McCauley, et al., Lancet, 1990, 335, 674) and systemic lupus erythematosus (K. Takabayashi, et al., *Clin. Immunol. Immunopathol.*, 1989, 51, 110–117) multidrug resistance (M. Naito, et al., *Cancer Chemother, Pharmacol.,* 1992, 29, 195–200), inflammation of mucosa and blood vessels (*PCT Publication WO* 91/17754), cytomegalovirus infection (*UK Publication GB* 2,247,620A), and idiopathic thrombocytophenic purpura and Basedow's disease (PCT Publication WO 91/19495).

BACKGROUND OF THE INVENTION

Inununoregulatory abnormalities have been shown to exist in a wide variety of "autoimmune" and chronic inflammatory diseases, including systemic lupus erythematosis, chronic rheumatoid arthritis, type I and II diabetes mellitus, inflammatory bowel disease, biliary cirrhosis, uveitis, multiple sclerosis and other disorders such as Crohn's disease, ulcerative colitis, bullous pemphigoid, sarcoidosis, psoriasis, ichthyosis, and Graves ophthalmopathy. Although the underlying pathogenesis of each of these conditions may be quite different, they have in common the appearance of a variety of autoantibodies and self-reactive lymphocytes. Such self-reactivity may be due, in part, to a loss of the homeostatic controls under which the normal immune system operates.

Similarly, following a bone-marrow or an organ transplantation, the host lymphocytes recognize 16/JET100 - 7 - 18513IB the foreign tissue antigens and begin to produce antibodies which lead to graft rejection.

One end result of an autoimmune or a rejection process is tissue destruction caused by inflammatory cells and the mediators they release. Antiinflammatory agents such as NSAID's and corticosteroids act principally by blocking the effect or secretion of these mediators but do nothing to modify the immunologic basis of the disease. On the other hand, cytotoxic agents such as cyclophosphamide, act in such a nonspecific fashion that both the normal and autoimmune responses are shut off. Indeed, patients treated with such nonspecific immunosuppressive agents are as likely to succumb from infection as they are from their autoimmune disease.

Cyclosporin A which was approved by the US FDA in 1983 is currently the leading drug used to prevent rejection of transplanted organs. The drug acts by inhibiting the body's immune system from mobilizing its vast arsenal of natural protecting agents to reject the transplant's foreign protein. Though cyclosporin A is effective in fighting transplant rejection, it is nephrotoxic and is known to cause several undesirable side effects including kidney failure, abnormal liver function and gastrointestinal discomfort.

Newer, safer drugs exhibiting less side effects are constantly being searched for in the field.

The 23-membered tricyclo-macrolide inununosuppressant, tacrolimus, FR-900506, FK-506,

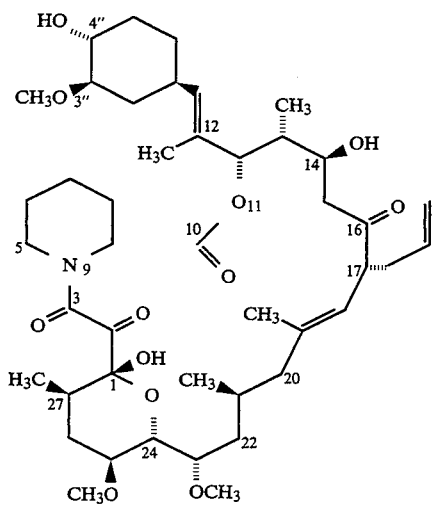

(17-allyl-1,14-dihydroxy-12-[2'-(4"-hydroxy-3"-methoxy-cyclohexyl) -1'-methylvinyl]-23,25-dimethoxy-13,19,21,27-tetramethyl-11,28-dioxa-4-azatricyclo[22-3.1.0$^{4,9}$]-octacos-18-ene-2,3,10,16-tetraone) and related compounds which were isolated and characterized by Tanaka, Kuroda, and co-workers at Fujisawa Pharmaceutical Co. in Japan, see J. Am. Chem. Soc., 1987, 109, 5031, and U.S. Pat. No. 4,894,366, issued Jan. 16, 1990) have been shown to possess exceptional immunosuppressive activity. Fujisawa United States patents (U.S. Pat. No. 4,929,611, issued May 29, 1990 U.S. Pat. No. 4,956,352, issued Sep. 11, 1990, and U.S. Pat. No. 5,110,811, issued May 5, 1992) disclose the use of FK-506-type compounds in treating resistance to transplantation. In particular, the compound FR-900506 has been reported to be 100 times more effective than cyclosporin in the supression of in vitro immune systems (*J. Antibiotics* 1987, 40, 1256). In addition, these compounds are reputed to possess topical activity in the treatment of inflammatory and hyperproliferative skin diseases and cutaneous manifestations of immunologically-mediated illnesses (EPO Pub. No. 0,315,978).

The compound FK-506 and related compounds further have been suggested to be useful in the treatment of obstructive airways disease, particularly asthma (*PCT Publication WO* 90/14826), male pattern alopecia or alopecia senilis (*EPO Publication No.* 0,423,714), rheumatoid arthitis (C. Arita, et al., *Clincial exp. Immunol.,* 1990, 82, 456–461; N. Inamura, et al., *Clin. Immunol. Immunopathol.* 1988, 46, 82–90), recent-onset diabetes (N. Murase, et al., Diabetes, 1990, 39, 1584–86; N. Murase, et al., Lancet, 1990, 336, 373–74), posterior uveitis (H. Kawashima, *Invest. Ophthalmol. Vis. Sci.,* 1988, 29, 1265–71), hepatic injury associated with ischemia (M. Sakr, et al., Life Sci., 1990, 47, 687–91) allergic encephalomyelitis (K, Deguchi, et al., *Brain Nerve,* 1990, 42, 391–97), glomerulonephritis (J. McCauley, et al., Lancet, 1990, 335, 674) systemic lupus erythematosus (K. Takabayashi, et al., *Clin. Immunol. Immunopathol.,* 1989, 51, 110–117) multidrug resistance (M. Naito, et al., *Cancer Chemother. Pharmacol.,* 1992, 29, 195–200), inflammation of mucosa and blood vessels (*PCT Publication WO* 92/17754), cytomegalovirus infection (*UK Publication GB* 2,247,620A), and idiopathic thrombocytophenic purpura and Basedow's disease (*PCT Publication WO* 91/19495).

Baldness or alopecia, in addition to male pattern alopecia, female pattern alopecia, and alopecia senilis, includes *alopecia areta,* and further, diseases accompanied by the basic skin lesions such as cicatrix or infectious tumors, or accompanied by systemic disorder, for example, an internal secretion abnormality or nutritional disorder.

In regard to alopecia areata, it is considered that an autoimmune phenomenon participates therein, and therefore, the administration of a substance having an inunmunosuppressive action can have therapeutical effect on alopecia areata.

The causes of human pattern alopecia (also called "androgenic alopecia") and alopecia senills are considered to be: an activation of male hormones at organs such as hair roots and the sebun gland; a lowering in the amount of blood reaching the hair follicles; a scalp abnormality caused by an excessive secretion of sebun, a formation or peroxides, or a propagation of bacteria; genetic causes; and aging.

The compound minoxidil (6-amino-1,2-dihydro -1- hydroxy-2-imino-4-piperidino-pyrimidine) was approved by the FDA for the treatment of male pattern baldness in August 1988. Minoxidil was also approved by the FDA for the treatment of female adrogenetic alopecia on Aug. 13, 1991. The preparation of minoxidil is described in U.S. Pat. Nos. 3,382,247, 3,644,364 and 4,098,791. Upjohn United States Patents (U.S. Pat. Nos. 4,139,619and 4,596,812) discloses the use of minoxidil in the topical treatment of human baldness. Similarly, an Upjohn United States Patent (U.S. Pat. No. 5,026,691) discloses the use of minoxidil and an antiinflammatory agent for the treatment of patterned male and female alopecia. Japanese patent Kokai 61-260010 states that topical minoxidil formulations containing other specified agents may be prepared. An Upjohn WIPO patent application (PCT Publication No. WO 92/09259) discloses a method and composition for promoting hair growth in mammals comprising the administration of a potassium channel opener and an androgen receptor blocker. A University of Miami WIPO patent application (PCT Publication No. WO 92/12703) discloser a method of stimulating hair growth comprising the topical application of a phospholipid.

Merck U.S. Pat. No. 4,760,071 discloses the 5α-reductase inhibitor 17β-(N-tert-butylcarbamoyl) -4-aza-5α-androst-1-en-3-one. Harris, et al., (*Proc. Natl. Acad. Sci. USA,* 89, 10787–10791 (Nov. 1992)) and Melin, et al. (*J. Steroid Biochem. Molec. Biol.,* 44(2), 121–131 (1993)) disclose the use of scalp-selective 5α-reductase inhibitors in the treatment of male pattern baldness, acne and hirsutism.

DETAILED DESCRIPTION OF THE INVENTION

A. Scope of the Invention

The present invention is directed to a compound of structural Formula I:

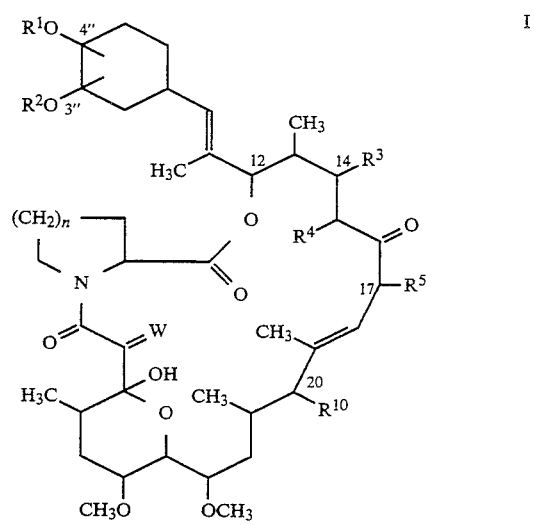

or a pharmaceutically acceptable salt thereof, wherein:
$R^1$ is selected from:
(1) heteroaryl;
(2) substituted heteroaryl in which the substituents are X, Y and Z;
(3) heteroaryl-$C_{1-10}$alkyl;
(4) substituted heteroaryl-$C_{1-10}$alkyl in which the heteroaryl group is substituted by X, Y and Z and the alkyl portion may be substituted with one or more of the substituent(s) selected from:
 (a) hydroxy,
 (b) OXO,
 (c) $C_{1-6}$-alkoxy,
 (d) aryl-$C_{1-3}$alkoxy,
 (e) substituted aryl-$C_{1-3}$alkoxy, in which the substituents on aryl are X, Y and Z,
 (f) unsubstituted or substituted aryloxy, in which the substituents on aryl are X, Y and Z,
 (g) —OCO-$C_{1-6}$alkyl,
 (h) —$NR^6R^7$, wherein $R^6$ and $R^7$ are independently selected from
   (i) hydrogen,
   (ii) $C_{1-10}$alkyl unsubstituted or substituted with one or more of the substituent(s) selected from:
     (a') aryl, which is unsubstituted or substituted with X, Y and Z,
     (b') heteroaryl, which is unsubstituted or substituted with X, Y and Z,
     (c') —OH,
     (d') $C_{1-6}$alkoxy,
     (e') —$CO_2H$, (f') —CO₂—C₁₋₆alkyl,
(g') —C₃₋₇cycloalkyl, and
(h') —OR¹¹,
(iii) C₃₋₁₀alkenyl unsubstituted or substituted with one or more of the substituent(s) selected from:
(a') aryl, which is unsubstituted or substituted with X, Y and Z,
(b') heteroaryl, which is unsubstituted or substituted with X, Y and Z,
(c') —OH,
(d') C₁₋₆alkoxy,
(e') —CO₂H,
(f') —CO₂—C₁₋₆alkyl,
(g') —C₃₋₇cycloalkyl, and
(h') —OR¹¹,
(iv) or where R⁶ and R⁷ and the N to which they are attached may form an unsubstituted or substituted 3-7-membered heterocyclic ring which may include one or two additional heteroatoms independently selected from the group consisting of O, S(O)p, NR¹⁴ wherein R¹⁴ is hydrogen or C₁₋₆ alkyl unsubstituted or substituted by phenyl, and p is 1 or 2, such as morpholine, thiomorpholine, piperidine, or piperizine,
(i) —NR⁶CO—C₁₋₆alkyl-R⁷, wherein R⁶ and R⁷ are as defined above,
(j) —NR⁶CO₂—C₁₋₆alkyl-R⁷,
(k) —NR⁶CONR⁶R⁷,
(l) —OCONR⁶R⁷,
(m) —COOR⁶,
(n) —CHO,
(o) aryl,
(p) substituted aryl in which the substituents are X, Y and Z,
(q) —OR¹¹, and
(r) —S(O)$_p$—C₁₋₆alkyl;
(5) heteroaryl-C₁₋₁₀alkyl wherein one or more of the alkyl carbons is replaced by a group selected from: —NR⁶—, —O—, —S(O)$_p$—, —CO₂—, —O₂C—, —CONR⁶—, —NR⁶CO—, —NR⁶CONR⁷—;
(6) substituted heteroaryl-C₁₋₁₀alkyl wherein one or more of the alkyl carbons is replaced by a group selected from: —NR⁶—, —O—, —S(O)$_p$—, —CO₂—, —O₂C—, —CONR⁶—, —NR⁶CO—, and —NR⁶CONR⁷—, the heteroaryl group is substituted with X, Y, and Z, and the alkyl group may be substituted with one or more of the substituent(s) selected from:
(a) hydroxy,
(b) oxo,
(c) C₁₋₆alkoxyl
(d) aryl-C₁₋₃alkoxyl
(e) substituted aryl-C₁₋₃alkoxy, in which the substituents on aryl are X, Y and Z,
(f) unsubstituted or substituted aryloxy, in which the substituents on aryl are X, Y and Z,
(g) —OCO—C₁₋₆alkyl,
(h) —NR⁶R⁷, wherein R⁶ and R⁷ are as defined above,
(i) —NR⁶CO—C₁₋₆alkyl-R⁷,
(j) —NR⁶CO₂—C₁₋₆alkyl-R⁷,
(k) —NR⁶CONR⁶R⁷,
(l) —OCONR⁶R⁷,
(m) —COOR⁶,
(n) —CHO,
(o) aryl,
(p) substituted aryl in which the substituents are X, Y and Z,
(q) —OR¹¹, and
(r) —S(O)$_p$—C₁₋₆alkyl;
(7) heteroaryl-C₃₋₁₀alkenyl wherein alkenyl contains one to four double bonds;
(8) heteroaryl-C₃₋₁₀alkenyl wherein alkenyl contains one to four double bonds and wherein one or more of the alkyl carbons is replaced by a group selected from: —NR⁶—, —O—, —S(O)$_p$—, —CO₂—, —O₂C—, —CONR⁶—, —NR⁶CO—, and —NR⁶CONR⁷—;
(9) substituted heteroaryl-C₃₋₁₀alkenyl wherein alkenyl contains one to four double bonds and wherein one or more of the alkyl carbons may be replaced by a group selected from: —NR⁶—, —O—, —S(O)$_p$—, —CO₂—, —O₂C—, —CONR⁶—, —NR⁶CO—, and —NR⁶CONR⁷, the heteroaryl group is substituted with X, Y, and Z, and the alkyl group may be substituted with one or more of the substituent(s) selected from:
(a) hydroxy,
(b) oxo,
(c) C₁₋₆alkoxy,
(d) aryl-C₁₋₃alkoxyl,
(e) substituted aryl-C₁₋₃alkoxy, in which the substituents on aryl are X, Y and Z,
(f) unsubstituted or substituted aryloxy, in which the substituents on aryl are X, Y and Z,
(g) —OCO—C₁₋₆alkyl,
(h) —NR⁶R⁷, wherein R⁶ and R⁷ as defined above,
(i) —NR⁶CO—C₁₋₆alkyl, wherein R⁶ is as defined above,
(j) —NR⁶CO₂—C₁₋₆alkyl,
(k) —NR⁶CONR⁶R⁷,
(l) —OCONR⁶R⁷,
(m) —COOR⁶,
(n) —CHO,
(o) aryl,
(p) substituted aryl in which the substituents are X, Y and Z, and
(q) —OR¹¹, and
(r) —S(O)$_p$—C₁₋₆alkyl;
R² is selected from:
(1) the definitions of R¹;
(2) hydrogen;
(3) phenyl;
(4) substituted phenyl in which the substituents are X, Y and Z;
(5) 1- or 2-naphthyl;
(6) substituted 1- or 2-naphthyl in which the substituents are X, Y and Z;
(7) biphenyl;
(8) substituted biphenyl in which the substituents are X, Y and Z;
(9) C₁₋₁₀alkyl;
(10) substituted-C₁₋₁₀alkyl in which one or more substituent(s) is(are) selected from:
(a) hydroxy,
(b) oxo,
(c) C₁₋₆alkoxy,
(d) aryl-C₁₋₃alkoxy,
(e) substituted aryl-C₁₋₃alkoxy, in which the substituents on aryl are X, Y and Z,
(f) unsubstituted or substituted aryloxy, in which the substituents on aryl are X, Y and Z,
(g) —OCO—C₁₋₆alkyl, (h) —NR$^6$R$^7$, wherein R$^6$ and R$^7$ are as defined above
(i) —NR$^6$CO—C$_{1-6}$alkyl-R$^7$, wherein R$^6$ and R$^7$ are as defined above,
(j) —COOR$^6$, wherein R$^6$ is as defined above,
(k) —CHO,
(l) phenyl,
(m) substituted phenyl in which the substituents are X, Y and Z,
(n) 1- or 2-naphthyl,
(o) substituted 1- or 2-naphthyl in which the substituents are X, Y and Z,
(p) biphenyl,
(q) substituted biphenyl in which the substituents are X, Y and Z,
(r) —OR$^{11}$ and
(s) —S(O)$_p$—C$_{1-6}$alkyl;
(11) C$_{3-10}$alkenyl;
(12) substituted C$_{3-10}$alkenyl in which one or more substituent(s) is(are) selected from: (a) hydroxy,
(b) oxo,
(c) C$_{1-6}$alkoxy,
(d) Phenyl-C$_{1-3}$alkoxy,
(e) substituted phenyl-C$_{1-3}$alkoxy, in which the substituents on phenyl are X, Y and Z,
(f) —OCO—C$_{1-6}$alkyl,
(g) —NR$^6$R$^7$, wherein R$^6$ and R$^7$ are as defined above
(h) —NR$^6$CO—C$_{1-6}$alkyl, wherein R$^6$ is as defined above,
(i) —COOR$^6$, wherein R$^6$ is as defined above,
(j) —CHO,
(k) phenyl,
(l) substituted phenyl in which the substituents are X, Y and Z,
(m) 1- or 2-naphthyl,
(n) substituted 1- or 2-naphthyl in which the substituents are X, Y and Z,
(o) biphenyl,
(p) substituted biphenyl in which the substituents are X, Y and Z,
(q) —OR$^{11}$, and
(r) —S(O)$_p$—C$_{1-6}$alkyl;
(13) C$_{3-10}$alkynyl;
(14) substituted C$_{3-10}$alkynyl in which one or more substituent(s) is(are) selected from:
(a) hydroxy,
(b) oxo,
(c) C$_{1-6}$alkoxyl,
(d) phenyl-C$_{1-3}$alkoxyl,
(e) substituted phenyl-C$_{1-3}$alkoxy, in which the substituents on phenyl are X, Y and Z,
(f) —OCO—C$_{1-6}$alkyl,
(g) —NR$^6$R$^7$, wherein R$^6$ and R$^7$ are as defined above,
(h) —NR$^6$CO—C$_{1-6}$alkyl, wherein R$^6$ is as defined above,
(i) —COOR$^6$, wherein R$^6$ is as defined above,
(j) —CH0,
(k) phenyl,
(l) substituted phenyl in which the substituents are X, Y and Z,
(m) 1- or 2-naphthyl,
(n) substituted 1- or 2-naphthyl in which the substituents are X, Y and Z,
(o) biphenyl,
(p) substituted biphenyl in which the substituents are X, Y and Z,
(q) —OR$^{11}$; and
(15) —R$^{11}$;
R$^3$ is hydrogen, hydroxy, —OR$^{11}$ or C$_{1-6}$alkoxy;
R$^4$ is hydrogen, or R$^3$ and R$^4$ taken together form a double bond;
R$^5$ is methyl, ethyl, propyl or allyl;
R$^{10}$ is hydrogen, hydroxy, —OR$^{11}$ or fluoro;
R$^{11}$ is selected from:
(a) —PO(OH)O$^-$M$^+$, wherein M$^+$ is a positively charged inorganic or organic counterion,
(b) —SO$_3^-$M$^+$,
(c) —CO(CH2)$_q$CO$_2^-$M$^+$, wherein q is 1–3, and
(d) —CO—C$_{1-6}$alkyl-NR$^6$R$^7$, wherein R$^6$ and R$^7$ are as defined above and the alkyl is unsubstituted or substituted with one or more substituents selected from:
(i) hydroxy,
(ii) C$_{1-6}$alkoxyl,
(iii) —NR$^{16}$R$^{17}$, wherein R$^{16}$ and R$^{17}$ are independently selected from:
(a') hydrogen, and
(b') C$_{1-6}$alkyl,
(iv) —COOR$^6$, wherein R$^6$ is as defined above,
(v) phenyl,
(iv) substituted phenyl in which the substituents are X, Y and Z,
(vii) heteroaryl,
(viii) —SH, and
(ix) —S—C$_{1-6}$alkyl;
W is 0 or (H, OH);
X, Y and Z independently are selected from:
(a) hydrogen,
(b) C$_{1-10}$alkyl, unsubstituted or substituted with one or more substituents selected from:
(i) aryl,
(ii) substituted aryl in which the substituents are X', Y' and
(iii) heteroaryl,
(iv) substituted heteroaryl in which the substituents are X', Y', and Z',
(v) unsubstituted or substituted aryloxy, in which the substituents on aryl are X', Y' and Z',
(vi) —OR$^6$,
(vii) —OR$^{11}$
(viii) —OCOR$^6$,
(ix) —OCO$_2$R$^6$,
(x) —NR$^6$R$^7$,
(xi) —CHO,
(xii) —NR$^6$COC$_{1-6}$alkyl-R$^7$,
(xiii) —NR$^6$CO2C$_{1-6}$alkyl-R$^7$,
(xiv) —NR$^6$CONR$^6$R$^7$,
(xv) —OCONR$^6$R$^7$,
(xvi) —CONR$^6$R$^7$,
(c) C$_{1-10}$alkyl wherein one or more of the alkyl carbons is replaced by a group selected from —NR$^6$—, —O—, —S(O)$_p$—, —CO$_2$—, —O$_2$C—, —CONR$^6$—, —NR$^6$CO—, —NR$^6$CONR$^7$—, —CO—, —CH(OH)—, alkenyl or alkynyl and the alkyl may be unsubstituted or substituted with one or more substituents selected from:
(i) aryl,
(ii) substituted aryl in which the substituents are X', Y' and Z',
(iii) heteroaryl,
(iv) substituted heteroaryl in which the substituents are X', Y', and (v) unsubstituted or substituted aryloxy, in which the substituents on aryl are X', Y', and Z',
(vi) —$OR^6$,
(vii) —$OR^{11}$,
(viii) —$OCOR^6$,
(ix) —$OCO_2R^6$,
(x) —$NR^6R^7$,
(xi) —CHO
(xii) —$NR^6COC_{1-6}alkyl-R^7$,
(xiii) —$NR^6CO_2C_{1-6}alkyl-R^7$,
(xiv) —$NR^6CONR^6R^7$,
(xv) —$OCONR^6R^7$,
(xvi) —$CONR^6R^7$,
(d) halogen,
(e) —$NR^6R^7$,
(f) —CN,
(g) —CHO,
(h) —$CF_3$,
(i) —$SR^8$, wherein $R^8$ is hydrogen, $C_{1-6}$alkyl, trifluoromethyl, or phenyl,
(j) —$SOR^8$,
(k) —$SO_2R^8$,
(l) —$CONR^6R^7$,
(m) $R^9O(CH_2)_m$— wherein $R^9$ is hydrogen, $C_{1-6}$alkyl, hydroxy-$C_{2-3}$alkyl, —$CF_3$, phenyl, $R^{11}$ or naphthyl and m is 0, 1, 2, or 3,
(n) —$CH(OR^{12})(OR^{13})$, wherein $R^{12}$ and $R^{13}$ are $C_{1-3}$alkyl or taken together form an ethyl or propyl bridge,
(o)

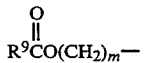

wherein $R^9$ and m are as defined above,
(p)

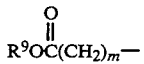

wherein $R^9$ and m are as defined above, and
(q) —$R^{11}$; or any two of X, Y and Z may be joined to form a saturated ring having 5, 6 or 7 ring atoms, said ring atoms comprising 1 or 2 oxygen atoms, the remaining ring atoms being carbon, such as dioxolanyl or dioxanyl;

X', Y' and Z' independently are selected from:
(a) hydrogen,
(b) $C_{1-7}$alkyl,
(c) $C_{2-6}$alkenyl,
(d) halogen,
(e) —$(CH_2)_m$—$NR^6R^7$ wherein $R^6$, $R^7$ and m are as defined above,
(f) —CN,
(g) —CHO,
(h) —$CF_3$,
(i) —$SR^8$ wherein $R^8$ is hydrogen, $C_{1-6}$alkyl, trifluoromethyl, or phenyl,
(j) —$SOR^8$ wherein $R^8$ is as defined above,
(k) —$SO_2R^8$, wherein $R^8$ is as defined above,
(l) —$CONR^6R^7$, wherein $R^6$ and $R^7$ are as defined above,
(m) $R^9O(CH_2)_m$— wherein $R^9$ and m are as defined above, (n) —$CH(OR^{12})(OR^{13})$, wherein $R^{12}$ and $R^{13}$ are as defined above,
(o)

wherein $R^9$ and m are as defined above,
(p)

wherein $R^9$ and m are as defined above, and
(q) —$R^{11}$;
n is 1 or 2.

The compounds of Formula I employed in the present invention have asymmetric centers and this invention includes all of the optical isomers and mixtures thereof.

In addition compounds of Formula I with carbon-carbon double bonds may occur in Z- and E-forms with all isomeric forms of the compounds being included in the present invention.

When any variable in Formula I (e.g., alkyl, aryl, $R^6$, $R^7$, $R^8$, $R^9$, $R^{10}$, $R^{11}$, etc.) occurs more than one time in any variable or in Formula I, its definition on each occurrence is independent of its definition at every other occurrence.

As used herein, the term "alkyl" includes those alkyl groups of a designated number of carbon atoms of either a straight, branched, or cyclic configuration. Examples of "alkyl" include methyl, ethyl, propyl, isopropyl, butyl, sec-and tert-butyl, pentyl, hexyl, heptyl, cyclopropyl, cyclobutyl, cyclopentyl, cyclohexyl, cycloheptyl, norbornyl, and the like. "Alkoxy" represents an alkyl group of indicated number of carbon atoms attached through an oxygen bridge, such as methoxy, ethoxy, propoxy, butoxy- and pentoxy. "Alkenyl" is intended to include hydrocarbon chains of a specified number of carbon atoms of either a straight- or branched-configuration and at least one unsaturation, which may occur at any point along the chain, such as ethenyl, propenyl, butenyl, pentenyl, dimethylpentyl, and the like, and includes E and Z forms, where applicable; and "heteroarylalkyl" represents heteroaryl groups as herein defined which are attached through a straight or branched chain alkyl group of from one to ten carbon atoms. "Halogen", as used herein, means fluoro, chloro, bromo and iodo, As will be understood by those skilled in the art, pharmaceutically acceptable salts include, but are not limited to salts with inorganic acids such as hydrochloride, sulfate, phosphate, diphosphate, hydrobromide, and nitrate or salts with an organic acid such as malate, maleate, fumarate, tartrate, succinate, citrate, acetate, lactate, methanesulfonate, p-toluenesulfonate or palmoate, salicylate and stearate. Similarly pharmaceutically acceptable cations include, but are not limited to sodium, potassium, calcium, aluminum, lithium and ammonium (especially ammonium salts with amines of the formula $HNR^6R^7$).

The heteroaryl group as used herein includes acridine, carbazole, cinnoline, dibenzofuran, dibenzothiophene, quinoxaline, pyrazole, indole, benzotriazole, furan, benzofuran, quinoline, isoquinoline, pyrazine, pyridazine, pyridine, pyrimidine, pyrrole which are optionally substituted.

In the compounds of Formula I the heteroaryl group may be optionally substituted with X, Y and Z at any available carbon atom or nitrogen atom (if present), but compounds bearing certain of X, Y and Z directly substituted to a nitrogen atom of the heteroaryl ring may be relatively unstable and are not preferred.

The term "heteroaryl" as utilized herein is intended to include the following heteraromatic groups which may include X, Y and Z substitution as indicated and wherein Q is —N(X)—, —O—, —S—, —DSO, or —SO$_2$—;

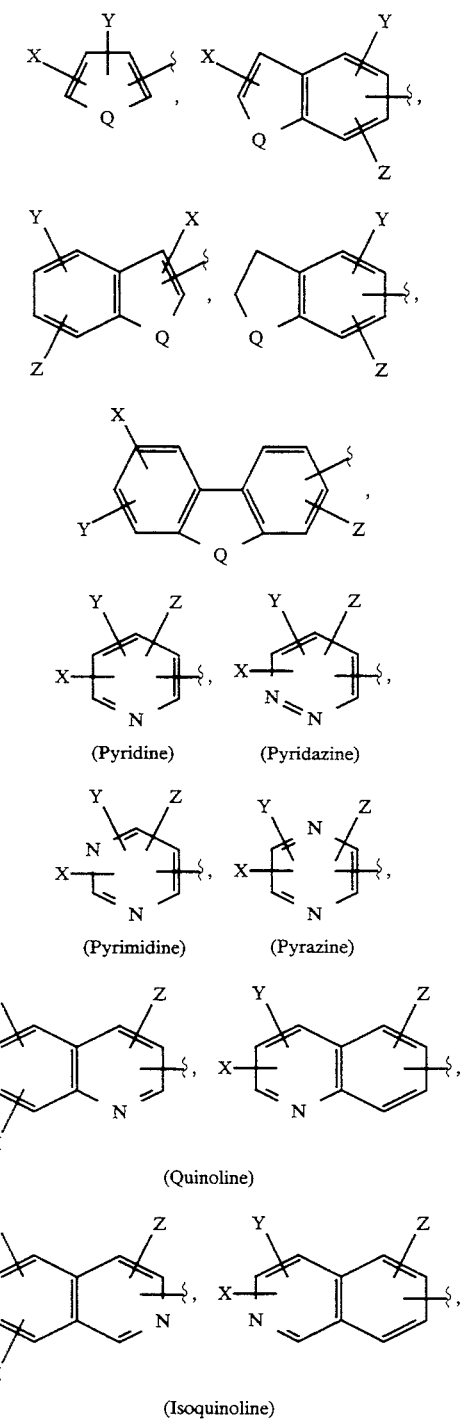

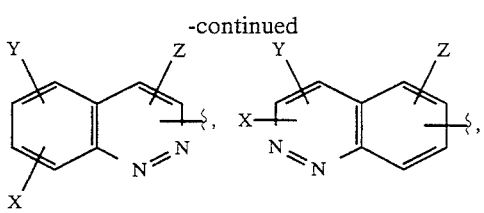

(Cinnoline)

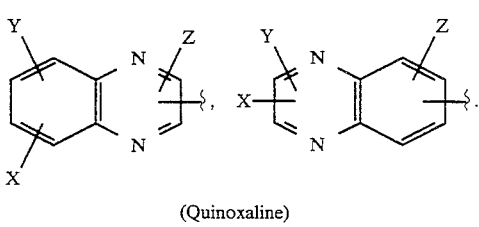

(Quinoxaline)

The aryl or aromatic group may include phenyl or naphthyl which are optionally substituted by from one- to three-members independently selected from the group consisting of: alkyl, alkenyl, halogen, carboxyl, $CH_0$, amino, mono-alkylamino, di-alkylamino, aminoalkyl, mono-alkylaminoalkyl, di-alkylaminoalkyl, alkylthio, alkylsulfinyl, alkysulfonyl, trifluoromethyl, amido, mono-alkylamido, dialkylamido, hydroxy, hydroxyalkyl, $R^{11}$O-alkyl, alkoxy, alkoxyalkyl, formamido, alkyl-CO$_2$—, formamidoalkyl, alkyl-CO$_2$-alkyl—, carboxyl, alkyl-CO$_2$H, alkyl-O$_2$C—, alkyl-O$_2$C-alkyl—, and OR$^{11}$.

In the compound of Formula I it is preferred that the heteroaryl is selected from the group consisting of:

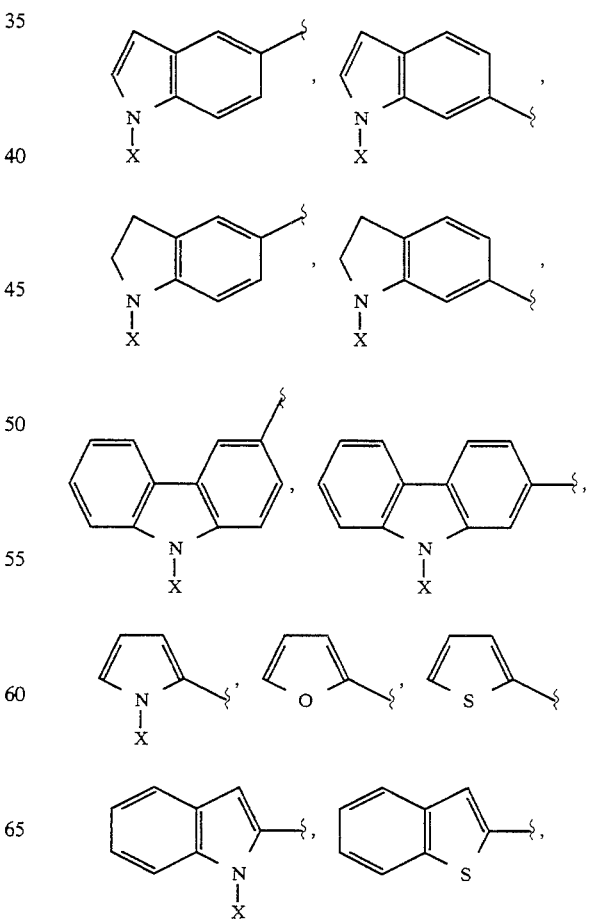

-continued

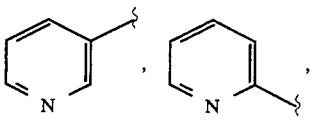

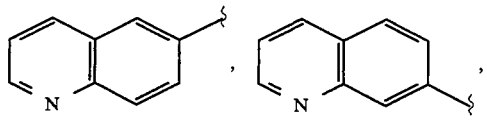

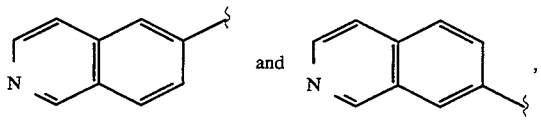

and wherein X is as defined above.

In the compound of formula I it is also preferred that $R^2$ is selected from:
(1) hydrogen,
(2) methyl,
(3) ethyl,
(4) propyl,
(5) allyl,
(6) $R^{11}$,
(7) —$C_{2-3}$alkyl-OH; and
(8) —$C_{2-3}$alkyl-$OR^{11}$;

$R^3$ is selected from:
(1) hydrogen,
(2) hydroxy,
(3) —$OR^{11}$, or $R^3$ and $R^4$ taken together form a double bond; $R^{10}$ is hydrogen, hydroxy, fluoro, or —$OR^{11}$;
W is 0; and
n is 2.

In one embodiment of the compound of Formula I, heteroaryl is indole, which may be represented by:

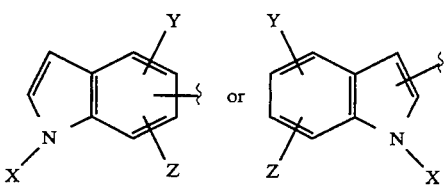

wherein $R^6$, X, Y and Z are as defined above,

In the instant combination, preferred compounds of Formula I are the compounds identified as follows:

17-Ethyl-1,14-dihydroxy-12-[2'-(4"-(2-furanyl)methoxy-3"-methoxycyclohexyl) -1'-methylvinyl]-23,25-dimethoxy-13,19,21,27-tetramethyl-11,28-dioxa-4-azatricyclo-[22.3.1.0⁴,⁹¹]octacos-18-ene-2,3,10,16-tetraone;

17-Ethyl-1,14-dihydroxy-12-[2'-(4"-(2-furanyl)methoxy-3"-hydroxycyclohexyl)-1'-methylvinyl]-23,25-dimethoxy-13,19,21,27-tetramethyl-11,28-dioxa-4-azatricyclo-[22.3.1.0⁴,⁹¹]octacos-18-ene-2,3,10,16-tetraone;

17-Ethyl-1,14-dihydroxy-12-[2'-(4"-hydroxy-3"-(2-furanyl) methoxycyclohexyl)-1'-methylvinyl]-23,25-dimethoxy-13,19,21,27-tetramethyl-11,28-dioxa-4-azatricyclo-[22.3.1.0⁴,⁹¹]octacos-18-ene-2,3,10,16-tetraone;

17-Ethyl-1,14-dihydroxy-12-[2'-(4"-(2-thiophene)-methoxy-3"-methoxycyclohexyl) -1'-methylvinyl]-23,25-dimethoxy-13,19,21,27-tetramethyl-11,28-dioxa-4-azatricyclo-[22.3.1.0⁴,⁹¹]octacos-18-ene-2,3,10,16-tetraone;

17-Ethyl-1,14-dihydroxy-12-[2'-(4"-(2-thiophene)-methoxy-3"-hydroxycyclohexyl) -1'-methylvinyl]-23,25-dimethoxy -13,19,21,27-tetramethyl-11,28-dioxa-4-aza-tricyclo [22.3.1.0⁴,⁹¹]octacos-18-ene-2,3,10,16-tetraone;

17-Ethyl-1,14-dihydroxy-12-[2'-(4"-(3-thiophene)-methoxy-3"-hydroxycyclohexyl) -1'-methylvinyl]-23,25-dimethoxy-13,19,21,27-tetramethyl-11,28-dioxa-4-aza-tricyclo [22.3.1.0⁴,⁹¹]octacos-18-ene-2,3,10,16-tetraone;

17-Ethyl-1,14-dihydroxy-12-[2'-(4"-hydroxy-3"-(2-thiophene) methoxycyclohexyl)-1'-methylvinyl]-23,25-dimethoxy -13,19,21,27-tetramethyl-11,28-dioxa-4-azatricyclo-22.3.1.0⁴,⁹¹]octacos-18-ene-2,3,10,16-tetraone;

17-Ethyl-1,14-dihydroxy-12-[2'-(4"-hydroxy-3"-(3-thiophene) methoxycyclohexyl)-1'-methylvinyl]-23,25-dimethoxy-13,19,21,27-tetramethyl -11,28-dioxa-4-azatricyclo-[22.3.1.0⁴,⁹¹]octacos-18-ene-2,3,10,16-tetraone;

17-Ethyl-1,14-dihydroxy-12-[2'-(4"-(2-thiophene)oxy-3"-methoxycyclohexyl) -1'-methylvinyl]-23,25-dimethoxy-13,19,21,27-tetramethyl-11,28-dioxa-4-azatricyclo-[22.3.1.0⁴,⁹¹]octacos-18-ene-2,3,10,16-tetraone;

17-Ethyl-1,14-dihydroxy-12-[2'-(4"-(2-benzothienyl)-oxy-3"-methoxycyclohexyl)-1'-methylvinyl]-23,25-dimethoxy-13,19,21,27-tetramethyl -11,28-dioxa-4-azatricyclo-[22.3.1.0⁴,⁹¹]octacos-18-ene-2,3,10,16-tetraone;

17-Ethyl-1,14-dihydroxy-12-[2'-(4"-(5-indolyl)oxy-3"-methoxycyclohexyl) -1'-methylvinyl]-23,25-dimethoxy-13,19,21,27-tetramethyl-11,28-dioxa-4-azatricyclo-[22.3.1.0⁴,⁹¹]octacos-18-ene-2,3,10,16-tetraone;

17-Ethyl-1,14-dihydroxy-12-[2'-(4"-(5-indolyl)oxy-3"-hydroxycyclohexyl) -1'-methylvinyl]-23,25-dimethoxy-13,19,21,27-tetramethyl-11,28-dioxa-4-azatricyclo-[22.3.1.0⁴,⁹¹]octacos-18-ene-2,3,10,16-tetraone;

17-Ethyl-1,14,20-trihydroxy-12-[2'-(4"-(5-indolyl)-oxy-3"-methoxycyclohexyl) -1'-methylvinyl]-23,25-di-methoxy-13,19,21,27-tetramethyl-11,28-dioxa-4-azatricyclo-[22.3.1.0⁴,⁹¹]octacos-18-ene-2,3,10,16-tetraone;

17-Ethyl-1,20-dihydroxy-12-[2'-(4"-(5-indolyl)oxy-3"-methoxycyclohexyl) -1'-methylvinyl]-23,25-dimethoxy-13,19,21,27-tetramethyl-11,28-dioxa-4-azatricyclo-[22.3.1.0⁴,⁹¹]octacos-18-ene-2,3,10,16-tetraone:

17-Ethyl-1-hydroxy-12-[2'-(4"-(5-indolyl)oxy-3"-methoxycyclohexyl) -1'-methylvinyl]-23,25-dimethoxy-13,19,21,27-tetramethyl -11,28-dioxa-4-azatricyclo-[22.3.1.0⁴,⁹¹]octacos-18-ene-2,3,10,16-tetraone;

17-Allyl-1,14-dihydroxy-12-[2'-(4"-(5-indolyl)oxy-3"-methoxycyclohexyl) -1'-methylvinyl]-23,25-dimethoxy-13,19,21,27-tetramethyl-11,28-dioxa-4-azatricyclo-[22.3.1.0⁴,⁹¹]octacos-18-ene-2,3,10,16-tetraone;

17-Allyl-1,14-dihydroxy-12-[2'-(4"-(5-indolyl)oxy-3"-hydroxycyclohexyl) -1'-methylvinyl]-23,25-dimethoxy-13,19,21,27-tetramethyl-11,28-dioxa-4-azatricyclo-[2.3.1.0⁴,⁹¹]octacos-18-ene-2,3,10,16-tetraone:

17-Allyl-1,14,20-trihydroxy-12-[2'-(4''-(5-indolyl)-oxy-3''-methoxycyclohexyl) -1'-methylvinyl]-23,25-dimethoxy-13,19,21,27-tetramethyl-11,28-dioxa-4-azatricyclo-[22.3.1.0⁴,⁹¹]octacos-18-ene-2,3,10,16-tetraone; 17-Allyl-1,20-dihydroxy-12-[2'-(4''-(5-indolyl)oxy-3''-methoxycyclohexyl) -1'-methylvinyl]-23,25-dimethoxy-13,19,21,27-tetramethyl-11,28-dioxa-4-azatricyclo-[22.3.1.0⁴,⁹¹]octacos-18-ene-2,3,10,16-tetraone;

17-Ethyl-1,14-dihydroxy-12-[2'-(4''-(5-indolyl)oxyl-3''-ethoxycyclohexyl) -1'-methylvinyl]-23,25-dimethoxy-13,19,21,27-tetramethyl-11,28-dioxa-4-azatricyclo-[22.3.1.0⁴,⁹¹]octacos-18-ene-2,3,10,16-tetraone;

17-Allyl-1,14-dihydroxy-12-[2'-(4''-(5-indolyl)oxy-3''-ethoxycyclohexyl) -1'-methylvinyl]-23,25-dimethoxy-13,19,21,27-tetramethyl-11,28-dioxa-4-azatricyclo-[22.3.1.0⁴,⁹¹]octacos-18-ene-2,3,10,16-tetraone:

17-Allyl-1-hydroxy-12-[2'-(4''-(5-indolyl)oxy-3''-methoxycyclohexyl) -1'-methylvinyl]-23,25-dimethoxy-13,19,21,27-tetramethyl-11,28-dioxa-4-azatricyclo-[22.3.1.0⁴,⁹¹]octacos-18-ene-2,3,10,16-tetraone:

17-Ethyl-1,14-dihydroxy-12-[2'-(4''-(1-N-methyl-5-indolyl) oxy-3''-methoxycyclohexyl)-1'-methylvinyl]-23,25-dimethoxy-13,19,21,27-tetramethyl-11,28-dioxa-4-azatricyclo [22.3.1.0⁴,⁹¹]octacos-18-ene-2,3,10,16-tetraone;

17-Ethyl-1,14-dihydroxy-12-[2'-(4''-(1-N-methyl-5-indolyl) oxy-3''-hydroxycyclohexyl)-1'-methylvinyl]-23,25-dimethoxy-13,19,21,27-tetramethyl-11,28-dioxa-4-azatricyclo [22.3.1.0⁴,⁹¹]octacos-18-ene-2,3,10,16-tetraone;

17-Ethyl-1,14,20-trihydroxy-12-[2'-(4''-(1-N-methyl-5-indolyl) oxy-3''-methoxycyclohexyl)-1'-methylvinyl]-23,25-dimethoxy-13,19,21,27-tetramethyl-11,28-dioxa-4-azatricyclo [22.3.1.0⁴,⁹¹]octacos-18-ene-2,3,10,16-tetraone;

17-Ethyl-1,14,20-trihydroxy-12-[2'-(4''-(1-N-methyl-5-indolyl) oxy-3''-hydroxycyclohexyl)-1'-methylvinyl]-23,25-dimethoxy-13,19,21,27-tetramethyl-11,28-dioxa-4-azatricyclo [22.3.1.0⁴,⁹¹]octacos-18-ene-2,3,10,16-tetraone;

17-Ethyl-1,20-dihydroxy-12-[2'-(4''-(1-N-methyl-5-indolyl) oxy-3''-methoxy-cyclohexyl)-1'-methylvinyl]-23,25-dimethoxy-13,19,21,27-tetramethyl-11,28-dioxa-4-azatricyclo [22.3.1.0⁴,⁹¹]octacos-18-ene-2,3,10,16-tetraone;

17-Ethyl-1,20-dihydroxy-12-[2'-(4''-(1-N-methyl-5-indolyl) oxy-3''-hydroxycyclohexyl)-1'-methylvinyl]-23,25-dimethoxy -13,19,21,27-tetramethyl-11,28-dioxa-4-azatricyclo[22.3.1.0⁴,⁹¹]octacos-18-ene-2,3,10,16-tetraone:

b 17-Allyl-1,14-dihydroxy-12-[2'-(4''-(1-N-methyl-5-indolyl) oxy-3''-methoxycyclohexyl)-1'-methylvinyl]-23,25-dimethoxy-13,19,21,27-tetramethyl-11,28-dioxa-4-azatricyclo [22.3.1.0⁴,⁹¹]octacos-18-ene-2,3,10,16-tetraone;

17-Allyl-1,14,20-trihydroxy-12-[2'-(4''-(1-N-methyl-5-indolyl)oxy-3''-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Allyl-1,20-dihydroxy-12-[2'-(4''-(1-N-methyl-5-indolyl)oxy-3''-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-1-hydroxy-12-[2'-(4''-(1-N-methyl-5-indolyl)oxy-3''-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-1,14-dihydroxy-12-[2'-(4''-(1-N-methyl-5-indolyl)oxy-3''-ethoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Allyl-1,14-dihydroxy-12-[2'-(4''-(1-N-methyl-5-indolyl)oxy-3''-ethoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-1,14-dihydroxy-12-[2'-(4''-(1-N-ethyl-5-indolyl)oxy-3''-ethoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Allyl-1-hydroxy-12-[2'-(4''-(1-N-methyl-5-indolyl)oxy-3''-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-1,14-dihydroxy-12-[2'-(4''-(1-N-methyl-5-indolyl)oxy-3''-allyloxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-1-hydroxy-12-[2'-(4''-(1-N-methyl-5-indolyl)oxy-3''-allyloxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-1,14-dihydroxy-12-[2'-(4''-(1-N-methyl-5-indolyl)oxy-3''-n-propyloxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-1-hydroxy-12-[2'-(4''-(1-N-methyl-5-indolyl)oxy-3''-n-propyloxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-1,14-dihydroxy-12-[2'-(4''-(1-N-methyl-5-indolyl)oxy-3''-i-propyloxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-1,14-dihydroxy-12-[2'-(4''-(1-N-ethyl-5-indolyl)oxy-3''-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-1,14,20-trihydroxy-12-[2'-(4''-(1-N-ethyl-5-indolyl)oxy-3''-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-1,20-dihydroxy-12-[2'-(4''-(1-N-ethyl-5-indolyl)oxy-3''-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-1,14-dihydroxy-12-[2'-(4''-(1-N-ethyl-5-indolyl)oxy-3''-hydroxycyclohexyl)-1'-methylvinyl]-23,25-dimethoxy-13,19,21,27-tetramethyl-11,28-dioxa-4-azatricyclo[22.3.1.0<sup>4,9</sup>]octacos-18-ene-2,3,10,16-tetraone;

17-Allyl-1,14-dihydroxy-12-[2'-(4''-(1-N-ethyl-5-indolyl)oxy-3''-methoxycyclohexyl)-1'-methylvinyl]-23,25-dimethoxy-13,19,21,27-tetramethyl-11,28-dioxa-4-azatricyclo[22.3.1.0<sup>4,9</sup>]octacos-18-ene-2,3,10,16-tetraone;

17-Allyl-1,14,20-trihydroxy-12-[2'-(4''-(1-N-ethyl-5-indolyl)oxy-3''-methoxycyclohexyl)-1'-methylvinyl]-23,25-dimethoxy-13,19,21,27-tetramethyl-11,28-dioxa-4-azatricyclo[22.3.1.0<sup>4,9</sup>]octacos-18-ene-2,3,10,16-tetraone;

17-Allyl -1,20-dihydroxy-12-[2'-(4''-(1-N-ethyl-5-indolyl)oxy-3''-methoxycyclohexyl)-1'-methylvinyl]-23,25-dimethoxy-13,19,21,27-tetramethyl-11,28-dioxa-4-azatricyclo[22.3.1.0<sup>4,9</sup>]octacos-18-ene-2,3,10,16-tetraone;

17-Allyl-1,14-dihydroxy-12-[2'-(4''-(1-N-ethyl-5-indolyl)oxy-3''-hydroxycyclohexyl)-1'-methylvinyl]-23,25-dimethoxy-13,19,21,27-tetramethyl-11,28-dioxa-4-azatricyclo[22.3.1.0<sup>4,9</sup>]octacos-18-ene-2,3,10,16-tetraone;

17-Ethyl-1-hydroxy-12-[2'-(4''-(1-N-ethyl-5-indolyl)oxy-3''-methoxycyclohexyl)-1'-methylvinyl]-23,25-dimethoxy-13,19,21,27-tetramethyl-11,28-dioxa-4-azatricyclo[22.3.1.0<sup>4,9</sup>]octacos-18-ene-2,3,10,16-tetraone;

17-Allyl-1-hydroxy-12-[2'-(4''-(1-N-ethyl-5-indolyl)oxy-3''-methoxycyclohexyl)-1'-methylvinyl]-23,25-dimethoxy-13,19,21,27-tetramethyl-11,28-dioxa-4-azatricyclo[22.3.1.0<sup>4,9</sup>]octacos-18-ene-2,3,10,16-tetraone;

17-Allyl-1,14-dihydroxy-12-[2'-(4''-(1-N-ethyl-5-indolyl)oxy-3''-ethoxycyclohexyl)-1'-methylvinyl]-23,25-dimethoxy-13,19,21,27-tetramethyl-11,28-dioxa-4-azatricyclo[22.3.1.0<sup>4,9</sup>]octacos-18-ene-2,3,10,16-tetraone;

17-Ethyl-1,14-dihydroxy-12-[2'-(4''-(1-N-propyl-5-indolyl)oxy-3''-methoxycyclohexyl)-1'-methylvinyl]-23,25-dimethoxy-13,19,21,27-tetramethyl-11,28-dioxa-4-azatricyclo[22.3.1.0<sup>4,9</sup>]octacos-18-ene-2,3,10,16-tetraone;

17-Ethyl-1,14,20-trihydroxy-12-[2'-(4''-(1-N-propyl-5-indolyl)oxy-3''-methoxycyclohexyl)-1'-methylvinyl]-23,25-dimethoxy-13,19,21,27-tetramethyl-11,28-dioxa-4-azatricyclo[22.3.1.0<sup>4,9</sup>]octacos-18-ene-2,3,10,16-tetraone;

17-Ethyl-1,20-dihydroxy-12-[2'-(4''-(1-N-propyl-5-indolyl)oxy-3''-methoxycyclohexyl)-1'-methylvinyl]-23,25-dimethoxy-13,19,21,27-tetramethyl-11,28-dioxa-4-azatricyclo[22.3.1.0<sup>4,9</sup>]octacos-18-ene-2,3,10,16-tetraone;

17-Ethyl-1,14-dihydroxy-12-[2'-(4''-(1-N-propyl-5-indolyl)oxy-3''-hydroxycyclohexyl)-1'-methylvinyl]-23,25-dimethoxy-13,19,21,27-tetramethyl-11,28-dioxa-4-azatricyclo[22.3.1.0<sup>4,9</sup>]octacos-18-ene-2,3,10,16-tetraone;

7-Ethyl-1,14,20-trihydroxy-12-[2'-(4''-(1-N-propyl-5-indolyl)oxy-3''-hydroxycyclohexyl)-1'-methylvinyl]-23,25-dimethoxy-13,19,21,27-tetramethyl-11,28-dioxa-4-azatricyclo[22.3.1.0<sup>4,9</sup>]octacos-18-ene-2,3,10,16-tetraone;

17-Ethyl-1,20-dihydroxy-12-[2'-(4''-(1-N-propyl-5-indolyl)oxy-3''-hydroxycyclohexyl)-1'-methylvinyl]-23,25-dimethoxy-13,19,21,27-tetramethyl-11,28-dioxa-4-azatricyclo[22.3.1.0<sup>4,9</sup>]octacos-18-ene-2,3,10,16-tetraone;

17-Allyl-1,14-dihydroxy-12-[2'-(4''-(1-N-propyl-5-indolyl)oxy-3''-methoxycyclohexyl)-1'-methylvinyl]-23,25-dimethoxy-13,19,21,27-tetramethyl-11,28-dioxa-4-azatricyclo[22.3.1.0<sup>4,9</sup>]octacos-18-ene-2,3,10,16-tetraone;

17-Allyl-1,14,20-trihydroxy-12-[2'-(4''-(1-N-propyl-5-indolyl)oxy-3''-methoxycyclohexyl)-1'-methylvinyl]-23,25-dimethoxy-13,19,21,27-tetramethyl-11,28-dioxa-4-azatricyclo[22.3.1.0<sup>4,9</sup>]octacos-18-ene-2,3,10,16-tetraone;

17-Allyl-1,20-dihydroxy-12-[2'-(4''-(1-N-propyl-5-indolyl)oxy-3''-methoxycyclohexyl)-1'-methylvinyl]-23,25-dimethoxy-13,19,21,27-tetramethyl-11,28-dioxa-4-azatricyclo[22.3.1.0<sup>4,9</sup>]octacos-18-ene-2,3,10,16-tetraone;

17-Allyl-1,14-dihydroxy-12-[2'-(4''-(1-N-propyl-5-indolyl)oxy-3''-hydroxycyclohexyl)-1'-methylvinyl]-23,25-dimethoxy-13,19,21,27-tetramethyl-11,28-dioxa-4-azatricyclo[22.3.1.0<sup>4,9</sup>]octacos-18-ene-2,3,10,16-tetraone;

17-Ethyl-1-hydroxy-12-[2'-(4''-(1-N-propyl-5-indolyl)oxy-3''-methoxycyclohexyl)-1'-methylvinyl]-23,25-dimethoxy-13,19,21,27-tetramethyl-11,28-dioxa-4-azatricyclo[22.3.1.0<sup>4,9</sup>]octacos-18-ene-2,3,10,16-tetraone;

17-Allyl-1-hydroxy-12-[2'-(4''-(1-N-propyl-5-indolyl)oxy-3''-methoxycyclohexyl)-1'-methylvinyl]-23,25-dimethoxy-13,19,21,27-tetramethyl-11,28-dioxa-4-azatricyclo[22.3.1.0<sup>4,9</sup>]octacos-18-ene-2,3,10,16-tetraone;

17-Ethyl-1,14-dihydroxy-12-[2'-(4''-(1-N-propyl-5-indolyl)oxy-3''-ethoxycyclohexyl)-1'-methylvinyl]-23,25-dimethoxy-13,19,21,27-tetramethyl-11,28-dioxa-4-azatricyclo[22.3.1.0<sup>4,9</sup>]octacos-18-ene-2,3,10,16-tetraone;

17-Allyl-1,14-dihydroxy-12-[2'-(4''-(1-N-propyl-5-indolyl)oxy-3''-ethoxycyclohexyl)-1'-methylvinyl]-23,25-dimethoxy-13,19,21,27-tetramethyl-11,28-dioxa-4-azatricyclo[22.3.1.0<sup>4,9</sup>]octacos-18-ene-2,3,10,16-tetraone;

17-Ethyl-1,14-dihydroxy-12-[2'-(4''-(1-N-allyl-5-indolyl)oxy-3''-methoxycyclohexyl)-1'-methylvinyl]-23,25-dimethoxy-13,19,21,27-tetramethyl-11,28-dioxa-4-azatricyclo[22.3.1.0<sup>4,9</sup>]octacos-18-ene-2,3,10,16-tetraone;

17-Ethyl-1,14,20-trihydroxy-12-[2'-(4''-(1-N-allyl-5-indolyl)oxy-3''-methoxycyclohexyl)-1'-methylvinyl]-23,25-dimethoxy-13,19,21,27-tetramethyl-11,28-dioxa-4-azatricyclo[22.3.1.0<sup>4,9</sup>]octacos-18-ene-2,3,10,16-tetraone;

17-Ethyl-1,20-dihydroxy-12-[2'-(4''-(1-N-allyl-5-indolyl)oxy-3''-methoxycyclohexyl)-1'-methylvinyl]-23,25-dimethoxy-13,19,21,27-tetramethyl-11,28-dioxa-4-azatricyclo[22.3.1.0<sup>4,9</sup>]octacos-18-ene-2,3,10,16-tetraone;

17-Ethyl-1,14-dihydroxy-12-[2'-(4''-(1-N-allyl-5-indolyl)oxy-3''-hydroxycyclohexyl)-1'-methylvinyl]-23,25-dimethoxy-13,19,21,27-tetramethyl-11,28-dioxa-4-azatricyclo[22.3.1.0<sup>4,9</sup>]octacos-18-ene-2,3,10,16-tetraone;

17-Ethyl-1,14,20-trihydroxy-12-[2'-(4''-(1-N-allyl-5-indolyl)oxy-3''-hydroxycyclohexyl)-1'-methylvinyl]-23,25-dimethoxy-13,19,21,27-tetramethyl-11,28-dioxa-4-azatricyclo[22.3.1.0<sup>4,9</sup>]octacos-18-ene-2,3,10,16-tetraone;

17-Ethyl-1,20-dihydroxy-12-[2'-(4"-(1-N-allyl-5-indolyl)oxy-3"-hydroxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Allyl-1,14-dihydroxy-12-[2'-(4"-(1-N-allyl-5-indolyl)oxy-3"-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Allyl-1,14,20-trihydroxy-12-[2'-(4"-(1-N-allyl-5-indolyl)oxy-3"-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Allyl-1,20-dihydroxy-12-[2'-(4"-(1-N-allyl-5-indolyl)oxy-3"-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Allyl-1,14-dihydroxy-12-[2'-(4"-(1-N-allyl-5-indolyl)oxy-3"-hydroxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-1-hydroxy-12-[2'-(4"-(1-N-allyl-5-indolyl)oxy-3"-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Allyl-1-hydroxy-12-[2'-(4"-(1-N-allyl-5-indolyl)oxy-3"-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-1,14-dihydroxy-12-[2'-(4"-(1-N-allyl-5-indolyl)oxy-3"-ethoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Allyl-1,14-dihydroxy-12-[2'-(4"-(1-N-allyl-5-indolyl)oxy-3"-ethoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-1,14-dihydroxy-12-[2'-(4"-(1-N-2-hydroxyethyl-5-indolyl)oxy-3"-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-1,14,20-trihydroxy-12-[2'-(4"-(1-N-2-hydroxyethyl-5-indolyl)oxy-3"-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-1,20-dihydroxy-12-[2'-(4"-(1-N-2-hydroxyethyl-5-indolyl)oxy-3"-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-1,14-dihydroxy-12-[2'-(4"-(1-N-2-hydroxyethyl-5-indolyl)oxy-3"-hydroxycyclohexyl-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-1,14,20-trihydroxy-12-[2'-(4"-(1-N-2-hydroxyethyl-5-indolyl)oxy-3"-hydroxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-1,20-dihydroxy-12-[2'-(4"-(1-N-2-hydroxyethyl-5-indolyl)oxy-3"-hydroxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Allyl-1,14-dihydroxy-12-[2'-(4"-(1-N-2-hydroxyethyl-5-indolyl)oxy-3"-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Allyl-1,14-dihydroxy-12-[2'-(4"-(1-N-hydroxyethyl-5-indolyl)oxy-3"-hydroxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-1,14-dihydroxy-12-[2'-(4"-(1-N-benzyl-5-indolyl)oxy-3"-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-1,14,20-trihydroxy-12-[2'-(4"-(1-N-benzyl-5-indolyl)oxy-3"-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-1,20-dihydroxy-12-[2'-(4"-(1-N-benzyl-5-indolyl)oxy-3"-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-1,14-dihydroxy-12-[2'-(4"-(1-N-benzyl-5-indolyl)oxy-3"-hydroxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-1,14,20-trihydroxy-12-[2'-(4"-(1-N-benzyl-5-indolyl)oxy-3"-hydroxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-1,20-dihydroxy-12-[2'-(4"-(1-N-benzyl-5-indolyl)oxy-3"-hydroxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Allyl-1,14-dihydroxy-12-[2'-(4"-(1-N-benzyl-5-indolyl)oxy-3"-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Allyl-1,14,20-trihydroxy-12-[2'-(4"-(1-N-benzyl-5-indolyl)oxy-3"-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Allyl-1,20-dihydroxy-12-[2'-(4"-(1-N-benzyl-5-indolyl)oxy-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Allyl-1,14-dihydroxy-12-[2'-(4''-(1-N-benzyl-5-indolyl)oxy-3''-hydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-1-hydroxy-12-[2'-(4''-(1-N-benzyl-5-indolyl)oxy-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Allyl-1-hydroxy-12-[2'-(4''-(1-N-benzyl-5-indolyl)oxy-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-1,14-dihydroxy-12-[2'-(4''-(1-N-benzyl-5-indolyl)oxy-3''-ethoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Allyl-1,14-dihydroxy-12-[2'-(4''-(1-N-benzyl-5-indolyl)oxy-3''-ethoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-1,14-dihydroxy-12-[2'-(4''-(1-N-cyclopropyl-5-indolyl)oxy-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-1,14-dihydroxy-12-[2'-(4''-(1-N-cyclopropyl-5-indolyl)oxy-3''-hydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Allyl-1,14-dihydroxy-12-[2'-(4''-(1-N-cyclopropyl-5-indolyl)oxy-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Allyl-1,14-dihydroxy-12-[2'-(4''-(1-N-cyclopropyl-5-indolyl)oxy-3''-hydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-1,14-dihydroxy-12-[2'-(4''-(1-N-cyclopropyl-5-indolyl)oxy-3''-ethoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Allyl-1,14-dihydroxy-12-[2'-(4''-(1-N-cyclopropyl-5-indolyl)oxy-3''-ethoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-1-hydroxy-12-[2'-(4''-(1-N-cyclopropyl-5-indolyl)oxy-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Allyl-1-hydroxy-12-[2'-(4''-(1-N-cyclopropyl-5-indolyl)oxy-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-1-hydroxy-12-[2'-(4''-(methoxy-N-tryptophanylcarbonylmethoxy-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-1-hydroxy-12-[2'-(4''-(3-indolyl)ethylaminocarbonylmethoxy-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-1,14-dihydroxy-12-[2'-(4''-(1-(3-hydroxypropyl)indol-5-yl)oxy-3''-methoxycyclohexyl)-1'-methyl-vinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-1,14-dihydroxy-12-[2'-(3''-hydroxy-4''-(1-hydroxyethylindol-5-yl)oxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-1,14-dihydroxy-12-[2'-(4''-(1-hydroxyethylindol-6-yl)oxy-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-1,14-dihydroxy-12-[2'-(4''-(1-methylindol-6-yl)oxy-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-1,14-dihydroxy-12-[2'-(4''-(1-dibenzylphosphonoxy-ethylindol-5-yl)oxy-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

Monopotassium salt of 17-Ethyl-1,14-dihydroxy-12-[2'-(4''-(1-phosphonoxy-ethylindol-5-yl)oxy-3''-methoxycyclohexyl)-1'-methylvinyl]-23,25-dimethoxy-13,19,21, 27-tetramethyl-11,28-dioxa-4-azatricyclo[22.3.1.0$^{4,9}$]octacos-18-ene-2,3,10,16-tetraone;

17-Ethyl-1,14-dihydroxy-12-[2'-(4'-'-(1-(N,N-dimethylglycyloxy)ethylindol-5-yl)oxy-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-1,14-dihydroxy-12-[2'-(4''-(1-succinyloxyethylindol-5-yl)oxy-3''-methoxycyclohexyl)-1'-methylvinyl]23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-1,14-dihydroxy-12-[2'-(4''-(1-methyl-3-phenylindol-5-yl)oxy-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-1,14-dihydroxy-12-[2'-(4''-(1-methyl-3-(2-hydroxyethyl)indol-5-yl)oxy-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-1,14-dihydroxy-12-[2'-(4''-(1,3-dimethylindol-5-yl)oxy-3''-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-1,14-dihydroxy-1-2-[2'-(4''-(9'-methylcarbazol-3'-yl)oxy-3''-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-1,14-dihydroxy-12-[2'-(4''-((2''''-(3'''''-diethylaminopropionyloxy)ethyl)indol-5'''-yl)oxy-3''-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-1,14-dihydroxy-12-[2'-(4''-((2''''-(3'''''-dimethylaminopropionyloxy)ethyl)indol-5'''-yl)oxy-3''-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-1,14-dihydroxy-12-[2'-(4''-((2''''-(3'''''-aminopropionyloxy)ethyl)indol-5'''-yl)oxy-3''-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-1,14-dihydroxy-12-[2'-(4''-((2''''-(3'''''-benzyloxycarbonyl-2'''''-benzyloxycarbonylaminopropionyloxy)ethyl)indol-5'''-yl)oxy-3''-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-1,14-dihydroxy-12-[2'-(4''-((2''''-(aspartyloxy)ethyl)indol-5'''-yl)oxy-3''-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-1,14-dihydroxy-12-[2'-(4''-((2''''-(1'''''-imidazolylcarbonyloxy)ethyl)indol-5'''-yl)oxy-3''-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-1,14-dihydroxy-12-[2'-(4''-((2''''-(1'''''-piperazinocarbonyloxy)ethyl)indol-5'''-yl)oxy-3''-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-1,14-dihydroxy-12-[2'-(4''-(1'''-(2''''-(2'''''-hydroxy)ethylaminocarbonyloxy)ethyl)indol-5'''-yl)oxy-3''-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-1,14-dihydroxy-12-[2'-(4''-(1'''-(2''''-(isopropylaminocarbonyloxy)ethyl)indol-5'''-yl)oxy-3''-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-1,14-dihydroxy-12-[2'-(4''-(1'''-(2''''-(1'''''-piperidinocarbonyloxy)ethyl)indol-5'''-yl)oxy-3''-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-1,14-dihydroxy-12-[2'-(4''-(1'''-(2''''-(1'''''-morpholinocarbonyloxy)ethyl)indol-5'''-yl)oxy-3''-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-1,14-dihydroxy-12-[2'-(4''-(1'''-(2''''-(diphenylaminocarbonyloxy)ethyl)indol-5'''-yl)oxy-3''-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-1,14-dihydroxy-12-[2'-(4''-(1'''-(2''''-(diethylaminocarbonyloxy)ethyl)indol-5'''-yl)oxy-3''-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-1,14-dihydroxy-12-[2'-(4''-(1'''-(2''''-methanesulfonyloxyethyl)indol-5'''-yl)oxy-3''-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-1,14-dihydroxy-12-[2'-(4''-(1'''-(2''''-azidoethyl)indol-5'''-yl)oxy-3''-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-1,14-dihydroxy-12-[2'-(4''-(1'''-(2''''-aminoethyl)indol-5'''-yl)oxy-3''-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-1,14-dihydroxy-12-[2'-(4''-(1'''-t-butyldimethylsilyloxyethoxyethylindol-5'''-yl)oxy-3''-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-1,14-dihydroxy-12-[2'-(4''-(1'''-hydroxyethoxyethylindol-5'''-yl)oxy-3''-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-1,14-dihydroxy-12-[2'-(3''-methoxy-4''-(1'''-(1''''-oxoprop-3''''-yl)indol-5'''-yl)oxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-1,14-dihydroxy-12-[2'-(3''-methoxy-4''-(1'''-(1''''-carboxyeth-2''''-yl)indol-5'''-yl)oxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-1,14-dihydroxy-12-[2'-(4''-(2'''-(3-pyridyl)-2'''-hydroxyethyloxy)-3''-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-1,14-dihydroxy-12-[2'-(4''-(2'''-(3-pyridyl)-2'''-oxoethyloxy)-3''-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-1,14-dihydroxy-12-[2'-(4''-(2'''-(2-thienyl)-2'''-hydroxyethyloxy)-3''-methoxycyclohexyl)-1'-methylvinyl]-23,23-dimethoxy-13,19,21, 27-tetramethyl-11, 28-dioxa-4-azatricyclo[22.3.1.0^{4,9}]octacos-18-ene-2,3, 10,16-tetraone;

17-Ethyl-1,14-dihydroxy-12-[2'-(4''-(2'''-(3-thienyl)-2'''-hydroxyethyloxy)-3''-methoxycyclohexyl)-1'-methylvinyl]-23,23-dimethoxy-13,19,21, 27-tetramethyl-11, 28-dioxa-4-azatricyclo[22.3.1.0^{4,9}]octacos-18-ene-2,3, 10,16-tetraone;

17-Ethyl-1,14-dihydroxy-12-[2'-(4''-(2'''(2-thienyl)-2'''-oxoethyloxy)-3''-methoxycyclohexyl)-1'-methylvinyl]-23,23-dimethoxy-13,19,21, 27-tetramethyl-11, 28-dioxa-4-azatricyclo[22.3.1.0^{4,9}]octacos-18-ene-2,3, 10,16-tetraone;

17-Ethyl-1,14-dihydroxy-12-[2'-(4''-(2'''-(3-thienyl)-2'''-oxoethyloxy)-3''-methoxycyclohexyl)-1'-methylvinyl]-23,23-dimethoxy-13,19,21, 27-tetramethyl-11, 28-dioxa-4-azatricyclo[22.3.1.0^{4,9}]octacos-18-ene-2,3, 10,16-tetraone;

17-Ethyl-1,14-dihydroxy-12-[2'-(4''-(2'''-(benzothien-2-yl)-2'''-hydroxyethyloxy)-3''-methoxycyclohexyl)-1'-methylvinyl]-23,23-dimethoxy-13,19,21,27-tetramethyl-11,28-dioxa-4-azatricyclo[22.3.1.0^{4,9}]octacos-18-ene-2,3,10,16-tetraone;

17-Ethyl-1,14-dihydroxy-12-[2'-(4''-(2'''-(benzothien-3-yl)-2'''-hydroxyethyloxy)-3''-methoxycyclohexyl)-1'-methylvinyl]-23,23-dimethoxy-13,19,21,27-tetramethyl-11,28-dioxa-4-azatricyclo[22.3.1.0^{4,9}]octacos-18-ene-2,3,10,16-tetraone;

17-Ethyl -1,14-dihydroxy-12-[2'-(4''-(2'''-(benzothien-5-yl)-2'''-hydroxyethyloxy)-3''-methoxycyclohexyl)-1'-methylvinyl]-23,23-dimethoxy-13,19,21,27-tetramethyl-11,28-dioxa-4-azatricyclo[22.3.1.0^{4,9}]octacos-18-ene-2,3,10,16-tetraone;

17-Ethyl-1,14-dihydroxy-12-[2'-(4''-(2'''-(benzothien-6-yl)-2'''-hydroxyethyloxy)-3''-methoxycyclohexyl)-1'-methylvinyl]-23,23-dimethoxy-13,19,21,27-tetramethyl-11,28-dioxa-4-azatricyclo[22.3.1.0^{4,9}]octacos-18-ene-2,3,10,16-tetraone;

17-Ethyl-1,14-dihydroxy-12-[2'-(4''-(2'''-(benzothien-2-yl)-2'''-oxoethyloxy)-3''-methoxycyclohexyl)-1'-methylvinyl]-23,23-dimethoxy-13,19,21,27-tetramethyl-11,28-dioxa-4-azatricyclo[22.3.1.0^{4,9}]octacos-18-ene-2,3,10,16-tetraone;

17-Ethyl-1,14-dihydroxy-12-[2'-(4''-(2'''-(benzothien-3-yl)-2'''-oxoethyloxy)-3''-methoxycyclohexyl)-1'-methylvinyl]-23,23-dimethoxy-13,19,21,27-tetramethyl-11,28-dioxa-4-azatricyclo[22.3.1.0^{4,9}]octacos-18-ene-2,3,10,16-tetraone;

17-Ethyl-1,14-dihydroxy-12-[2'-(4''-(2'''-(benzothien-5-yl)-2'''-oxoethyloxy)-3''-methoxycyclohexyl)-1'-methylvinyl]-23,23-dimethoxy-13,19,21,27-tetramethyl-11,28-dioxa-4-azatricyclo[22.3.1.0^{4,9}]octacos-18-ene-2,3,10,16-tetraone;

17-Ethyl-1,14-dihydroxy-12-[2'-(4''-(2'''-(benzothien-6-yl)-2'''-oxoethyloxy)-3''-methoxycyclohexyl)-1'-methylvinyl]-23,23-dimethoxy-13,19,21,27-tetramethyl-11,28-dioxa-4-azatricyclo[22.3.1.0^{4,9}]octacos-18-ene-2,3,10,16-tetraone;

17-Ethyl-1,14-dihydroxy-12-[2'-(4''-(2'''-(benzofuran-2-yl)-2'''-hydroxyethyloxy)-3''-methoxycyclohexyl)-1'-methylvinyl]-23,23-dimethoxy-13,19,21,27-tetramethyl-11,28-dioxa-4-azatricyclo[22.3.1.0^{4,9}]octacos-18-ene-2,3,10,16-tetraone;

17-Ethyl-1,14-dihydroxy-12-[2'-(4''-(2'''-(benzofuran-3-yl)-2'''-hydroxyethyloxy)-3''-methoxycyclohexyl)-1'-methylvinyl]-23,23-dimethoxy-13,19,21,27-tetramethyl-11,28-dioxa-4-azatricyclo[22.3.1.0^{4,9}]octacos-18-ene-2,3,10,16-tetraone;

17-Ethyl-1,14-dihydroxy-12-[2'-(4''-(2'''-(benzofuran-5-yl)-2'''-hydroxyethyloxy)-3''-methoxycyclohexyl)-1'-methylvinyl]-23,23-dimethoxy-13,19,21,27-tetramethyl-11,28-dioxa-4-azatricyclo[22.3.1.0^{4,9}]octacos-18-ene-2,3,10,16-tetraone;

17-Ethyl-1,14-dihydroxy-12-[2'-(4''-(2'''-(benzofuran-6-yl)-2'''-hydroxyethyloxy)-3''-methoxycyclohexyl)-1'-methylvinyl]-23,23-dimethoxy-13,19,21,27-tetramethyl-11,28-dioxa-4-azatricyclo[22.3.1.0^{4,9}]octacos-18-ene-2,3,10,16-tetraone;

17-Ethyl-1,14-dihydroxy-12-[2'-(4''-(2'''-(benzofuran-2-yl)-2'''-oxoethyloxy)-3''-methoxycyclohexyl)-1'-methylvinyl]-23,23-dimethoxy-13,19,21,27-tetramethyl-11,28-dioxa-4-azatricyclo[22.3.1.0^{4,9}]octacos-18-ene-2,3,10,16-tetraone;

17-Ethyl-1,14-dihydroxy-12-[2'-(4''-(2'''(benzofuran-3-yl)-2'''-oxoethyloxy)-3''-methoxycyclohexyl)-1'-methylvinyl]-23,23-dimethoxy-13,19,21,27-tetramethyl-11,28-dioxa-4-azatricyclo[22.3.1.0^{4,9}]octacos-18-ene-2,3,10,16-tetraone;

17-Ethyl-1,14-dihydroxy-12-[2'-(4''-(2'''-(benzofuran-5-yl)-2'''-oxoethyloxy)-3''-methoxycyclohexyl)-1'-methylvinyl]-23,23-dimethoxy-13,19,21,27-tetramethyl-11,28-dioxa-4-azatricyclo[22.3.1.0^{4,9}]octacos-18-ene-2,3,10,16-tetraone;

17-Ethyl-1,14-dihydroxy-12-[2'-(4''-(2'''-(benzofuran-6-yl)-2'''-oxoethyloxy)-3''-methoxycyclohexyl)-1'-methylvinyl]-23,23-dimethoxy-13,19,21,27-tetramethyl-11,28-dioxa-4-azatricyclo[22.3.1.0^{4,9}]octacos-18-ene-2,3,10,16-tetraone;

or a pharmaceutically acceptable salt thereof.

Representative compounds of the present invention include the compounds of Formula X, XI, XII and XIII:

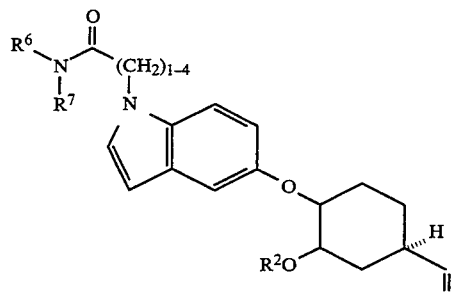

X

-continued
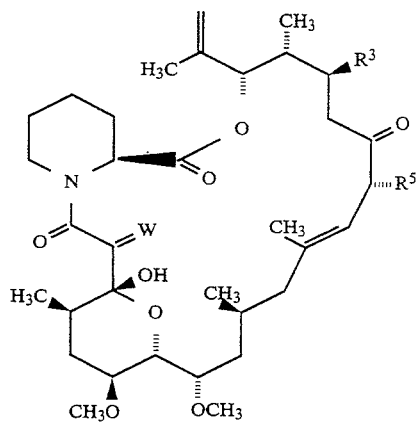
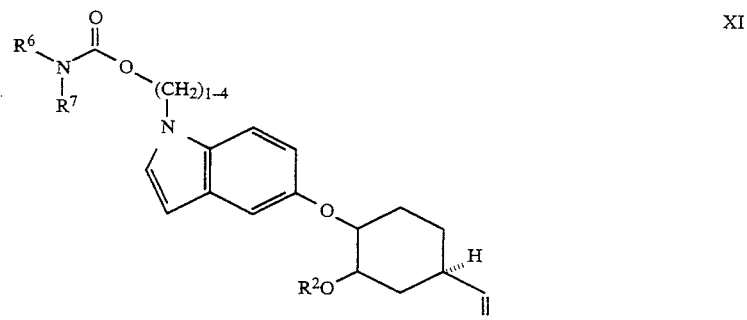
XI
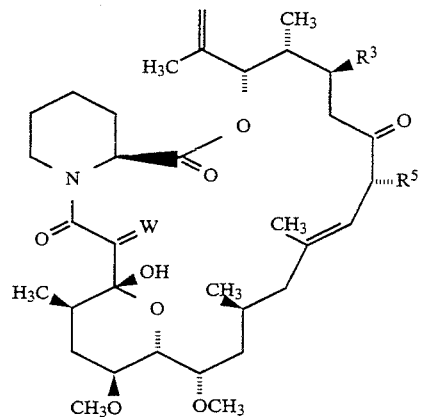
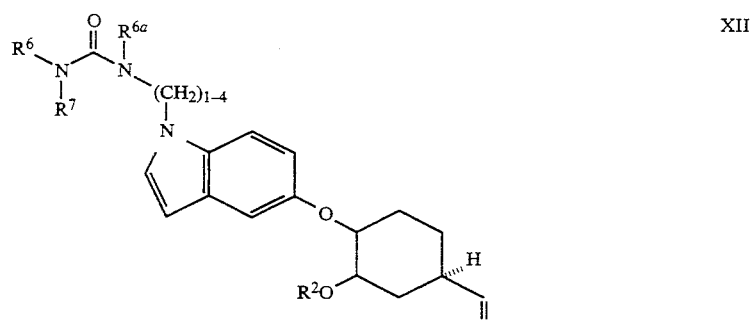
XII

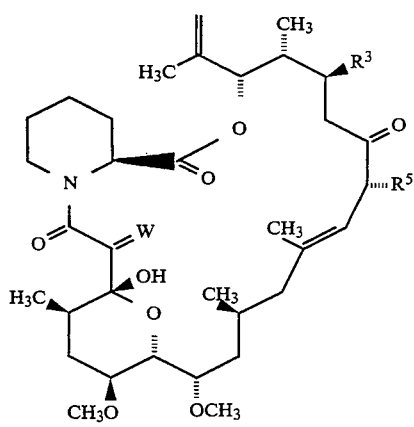

XIII

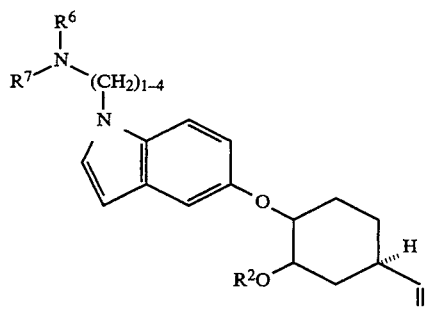

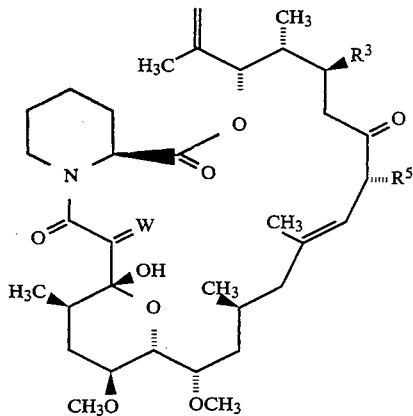

wherein $R^{6a}$ is H or $CH_3$ and the definitions of $R^2$, $R^3$, $R^5$, $R^6$ and $R^7$ are selected from the following groups of substituents:

| $R^6$ | $R^7$ | $R^2$ | $R^3$ | $R^5$ |
|---|---|---|---|---|
| phenyl | phenyl | $CH_3$ | OH | ethyl |
| phenyl | H | $CH_3$ | OH | ethyl |
| benzyl | H | $CH_3$ | OH | ethyl |
| 4-$HO_2$C-benzyl | H | $CH_3$ | OH | ethyl |
| 4-$H_2$NCO-benzyl | H | $CH_3$ | OH | ethyl |
| 4-$CH_3$O-benzyl | H | $CH_3$ | OH | ethyl |
| 4-HO-benzyl | H | $CH_3$ | OH | ethyl |
| 4-Cl-benzyl | H | $CH_3$ | OH | ethyl |
| 4-$(CH_3)_2$N-benzyl | H | $CH_3$ | OH | ethyl |
| 3-$HO_2$C-benzyl | H | $CH_3$ | OR | ethyl |
| 3-$H_2$NCO-benzyl | H | $CH_3$ | OH | ethyl |
| 3-$CH_3$O-benzyl | H | $CH_3$ | OH | ethyl |
| 3-HO-benzyl | H | $CH_3$ | OH | ethyl |
| 3-Cl-benzyl | H | $CH_3$ | OH | ethyl |
| 3-$(CH_3)_2$N-benzyl | H | $CH_3$ | OH | ethyl |
| 4-pyridyl | H | $CH_3$ | OH | ethyl |
| 3-pyridyl | H | $CH_3$ | OH | ethyl |
| 2-pyridyl | H | $CH_3$ | OH | ethyl |
| 4-pyridylmethyl | H | $CH_3$ | OH | ethyl |
| 3-pyridylmethyl | R | $CH_3$ | OH | ethyl |
| 2-pyridylmethyl | H | $CH_3$ | OH | ethyl |
| phenyl | phenyl | $CH_3$ | H | ethyl |
| phenyl | H | $CH_3$ | H | ethyl |
| benzyl | H | $CH_3$ | H | ethyl |
| 4-$HO_2$C-benzyl | H | $CH_3$ | H | ethyl |
| 4-$H_2$NCO-benzyl | H | $CH_3$ | H | ethyl |
| 4-$CH_3$O-benzyl | H | $CH_3$ | H | ethyl |
| 4-HO-benzyl | H | $CH_3$ | H | ethyl |
| 4-Cl-benzyl | H | $CH_3$ | H | ethyl |
| 4-$(CH_3)_2$N-benzyl | H | $CH_3$ | H | ethyl |
| 3-$HO_2$C-benzyl | H | $CH_3$ | H | ethyl |
| 3-$H_2$NCO-benzyl | H | $CH_3$ | H | ethyl |
| 3-$CH_3$O-benzyl | H | $CH_3$ | H | ethyl |
| 3-HO-benzyl | H | $CH_3$ | H | ethyl |
| 3-Cl-benzyl | H | $CH_3$ | H | ethyl |
| 3-$(CH_3)_2$N-benzyl | H | $CH_3$ | H | ethyl |
| 4-pyridyl | H | $CH_3$ | H | ethyl |
| 3-pyridyl | H | $CH_3$ | H | ethyl |
| 2-pyridyl | H | $CH_3$ | H | ethyl |
| 4-pyridylmethyl | H | $CH_3$ | H | ethyl |
| 3-pyridylmethyl | H | $CH_3$ | H | ethyl |
| 2-pyridylmethyl | H | $CH_3$ | H | ethyl |

-continued

| R⁶ | R⁷ | R² | R³ | R⁵ |
|---|---|---|---|---|
| phenyl | phenyl | CH₃ | OH | allyl |
| phenyl | H | CH₃ | OH | allyl |
| benzyl | H | CH₃ | OH | allyl |
| 4-HO₂C-benzyl | H | CH₃ | OH | allyl |
| 4-H₂NCO-benzyl | H | CH₃ | OH | allyl |
| 4-CH₃O-benzyl | H | CH₃ | OH | allyl |
| 4-HO-benzyl | H | CH₃ | OH | allyl |
| 4-Cl-benzyl | H | CH₃ | OH | allyl |
| 4-(CH₃)₂N-benzyl | H | CH₃ | OH | allyl |
| 3-HO₂C-benzyl | H | CH₃ | OH | allyl |
| 3-H₂NCO-benzyl | H | CH₃ | OH | allyl |
| 3-CH₃O-benzyl | H | CH₃ | OH | allyl |
| 3-HO-benzyl | H | CH₃ | OH | allyl |
| 3-Cl-benzyl | H | CH₃ | OH | allyl |
| 3-(CH₃)₂N-benzyl | H | CH₃ | OH | allyl |
| 4-pyridyl | H | CH₃ | OH | allyl |
| 3-pyridyl | H | CH₃ | OH | allyl |
| 2-pyridyl | H | CH₃ | OH | allyl |
| 4-pyridylmethyl | H | CH₃ | OH | allyl |
| 3-pyridylmethyl | H | CH₃ | OH | allyl |
| 2-pyridylmethyl | H | CH₃ | OH | allyl |
| CH₃ | H | CH₃ | OH | ethyl |
| CH₃CH₂ | H | CH₃ | OH | ethyl |
| CH₃CH₂CH₂ | H | CH₃ | OH | ethyl |
| (CH₃)₂CH | H | CH₃ | OH | ethyl |
| HO₂CCH₂CH₂ | H | CH₃ | OH | ethyl |
| H₂NCOCH₂CH₂ | H | CH₃ | OH | ethyl |
| HOCH₂CH₂ | H | CH₃ | OH | ethyl |
| HOCH₂CH₂CH₂ | H | CH₃ | OH | ethyl |
| CH₃ | CH₃ | CH₃ | OH | ethyl |
| CH₃CH₂ | CH₃CH₂ | CH₃ | OH | ethyl |
| CH₃CH₂CH₂ | CH₃CH₂CH₂ | CH₃ | OH | ethyl |
| HOCH₂CH₂ | HOCH₂CH₂ | CH₃ | OH | ethyl |
| HOCH₂CH₂CH₂ | HOCH₂CH₂CH₂ | CH₃ | OH | ethyl |
| CH₃ | H | CH₃ | H | ethyl |
| CH₃CH₂ | H | CH₃ | H | ethyl |
| CH₃CH₂CH₂ | H | CH₃ | H | ethyl |
| (CH₃)₂CH | H | CH₃ | H | ethyl |
| HO₂CCH₂CH₂ | H | CH₃ | H | ethyl |
| H₂NCOCH₂CH₂ | H | CH₃ | H | ethyl |
| HOCH₂CH₂ | H | CH₃ | H | ethyl |
| HOCH₂CH₂CH₂ | H | CH₃ | H | ethyl |
| CH₃ | CH₃ | CH₃ | H | ethyl |
| CH₃CH₂ | CH₃CH₂ | CH₃ | H | ethyl |
| CH₃CH₂CH₂ | CH₃CH₂CH₂ | CH₃ | H | ethyl |
| HOCH₂CH₂ | HOCH₂CH₂ | CH₃ | H | ethyl |
| HOCH₂CH₂CH₂ | HOCH₂CH₂CH₂ | CH₃ | H | ethyl |
| CH₃ | H | H | OH | ethyl |
| CH₃CH₂ | H | H | OH | ethyl |
| CH₃CH₂CH | H | H | OH | ethyl |
| (CH₃)₂CH | H | H | OH | ethyl |
| HO₂CCH₂CH₂ | H | H | OH | ethyl |
| H₂NCOCH₂CH₂ | H | H | OH | ethyl |
| HOCH₂CH₂ | H | H | OH | ethyl |
| HOCH₂CH₂CH₂ | H | H | OH | ethyl |
| CH₃ | CH₃ | H | OH | ethyl |
| CH₃CH₂ | CH₃CH₂ | H | OH | ethyl |
| CH₃CH₂CH₂ | CH₃CH₂CH₂ | H | OH | ethyl |
| HOCH₂CH₂ | HOCH₂CH₂ | H | OH | ethyl |
| HOCH₂CH₂CH₂ | HOCH₂CH₂CH₂ | H | OH | ethyl |
| —CH₂CH₂OCH₂CH₂— | | CH₃ | H | ethyl |
| —CH₂CH₂CH₂CH₂—CH₂— | | CH₃ | H | ethyl |
| —CH₂CH₂OCH₂CH₂— | | CH₃ | OH | ethyl |
| —CH₂CH₂CH₂CH₂CH₂— | | H | OH | ethyl |
| —CH₂CH₂OCH₂CH₂— | | H | OH | ethyl |
| —CH₂CH₂CH₂CH₂CH₂— | | H | OH | ethyl |
| —CH₂CH₂OCH₂CH₂— | | CH₃ | H | allyl |
| —CH₂CH₂CH₂CH₂CH₂— | | CH₃ | H | allyl |
| —CH₂CH₂OCH₂CH₂— | | CH₃ | OH | allyl |
| —CH₂CH₂OCH₂CH₂— | | H | OH | allyl |
| —CH₂CH₂OCH₂CH₂— | | H | OH | allyl |
| —CH₂CH₂CH₂CH₂CH₂— | | H | OH | allyl |

Representative compounds of the present invention include the compounds of formula XIV, XV, XVI and XVII:

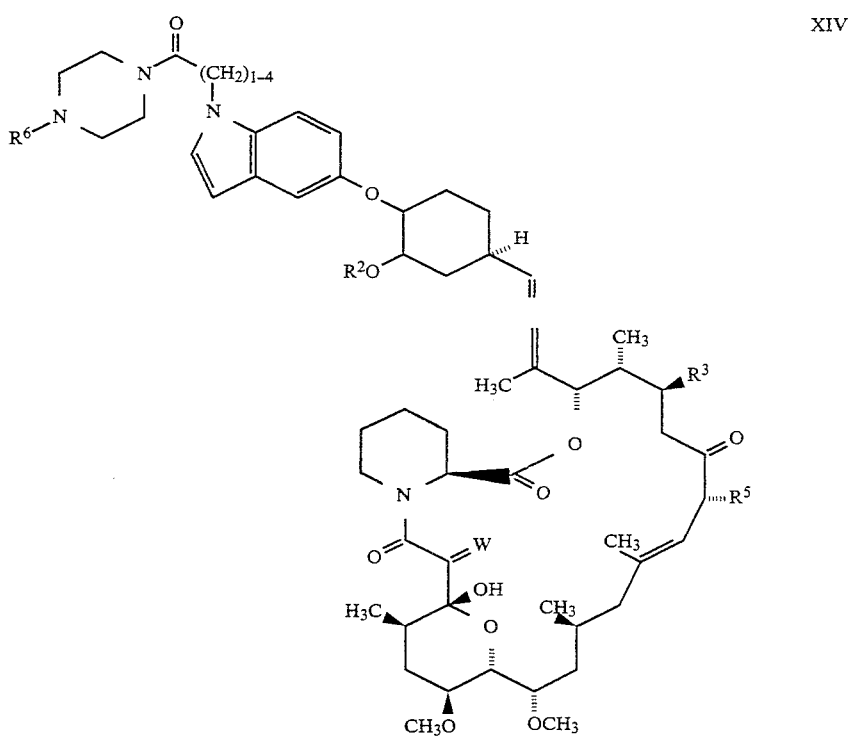

XIV

-continued
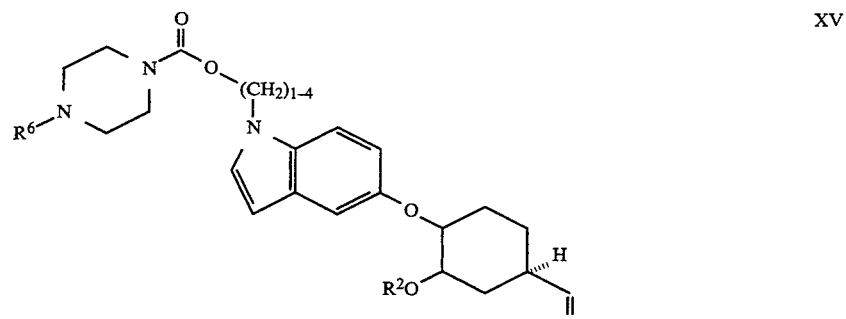
XV
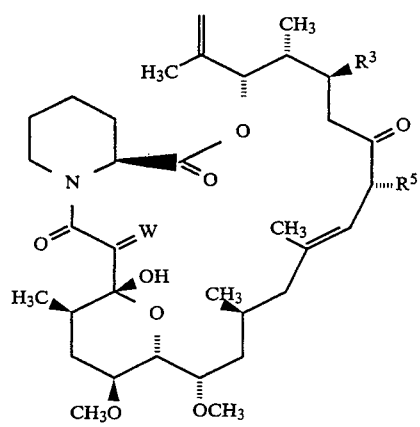
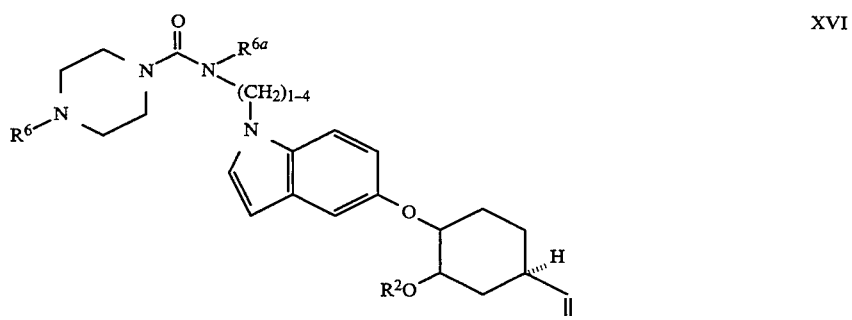
XVI
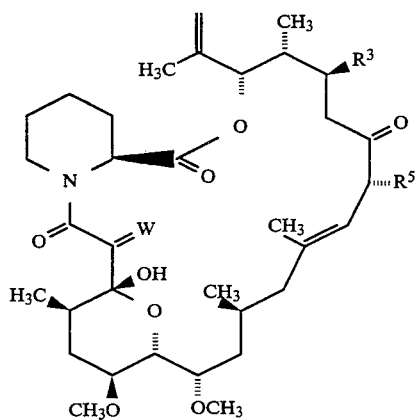

XVII

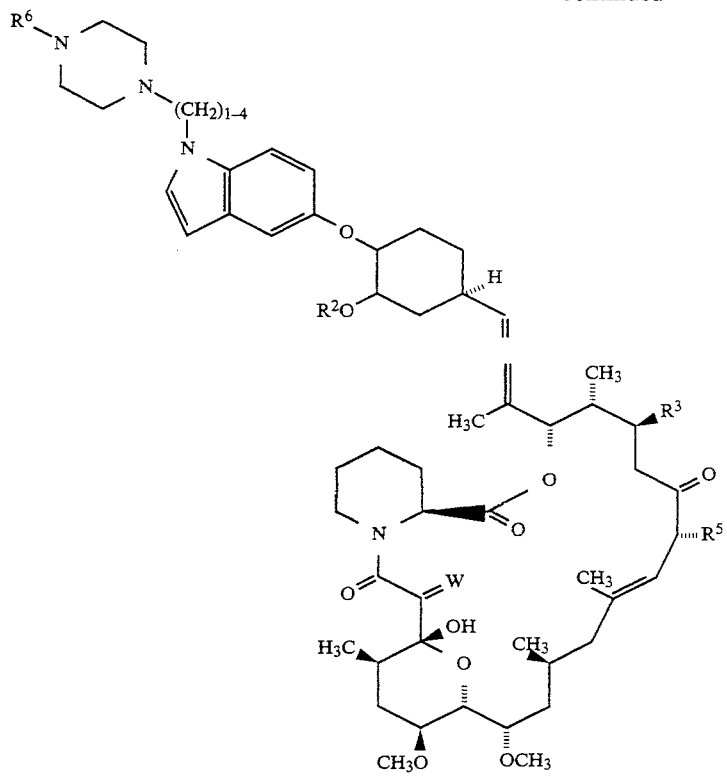

wherein $R^{6a}$ is H or $CH_3$ and $R^2$, $R^3$, $R^5$ and $R^6$ are selected from the following groups of substituents:

| $R^6$ | $R^2$ | $R^3$ | $R^5$ |
|---|---|---|---|
| H | $CH_3$ | OH | ethyl |
| $CH_3$ | $CH_3$ | OH | ethyl |
| $CH_3CH_2$ | $CH_3$ | OH | ethyl |
| $CH_2$=$CHCH_2$ | $CH_3$ | OH | ethyl |
| $CH_3CH_2CH_2$ | $CH_3$ | OH | ethyl |
| $(CH_3)_2CH$ | $CH_3$ | OH | ethyl |
| $HO_2CCH_2CH_2$ | $CH_3$ | OH | ethyl |
| $H_2NCOCH_2CH_2$ | $CH_3$ | OH | ethyl |
| $HOCH_2CH_2$ | $CH_3$ | OH | ethyl |
| $HOCH_2CH_2CH_2$ | $CH_3$ | OH | ethyl |
| $(CH_3)_2CH_2$ | $CH_3$ | OH | ethyl |
| phenyl | $CH_3$ | OH | ethyl |
| 4-pyridyl | $CH_3$ | OH | ethyl |
| 3-pyridyl | $CH_3$ | ON | ethyl |
| 2-pyridyl | $CH_3$ | OH | ethyl |
| 4-pyridylmethyl | $CH_3$ | OH | ethyl |
| 3-pyridylmethyl | $CH_3$ | OH | ethyl |
| 2-pyridylmethyl | $CH_3$ | OH | ethyl |
| benzyl | $CH_3$ | OH | ethyl |
| 4-$HO_2C$-benzyl | $CH_3$ | OH | ethyl |
| 4-$H_2NCO$-benzyl | $CH_3$ | OH | ethyl |
| 4-$CH_3O$-benzyl | $CH_3$ | OH | ethyl |
| 4-HO-benzyl | $CH_3$ | OH | ethyl |
| 4-Cl-benzyl | $CH_3$ | OH | ethyl |
| 4-$(CH_3)_2N$-benzyl | $CH_3$ | OH | ethyl |
| 3-$HO_2C$-benzyl | $CH_3$ | OH | ethyl |
| 3-$H_2NCO$-benzyl | $CH_3$ | OH | ethyl |
| 3-$CH_3$-benzyl | $CH_3$ | OH | ethyl |
| 3-HO-benzyl | $CH_3$ | OH | ethyl |
| 3-Cl-benzyl | $CH_3$ | OH | ethyl |
| 3-$(CH_3)_2N$-benzyl | $CH_3$ | OH | ethyl |
| 2-HO-benzyl | $CH_3$ | OH | ethyl |
| 2-Cl-benzyl | $CH_3$ | OH | ethyl |
| 2-$(CH_3)_2N$-benzyl | $CH_3$ | OH | ethyl |
| $CH_3$ | $CH_3$ | H | ethyl |
| $CH_3CH_2$ | $CH_3$ | H | ethyl |
| $CH_2$=$CHCH_2$ | $CH_3$ | H | ethyl |
| $CH_3CH_2CH_2$ | $CH_3$ | H | ethyl |
| $(CH_3)_2CH$ | $CH_3$ | H | ethyl |
| $HO_2CCH_2CH_2$ | $CH_3$ | H | ethyl |
| $H_2NCOCH_2CH_2$ | $CH_3$ | H | ethyl |
| $HOCH_2CH_2$ | $CH_3$ | H | ethyl |
| $HOCH_2CH_2CH_2$ | $CH_3$ | H | ethyl |
| $(CH_3)_2CH_2$ | $CH_3$ | H | ethyl |
| phenyl | $CH_3$ | H | ethyl |
| 4-pyridyl | $CH_3$ | H | ethyl |
| 3-pyridyl | $CH_3$ | H | ethyl |
| 2-pyridyl | $CH_3$ | H | ethyl |
| 4-pyridylmethyl | $CH_3$ | H | ethyl |
| 3-pyridylmethyl | $CH_3$ | H | ethyl |
| 2-pyridylmethyl | $CH_3$ | H | ethyl |
| benzyl | $CH_3$ | H | ethyl |
| 4-$HO_2C$-benzyl | $CH_3$ | H | ethyl |
| 4-$H_2NCO$-benzyl | $CH_3$ | H | ethyl |
| 4-$CH_3O$-benzyl | $CH_3$ | H | ethyl |
| 4-HO-benzyl | $CH_3$ | H | ethyl |
| 4-Cl-benzyl | $CH_3$ | H | ethyl |
| 4-$(CH_3)_2N$-benzyl | $CH_3$ | H | ethyl |
| 3-$HO_2C$-benzyl | $CH_3$ | H | ethyl |
| 3-$H_2NCO$-benzyl | $CH_3$ | H | ethyl |
| 3-$CH_3O$-benzyl | $CH_3$ | H | ethyl |
| 3-HO-benzyl | $CH_3$ | H | ethyl |
| 3-Cl-benzyl | $CH_3$ | H | ethyl |
| 3-$(CH_3)_2N$-benzyl | $CH_3$ | H | ethyl |
| 2-$HO_2C$-benzyl | $CH_3$ | H | ethyl |
| 2-$H_2NCO$-benzyl | $CH_3$ | H | ethyl |
| 2-$CH_3O$-benzyl | $CH_3$ | H | ethyl |
| 2-HO-benzyl | $CH_3$ | H | ethyl |
| 2-Cl-benzyl | $CH_3$ | H | ethyl |
| 2-$(CH_3)_2N$-benzyl | $CH_3$ | H | ethyl |
| $CH_3$ | $CH_3$ | OH | allyl |
| $CH_3CH_2$ | $CH_3$ | OH | allyl |
| $CH_2$=$CHCH_2$ | $CH_3$ | OH | allyl |
| $CH_3CH_2CH_2$ | $CH_3$ | OH | allyl |
| $(CH_3)_2CH$ | $CH_3$ | OH | allyl |
| $HO_2CCH_2CH_2$ | $CH_3$ | OH | allyl |
| $H_2NCOCH_2CH_2$ | $CH_3$ | OH | allyl |
| $HOCH_2CH_2$ | $CH_3$ | OH | allyl |
| $HOCH_2CH_2CH_2$ | $CH_3$ | OH | allyl |
| $(CH_3)_2CH_2$ | $CH_3$ | OH | allyl |
| phenyl | $CH_3$ | OH | allyl |
| 4-pyridyl | $CH_3$ | OH | allyl |

-continued

| $R^6$ | $R^2$ | $R^3$ | $R^5$ |
|---|---|---|---|
| 3-pyridyl | $CH_3$ | OH | allyl |
| 2-pyridyl | $CH_3$ | OH | allyl |
| 4-pyridylmethyl | $CH_3$ | OH | allyl |
| 3-pyridylmethyl | $CH_3$ | OH | allyl |
| 2-pyridylmethyl | $CH_3$ | OH | allyl |
| benzyl | $CH_3$ | OH | allyl |
| 4-$HO_2$C-benzyl | $CH_3$ | OH | allyl |
| 4-$H_2$NCO-benzyl | $CH_3$ | OH | allyl |
| 4-$CH_3$O-benzyl | $CH_3$ | OH | allyl |
| 4-HO-benzyl | $CH_3$ | OH | allyl |
| 4-Cl-benzyl | $CH_3$ | OH | allyl |
| 4-$(CH_3)_2$N-benzyl | $CH_3$ | OH | allyl |
| 3-$HO_2$C-benzyl | $CH_3$ | OH | allyl |
| 3-$H_2$NCO-benzyl | $CH_3$ | OH | allyl |

-continued

| $R^6$ | $R^2$ | $R^3$ | $R^5$ |
|---|---|---|---|
| 3-$CH_3$O-benzyl | $CH_3$ | OH | allyl |
| 3-HO-benzyl | $CH_3$ | OH | allyl |
| 3-Cl-benzyl | $CH_3$ | OH | allyl |
| 3-$(CH_3)_2$N-benzyl | $CH_3$ | OH | allyl |
| 2-$HO_2$C-benzyl | $CH_3$ | OH | allyl |
| 2-$H_2$NCO-benzyl | $CH_3$ | OH | allyl |
| 2-$CH_3$O-benzyl | $CH_3$ | OH | allyl |
| 2-HO-benzyl | $CH_3$ | OH | allyl |
| 2-Cl-benzyl | $CH_3$ | OH | allyl |
| 2-$(CH_3)_2$N-benzyl | $CH_3$ | OH | allyl. |

Representative compounds of the present invention include the compounds of Formula XVIII, XIX, XX and XXI:

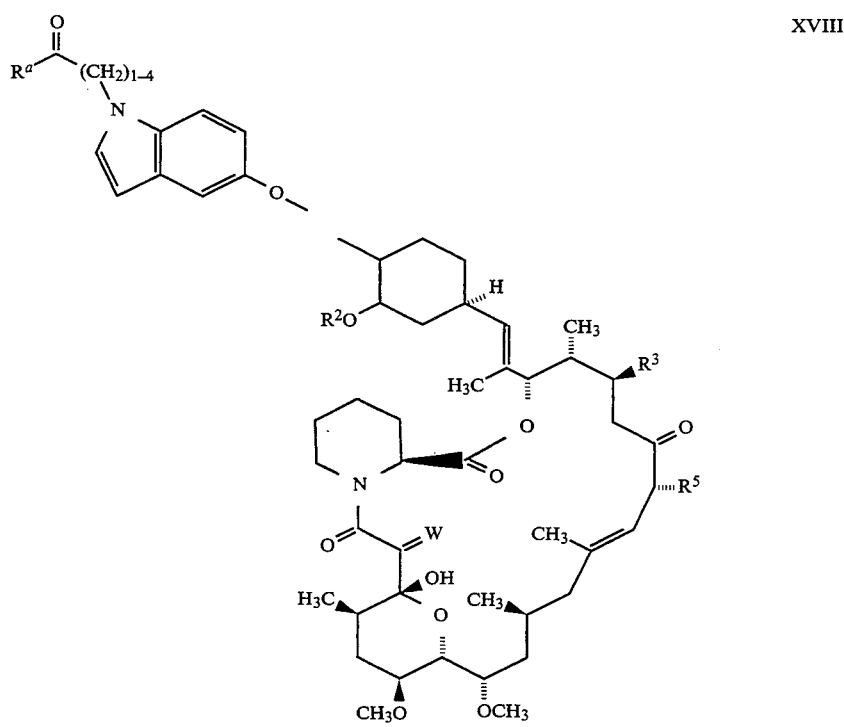

XVIII

XVIII

-continued
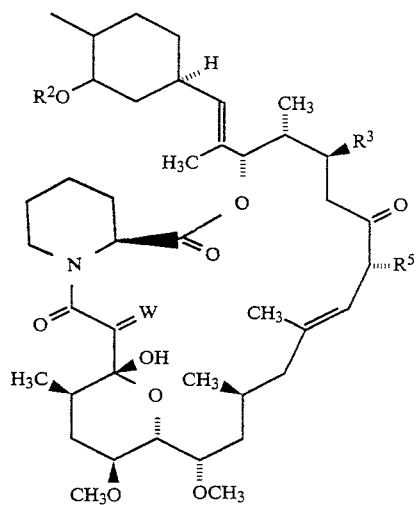
XX
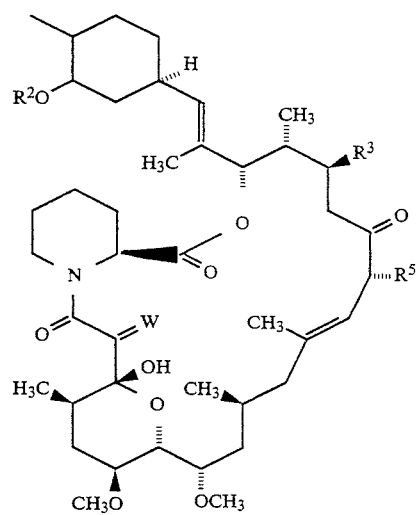
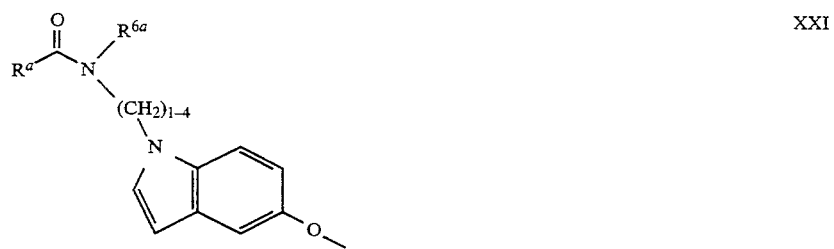
XXI

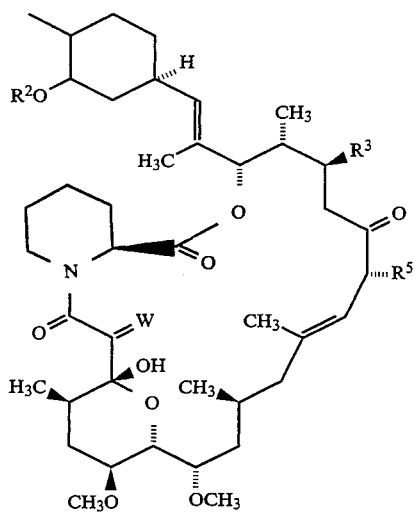

wherein $R^{6a}$ is H or $CH_3$ and R, $R^2$, $R^3$ and $R^5$ are selected from the following groups of substituents:

| $R^a$ | $R^2$ | $R^3$ | $R^5$ |
|---|---|---|---|
| $CH_3$ | $CH_3$ | OH | ethyl |
| $CH_3CH_2$ | $CH_3$ | OH | ethyl |
| $CH_2$=$CHCH_2$ | $CH_3$ | OH | ethyl |
| $CH_3CH_2CH_2$ | $CH_3$ | OH | ethyl |
| $(CH_3)_2CH$ | $CH_3$ | OH | ethyl |
| $HO_2CCH_2CH_2$ | $CH_3$ | OH | ethyl |
| $H_2NCOCH_2CH_2$ | $CH_3$ | OH | ethyl |
| $HOCH_2CH_2$ | $CH_3$ | OH | ethyl |
| $HOCH_2CH_2CH_2$ | $CH_3$ | OH | ethyl |
| $(CH_3)_2CH_2$ | $CH_3$ | OH | ethyl |
| phenyl | $CH_3$ | OH | ethyl |
| 4-pyridyl | $CH_3$ | OH | ethyl |
| 3-pyridyl | $CH_3$ | OH | ethyl |
| 2-pyridyl | $CH_3$ | OH | ethyl |
| 4-pyridylmethyl | $CH_3$ | OH | ethyl |
| 3-pyridylmethyl | $CH_3$ | OH | ethyl |
| 2-pyridylmethyl | $CH_3$ | OH | ethyl |
| benzyl | $CH_3$ | OH | ethyl |
| 4-$HO_2C$-benzyl | $CH_3$ | OH | ethyl |
| 4-$H_2NCO$-benzyl | $CH_3$ | OH | ethyl |
| 4-$CH_3O$-benzyl | $CH_3$ | OH | ethyl |
| 4-HO-benzyl | $CH_3$ | OH | ethyl |
| 4-Cl-benzyl | $CH_3$ | OH | ethyl |
| 4-$(CH_3)_2N$-benzyl | $CH_3$ | OH | ethyl |
| 3-$HO_2C$-benzyl | $CH_3$ | OH | ethyl |
| 3-$H_2NCO$-benzyl | $CH_3$ | OH | ethyl |
| 3-$CH_3O$-benzyl | $CH_3$ | OH | ethyl |
| 3-HO-benzyl | $CH_3$ | OH | ethyl |
| 3-Cl-benzyl | $CH_3$ | OH | ethyl |
| 3-$(CH_3)_2N$-benzyl | $CH_3$ | OH | ethyl |
| 2-$HO_2C$-benzyl | $CH_3$ | OH | ethyl |
| 2-$H_2NCO$-benzyl | $CH_3$ | OH | ethyl |
| 2-$CH_3O$-benzyl | $CH_3$ | OH | ethyl |
| 2-HO-benzyl | $CH_3$ | OH | ethyl |
| 2-Cl-benzyl | $CH_3$ | OH | ethyl |
| 2-$(CH_3)_2N$-benzyl | $CH_3$ | OH | ethyl |
| $CH_3$ | $CH_3$ | H | ethyl |
| $CH_3CH_2$ | $CH_3$ | H | ethyl |
| $CH_2$=$CHCH_2$ | $CH_3$ | H | ethyl |
| $CH_3CH_2CH_2$ | $CH_3$ | H | ethyl |
| $(CH_3)_2CH$ | $CH_3$ | H | ethyl |
| $HO_2CCH_2CH_2$ | $CH_3$ | H | ethyl |
| $H_2NCOCH_2CH_2$ | $CH_3$ | H | ethyl |
| $HOCH_2CH_2$ | $CH_3$ | H | ethyl |
| $HOCH_2CH_2CH_2$ | $CH_3$ | H | ethyl |
| $(CH_3)_2CH_2$ | $CH_3$ | H | ethyl |
| phenyl | $CH_3$ | H | ethyl |
| 4-pyridyl | $CH_3$ | H | ethyl |
| 3-pyridyl | $CH_3$ | H | ethyl |
| 2-pyridyl | $CH_3$ | H | ethyl |
| 4-pyridylmethyl | $CH_3$ | H | ethyl |
| 3-pyridylmethyl | $CH_3$ | H | ethyl |
| 2-pyridylmethyl | $CH_3$ | H | ethyl |
| benzyl | $CH_3$ | H | ethyl |
| 4-$HO_2C$-benzyl | $CH_3$ | H | ethyl |
| 4-$H_2NCO$-benzyl | $CH_3$ | H | ethyl |
| 4-$CH_3O$-benzyl | $CH_3$ | H | ethyl |
| 4-HO-benzyl | $CH_3$ | H | ethyl |
| 4-Cl-benzyl | $CH_3$ | H | ethyl |
| 4-$(CH_3)_2N$-benzyl | $CH_3$ | H | ethyl |
| 3-$HO_2C$-benzyl | $CH_3$ | H | ethyl |
| 3-$H_2NCO$-benzyl | $CH_3$ | H | ethyl |
| 3-$CH_3O$-benzyl | $CH_3$ | H | ethyl |
| 3-HO-benzyl | $CH_3$ | H | ethyl |
| 3-Cl-benzyl | $CH_3$ | H | ethyl |
| 3-$(CH_3)_2N$-benzyl | $CH_3$ | H | ethyl |
| 2-$HO_2C$-benzyl | $CH_3$ | H | ethyl |
| 2-$H_2NCO$-benzyl | $CH_3$ | H | ethyl |
| 2-$CH_3O$-benzyl | $CH_3$ | H | ethyl |
| 2-HO-benzyl | $CH_3$ | H | ethyl |
| 2-Cl-benzyl | $CH_3$ | H | ethyl |
| 2-$(CH_3)_2N$-benzyl | $CH_3$ | H | ethyl |
| $CH_3$ | $CH_3$ | OH | allyl |
| $CH_3CH_2$ | $CH_3$ | OH | allyl |
| $CH_2$=$CHCH_2$ | $CH_3$ | OH | allyl |
| $CH_3CH_2CH_2$ | $CH_3$ | OH | allyl |
| $(CH_3)_2CH$ | $CH_3$ | OH | allyl |
| $HO_2CCH_2CH_2$ | $CH_3$ | OH | allyl |
| $H_2NCOCH_2CH_2$ | $CH_3$ | OH | allyl |
| $HOCH_2CH_2$ | $CH_3$ | OH | allyl |
| $HOCH_2CH_2CH_2$ | $CH_3$ | OH | allyl |
| $(CH_3)_2CH_2$ | $CH_3$ | OH | allyl |
| phenyl | $CH_3$ | OH | allyl |
| 4-pyridyl | $CH_3$ | OH | allyl |
| 3-pyridyl | $CH_3$ | OH | allyl |
| 2-pyridyl | $CH_3$ | OH | allyl |
| 4-pyridylmethyl | $CH_3$ | OH | allyl |
| 3-pyridylmethyl | $CH_3$ | OH | allyl |
| 2-pyridylmethyl | $CH_3$ | OH | allyl |
| benzyl | $CH_3$ | OH | allyl |
| 4-$HO_2C$-benzyl | $CH_3$ | OH | allyl |
| 4-$H_2NCO$-benzyl | $CH_3$ | OH | allyl |
| 4-$CH_3O$-benzyl | $CH_3$ | OH | allyl |
| 4-HO-benzyl | $CH_3$ | OH | allyl |
| 4-Cl-benzyl | $CH_3$ | OH | allyl |
| 4-$(CH_3)_2N$-benzyl | $CH_3$ | OH | allyl |
| 3-$HO_2C$-benzyl | $CH_3$ | OH | allyl |
| 3-$H_2NCO$-benzyl | $CH_3$ | OH | allyl |
| 3-$CH_3O$-benzyl | $CH_3$ | OH | allyl |
| 3-HO-benzyl | $CH_3$ | OH | allyl |
| 3-Cl-benzyl | $CH_3$ | | |
| 3-$(CH_3)_2N$-benzyl | $CH_3$ | OH | allyl |
| 2-$HO_2C$-benzyl | $CH_3$ | OH | allyl |
| 2-$H_2NCO$-benzyl | $CH_3$ | OH | allyl |
| 2-$CH_3O$-benzyl | $CH_3$ | OH | allyl |

-continued

| $R^a$ | $R^2$ | $R^3$ | $R^5$ |
|---|---|---|---|
| 2-HO-benzyl | $CH_3$ | OH | allyl |
| 2-Cl-benzyl | $CH_3$ | OH | allyl |
| 2-$(CH_3)_2$N-benzyl | $CH_3$ | OH | allyl |

Representative compounds of the present invention include the compounds of Formula XVIII:

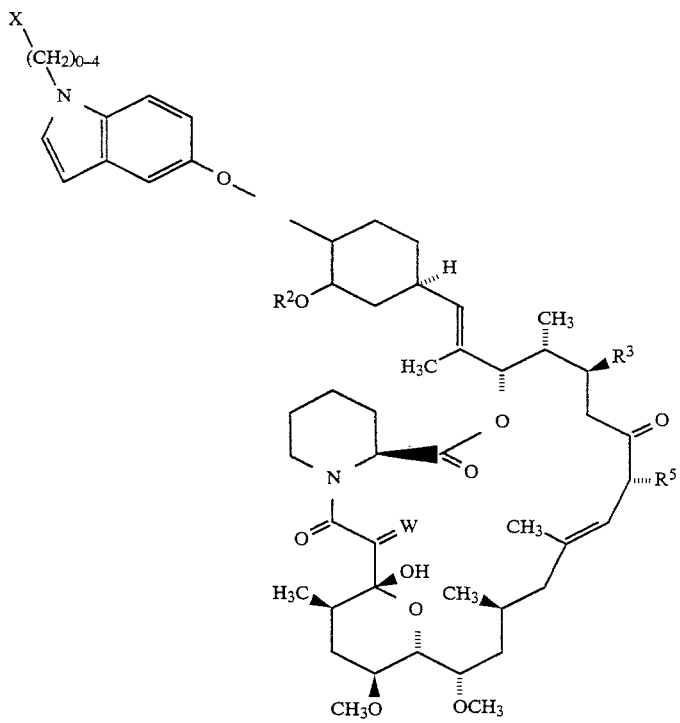

XVIII wherein X, $R^2$, $R^3$ and $R^5$ are selected from the following groups of substituents:

| X | $R^2$ | $R^3$ | $R^5$ |
|---|---|---|---|
| 1-imidazolylmethyl | $CH_3$ | OH | ethyl |
| 2-imidazolylmethyl | $CH_3$ | OH | ethyl |
| 3-thiazolylmethyl | $CH_3$ | OH | ethyl |
| 2-thiazolylmethyl | $CH_3$ | OH | ethyl |
| 2-oxazolylmethyl | $CH_3$ | OH | ethyl |
| 5-tetrazolylmethyl | $CH_3$ | OH | ethyl |
| 4-pyridylmethyl | $CH_3$ | OH | ethyl |
| 3-pyridylmethyl | $CH_3$ | OH | ethyl |
| 2-pyridylmethyl | $CH_3$ | OH | ethyl |
| benzyl | $CH_3$ | OH | ethyl |
| 4-$HO_2$C-benzyl | $CH_3$ | OH | ethyl |
| 4-$H_2$NCO-benzyl | $CH_3$ | OH | ethyl |
| 4-$CH_3$O-benzyl | $CH_3$ | OH | ethyl |
| 4-HO-benzyl | $CH_3$ | OH | ethyl |
| 4-$R^{11}$O-benzyl | $CH_3$ | OH | ethyl |
| 4-Cl-benzyl | $CH_3$ | OH | ethyl |
| 4-$(CH_3)_2$N-benzyl | $CH_3$ | OH | ethyl |
| 3-$HO_2$C-benzyl | $CH_3$ | OH | ethyl |
| 3-$H_2$NCO-benzyl | $CH_3$ | OH | ethyl |
| 3-$CH_3$O-benzyl | $CH_3$ | OH | ethyl |
| 3-HO-benzyl | $CH_3$ | OH | ethyl |
| 3-$R^{11}$O-benzyl | $CH_3$ | OH | ethyl |
| 3-Cl-benzyl | $CH_3$ | OH | ethyl |
| 3-$(CH_3)_2$N-benzyl | $CH_3$ | OH | ethyl |
| 2-$HO_2$C-benzyl | $CH_3$ | OH | ethyl |
| 2-$H_2$NCO-benzyl | $CH_3$ | OH | ethyl |
| 2-$CH_3$O-benzyl | $CH_3$ | OH | ethyl |
| 2-HO-benzyl | $CH_3$ | OH | ethyl |
| 2-$R^{11}$O-benzyl | $CH_3$ | OH | ethyl |
| 2-Cl-benzyl | $CH_3$ | OH | ethyl |
| 2-$(CH_3)_2$N-benzyl | $CH_3$ | OH | ethyl |
| 3-(4-pyridyl)-imidazol-2-ylmethyl | $CH_3$ | OH | ethyl |
| 3-(3-pyridyl)-imidazol-2-ylmethyl | $CH_3$ | OH | ethyl |
| 3-(2-pyridyl)-imidazol-2 ylmethyl | $CH_3$ | OH | ethyl |
| 3-phenylimidazol-2-ylmethyl | $CH_3$ | OH | ethyl |
| 3-(4-$HO_2$C-phenyl)-imidazol-2-ylmethyl | $CH_3$ | OH | ethyl |
| 3-(4-$H_2$NCO-phenyl)-imidazol-2-ylmethyl | $CH_3$ | OH | ethyl |
| 3-(4-$CH_3$O-phenyl)-imidazol-2-ylmethyl | $CH_3$ | OH | ethyl |
| 3-(4-HO-phenyl)-imidazol-2-ylmethyl | $CH_3$ | OH | ethyl |
| 3-(4-$R^{11}$O-phenyl)-imidazol-2-ylmethyl | $CH_3$ | OH | ethyl |
| 3-(4-Cl-phenyl)-imidazol-2-ylmethyl | $CH_3$ | OH | ethyl |
| 3-(4-$(CH_3)_2$N-phenyl)-imidazol-2-ylmethyl | $CH_3$ | OH | ethyl |
| 3-(3-$HO_2$C-phenyl)-imidazol-2-ylmethyl | $CH_3$ | OH | ethyl |
| 3-(3-$H_2$NCO-phenyl)-imidazol-2-ylmethyl | $CH_3$ | OH | ethyl |
| 3-(3-$CH_3$O-phenyl)-imidazol-2-ylmethyl | $CH_3$ | OH | ethyl |
| 3-(3-HO-phenyl)-imidazol-2-ylmethyl | $CH_3$ | OH | ethyl |
| 3-(3-$R^{11}$O-phenyl)-imidazol-2-ylmethyl | $CH_3$ | OH | ethyl |
| 3-(3-Cl-phenyl)-imidazol-2-ylmethyl | $CH_3$ | OH | ethyl |
| 3-(3-$(CH_3)_2$N-phenyl)-imidazol-2-ylmethyl | $CH_3$ | OH | ethyl |
| 3-(2-$HO_2$C-phenyl)-imidazol-2-ylmethyl | $CH_3$ | OH | ethyl |
| 3-(2-$H_2$NCO-phenyl)-imidazol-2-ylmethyl | $CH_3$ | OH | ethyl |
| 3-(2-$CH_3$O-phenyl)-imidazol-2-ylmethyl | $CH_3$ | OH | ethyl |
| 3-(2-HO-phenyl)-imidazol-2-ylmethyl | $CH_3$ | OH | ethyl |
| 3-(2-$R^{11}$O-phenyl)-imidazol-2-ylmethyl | $CH_3$ | OH | ethyl |
| 3-(2-Cl-phenyl)-imidazol-2-ylmethyl | $CH_3$ | OH | ethyl |
| 3-(2-$(CH_3)_2$N-phenyl)-imidazol-2-ylmethyl | $CH_3$ | OH | ethyl |
| 1-imidazolylmethyl | $CH_3$ | H | ethyl |
| 2-imidazolylmethyl | $CH_3$ | H | ethyl |
| 3-thiazolylmethyl | $CH_3$ | H | ethyl |
| 2-thiazolylmethyl | $CH_3$ | H | ethyl |
| 2-oxazolylmethyl | $CH_3$ | H | ethyl |
| 5-tetrazolylmethyl | $CH_3$ | H | ethyl |
| 4-pyridylmethyl | $CH_3$ | H | ethyl |
| 3-pyridylmethyl | $CH_3$ | H | ethyl |
| 2-pyridylmethyl | $CH_3$ | H | ethyl |
| benzyl | $CH_3$ | H | ethyl |
| 4-$HO_2$C-benzyl | $CH_3$ | H | ethyl |
| 4-$H_2$NCO-benzyl | $CH_3$ | H | ethyl |
| 4-$CH_3$O-benzyl | $CH_3$ | H | ethyl |
| 4-HO-benzyl | $CH_3$ | H | ethyl |
| 4-$R^{11}$O-benzyl | $CH_3$ | H | ethyl |
| 4-Cl-benzyl | $CH_3$ | H | ethyl |
| 4-$(CH_3)_2$N-benzyl | $CH_3$ | H | ethyl |
| 3-$HO_2$C-benzyl | $CH_3$ | H | ethyl |
| 3-$H_2$NCO-benzyl | $CH_3$ | H | ethyl |

-continued

| X | R² | R³ | R⁵ |
|---|---|---|---|
| 3-CH₃O-benzyl | CH₃ | H | ethyl |
| 3-HO-benzyl | CH₃ | H | ethyl |
| 3-R¹¹O-bezyl | CH₃ | H | ethyl |
| 3-Cl-benzyl | CH₃ | H | ethyl |
| 3-(CH₃)₂N-benzyl | CH₃ | H | ethyl |
| 2-HO₂C-benzyl | CH₃ | H | ethyl |
| 2-H₂NCO-benzyl | CH₃ | H | ethyl |
| 2-CH₃O-benzyl | CH₃ | H | ethyl |
| 2-HO-benzyl | CH₃ | H | ethyl |
| 2-R¹¹O-benzyl | CH₃ | H | ethyl |
| 2-Cl-benzyl | CH₃ | H | ethyl |
| 2-(CH₃)₂N-benzyl | CH₃ | H | ethyl |
| 3-(4-pyridyl)-imidazol-2-ylmethyl | CH₃ | H | ethyl |
| 3-(3-pyridyl)-imidazol-2-ylmethyl | CH₃ | H | ethyl |
| 3-(2-pyridyl)-imidazol-2-ylmethyl | CH₃ | H | ethyl |
| 3-phenylimidazol-2-ylmethyl | CH₃ | H | ethyl |
| 3-(4-HO₂C-phenyl)-imidazol-2-ylmethyl | CH₃ | H | ethyl |
| 3-(4-H₂NCO-phenyl)-imidazol-2-ylmethyl | CH₃ | H | ethyl |
| 3-(4-CH₃O-phenyl)-imidazol-2-ylmethyl | CH₃ | H | ethyl |
| 3-(4-HO-phenyl)-imidazol-2-ylmethyl | CH₃ | H | ethyl |
| 3-(4-R¹¹O-phenyl)-imidazol-2-ylmethyl | CH₃ | H | ethyl |
| 3-(4-Cl-phenyl)-imidazol-2-ylmethyl | CH₃ | H | ethyl |
| 3-(4-(CH₃)₂N-phenyl)-imidazol-2-ylmethyl | CH₃ | H | ethyl |
| 3-(3-HO₂C-phenyl)-imidazol-2-ylmethyl | CH₃ | H | ethyl |
| 3-(3-H₂NCO-phenyl)-imidazol-2-ylmethyl | CH₃ | H | ethyl |
| 3-(3-CH₃O-phenyl)-imidazol-2-ylmethyl | CH₃ | H | ethyl |
| 3-(3-HO-phenyl)-imidazol-2-ylmethyl | CH₃ | H | ethyl |
| 3-(3-R¹¹O-phenyl)-imidazol-2-ylmethyl | CH₃ | H | ethyl |
| 3-(3-Cl-phenyl)-imidazol-2-ylmethyl | CH₃ | H | ethyl |
| 3-(3-(CH₃)₂N-phenyl)-imidazol-2-ylmethyl | CH₃ | H | ethyl |
| 3-(2-HO₂C-phenyl)-imidazol-2-ylmethyl | CH₃ | H | ethyl |
| 3-(2-H₂NCO-phenyl)-imidazol-2-ylmethyl | CH₃ | H | ethyl |
| 3-(2-CH₃O-phenyl)-imidazol-2-ylmethyl | CH₃ | H | ethyl |
| 3-(2-HO-phenyl)-imidazol-2-ylmethyl | CH₃ | H | ethyl |
| 3-(2-R¹¹O-phenyl)-imidazol-2-ylmethyl | CH₃ | H | ethyl |
| 3-(2-Cl-phenyl)-imidazol-2-ylmethyl | CH₃ | H | ethyl |
| 3-(2-(CH₃)₂N-phenyl)-imidazol-2-ylmethyl | CH₃ | H | ethyl |
| 1-imidazolylmethyl | H | OH | ethyl |
| 2-imidazolylmethyl | H | OH | ethyl |
| 3-thiazolylmethyl | H | OH | ethyl |
| 2-thiazolylmethyl | H | OH | ethyl |
| 2-oxazolylmethyl | H | OH | ethyl |
| 5-tetrazolylmethyl | H | OH | ethyl |
| 4-pyridylmethyl | H | OH | ethyl |
| 3-pyridylmethyl | H | OH | ethyl |
| 2-pyridylmethyl | H | OH | ethyl |
| benzyl | H | OH | ethyl |
| 4-HO₂C-benzyl | H | OH | ethyl |
| 4-H₂NCO-benzyl | H | OH | ethyl |
| 4-CH₃O-benzyl | H | OH | ethyl |
| 4-HO-benzyl | H | OH | ethyl |
| 4-R¹¹O-benzyl | H | OH | ethyl |
| 4-Cl-benzyl | H | OH | ethyl |
| 4-(CH₃)-2-benzyl | H | OH | ethyl |
| 3-HO₂C-benzyl | H | OH | ethyl |
| 3-H₂NCO-benzyl | H | OH | ethyl |
| 3-CH₃O-benzyl | H | OH | ethyl |
| 3-HO-benzyl | H | OH | ethyl |
| 3-R¹¹O-benzyl | H | OH | ethyl |
| 3-Cl-benzyl | H | OH | ethyl |
| 3-(CH₃)₂N-benzyl | H | OH | ethyl |
| 2-HO₂C-benzyl | H | OH | ethyl |
| 2-H₂NCO-benzyl | H | OH | ethyl |
| 2-CH₃O-benzyl | H | OH | ethyl |
| 2-HO-benzyl | H | OH | ethyl |
| 2-R¹¹O-benzyl | H | OH | ethyl |
| 2-Cl-benzyl | H | OH | ethyl |
| 2-(CH₃)₂N-benzyl | H | OH | ethyl |
| 3-(4-pyridyl)-imidazol-2-ylmethyl | H | OH | ethyl |
| 3-(3-pyridyl)-imidazol-2-ylmethyl | H | OH | ethyl |
| 3-(2-pyridyl)-imidazol-2-ylmethyl | H | OH | ethyl |
| 3-phenylimidazol-2-ylmethyl | H | OH | ethyl |
| 3-(4-HO₂C-phenyl)-imidazol-2-ylmethyl | H | OH | ethyl |
| 3-(4-H₂NCO-phenyl)-imidazol-2-ylmethyl | H | OH | ethyl |
| 3-(4-CH₃O-phenyl)-imidazol-2-ylmethyl | H | OH | ethyl |
| 3-(4-HO-phenyl)-imidazol-2-ylmethyl | H | OH | ethyl |
| 3-(4-R¹¹O-phenyl)-imidazol-2-ylmethyl | H | OH | ethyl |
| 3-(4-Cl-phenyl)-imidazol-2-ylmethyl | H | OH | ethyl |
| 3-(4-(CH₃)₂N-phenyl)-imidazol-2-ylmethyl | H | OH | ethyl |
| 3-(3-HO₂C-phenyl)-imidazol-2-ylmethyl | H | OH | ethyl |
| 3-(3-H₂NCO-phenyl)-imidazol-2-ylmethyl | H | OH | ethyl |
| 3-(3-CH₃O-phenyl)-imidazol-2-ylmethyl | H | OH | ethyl |
| 3-(3-HO-phenyl)-imidazol-2-ylmethyl | H | OH | ethyl |
| 3-(3-R¹¹O-phenyl)-imidazol-2-ylmethyl | H | OH | ethyl |
| 3-(3-Cl-phenyl)-imidazol-2-ylmethyl | H: | OH | ethyl |
| 3-(3-(CH₃)₂N-phenyl)-imidazol-2-ylmethyl | H | OH | ethyl |
| 3-(2-HO₂C-phenyl)-imidazol-2-ylmethyl | H | OH | ethyl |
| 3-(2-H₂NCO-phenyl)-imidazol-2-ylmethyl | H | OH | ethyl |
| 3-(2-CH₃O-phenyl)-imidazol-2-ylmethyl | H | OH | ethyl |
| 3-(2-HO-phenyl)-imidazol-2-ylmethyl | H | OH | ethyl |
| 3-(2-R¹¹O-phenyl)-imidazol-2-ylmethyl | H | OH | ethyl |
| 3-(2-Cl-phenyl)-imidazol-2-ylmethyl | H | OH | ethyl |
| 3-(2-(CH₃)₂N-phenyl)-imidazol-2-ylmethyl | H | OH | ethyl |
| 1-imidazolylmethyl | H | H | ethyl |
| 2-imidazolylmethyl | H | H | ethyl |
| 3-thiazolylmethyl | H | H | ethyl |
| 2-thiazolylmethyl | H | H | ethyl |
| 2-oxazolylmethyl | H | H | ethyl |
| 5-tetrazolylmethyl | H | H | ethyl |
| 4-pyridylmethyl | H | H | ethyl |
| 3-pyridylmethyl | H | H | ethyl |
| 2-pyridylmethyl | H | H | ethyl |
| benzyl | H | H | ethyl |
| 4-HO₂C-benzyl | H | H | ethyl |
| 4-H₂NCO-benzyl | H | H | ethyl |
| 4-CH₃O-benzyl | H | H | ethyl |
| 4-HO-benzyl | H | H | ethyl |
| 4-R¹¹O-benzyl | H | H | ethyl |
| 4-Cl-benzyl | H | H | ethyl |
| 4-(CH₃)₂N-benzyl | H | H | ethyl |
| 3-HO₂C-benzyl | H | H | ethyl |
| 3-H₂NCO-benzyl | H | H | ethyl |
| 3-CH₃O-benzyl | H | H | ethyl |
| 3-HO-benzyl | H | H | ethyl |
| 3-R¹¹O-benzyl | H | H | ethyl |
| 3-Cl-benzyl | H | H | ethyl |
| 3-(CH₃)₂N-benzyl | H | H | ethyl |
| 2-HO₂C-benzyl | H | H | ethyl |
| 2-H₂NCO-benzyl | H | H | ethyl |
| 2-CH₃O-benzyl | H | H | ethyl |
| 2-HO-benzyl | H | H | ethyl |
| 2-R¹¹O-benzyl | H | H | ethyl |
| 2-Cl-benzyl | H | H | ethyl |
| 2-(CH₃)₂N-benzyl | H | H | ethyl |
| 3-(4-pyridyl)-imidazol-2-ylmethyl | H | H | ethyl |
| 3-(3-pyridyl)-imidazol-2-ylmethyl | H | H | ethyl |
| 3-(2-pyridyl)-imidazol-2-ylmethyl | H | H | ethyl |
| 3-phenylimidazol-2-ylmethyl | H | H | ethyl |
| 3-(4-HO₂C-phenyl)-imidazol-2-ylmethyl | H | H | ethyl |
| 3-(4-H₂NCO-phenyl)-imidazol-2-ylmethyl | H | H | ethyl |
| 3-(4-CH₃O-phenyl)-imidazol-2-ylmethyl | H | H | ethyl |
| 3-(4-HO-phenyl)-imidazol-2 ylmethyl | H | H | ethyl |
| 3-(4-R¹¹O-phenyl)-imidazol-2-ylmethyl | H | H | ethyl |
| 3-(4-Cl-phenyl)-imidazol-2-ylmethyl | H | H | ethyl |
| 3-(4-(CH₃)₂N-phenyl)-imidazol-2-ylmethyl | H | H | ethyl |
| 3-(3-HO₂C-phenyl)-imidazol-2-ylmethyl | H | H | ethyl |
| 3-(3-H₂NCO-phenyl)-imidazol-2-ylmethyl | H | H | ethyl |
| 3-(3-CH₃O-phenyl)-imidazol-2-ylmethyl | H | H | ethyl |
| 3-(3-HO-phenyl-imidazol-2-ylmethyl | H | H | ethyl |
| 3-(3-R¹¹O-phenyl)-imidazol-2-ylmethyl | H | H | ethyl |
| 3-(3-Cl-phenyl)-imidazol-2-ylmethyl | H | H | ethyl |
| 3-(3-(CH₃)₂N-phenyl)-imidazol-2-ylmethyl | H | H | ethyl |
| 3-(2-HO₂C-phenyl)-imidazol-2-ylmethyl | H | H | ethyl |
| 3-(2-H₂NCO-phenyl)-imidazol-2-ylmethyl | H | H | ethyl |
| 3-(2-CH₃O-phenyl)-imidazol-2-ylmethyl | H | H | ethyl |
| 3-(2-HO-phenyl)-imidazol-2-ylmethyl | H | H | ethyl |
| 3-(2-R¹¹O-phenyl)-imidazol-2-ylmethyl | H | H | ethyl |
| 3-(2-Cl-phenyl)-imidazol-2-ylmethyl | H | H | ethyl |
| 3-(2-(CH₃)₂N-phenyl)-imidazol-2-ylmethyl | H | H | ethyl |
| 1-imidazolylmethyl | CH₃ | OH | allyl |
| 2-imidazolylmethyl | CH₃ | OH | allyl |
| 3-thiazolylmethyl | CH₃ | OH | allyl |
| 2-thiazolylmethyl | CH₃ | OH | allyl |
| 2-oxazolylmethyl | CH₃ | OH | allyl |
| 5-tetrazolylmethyl | CH₃ | OH | allyl |
| 4-pyridylmethyl | CH₃ | OH | allyl |
| 3-pyridylmethyl | CH₃ | OH | allyl |
| 2-pyridylmethyl | CH₃ | OH | allyl |
| benzyl | CH₃ | OH | allyl |
| 4-HO₂C-benzyl | CH₃ | OH | allyl |
| 4-H₂NCO-benzyl | CH₃ | OH | allyl |
| 4-CH₃O-benzyl | CH₃ | OH | allyl |

-continued

| X | R² | R³ | R⁵ |
|---|---|---|---|
| 4-HO-benzyl | CH₃ | OH | allyl |
| 4-R¹¹O-benzyl | CH₃ | OH | allyl |
| 4-Cl-benzyl | CH₃ | OH | allyl |
| 4-(CH₃)₂N-benzyl | CH₃ | OH | allyl |
| 3-HO₂C-benzyl | CH₃ | OH | allyl |
| 3-H₂NCO-benzyl | CH₃ | OH | allyl |
| 3-CH₃O-benzyl | CH₃ | OH | allyl |
| 3-HO-benzyl | CH₃ | OH | allyl |
| 3-R¹¹O-benzyl | CH₃ | OH | allyl |
| 3-Cl-benzyl | CH₃ | OH | allyl |
| 3-(CH₃)₂N-benzyl | CH₃ | OH | allyl |
| 2-HO₂C-benzyl | CH₃ | OH | allyl |
| 2-H₂NCO-benzyl | CH₃ | OH | allyl |
| 2-CH₃O-benzyl | CH₃ | OH | allyl |
| 2-HO-benzyl | CH₃ | OH | allyl |
| 2-R¹¹O-benzyl | CH₃ | OH | allyl |
| 2-Cl-benzyl | CH₃ | OH | allyl |
| 2-(CH₃)₂N-benzyl | CH₃ | OH | allyl |
| 3-(4-pyridyl)-imidazol-2-ylmethyl | CH₃ | OH | allyl |
| 3-(3-pyridyl)-imidazol-2-ylmethyl | CH₃ | OH | allyl |
| 3-(2-pyridyl)-imidazol-2-ylmethyl | CH₃ | OH | allyl |
| 3-phenylimidazol-2-ylmethyl | CH₃ | OH | allyl |
| 3-(4-HO₂C-phenyl)-imidazol-2-ylmethyl | CH₃ | OH | allyl |
| 3-(4-H₂NCO-phenyl)-imidazol-2-ylmethyl | CH₃ | OH | allyl |
| 3-(4-CH₃O-phenyl)-imidazol-2-ylmethyl | CH₃ | OH | allyl |
| 3-(4-HO-phenyl)-imidazol-2-ylmethyl | CH₃ | OH | allyl |
| 3-(4-R¹¹O-phenyl)-imidazol-2-ylmethyl | CH₃ | OH | allyl |
| 3-(4-Cl-phenyl)-imidazol-2-ylmethyl | CH₃ | OH | allyl |
| 3-(4-(CH₃)₂N-phenyl)-imidazol-2-ylmethyl | CH₃ | OH | allyl |
| 3-(3-HO₂C-phenyl)-imidazol-2-ylmethyl | CH₃ | OH | allyl |
| 3-(3-H₂NCO-phenyl)-imidazol-2-ylmethyl | CH₃ | OH | allyl |
| 3-(3-CH₃O-phenyl)-imidazol-2-ylmethyl | CH₃ | OH | allyl |
| 3-(3-HO-phenyl)-imidazol-2-ylmethyl | CH₃ | OH | allyl |
| 3-(3-R¹¹O-phenyl)-imidazol-2-ylmethyl | CH₃ | OH | allyl |
| 3-(3-Cl-phenyl)-imidazol-2-ylmethyl | CH₃ | OH | allyl |
| 3-(3-(CH₃)₂N-phenyl)-imidazol-2-ylmethyl | CH₃ | OH | allyl |
| 3-(2-HO₂C-phenyl)-imidazol-2-ylmethyl | CH₃ | OH | allyl |
| 3-(2-H₂NCO-phenyl)-imidazol-2-ylmethyl | CH₃ | OH | allyl |
| 3-(2-CH₃O-phenyl)-imidazol-2-ylmethyl | CH₃ | OH | allyl |
| 3-(2-HO-phenyl)-imidazol-2-ylmethyl | CH₃ | OH | allyl |
| 3(2-R¹¹O-phenyl)-imidazol-2-ylmethyl | CH₃ | OH | allyl |
| 3(2-Cl-phenyl)-imidazol-2-ylmethyl | CH₃ | OH | allyl |
| 3-(2-(CH₃)₂N-phenyl)-imidazol-2-ylmethyl | CH₃ | OH | allyl |
| 1-imidazolylmethyl | CH₃ | H | allyl |
| 2-imidazolylmethyl | CH₃ | H | allyl |
| 3-thiazolylmethyl | CH₃ | H | allyl |
| 2-thiazolylmethyl | CH₃ | H | allyl |
| 2-oxazolylmethyl | CH₃ | H | allyl |
| 5-tetrazolylmethyl | CH₃ | H | allyl |
| 4-pyridylmethyl | CH₃ | H | allyl |
| 3-pyridylmethyl | CH₃ | H | allyl |
| 2-pyridylmethyl | CH₃ | H | allyl |
| benzyl | CH₃ | H | allyl |
| 4-HO₂C-benzyl | CH₃ | H | allyl |
| 4-H₂NCO-benzyl | CH₃ | H | allyl |
| 4-CH₃O-benzyl | CH₃ | H | allyl |
| 4-HO-benzyl | CH₃ | H | allyl |
| 4-R¹¹O-benzyl | CH₃ | H | allyl |
| 4-Cl-benzyl | CH₃ | H | allyl |
| 4-(CH₃)₂N-benzyl | CH₃ | H | allyl |
| 3-HO₂C-benzyl | CH₃ | H | allyl |
| 3-H₂NCO-benzyl | CH₃ | H | allyl |
| 3-CH₃O-benzyl | CH₃ | H | allyl |
| 3-HO-benzyl | CH₃ | H | allyl |
| 3-R¹¹O-benzyl | CH₃ | H | allyl |
| 3-Cl-benzyl | CH₃ | H | allyl |
| 3-(CH₃)₂N-benzyl | CH₃ | H | allyl |
| 2-HO₂C-benzyl | CH₃ | H | allyl |
| 2-H₂NCO-benzyl | CH₃ | H | allyl |
| 2-CH₃O-benzyl | CH₃ | H | allyl |
| 2-HO-benzyl | CH₃ | H | allyl |
| 2-R¹¹O-benzyl | CH₃ | H | allyl |
| 2-Cl-benzyl | CH₃ | H | allyl |
| 2-(CH₃)₂N-benzyl | CH₃ | H | allyl |
| 3-(4-pyridyl)-imidazol-2-ylmethyl | CH₃ | H | allyl |
| 3-(3-pyridyl)-imidazol-2-ylmethyl | CH₃ | H | allyl |
| 3-(2-pyridyl)-imidazol-2-ylmethyl | CH₃ | H | allyl |
| 3-phenylimidazol-2-ylmethyl | CH₃ | H | allyl |
| 3-(4-HO₂C-phenyl)-imidazol-2-ylmethyl | CH₃ | H | allyl |
| 3-(4-H₂NCO-phenyl)-imidazol-2-ylmethyl | CH₃ | H | allyl |
| 3-(4-CH₃O-phenyl)-imidazol-2-ylmethyl | CH₃ | H | allyl |
| 3-(4-HO-phenyl)-imidazol-2-ylmethyl | CH₃ | H | allyl |
| 3-(4-R¹¹O-phenyl)-imidazol-2-ylmethyl | CH₃ | H | allyl |
| 3-(4-Cl-phenyl)-imidazol-2-ylmethyl | CH₃ | H | allyl |
| 3-(4-(CH₃)₂N-phenyl)-imidazol-2-ylmethyl | CH₃ | H | allyl |
| 3-(3-HO₂C-phenyl)-imidazol-2-ylmethyl | CH₃ | H | allyl |
| 3-(3-H₂NCO-phenyl)-imidazol-2-ylmethyl | CH₃ | H | allyl |
| 3-(3-CH₃O-phenyl)-imidazol-2-ylmethyl | CH₃ | H | allyl |
| 3-(3-HO-phenyl)-imidazol-2-ylmethyl | CH₃ | H | allyl |
| 3-(3-R¹¹O-phenyl)-imidazol-2-ylmethyl | CH₃ | H | allyl |
| 3-(3-Cl-phenyl)-imidazol-2-ylmethyl | CH₃ | H | allyl |
| 3-(3-(CH₃)₂N-phenyl)-imidazol-2-ylmethyl | CH₃ | H | allyl |
| 3-(2-HO₂C-phenyl)-imidazol-2-ylmethyl | CH₃ | H | allyl |
| 3-(2-H₂NCO-phenyl)-imidazol-2-ylmethyl | CH₃ | H | allyl |
| 3-(2-CH₃O-phenyl)-imidazol-2-ylmethyl | CH₃ | H | allyl |
| 3-(2-HO-phenyl)-imidazol-2-ylmethyl | CH₃ | H | allyl |
| 3-(2-R¹¹O-phenyl)-imidazol-2-ylmethyl | CH₃ | H | allyl |
| 3-(2-Cl-phenyl)-imidazol-2-ylmethyl | CH₃ | H | allyl |
| 3-(2-(CH₃)₂N-phenyl)-imidazol-2-ylmethyl | CH₃ | H | allyl |
| 1-imidazolylmethyl | H | OH | allyl |
| 2-imidazolylmethyl | H | OH | allyl |
| 3-thiazolylmethyl | H | OH | allyl |
| 2-thiazolylmethyl | H | OH | allyl |
| 2-oxazolylmethyl | H | OH | allyl |
| 5-tetrazolylmethyl | H | OH | allyl |
| 4-pyridylmethyl | H | OH | allyl |
| 3-pyridylmethyl | H | OH | allyl |
| 2-pyridylmethyl | H | OH | allyl |
| benzyl | H | OH | allyl |
| 4-HO₂C-benzyl | H | OH | allyl |
| 4-H₂NCO-benzyl | H | OH | allyl |
| 4-CH₃O-benzyl | H | OH | allyl |
| 4-HO-benzyl | H | OH | allyl |
| 4-R¹¹O-benzyl | H | OH | allyl |
| 4-Cl-benzyl | H | OH | allyl |
| 4-(CH₃)₂N-benzyl | H | OH | allyl |
| 3-HO₂C-benzyl | H | OH | allyl |
| 3-H₂NCO-benzyl | H | OH | allyl |
| 3-CH₃O-benzyl | H | OH | allyl |
| 3-HO-benzyl | H | OH | allyl |
| 3-R¹¹O-benzyl | H | OH | allyl |
| 3-Cl-benzyl | H | OH | allyl |
| 3-(CH₃)₂N-benzyl | H | OH | allyl |
| 2-HO₂C-benzyl | H | OH | allyl |
| 2-H₂NCO-benzyl | H | OH | allyl |
| 2-CH₃O-benzyl | H | OH | allyl |
| 2-HO-benzyl | H | OH | allyl |
| 2-R¹¹O-benzyl | H | OH | allyl |
| 2-Cl-benzyl | H | OH | allyl |
| 2-(CH₃)₂N-benzyl | H | OH | allyl |
| 3-(4-pyridyl)-imidazol-2-ylmethyl | H | OH | allyl |
| 3-(3-pyridyl)-imidazol-2-ylmethyl | H | OH | allyl |
| 3-(2-pyridyl)-imidazol-2-ylmethyl | H | OH | allyl |
| 3-phenylimidazol-2-ylmethyl | H | OH | allyl |
| 3-(4-HO₂C-phenyl)-imidazol-2-ylmethyl | H | OH | allyl |
| 3-(4-H₂NCO-phenyl)-imidazol-2-ylmethyl | H | OH | allyl |
| 3-(4-CH₃O-phenyl)-imidazol-2-ylmethyl | H | OH | allyl |
| 3-(4-HO-phenyl)-imidazol-2-ylmethyl | H | OH | allyl |
| 3-(4-R¹¹O-phenyl)-imidazol-2-ylmethyl | H | OH | allyl |
| 3-(4-Cl-phenyl)-imidazol-2-ylmethyl | H | OH | allyl |
| 3-(4-(CH₃)₂N-phenyl)-imidazol-2-ylmethyl | H | OH | allyl |
| 3-(3-HO₂C-phenyl)-imidazol-2-ylmethyl | H | OH | allyl |
| 3-(3-H₂NCO-phenyl)-imidazol-2-ylmethyl | H | OH | allyl |
| 3-(3-CH₃O-phenyl)-imidazol-2-ylmethyl | H | OH | allyl |
| 3-(3-HO-phenyl)-imidazol-2-ylmethyl | H | OH | allyl |
| 3-(3-R¹¹O-phenyl)-imidazol-2-ylmethyl | H | OH | allyl |
| 3-(3-Cl-phenyl)-imidazol-2-ylmethyl | H | OH | allyl |
| 3-(3-(CH₃)₂N-phenyl)-imidazol-2-ylmethyl | H | OH | allyl |
| 3-(2-HO₂C-phenyl)-imidazol-2-ylmethyl | H | OH | allyl |
| 3-(2-H₂NCO-phenyl)-imidazol-2-ylmethyl | H | OH | allyl |
| 3-(2-CH₃O-phenyl)-imidazol-2-ylmethyl | H | OH | allyl |
| 3-(2-HO-phenyl)-imidazol-2-ylmethyl | H | OH | allyl |
| 3-(2-R¹¹O-phenyl)-imidazol-2-ylmethyl | H | OH | allyl |
| 3-(2-Cl-phenyl)-imidazol-2-ylmethyl | H | OH | allyl |
| 3-(2-(CH₃)₂N-phenyl)-imidazol-2-ylmethyl | H | OH | allyl |
| 1-imidazolylmethyl | H | H | allyl |
| 2-imidazolylmethyl | H | H | allyl |
| 3-thiazolylmethyl | H | H | allyl |
| 2-thiazolylmethyl | H | H | allyl |
| 2-oxazolylmethyl | H | H | allyl |
| 5-tetrazolylmethyl | H | H | allyl |
| 4-pyridylmethyl | H | H | allyl |

-continued

| X | R² | R³ | R⁵ |
|---|----|----|----|
| 3-pyridylmethyl | H | H | allyl |
| 2-pyridylmethyl | H | H | allyl |
| benzyl | H | H | allyl |
| 4-HO₂C-benzyl | H | H | allyl |
| 4-H₂NCO-benzyl | H | H | allyl |
| 4-CH₃O-benzyl | H | H | allyl |
| 4-HO-benzyl | H | H | allyl |
| 4-R¹¹O-benzyl | H | H | allyl |
| 4-Cl-benzyl | H | H | allyl |
| 4-(CH₃)₂N-benzyl | H | H | allyl |
| 3-HO₂C-benzyl | H | H | allyl |
| 3-H₂NCO-benzyl | H | H | allyl |
| 3-CH₃O-benzyl | H | H | allyl |
| 3-HO-benzyl | H | H | allyl |
| 3-R¹¹O-benzyl | H | H | allyl |
| 3-Cl-benzyl | H | H | allyl |
| 3-(CH₃)₂N-benzyl | H | H | allyl |
| 2-HO₂C-benzyl | H | H | allyl |
| 2-H₂NCO-benzyl | H | H | allyl |
| 2-CH₃O-benzyl | H | H | allyl |
| 2-HO-benzyl | H | H | allyl |
| 2-R¹¹O-benzyl | H | H | allyl |
| 2-Cl-benzyl | H | H | allyl |
| 2-(CH₃)₂N-benzyl | H | H | allyl |
| 3-(4-pyridyl)-imidazol-2-ylmethyl | H | H | allyl |
| 3-(3-pyridyl)-imidazol-2-ylmethyl | H | H | allyl |
| 3-(2-pyridyl)-imidazol-2-ylmethyl | H | H | allyl |
| 3-phenylimidazol-2-ylmethyl | H | H | allyl |
| 3-(4-HO₂C-phenyl)-imidazol-2-ylmethyl | H | H | allyl |
| 3-(4-H₂NCO-phenyl)-imidazol-2-ylmethyl | H | H | allyl |
| 3-(4-CH₃O-phenyl)-imidazol-2-ylmethyl | H | H | allyl |
| 3-(4-HO-phenyl)-imidazol-2-ylmethyl | H | H | allyl |
| 3-(4-R¹¹O-phenyl)-imidazol-2-ylmethyl | H | H | allyl |
| 3-(4-Cl-phenyl)-imidazol-2-ylmethyl | H | H | allyl |
| 3-(4-(CH₃)₂N-phenyl)-imidazol-2-ylmethyl | H | H | allyl |
| 3-(3-HO₂C-phenyl)-imidazol-2-ylmethyl | H | H | allyl |
| 3-(3-H₂NCO-phenyl)-imidazol-2-ylmethyl | H | H | allyl |
| 3-(3-CH₃O-phenyl)-imidazol-2-ylmethyl | H | H | allyl |
| 3-(3-HO-phenyl)-imidazol-2-ylmethyl | H | H | allyl |
| 3-(3-R¹¹O-phenyl)-imidazol-2-ylmethyl | H | H | allyl |
| 3-(3-Cl-phenyl)-imidazol-2-ylmethyl | H | H | allyl |
| 3-(3-(CH₃)₂N-phenyl)-imidazol-2-ylmethyl | H | H | allyl |
| 3-(2-HO₂C-phenyl)-imidazol-2-ylmethyl | H | H | allyl |
| 3-(2-H₂NCO-phenyl)-imidazol-2-ylmethyl | H | H | allyl |
| 3-(2-CH₃O-phenyl)-imidazol-2-ylmethyl | H | H | allyl |
| 3-(2-HO-phenyl)-imidazol-2-ylmethyl | H | H | allyl |
| 3-(2-R¹¹O-phenyl)-imidazol-2-ylmethyl | H | H | allyl |
| 3-(2-Cl-phenyl)-imidazol-2-ylmethyl | H | H | allyl |
| 3-(2-(CH₃)₂N-phenyl)-imidazol-2-ylmethyl | H | H | allyl. |

B. Preparation of Compounds Within the Scope of the Present Invention

The starting materials for the preparation of the compounds of Formula I are represented by Formula II:

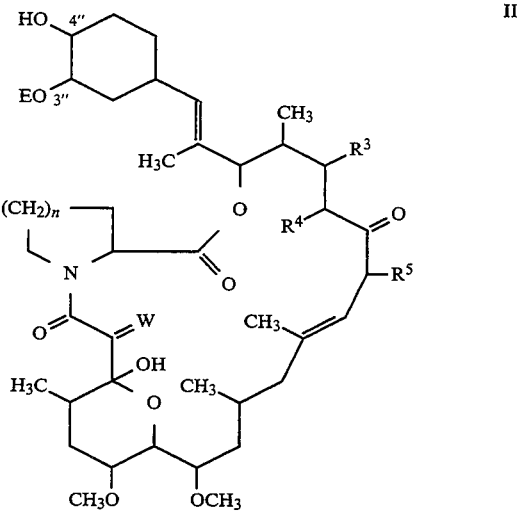

wherein:

E is hydrogen or methyl;

W is O or (H, OH);

$R^3$ is hydrogen, hydroxy, or $C_{1-6}$ alkoxy;

$R^4$ is hydrogen, or $R^3$ and $R^4$ taken together form a double bond;

$R^5$ is methyl, ethyl, propyl or allyl; and n is 1 or 2.

The production and characterization of compounds of Formula II is well known in the literature (see U.S. Pat. No. 4,894,366 issued Jan. 16, 1990; U.S. Pat. No. 4,929,611 issued May 29, 1990; U.S. Pat. No. 3,244,592 issued Apr. 15, 1966; EPO Publication No. 0,323,042,; EPO Publication No. 0,356, 399; PBJ Disclo sure 63-17884; J. Am. Chem. Soc., 1987, 109, 5031; J. Antibiotics, 1987, 40, 1249; J. Antibiotics, 1988, 41(11), 1952; and J. Anibiotics, 1992, 45(1), 118). Both biological fermentation and synthetic processes may be found. A synthetic route to compounds of Formula II can involve modifications of a route described in J. Am. Chem. Soc., 1989, 111, 1157.

Biological fermentation followed by synthetic modification is presently favored in the art as the method to produce compounds of Formula II. Organisms belonging to the genus Streptomyces such as Streptomyces tsukubaensis, No. 9993 and Streptomyces hygroscopicus, var. ascomycetis, No. 14891 placed in an aqueous nutrient medium will produce desired compounds in isolable amounts. The nutrient medium contains sources of assimilable carbon and nitrogen, preferably under aerobic conditions. Produced in fermentation are four compounds of Formula II, (A) where E is methyl, W is O, $R^3$ is hydroxyl, $R^4$ is hydrogen, $R^5$ is allyl and n is 2; (B) where E is methyl, W is O, $R^3$ is hydroxyl, $R^4$ is hydrogen, $R^5$ is ethyl and n is 2; (C) where E is methyl, W is O, $R^3$ is hydroxyl, $R^4$ is hydrogen, $R^5$ is methyl and n is 2; and (D) where E is methyl W is O, $R^3$ is hydroxyl, $R^4$ is hydrogen, $R^5$ is allyl and n is 1.

A lyophilized sample of the isolated Streptomyces tsukubaensis, No. 9993 was deposited with the Fermentation Research Institute, Agency of Industrial Science and Technology (No. 1-3, Higashi 1-chome, Yatabemachi Tsukuba-gun, Ibaraki Prefecture, Japan) under the deposit number of FERM P-7886 (deposit date: Oct. 5th, 1984), and then converted to Budapest Treaty route of the same depository on Oct. 19, 1985 under the new deposit number of FERM BP-927.

Using the four compounds produced in fermentation above, the remaining compounds of Formula II may be easily produced. The allyl of $R^5$ may be conveniently reduced to propyl by well known methods, for example as described in U.S. Pat. No. 4,894,366. The hydroxy of $R^3$ may be protected by well known methods, for example as disclosed in EPO Publication No. 0,323,042. Likewise, the hydroxyl at C-4'' may also be protected. In addition, the hydroxy of $R^3$ may be reduced to a hydrogen or eliminated to form a double bond with $R^4$ (by methods disclosed in U.S. Pat. No. 4,894,366, EPO Publication No. 0,323,042 or EPO Publication No. 0,413,532). The carbonyl of W may be reduced to the alcohol by methods disclosed in EPO Publication No. 0,323,042 or by methods disclosed in EPO Publication No. 0,323,042 or by methods disclosed in EPO Publication No. 0,445,975.

The methyl of E as produced may be replaced with hydrogen or demethylated and subsequently protected as desired, if necessary. This demethylation of compounds wherein E is methyl may be carried out in a fermentation reaction using the compounds of Formula II as a feedstock. For instance, compound A named under Formula II above may be demethylated at E above by using the microorganism *Actinomycetales* ATCC No. 53771 (described in U.S. Pat. No. 4,981,792) or by using the microorganism *Streptomyce tsukubaensis* No. 9993 (described in EPO Publication No. 0,353,678). Similarly, compound B named under Formula II above may be demethylated at E above using the microorganism *Actinoplanacete sp.* ATCC No. 53771 (described in EPO Publication No. 0,349,061). In addition the compound of Formula II wherein E is H, W is O, $R^3$ is hydroxy, $R^4$ is hydrogen, $R^5$ is ethyl and n is 2 may be produced directly by fermentation using the mutant microorganism *Streptomyces hygroscopicus sup. ascomyceticus*, No. 53855 (being a blocked mutant of *Streptomyces hygroscopicus sup. ascomyceticus*, No. 14891) (as described in EPO Publication No. 0,388,152). Similarly, the compound of Formula II wherein E is hydrogen, W is O, $R^3$ is hydroxy, $R^4$ is hydrogen, $R^5$ is methyl and n is 2 may be produced directly by fermentation using the mutant microorganism *Streptomyces hygroscopicus sup. ascomyceticus*, No. 53855 (being a blocked mutant of *Streptomyces hygroscopicus sup. ascomyceticus*, No. 4891) (EPO Publication No. 0 388,153). The hydroxy of C-3'' may be protected by methods similar to those known for the protection of the hydroxyl groups of $R^3$ and/or C-4'', for example as disclosed in U.S Pat. No. 4,894,366.

Suitable protecting groups for hydroxyl include those groups well known in the art such as: methylthiomethyl, ethylthiomethyl; trisubstituted silyl such as trimethylsilyl, triethylsilyl, tributylsilyl, tri-i-propylsilyl, t-butyldimethylsilyl, tri-t-butylsilyl, methyldiphenylsilyl, ethyldiphenylsilyl, t-butyldiphenylsilyl, and the like; acyl such as acetyl, pivaloyl benzoyl, 4-methoxybenzoyl, 4-nitrobenzoyl and aliphatic acyl substituted with aromatic group, which are derived from carboxylic acids; and the like.

Compounds A, B, C and D of Formula II, organisms to produce the same, conditions of fermentation, separation techniques, and chemical modification of the products are fully described in U.S. Pat. No. 4,894,366, dated Jan. 16, 1990, U.S. Pat. No. 4,929,611, issued May 29, 1990 and U.S Pat. No. 5,110,811, issued May 5, 1992.

The 5α-reductase inhibitor may be an inhibitor of 5α-reductase isozyme 1 and/or 5α-reductase isozyme 2, A preferred 5α-reductase inhibitor is finasteride. It is also preferred that the 5α-reductase inhibitor be selective for the scalp-associated enzyme 5α-reductase isozyme 1.

4-Aza steriod compounds are known in the art as 5α-reductase inhibitors. For example, See U.S Pat. Nos. 2,227,876, 3,239,417, 3,264,301 and 3,285,918; French Patent No. 1,465,544; Doorenbos and Solomons, *J. Pharm. Sci.* 62, 4 pp. 638–640 (1973); Doorenbos and Brown, *J. Pharm. Sci.*, 60, 8, pp. 1234–1235 (1971); and Doorenbos and Kim, *J. Pharm. Sci.* 63, 4, pp. 620–622 (1974).

In addition, U.S. Pat. Nos. 4,377 584, 4220,775, 4,859,681, 4,760,071 and the articles *J. Med. Chem.* 27, p. 1690–1701 (1984) and *J. Med. Chem.* 29, 2998–2315 (1986) of Rasmusson, et al., U.S. Pat. No. 4,845,104 to Carlin, et al., and U.S. Pat. No. 4,732,897 to Cainelli, et al. described 4-aza 17β-substituted-5α-androstan-3-ones useful in the treatment of DHT-related hyper androgenic conditions.

Cyclosporin may be prepared essentially as described in U.S. Pat. No. 4,117,118 or by R. Wenger, Transplant. Proc., 15 (4), Suppl. 1, 2230 (1983) and is available from Sandoz Pharmaceuticals, East Hanover, N.J.

The potassium channel opener may be minoxidil, cromakalim, pinacidil, a triazine compound, a thiane-1-oxide, or other compounds.

Chemically minoxidil is 6-amino-1,2-dihydrohydroxy-2-imino-4-piperidinopyrimidine and analogs thereof. The preparation of these compounds are described in U.S Pat. Nos. 3,382,247, 3,461,461 and 3,644,364 and J. M. McCall, et al., *J. Org. Chem.*, 40, 3304 (1975). Related compounds are sulfoxypyrimidinium, -pyridinium, and -triazinium which are described in U.S. Pat. No. 4,287,338. The term "minoxidil" includes any of the various forms of 6-amino-1,2-dihydro-hydroxy-2-imino-4-piperidinopyrimidine derivatives and analogs thereof. Minoxidil is distributed by The Upjohn Company, Kalamazoo, Mich.

Chemically cromakalim is (3S-trans) 3,4-dihydro-3-hydroxy-2, 2-dimethyl-4-(2-oxo-1-pyrrolidinyl)2H-1-benxopyran-6-carbonitrile. Cromakalim is distributed by SmithKline Consumer Products, Philadelphia, Pa.

Pinacidil is chemically, N-cyano-N'-4-pyridinyl-N''-(1,2,2-trimethylpropyl)-guanidine monohydrate. The preparation of pinacidil is described in U.S. Pat. No. 4,057,636 and is distributed by Eli Lilly and Company, Indianapolis, Ind.

S-Triazine compounds or 2,6-diamino-4-substituted-s-triazine-l-oxides are described in U.S. Pat. No. 3,270,014 assigned to The Upjohn Company, Kalamazoo, Mich. Specific examples of these compounds include: N4-hexyl-2,4,6-triamino-1,3,5-triazine1-oxide; N4-butyl-2,4,6-triamino-1,3,5-triazine-1oxide; N4-Pentyl-2,4,6-triamino-1,3,5-triazine-1oxide; 4-(N,N-dipropyl)-2,6-diamino-1,3,5-triazine1-oxide; 4-<N,N-dibutyl>-2,6-diamino-1,3,5-triazine 1-oxide; 4-(1-Pyrollidinyl)-2,6-diamino-1,3,5-triazine-1-oxide; 4-(N,N-di(2-methyl-2-proppenyl)amino)-2,6-diamino-1,3,5-triazine-1-oxide; 4-(N,N-(diallylamino) -2,6-diamino-1,3,5-triazine-1-oxide; 4-(N,N- dimethylamino)-2,6-diamino-1,3,5-triazine-1-oxide; 4(1-piperidinyl)-2,6-diamino-1,3,5-triazine-1oxide; N4-ProPY1-2,4,6-triamino-1,3,5-triazine-1-oxide; N4- ethyl-2,4,6-triamino-1,3,5-triazine-1-oxide; N4(1,1,4,4-tetramethylbutyl)-2,4 ,6-triamino-1,3,5-triazine-1-oxide; and N4-heptyl-2,4,6-triamino-1,3,5-triazine-1-oxide.

Thiane-1-oxide compounds are described in U.S. Pat. No. 4,568,682 assigned to Rhone-Poulenc Sante, Courbevoie, France. An example of such a compound contemplated by the subject invention is N-methyl-2-Pyridin-3-yl)tetrahydrothiopyran-2-carbothioamide1-oxide. Other derivatives include those disclosed in patent applications EP 0,321,274, A, EP 0,321,273 A, and EP 0,326,297 A.

Other potassium channel openers include pyranopyridine derivatives described in patent applications GB 2 204 868 A and benzopyran derivatives described in patent applications GB 2,204, 868 A, EP 0,314,446 A2, EP 0,339,562 A, EP 0,340,718 A, EP 0,337,179, AU A 18556/88, JA 1294, 677 A, EP 0,359,537 A, and U.S. Pat. No. 4,900,752.

The phospholipids used herein may be obtained from commercial sources. The phospholipids may also be isolated from natural sources (for example, egg yolk, soybean or other oily seed including safflower, sunflower and olive, and brain tissue) or may be produced synthetically. In either case, known techniques can be used for purification of the phospholipids (see, for example, *J. of American Oil Chemists Soc.* 42:53–56 (1965)).

The processes for preparing the compounds of Formula I are illustrated as follows, wherein $R^1$, $R^2$, $R^3$, $R^5$, $R^6$, $R^7$, $R^8$, $R^9$, $R^{10}$, $R^{11}$, E, W and n are as defined above unless otherwise indicated. It will be readily apparent to one of ordinary skill in the art reviewing the synthetic route depicted below that other compounds within Formula I can be synthesized by substitution of appropriate reactants and agents in the synthesis shown below.

REACTION SCHEME A

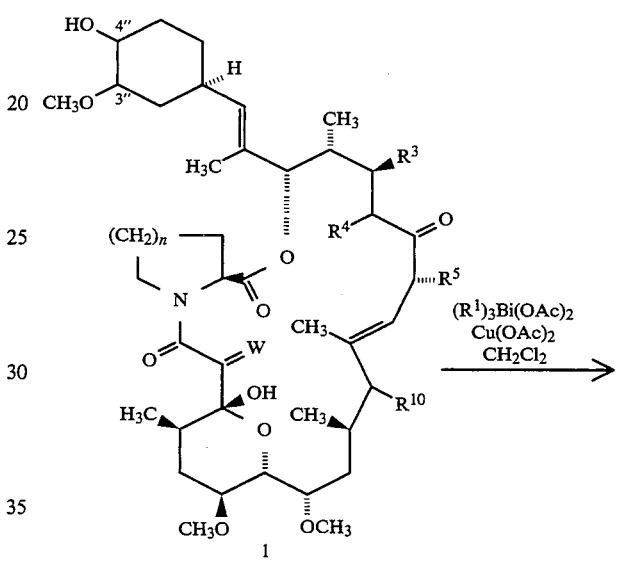

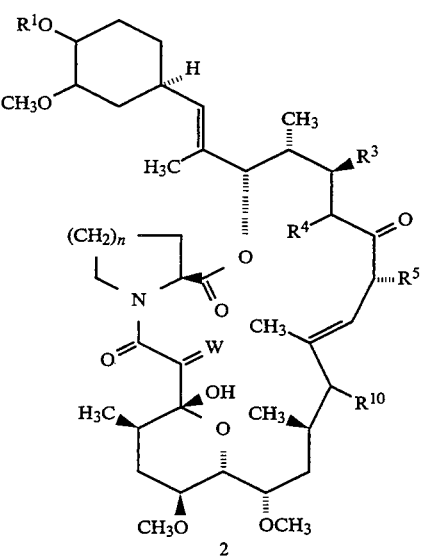

REACTION SCHEME B
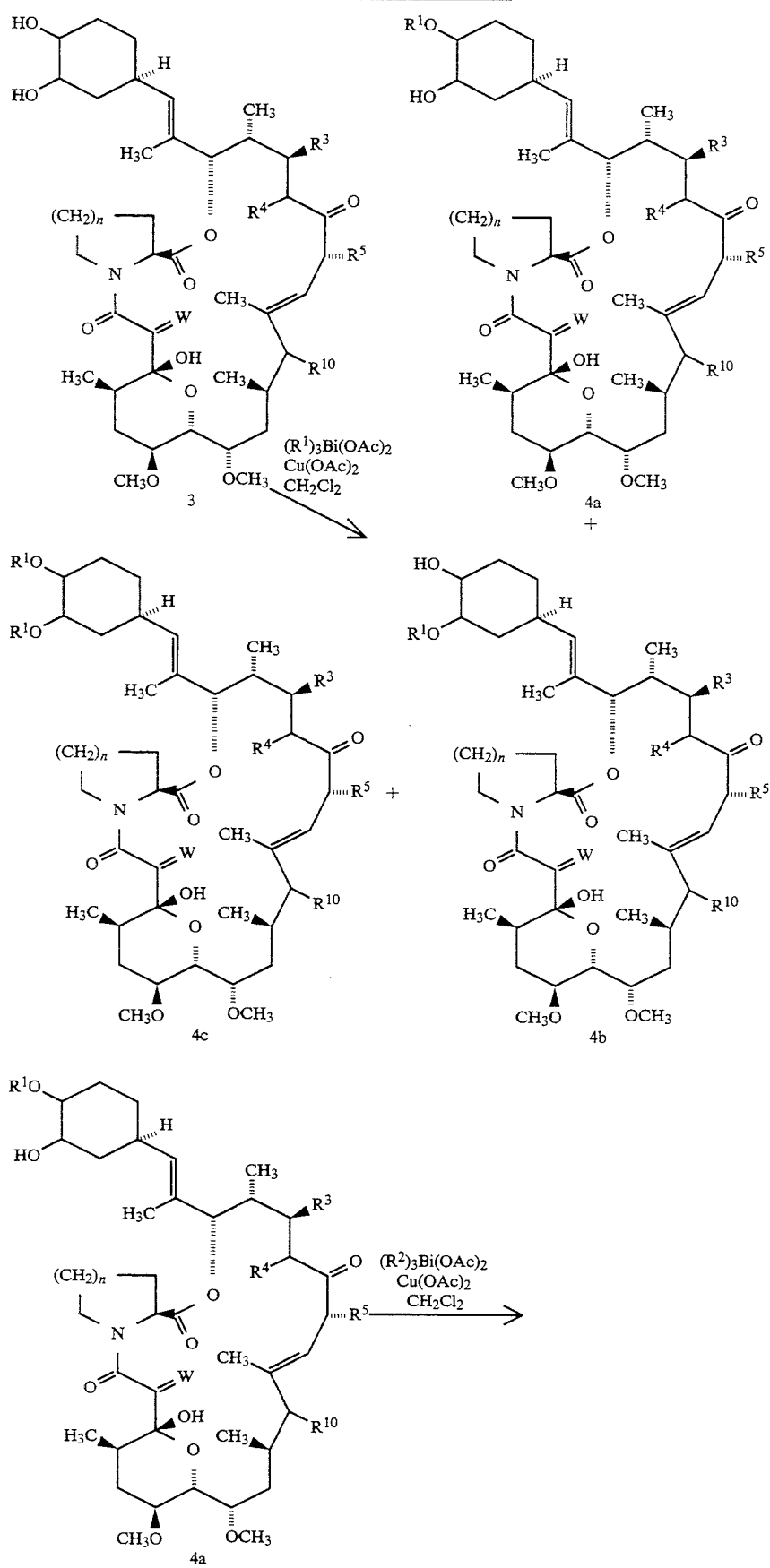

-continued
REACTION SCHEME B
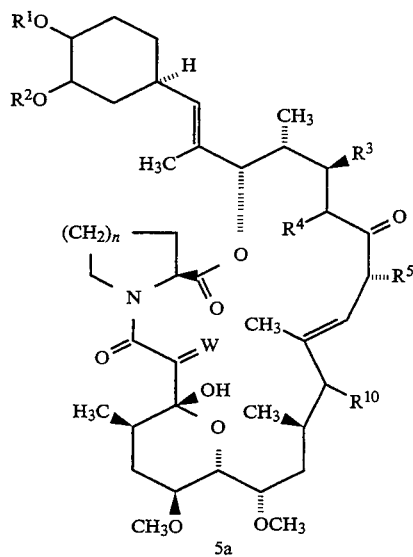
5a
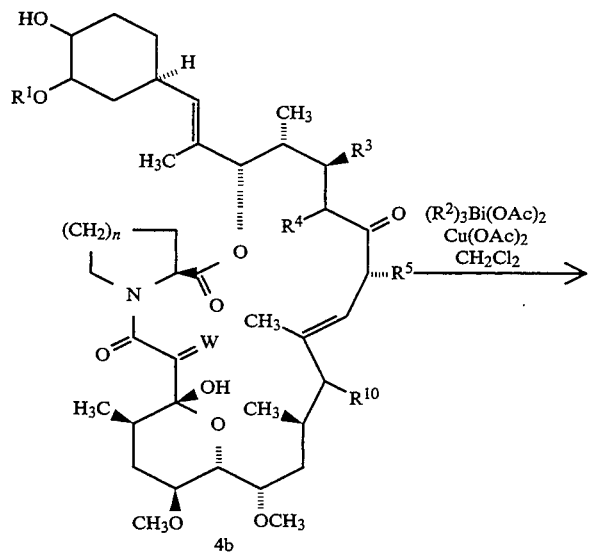
4b
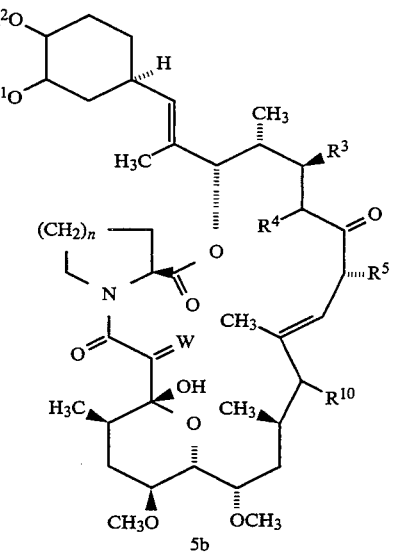
5b

REACTION SCHEME C
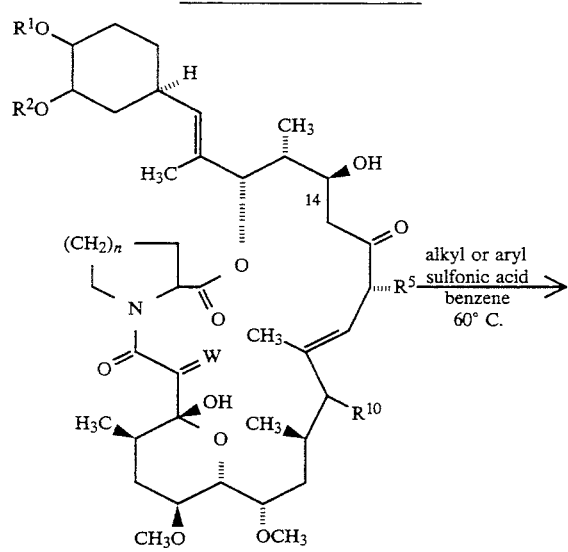
61
alkyl or aryl sulfonic acid
benzene
60° C.
-continued
REACTION SCHEME C
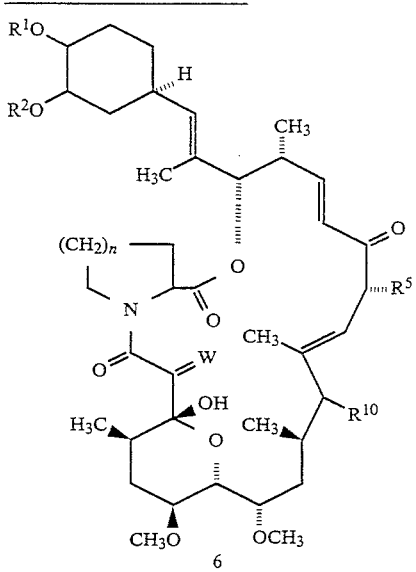
62
REACTION SCHEME D
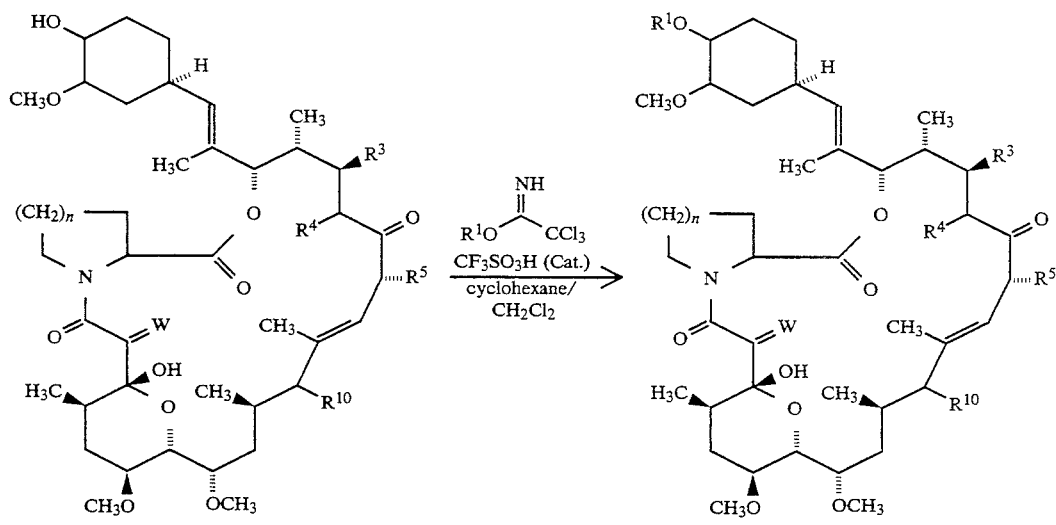

REACTION SCHEME E
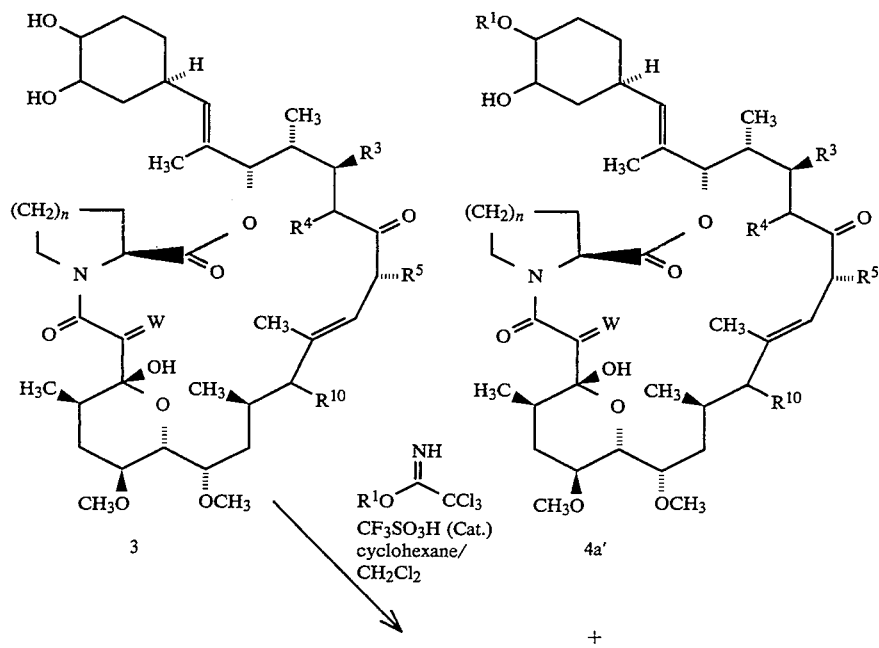
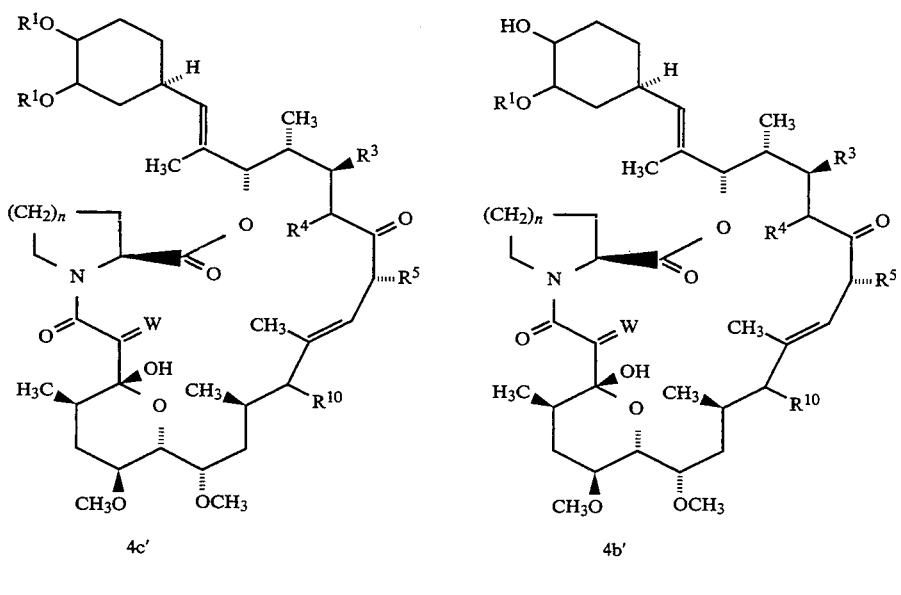

-continued
REACTION SCHEME E
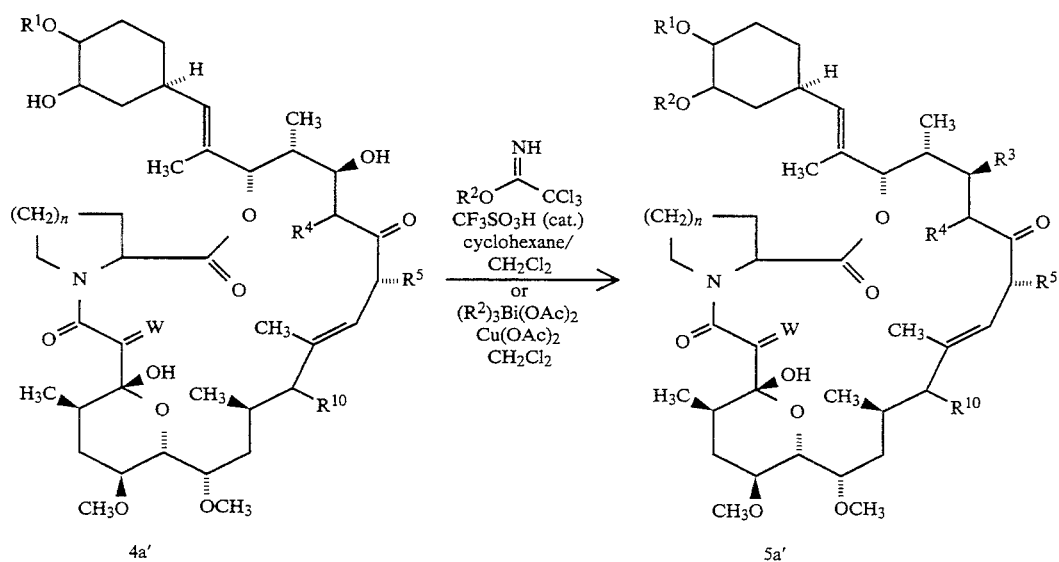
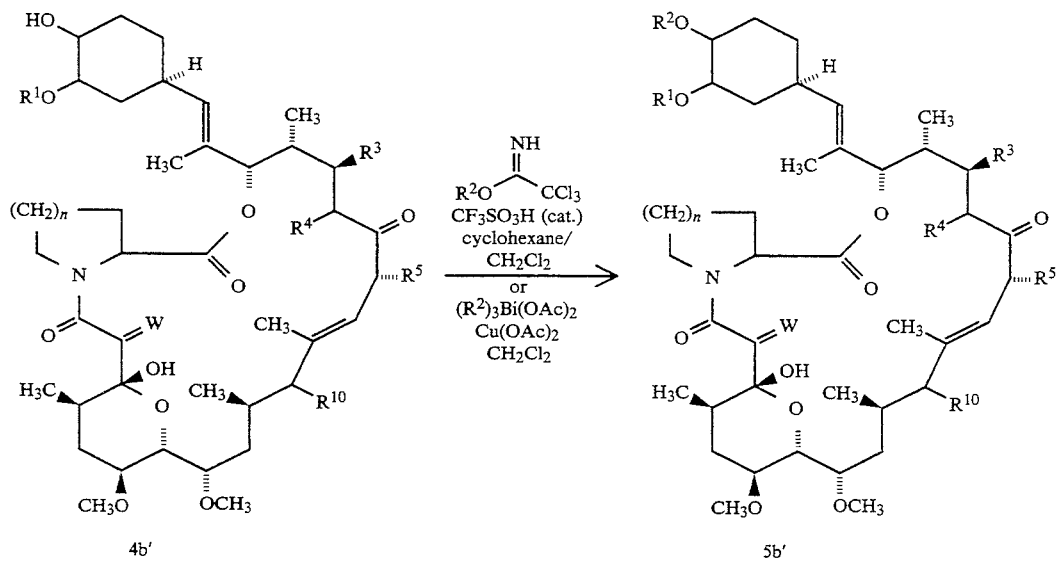

REACTION SCHEME F
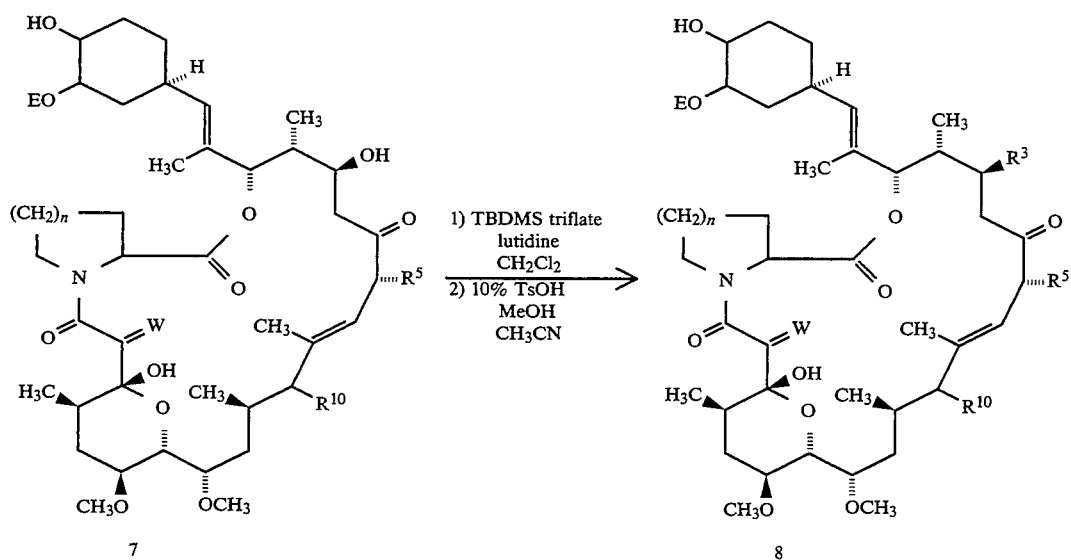
REACTION SCHEME G
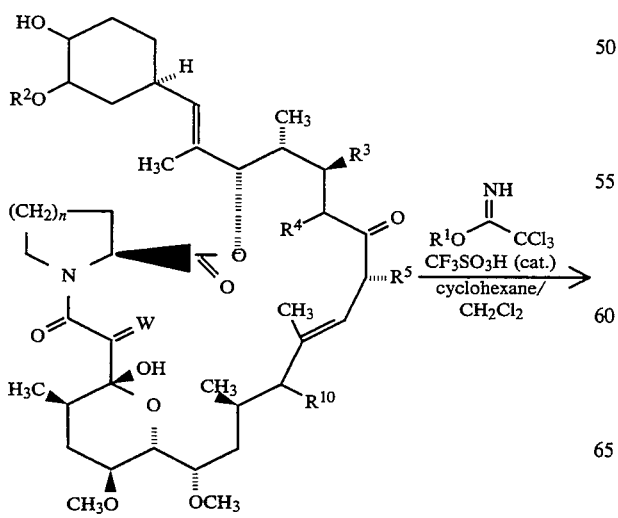
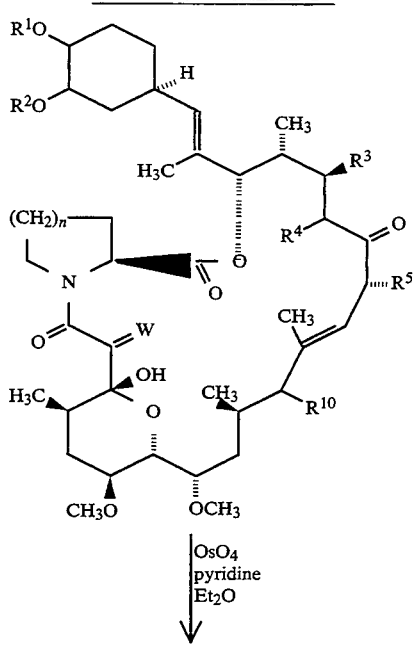

REACTION SCHEME G
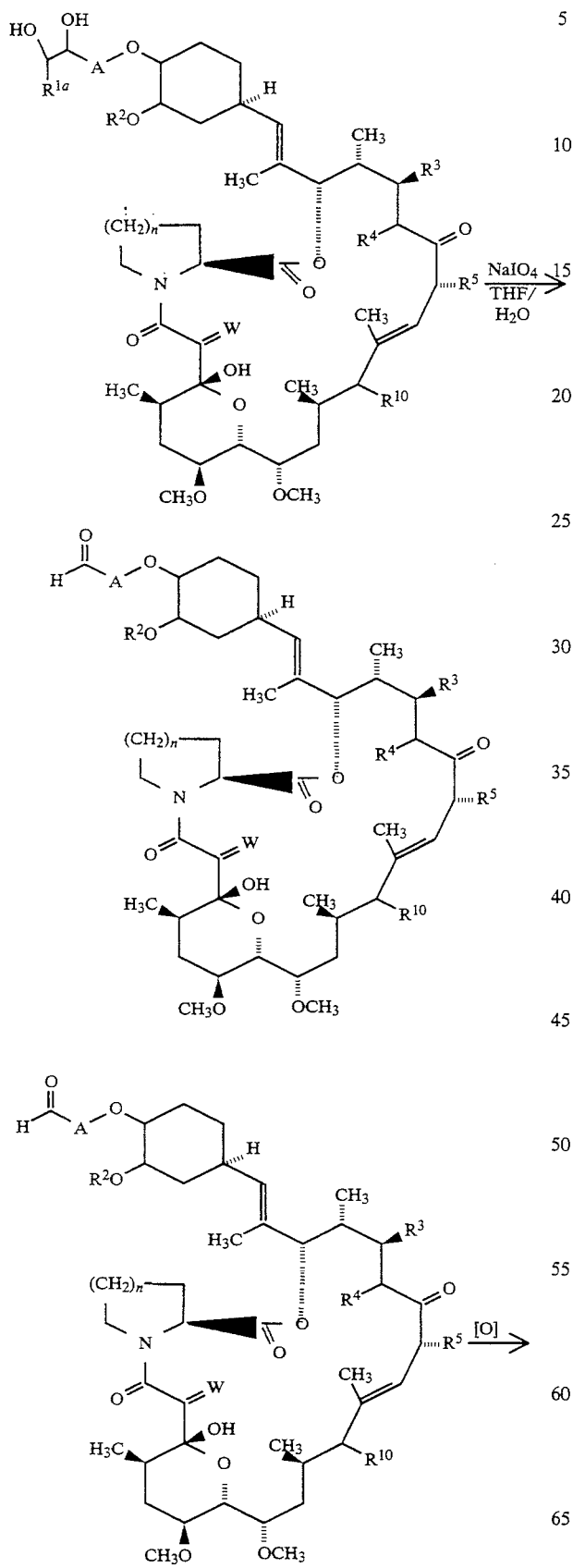
REACTION SCHEME G
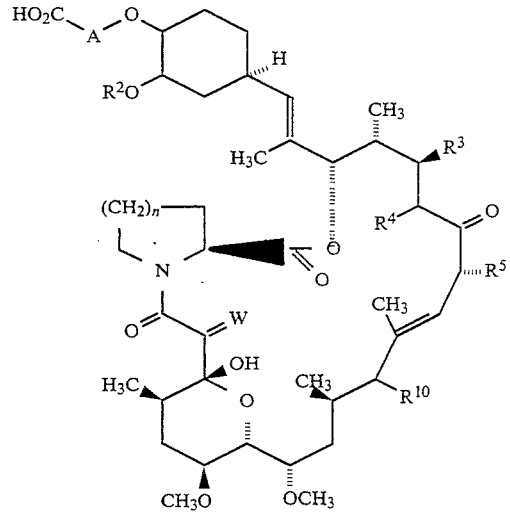
REACTION SCHEME H
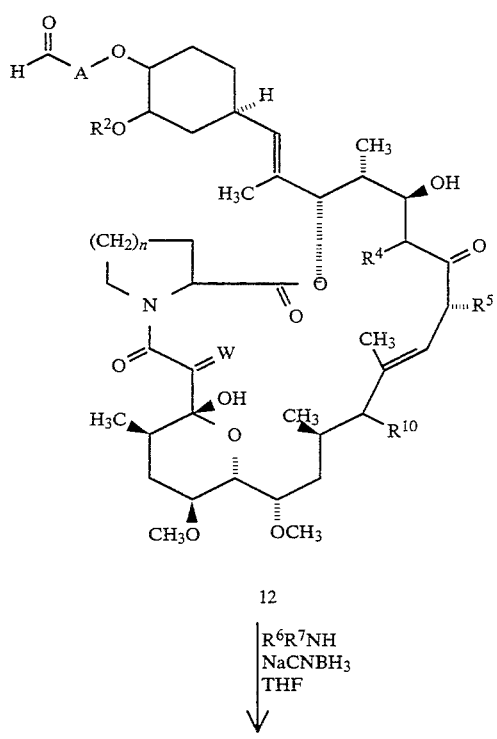

-continued
REACTION SCHEME H
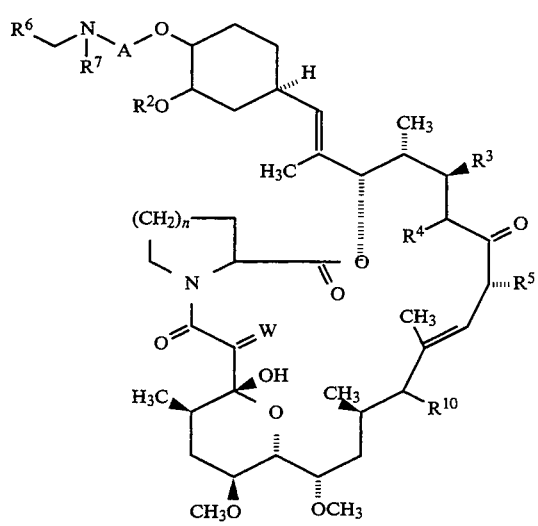
14
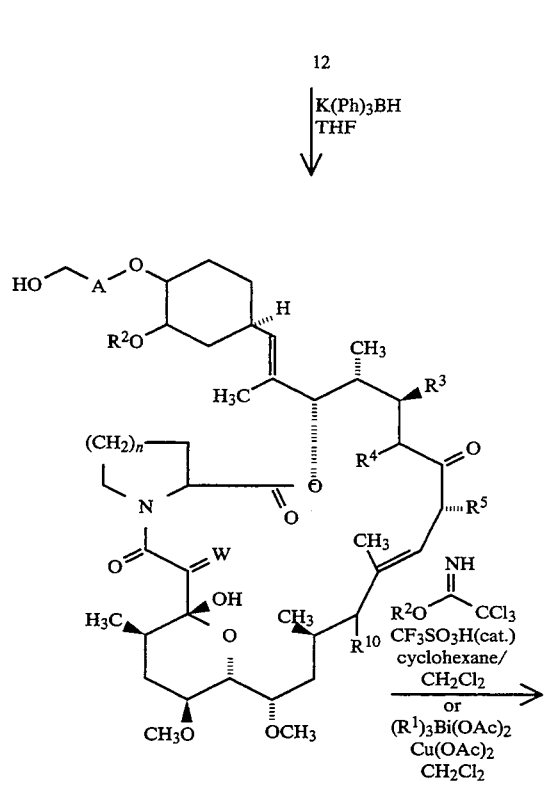
15
-continued
REACTION SCHEME H
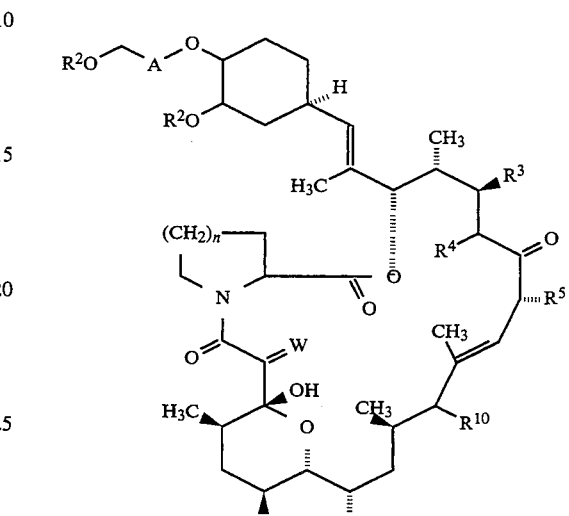
16
REACTION SCHEME I
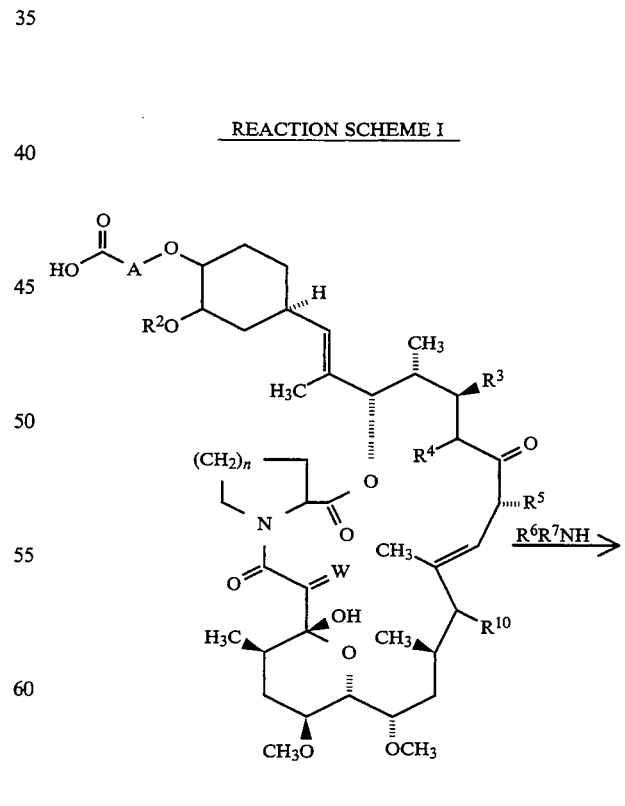

-continued
REACTION SCHEME I
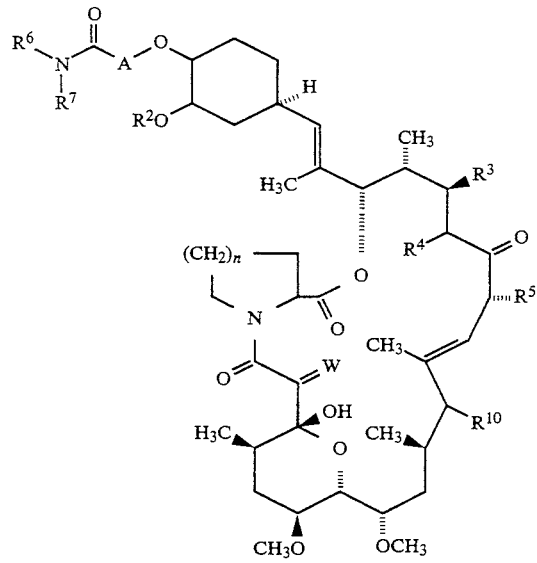
REACTION SCHEME J
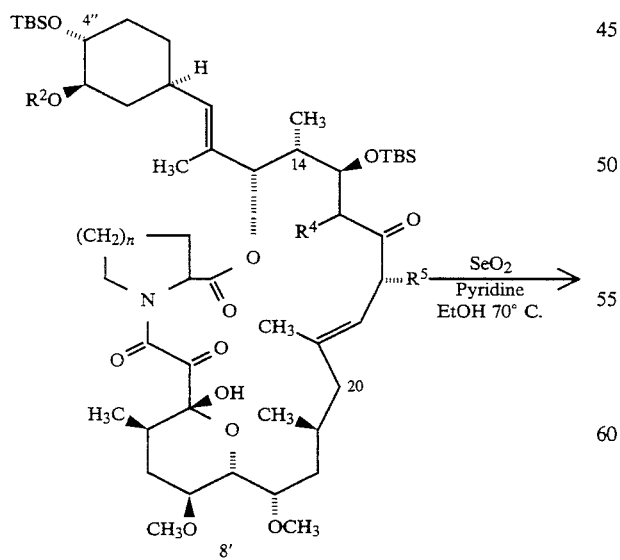
-continued
REACTION SCHEME J
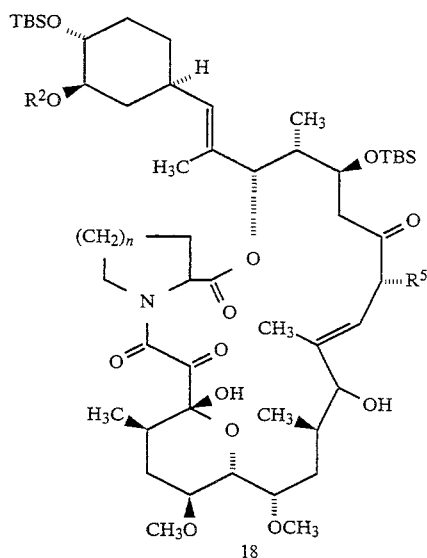
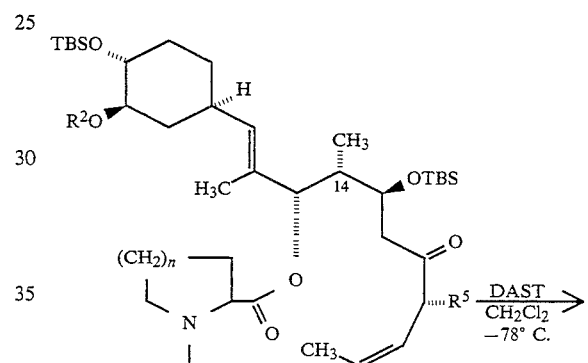
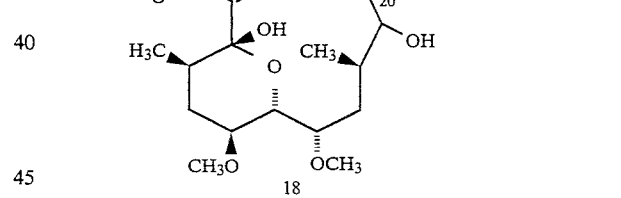
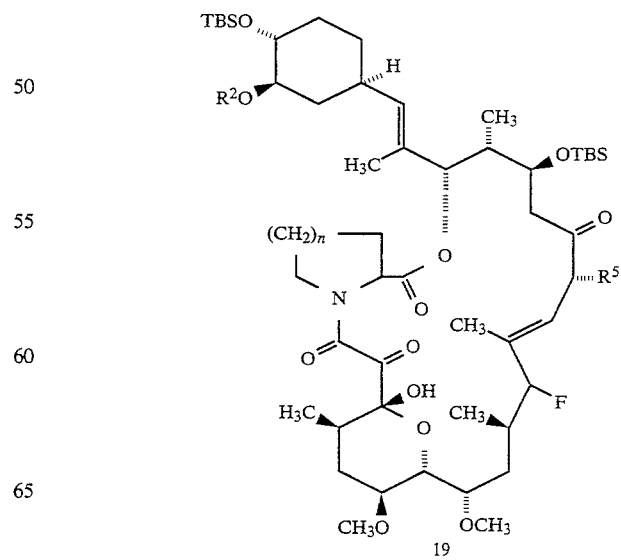

-continued
REACTION SCHEME J

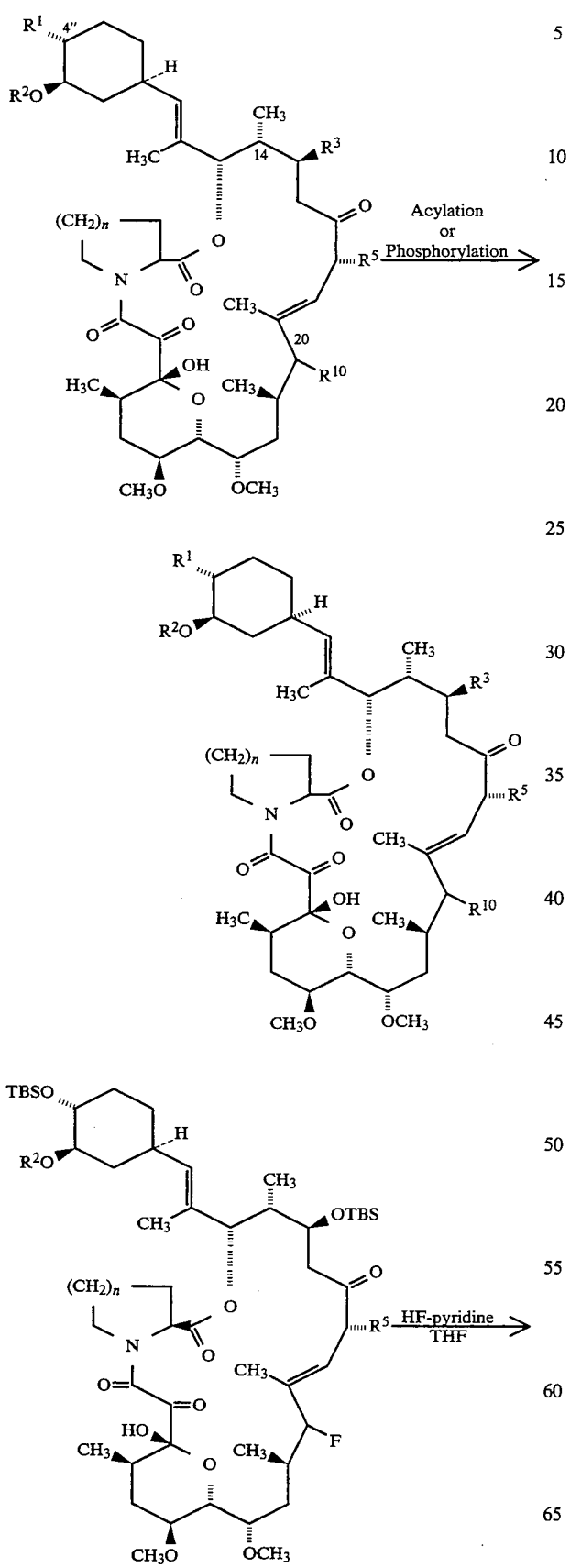

-continued
REACTION SCHEME J

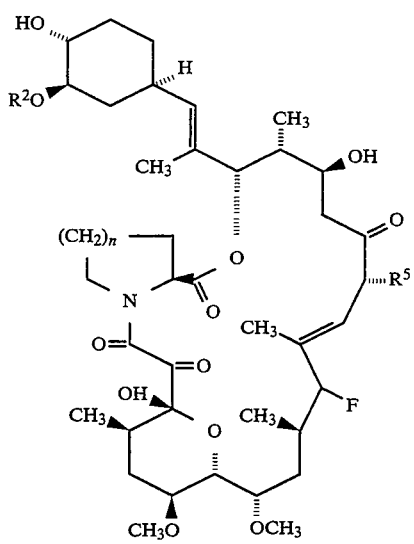

REACTION SCHEME A

As shown in Reaction Scheme A, a solution of 4"-hydroxy-3-methoxy macrolide 1 in an inert organic solvent such as methylene chloride, benzene, toluene, chloroform, or the like or mixtures thereof is treated with a triheteroarylbismuth diacetate reagent (wherein $R^1$ is heteroaryl) (prepared immediately prior to use by the addition of acetic acid to a suspension of a triheteroarylbismuth carbonate in an inert organic solvent such as methylene chloride, chooform or the like or mixture thereof) in the presence of a catalytic amount of copper(II) acetate at a temperature of 20–50° C., preferably room temperature, for a period of one hour to seven days, preferably one day, to give the 4"-O-heteroaryl-3"-methoxy macrolide 2. Alternatively, the triheteroarylbismuth(V) reagent can be prepared by treatment of a triheteroarylbismuthine with a suitable oxidant such as peracetic acid, iodobenzene diacetate, bis(trifluoroacetoxy) iodobenzene and the like in an inert solvent such as methylene chloride, chloroform, benzene, toluene and the like. The triheteroarylbismuth(V) reagent can be used without purification or can be purified by silica gel chromatography. Triheteroarylbismuthines may be prepared by the reaction of an appropriate heteroaryl Grignard reagent or lithiated heteroaryl species with bismuth trichloride in an inert organic solvent such as tetrahydrofuran, diethyl ether, or 1,4-dioxane, or mixtures thereof, at or near room temperature for a period of 1 to 48 hours. General procedures for the preparation and use of triheteroaryl bismuth reagents may be found in Barton, D.H.E., et al., J. Chem. Soc. Chem. Commun., 1986, 65 and references cited therein.

Reaction Scheme B

Similarly, as shown in Reaction Scheme B, a solution of the 3", 4"-dihydroxy macrolide 3 treated with a triheteroarylbismuth diacetate reagent as described in Reaction Scheme A, to give a mixture of the 3"-hydroxy-4"-O-heteroaryl macrolide 4a, the 3"-O-heteroaryl-4"-hydroxy macrolids 4b, and the 3", 4"-di-O-heteroaryl macrolide 4c. At this stage, a solution of 3"-hydroxy-4"-O-heteroaryl macrolide 4a, or 3"-O- heteroaryl-4"-hydroxy macrolide 4b can be treated with a triarylbismuth diacetate reagent (prepared immediately prior to use by procedures analogous to those disclosed above), to give 3"-O-aryl-4"-O-heteroaryl macrolide 5a, or 3"-O-heteroaryl-4"-O-aryl macrolide 5a, respectively.

Reaction Scheme C

As shown in Reaction Scheme C the 14-hydroxy group of a macrolide 5a or 5b (wherein $R^1$, $R^2, R^5$, $R^{10}$, W and n are as defined above) may be eliminated by treatment with p-toluenesulfonic acid, benzenesulfonic acid or methanesulfonic acid in an inert organic solvent such as benzene, or toluene at from 40° C. to 60° C., for about 0.5 to 6 hours , or a sufficient period of time to eliminate the 14-hydroxy group. Neutralization with an aqueous solution of a weak base such as aqueous saturated sodium bicarbonate gives the 14,15-dehydro macrolides 6a or 6b. The 14-hydroxy group may also be eliminated by activation followed by basic elimination, as described in U.S. Pat. No. 4,894,366.

By changing the sequence of synthetic steps, all possible variations of substitution can be achieved.

Reaction Scheme D

As shown in Reaction Scheme D, a solution of the 4"-hydroxy 3"-methoxy macrolide 1 in an inert organic solvent such as methylene chloride, chloroform, pentane, hexane, cyclohexane, heptane or mixtures thereof is treated with a heteroarylalkyl, heteroarylalkenyl or heteroalylalkynyl trichloroacetimidate reagent (prepared by the reaction of an appropriate sodium alkoxide with trichloroacetonitrile, such as described by Wessel, H. P., Iversen, T., Bundle, D. R., *J. Chem. Soc., Perkin Trans. I*, 1985, 2247) in the presence of a mild acid catalyst such as trifluoro-methanesulfonic acid, p-toluenesulfonic acid, methanesulfonic acid, or mixtures thereof at a temperature of 20–50° C. for a period of from one hour to seven days to give the 4"-O-heteroarylalkyl-, 4"-O-heteroarylalkenyl- or 4"-O-heteroarylalkynyl-3"-methoxy macrolide 2a.

Reaction Scheme E

Similarly, as shown in Reaction Scheme E, a solution of the 3", 4"-dihydroxy macrolide 3 in an inert organic solvent such as methylene chloride, chloroform, pentane, hexane, cyclohexane, heptane or the like or mixtures thereof is treated with a heteroarylalkyl, heteroarylalkenyl or heteroarylalkynyl trichloroacetimidate (prepared as described in Reaction Scheme D) at a temperature of 20–50° C., preferably 40° C., for a period of one hour to seven days, preferably 6 hours, to give a mixture of ythe 4"-O-heteroarylalkyl, 4"-O-heteroarylalkenyl, or 4"-O-heteroarylalkynyl-3-hydroxy macrolide 4a', 3"-O-heteroarylalkyl, 3"-O-heteroarylalkenyl, or 3"-O-heteroarylalkynyl-4"-hydroxymacrolide 4b'and the 3", 4"-di-O-heteroarylalkyl,-heteroarylalkenyl or -heteroarylalkynyl macrolide 4c'. Subsequently, a solution of 4"-O-heteroaryl, 4"-O-heteroarylalkyl, 4"-O-heteroarylalkenyl or 4"-O -heteroarylalkynyl-3-hydroxy macrolide 4a (from Reaction Scheme B or 4a', or 3"-O-heteroaryl-, 3"-O-heteroarylalkyl, 3"-O-heteroarylalkenyl, 3"-O-heteroarylalkynyl-4"hydroxymacrolide 4b from Reaction Scheme B or 4b'can be treated with an arylalkyl, alkenyl or alkynyl trichloroacetimidate by procedures described above.) to give macrolides 5a'or 5b '.

The procedures described in Reaction Schemes C and D may optionally be conducted following the procedures of Reaction Scheme E or F. Alternatively, the procedures described in Reaction Scheme F may be performed.

In any of the aforementioned Reaction Schemes, the macrolide (wherein $R^1$ and/or $R^2$ contains an alkenyl, substituted alkenyl, alkynyl or substituted alkynyl and wherein $R^3$ is hydroxy or $C_{1-6}$ alkoxy, $R^4$ is hydrogen, or $R^3$ and $R^4$ taken together form a double bond) can be reduced with tri-n-butyltin hydride in the presence of tetrakis (triphenylphosphine) palladium (0) catalyst and acetic acid in an organic solvent such as toluene or tetrahydrofuran at or near room temperature for about 2 to 10 hours to give the reduced macrolide.

The procedures described in Reaction Scheme F may be conducted on the mono-substituted products of Reaction Scheme B (and visa versa) to obtain the mixed disubstituted compounds. In fact, within Reaction Schemes B and F, treatment of the mono-substituted product with a different reagent will afford the mixed disubstituted compounds.

Reaction Scheme F

Protection of the C-3", C-4"and/or the C-14 hydroxyl group(s) may be accomplished by methods known in the prior art for compounds of Formula II such as by treatment with: 2,6-lutidine and triisopropylsilyl trifluoromethanesulfonate in a solution of methylene chloride; 2,6-lutidine and t-butyldimethylsilyl trifluoromethanesulfonate in a solution of methylene chloride; pyridine and acetic anhydride in a solution of methylene chloride; pyridine and benzoyl chloride in a solution of dichloromethane; pyridine and p-nitrobenzoyl chloride in a solution of dichloromethane; imidazole and t-butyldiphenylsilyl chloride in a solution of methylene chloride; and the like. For example, as shown in Reaction Scheme F, the C-4", 14-dihydroxy-C-3"-methoxy macrolide 7 may be protected at C-14 as the t-butyldimethylsilyl ether by treatment with t-butyldimethylsilyl trifluoromethanesulfonate in methylene chloride to give the C-4", 14-di-O-TBDMS macrolide. Treatment with toluenesulfonic acid in methanol results in selective removal of the C-4"silyl ether to give the C-14-O-TBDMS macrolide 8.

Reaction Scheme G

As shown in Reaction Scheme H, the 4"-hydroxy-3"-$R^2O$ macrolide 9 or alternatively the 3"-hydroxy-4"-$R^2O$ macrolide (not depicted ) (wherein $R^3$ is protected hydroxy or hydrogen) may be reacted with an alkenyl trichloroacetimidate (wherein alkenyl is $C_{314\,10}$ alkenyl) under conditions described in Reaction Scheme E to give the O-alkenyl macrolide 10. Treatment with a stoichiometric amount of osmium tetroxide in an inert organic solvent, such as diethyl ether or tetrahydrofuran, in the presence of an amine base, such as pyridine, at or near room temperature gives the corresponding glycol 11 (wherein A is $C_{1-8}$ alkyl). Treatment of glycol 11 with sodium metaperiodate in a solution of tetrahydrofuran/water gives aldehyde 12. Alternatively, the alkenyl macrolide 10 may be treated with sodium metaperiodate in the presence of a catalytic amount of osmium tetroxide in an organic solvent to give the aldehyde directly. Aldehyde 12·can be further oxidized to carboxylic acid 13 by any number of methods commonly used.

Reaction Scheme H

A variety of compounds may be prepared from aldehyde 12 as illustrated in Reaction Scheme H. Aldehyde 12 may be reacted with a primary or secondary amine, $HNR^6R^7$ (wherein $R^6$ and/or $R^7$ are as defined and contain(s) a heteroaryl group) in an organic solvent such as tetrahydrofuran to give an imine which is reduced in situ with a hydride reducing agent, such as sodium cyanoborohydride, to give macrolide 1 bearing an aminoalkoxy functionality at C-4". Aldehyde 12 may also be reduced to the corresponding alcohol 15 by treatment with a hydride reducing agent, such as potassium triphenyl borohydride or sodium cyanoborohydride in an organic solvent such as tetrahydrofuran. Alcohol 15 may be further modified by utilizing the methods of Reaction Scheme B (wherein $R^1$ is as defined) or Reaction Scheme E to produce macrolide 16. The procedures described in Reaction Scheme H are readily applicable to the preparation of compounds bearing analagous functionality at C-3".

REACTION SCHEME I

Amide derivatives may be prepared from the carboxylic acid 13 as illustrated in Reaction Scheme I. The carboxylic acid 13 may be coupled with a primary or secondary amine, $HNR^6R^7$ (wherein $R^6$ and/or $R^7$ are as defined and contain(s) a heteroaryl group) by any of the peptide coupling methods commonly used in the art, such as with BOP reagent or DCC/HOBT.

REACTION SCHEME J

A hydroxyl or fluoro group may be introduced at C-20 essentially by the procedures of Reaction Scheme J. As shown in Reaction Scheme R the 4", 14-dihydroxy macrolide (or the 14-deoxymacrolide) is protected as the di(t-butyldimethylsilyl ether) by treatment with t-butyldimethylsilyl triflate in an inert organic solvent such as methylene chloride, chloroform or the like in the presence of a non-nucleophillic base such as 2,6-lutidine. The diprotected macrolide is oxidized at C-20 as further shown in Reaction Scheme J by treatment with selenium dioxide in an alcoholic solvent such as ethanol in the presence of pyridine at solvent reflux temperature to give the 20-hydroxy macrolide (18). The 20-hydroxy macrolide may be further derivatized at C-20 by alkylation, acylation or phosphorylation to give ether, ester or phosphate derivatives by procedures well known to the practitioner of the art. As further illustrated, treatment of the 20-hydroxy 4", 14-di-OTBS macrolide with diethylaminosulfur trifluoride in an inert organic solvent such as methylene chloride, chloroform or the like at-a temperature of about 0° C. to −90° C., preferably about −78° C., gives the 20-fluoro 4", 14-di-OTBS macrolide (19). Removal of the silyl ether protecting groups by treatment with hydrogen fluoride-pyridine complex in tetrahydrofuran gives the 20-fluoro 4", 14-dihydroxy macrolide which may be further derivatized by any of the methods previously described. Reaction Scheme J may also be performed on the 3", 4", 14-trihydroxy macrolide to give the 20-fluoro 3", 4", 14-trihydroxy macrolide. The procedures of Reaction Scheme J may be conducted prior to, concurrent with, or subsequent to the procedures of Reaction Schemes A-I.

The object compounds of Formula I obtained according to the reactions as explained above can be isolated and purified in a conventional manner, for example, extraction, precipitation, fractional crystallization, recrystallization, chromatography, and the like.

In the compounds of Formula I, $OR^1$ may be substituted at C-4"or C-3", or both C-4"and C-3"(wherein $R^2$ is independently selected from the definitions of $R^1$), but it is preferred that $-OR^1$ is substituted at C-4".

It is to be noted that in the aforementioned reactions and the post-treatment of the reaction mixture therein, the stereoisomer(s) of starting and object compounds due to asymmetric carbon atom(s) or double bond(s) of the object compounds of Formula I may occasionally be transformed into the other stereo isomer(s), and such cases are also included within the scope of the present invention.

In the present invention, compounds of Formula I with asymmetric centers may occur as racemates, as diastereomeric mixtures and as individual diastereomers, with all isomeric forms of the compounds being included in the present invention. These may be prepared by methods such as those disclosed in publications which describe synthetic routes to fragments of the macrolide FR-900506 and the total synthesis of the macrolide FR-900506 itself (*J. Am. Chem. Soc.* 1989, 111, 1157; *J. Am. Chem. Soc.* 1990, 112, 2998; *J. Org. Chem.* 1990, 55, 2786; *J. Am. Chem. Soc.* 1990, 112, 5583. *Tetrahedron Lett.* 1988, 29, 277; *Tetrahedron Lett.* 1988, 29, 281; *Tetrahedron Lett.* 1988, 29, 3895; *Org. Chem.* 1988, 53, 4643; *Tetrahedron Lett.* 1988, 29, 4245; *Tetrahedron Lett.* 1988, 29, 4481; *J. Org. Chem.* 1989, 54, 9; *J. Org. Chem.* 1989, 54, 11; *J. Org. Chem.* 1989, 54, 12; *J. Org. Chem.* 1989, 54, 15; *J. Org. Chem.* 1989, 54, 17; *Tetrahedron Lett.* 1989, 30, 919; *Tetrahedron Lett.* 1989, 30, 1037; *J. Org. Chem.* 1989, 54, 2785; *J. Org. Chem.* 1989, 54, 4267; *Tetrahedron Lett.* 1989, 30, 5235; *Tetrahedron Lett.* 1989, 30, 6611; *Tetrahedron Lett.* 1989, 30, 6963; *Synlett* 1990, 38; *J. Org. Chem.* 1990, 55, 2284; *Org. Chem.* 1990, 55, 2771; *J. Org. Chem.* 1990, 55, 2776; *Tetrahedron Lett.* 1990, 31, 1439; *Tetrahedron Lett.* 1990, 31, 1443; *Tetrahedron Lett.* 1990, 3007; *Tetrahedron Lett.* 1990, 31, 3283, 3287).

The compounds of Formula I are capable of forming salts with various inorganic and organic acids and bases and such salts are also within the scope of this invention. Examples of such acid addition salts (which are negative counterions defined herein as $M^-$) include acetate, adipate, benzoate, benzenesulfonate, bisulfate, butyrate, citrate, camphorate, camphorsulfonate, ethanesulfonate, fumarate, hemisulfate, heptanoate, hexanoate, hydrochloride, hydrobromide, hydroiodide, methanesulfonate, lactate, maleate, methanesulfonate, 2-naphthalenesulfonate, oxalate, pamoate, persulfate, picrate, pivalate, propionate, succinate, tartrate, rosylate, and undecanoate. Base salts (which are positive counterions defined herein as $M^+$) include ammonium salts, alkali metal salts such as sodium, lithium and potassium salts, alkaline earth metal salts such as calcium and magnesium salts, salts with organic bases such as dicyclohexylamine salts, N-methyl-D-glucamine, and salts with amino acids such as arginine, lysine and so forth. Also, the basic nitrogen-containing groups may be quaternized with such agents as: lower alkyl halides, such as methyl, ethyl, propyl, and butyl chloride, bromides and iodides; dialkyl sulfates like dimethyl, diethyl, dibutyl; diamyl sulfates; long chain halides such as decyl, lauryl, myristyl and stearyl chlorides, bromides and iodides: aralkyl halides like benzyl bromide and others. The non-toxic physiologically acceptable salts are preferred, although other salts are also useful, such as in isolating or purifying the product.

The salts may be formed by conventional means, such as by reacting the free base form of the product with one or more equivalents of the appropriate acid in a solvent or medium in which the salt is insoluble, or in a solvent such as water which is removed in vacuo or by freeze drying or by exchanging the anions of an existing salt for another anion on a suitable ion exchange resin.

C. Utility of the compounds within the scope of the invention

The compounds of Formula I may be employed as immunosuppressants or antimicrobial compounds by methods and in dosages known in the prior art for compounds of Formula II. These compounds possess pharmacological activity such as immunosuppressive activity, antimicrobial activity, and the like, and therefore are useful for the treatment and prevention of the resistance to transplantation or transplantation rejection of organs or tissues (such as heart, kidney, liver, lung, bone marrow, cornea, pancreas, intestinum tenue, limb, muscle, nervus, medulla ossium, duodenum, small-bowel, medulla ossium, skin, pancreatic islet-cell, etc. including xeno transplantation), graft-versus-host diseases by medulla ossium transplantation, autoimmune diseases such as rheumatoid arthritis, systemic lupus erythematosis, nephrotic syndrome lupus, Hashimoto's thyroidiris, multiple sclerosis, myasthenia gravis, type I diabetes mellitus, type II adult onset diabetes, uveitis, nephrotic syndrome, steroid-dependent and steroid-resistant nephrosis, Palmo-planter pustulosis, allergic encephalomyelitis, glomerulonephritis, etc., and infectious diseases caused by pathogenic microorganisms.

The compounds of Formula I are also useful for treating inflammatory, proliferative and hyperproliferative skin diseases and cutaneous manifestations of immunologically-mediated illnesses such as: psoriasis, psoriatic arthritis, atopical dermatitis, contact dermatitis and further eczematous dermatitises, seborrhoeic dermatitis, Lichen planus, Pemphigus, bullous Pemphigoid, Epidermolysis bullosa, urticaria, angioedemas, vasculitides, erythemas, cutaneous eosinophilias, acne Alopecia areata, eosinophilic fasciitis, and atherosclerosis. More particularly, the compounds of Formula I are useful in hair revitalizing, such as in the treatment of male or female pattern alopecia or alopecia senilis, by providing epilation prevention, hair germination, and/or a promotion of hair generation and hair growth.

The compounds of Formula I are further useful in the treatment of respiratory diseases, for example sarcoidosis, fibroid lung, idiopathic interstitial pneumonia, and reversible obstructive airways disease, including conditions such as asthma, including bronchial asthma, allergic asthma, intrinsic asthma, extrinsic asthma and dust asthma, particularly chronic or inveterate asthma (for example late asthma and airway hyperreponsiveness), bronchitis and the like. The compounds of Formula I may also be useful for treating hepatic injury associated with ischemia.

The compounds of the invention are also indicated in certain eye diseases such as keratoconjunctivitis, vernal conjunctivitis, uveitis associated with Behcet's disease, keratitis, herpetic keratitis, conical cornea, dystorphia epithelialis corneae, corneal leukoma, ocular pemphigus, Mooren's ulcer, Scleritis, Graves' ophthalmopathy, severe intraocular inflammation, and the like.

The compounds of Formula I are also useful for treating multidrug resistance of tumor cells, (i.e. enhancing the activity and/or sensitivity of chemotherapeutic agents), preventing or treating inflammation of mucosa or blood vessels (such as leukotriene B4-mediated diseases, gastric ulcers, vascular damage caused by ischemic diseases and thrombosis, ischemic bowel disease, inflammatory bowel disease (e.g., Crohn's disease and ulcerative coliris) necrotizing enterocolitis), or intestinal lesions associated with thermal burns, cytomegalovirus infection, particularly HCMV infection.

Further, the compounds of Formula I are also useful for treating or preventing renal diseases including interstitial nephritis, Goodpasture's syndrome, hemolyticuremic syndrome and diabetic nephropathy; nervous diseases selected from multiple myositis, Guillain-Barre syndrome, Meniere's disease and radiculopathy; endocrine diseases including hyperthyroidism and Basedow's disease; hematic diseases including pure red cell aplasia, aplastic anemia, hypoplastic anemia, idiopathic thrombocytopenic purpura, autoimmune hemolytic anemia, agranulocytosis and anerythroplasia; bone diseases including osteoporosis; respiratory diseases including sarcoidosis, fibroid lung and idiopathic interstitial pneumonia; skin diseases including dermato,myositis, leukoderma vulgaris, ichthyosis vulgaris, photoallergic sensitivity and cutaneous T cell lymphoma; circulatory diseases including arteriosclerosis, aortitis syndrome, polyarteritis nodosa and myocardosis; collagen including scleroderma, Wegener's granuloma and Sjogren's syndrome; adiposis; eosinophilic fasciitis; periodontal disease; nephrotic syndrome; hemolytic-uremic syndrome; and muscular dystrophy.

Further, the compounds of the invention are indicated in the treatment of diseases including intestinal inflammations/allergies such as Coeliac disease, proctitis, eosinophilic gastroenteritis, mastocytosis, Crohn's disease and ulcerative colitis; and food related allergic diseases which have symptomatic manifestation remote from the gastrointestinal tract, for example migraine, rhinitis and eczema.

The compounds of the invention also have liver regenerating activity and/or activity in stimulating hypertrophy and hyperplasia of hepatocytes. Therefore, they are useful for the treatment and prevention of hepatic diseases such as immunogenic diseases (e.g. chronic autoimmune liver diseases including autoimmune hepatitis, primary biliary cirrhosis and sclerosing cholangitis), partial liver resection, acute liver necrosis (e.g. necrosis caused by toxins, viral hepatitis, shock or anoxia), B-virus hepatitis, non-A/non-B hepatitis and cirrhosis.

The compounds of the invention are also indicated for use as antimicrobial agents, and thus may be used in the treatment of diseases caused by pathogenic microorganisms and the like.

The compounds of Formula I may also be useful in the prevention or treatment of immunodepression (such as AIDS, HIV infection, cancer, senile dementia, trauma (including wound healing, surgery and shock), chronic bacterial infection and certain central nervous system disorders), overdosages or toxicity of such immunosuppressive compounds, and as an adjunct to the administration of an antigen in vaccination.

The pharmaceutical compositions of this invention can be used in the form of a pharmaceutical preparation, for example, in solid, semisolid or liquid form, which contains one or more of the compounds of the present invention, as an active ingredient, in admixture with an organic or inorganic carrier or excipient suitable for external, enteral or parenteral applications. The active ingredient may be compounded, for example, with the usual non-toxic, pharmaceutically acceptable carriers for tablets, pellets, capsules, suppositories, solutions, emulsions, suspensions, and any other form suitable for use. The carriers which can be used are water, glucose, lactose, gum acacia, gelatin, mannitol, starch paste, magnesium trisilicate, talc, corn starch, keratin, colloidal silica, potato starch, urea and other carriers suitable for use in manufacturing preparations, in solid, semisolid, or liquid form, and in addition auxiliary, stabilizing, thickening and coloring agents and perfumes may be used. For example, the compounds of Formula I may be utilized with hydroxypropyl methylcellulose essentially as described in U.S Pat. No. 4,916,138, issued Apr. 10, 1990, or with a surfactant essentially as described in EPO Publication 0,428,169. Oral dosage forms may be prepared essentially as described by T. Hondo, et al., *Transplantation Proceedings*, 1987, XIX, Supp. 6, 17–22. Dosage forms for external application may be prepared essentially as described in EPO Publication 0,423,714. The active object compound is included in the pharmaceutical composition in an amount sufficient to produce the desired effect upon the process or condition of diseases.

For the treatment of these conditions and diseases caused by immunoirregularity a compound of Formula I may be administered orally, topically, parenterally, by inhalation spray or rectally in dosage unit formulations containing conventional non-toxic pharmaceutically acceptable carriers, adjuvants and vehicles. The term parenteral as used herein includes subcutaneous injections, intravenous, intramuscular, intrasternal injection or infusion techniques.

For the treatment of reversible obstructive airways disease, it is preferable that the compound of Formula I be administered by inhalation to the lung, especially in the form of a powder.

For modifying the activity and/or toxicity of FK-506-type immunosuppressants, a compound of Formula I may be administered prior to, in conjuction with or subsequent to the administration of an FK-506-type of a compound.

The compounds of Formula I may optionally be employed in co-therapy with anti-proliferative agents. Particularly preferred is co-therapy with an antiproliferative agent selected from the group consisting of azathioprine (AZA), brequinar sodium, deoxyspergualin (DSG), mizaribine, mycophenolic acid morpholino ester (RS-61443), cyclosporin and rapamycin.

The compounds of Formula I may also be employed in conjunction with (or in a pharmaceutical composition additionally comprising):

(1) a 5α-reductase inhibitor,
(2) a cyclosporin,
(3) a potassium channel opener (such as minoxidil), or
(4) a phospholipid.

Such co-therapy is particularly useful in hair revitalizing, such as in the treatment of male pattern alopecia, female pattern alopecia, alopecia senilis or alopecia areata, by providing epilation prevention, hair germination, and/or a promotion of hair generation and hair growth.

Such co-therapy is further useful in treating the hyperandrogenic conditions of androgenic alopecia, acne vulgaris, seborrhea, and female hirsutism.

For co-therapy of these conditions and diseases a compound of Formula I may be administered in combination with prior to, concurrent to, or subsequent to the administration of other agent(s).

For hair revitalizing the compound of Formula I may be administered topically or orally. Cyclosporin may be administered topically or orally. Although the 5α-reductase inhibitor or the potassium channel opener may be administered topically or orally, it is preferable that it be administered topically to the scalp. For unitary formulation, however, the preferred mode of administration is topically. It is especially preferred that the hair revitalizing composition of the present invention is administered by a percutaneous administration or by spraying onto the skin.

Dosage levels of the compounds of the present invention are of the order from about 0.005 mg to about 50 mg per kilogram of body weight per day, preferably from about 0.1 mg to about 10 mg per kilogram of body weight per day, are useful in the treatment of the above-indicated conditions (from about 0.7 mg to about 3.5 mg per patient per day, assuming a 70 kg patient). In addition, the compounds of the present invention may be administered on an intermittent basis; i.e. at daily, semi-weekly, weekly, semi-monthly or monthly intervals.

The amount of active ingredient that may be combined with the carrier materials to produce a single dosage form will vary depending upon the host treated and the particular mode of administration. For example, a formulation intended for the oral administration of humans may contain from 0.5 mg to 5 gm of active agent compounded with an appropriate and convenient amount of carrier material which may vary from about 5 to about 95 percent of the total composition. Dosage unit forms will generally comprise from about 0.01 mg to about 500 mg, and preferably about 0.5 mg to about 100 mg of active ingredient. For external administration the compound of Formula I may be formulated within the range of, for example, 0.0001% to 60% by weight, preferably from 0.001 to 10% by weight, and most preferably from about 0.005 to 0.8% by weight.

It will be understood, however, that the specific dose level for any particular patient will depend on a variety of factors including the activity of the specific compound employed, the age, body weight, general health, sex, diet, time of administration, route of administration, rate of excretion, drug combination and the severity of the particular disease undergoing therapy.

The following examples are given for the purpose of illustrating the present invention and shall not be construed as being limitations on the scope or spirit of the instant invention.

PREPARATION OF STARTING INTERMEDIATES

17-Ethyl-1-hydroxy-12-[2'-(4'-hydroxy-3'-methoxycyclohexyl)
-1'-methylvinyl]-23,25-dimethoxy-13,19,21,27-tetramethyl-11,28-dioxa-4-azatricyclo-[22.3.1.0$^{4,9}$]-octacos-18-ene-2,3,10,16-tetraone A solution of 500 mg of 17-ethyl-1,14-di -hydroxy-12-[2'-(4"-hydroxy-3"-methoxycyclohexyl)-1'-methylvinyl]-23,25-dimethoxy-13,19,21,27-tetramethyl -11,28-dioxa-4-azatricyclo[22.3.1.0$^{4,9}$]octacos-18-ene-2,3,10,16-tetraone in 7 ml of benzene was treated with 10 mg of p-toluenesulfonic acid and the solution was heated at 60° C. for two hours. The reaction mixture was quenched into saturated sodium bicarbonate solution and extracted with ethyl acetate. The combined organic layers were washed with water and saturated sodium chloride solution, dried with anhydrous magnesium sulfate and concentrated. The residue was chromatographed on silica gel (66% ethyl acetate: 33% hexane: 1% methanol) to give 350 mg of product. This material was dissolved in 10 ml of ethyl acetate and treated with 15 mg of 5% Rh/C. A balloon containing hydrogen was placed over the reaction mixture and the mixture stirred until the reaction was complete. The mixture was filtered through diatomaceous earth, concentrated and the residue subjected to chromatography (75% $CH_2Cl_2$: 5% MeOH: 20% Hexane) to give 294 mg of product.

17-Ethyl-1-hydroxy-12-[2'-(4'',3''-dihydroxyoxycyclo -hexyl)-1'-methylvinyl]-23,25-dimethoxy-13,19,21,27- tetramethyl-11,28-dioxa-4-azatricyclo -[22.3.1.0$^{4,9}$]octacos-18-ene-2,3,10,16-tetraone A solution of 17-ethyl-1,14-dihydroxy-12-[2'-(4''-hydroxy-3''-hydroxycyclohexyl)-1'-methylvinyl]-23,25-dimethoxy-13,19,21,27-tetramethyl-11,28-dioxa -4-azatricyclo-[22.3.1.0$^{4,9}$]octacos-18-ene-2,3,10,16-tetraone (210 mg) and a catalytic amount of p-toluenesulfonic acid in 40 ml of benzene was refluxed for 4 hours under a nitrogen atmosphere. The solvent was removed under reduced pressure and the dark residue was purified by chromatography (silica gel, 7% i-propanol/$CH_2Cl_2$) to give 17-ethyl-1-hydroxy-12-[2'-(4''-hydroxy-3''-isopropyloxy-cyclohexyl) -1'-methylvinyl]-23,25-dimethoxy-13,19,21,27-tetramethyl-11,28-dioxa-4-azatricyclo -[22.3.1.0$^{4,9}$]octacos-14,18-diene-2,3,10,16-tetraone (180 mg) as a white solid. This material was dissolved in ethanol (20 ml) and treated with 5% Rh/C (40 mg). Hydrogen was introduced via balloon for 30 min. and the mixture was filtered through celite. Removal of solvent followed by chromatography (silica gel) gave 172 mg of the title compound. Mass, $^1$H and $^{13}$C NMR data were consistant with the title structure.

17-Ethyl-1-hydroxy-12-[2'-(4''-triisopropylsilyloxy-3''-methoxycyclohexyl)-1'-methylvinyl]-14-triisopropyl -silyloxy-23,25-dimethoxy-13,19,21,27-tetramethyl- 11,28 -dioxa-4-azatricyclo-[22.3.1.0$^{4,9}$]octacos-18-ene -2,3,10,16-tetraone To a cooled solution (0° C.) of 17-ethyl-1,14-dihydroxy-12-[2'-(4''-hydroxy-3''-methoxycyclohexyl) -1'-methylvinyl]-23,25-dimethoxy-13,19,21,27-tetra -methyl-11,28-dioxa-4-azatricyclo[22.3.1.0$^{4,9}$]-octacos-18-ene- 2,3,10,16-tetraone (120 mg) in dry methylene chloride (15 ml) was added 2,6-lutidine (64.3 mg) followed by triisopropylsilyl trifluoro-methanesulfonate (184 mg). Reaction temperature was raised to r.t. and stirred overnight under nitrogen atmosphere. The reaction was quenched with 10 ml of water and extracted with ethyl acetate. Organic layer was washed (water, sat'd NaHCO$_3$, sat'd NaCl) and dried (anhydrous MgSO$_4$). Removal of solvent followed by chromatography on silica gel (70% hexane/ethyl acetate) gave 150 mg of product.

MASS: (FAB) 1110 (M+ +Li).

17-Ethyl-1-hydroxy-12-[2'-(4''-hydroxy -3''-methoxycyclohexyl)-1'-methylvinyl]-14-triisopropyl -silyloxy-23,25-dimethoxy-13,19,21,27-tetramethyl- 11,28-dioxa-4-azatricyclo[22.3.1.0$^{4,9}$]-octacos-18-ene -2,3,10,16-tetraone The title compound from the previous preparation (680 mg) was dissolved in methylene chloride (45 ml) and 10% solution of p-toluenesulfonic acid in methanol (45 ml) was added with stirring. The mixture was stirred at room temperature and the progress was followed by tlc analysis. After 4 hr, reaction was quenched with sat'd sodium bicarbonate and extracted with ethyl acetate three times. Normal work-up and removal of solvent followed by purification on silica gel column (80% ethyl acetate/hexane) gave 560 mg of the product (2a) as a white solid. MASS: (FAB) 954 (M+ +Li).

17-Ethyl-1-hydroxy-12-[2'-(4''-t-butyl -dimethylsilyloxy-3''-methoxycyclohexyl)-1'-methylvinyl]-14-t-butyldimethylsilyloxy-23,25-dimethoxy -13,19,21,27-tetramethyl-11, 28-dioxa-4-azatri-cyclo -[22.3.1.0$^{4,9}$]octacos-18-ene-2,3,10,16-tetraone To a cooled solution (0° C.) of 17-ethyl -1,14-dihydroxy-12-[2'-(4''-hydroxy-3''-methoxycyclo -hexyl)-1'-methylvinyl ]-23,25-dimethoxy-13,19,21,27-tetra-methyl-11,28-dioxa-4-azatricyclo[22.3.1.0$^{4,9}$]-octacos-18-ene- 2,3,10,16-tetraone (1a) (395 mg) in dry methylene chloride (15 ml) was added 2,6-lutidine (160 mg) followed by t-butyldimethylsilyl triflouromethanesulfonate (250 mg). Reaction temperature was raised to r.t. and stirred under nitrogen atmosphere. After 6 hr, the reaction was quenched with 10 ml of water and extracted with ethyl acetate. Organic layer was washed (water, saturated NaHCO$_3$, saturated NaCl) and dried (anhydrous MgSO$_4$). Removal of solvent under reduced pressure gave 500 mg of crude product. MASS: (FAB) 1023 (M+ +Li).

17-Ethyl-1-hydroxy-12-[2'-(4''-hydroxy -3''-methoxycyclohexyl)-1'-methylvinyl]-14-t-butyl -dimethylsilyloxy-23, 25-dimethoxy-13,19,21,27-tetramethyl -11,28-dioxa-4-azatricyclo[22.3.1.0$^{4,9}$]-octacos-18ene- 2,3,10,16-tetraone The product from the previous example (500 mg) was dissolved in acetonitrile (20 ml) and 100 ml of hydrogen fluoride (48%) was added. Reaction was stirred for 20 minutes at room temperature, quenched with saturated sodium bicarbonate, then extracted with ethyl acetate. Removal of solvent in vacuo followed by chromatography on silica gel (80% ethyl acetate/hexane) gave 300 mg of product (Mass, $^1$H and $^{13}$C NMR data consistent with the title compound.

17-Ethyl-1-hydroxy-12-[2'- (4''-(tert-butyldimethylsiloxy) -3''-hydroxycyclohexyl) -1'-methylvinyl]-23,25-dimethoxy-13,19,21,27-tetramethyl-11,28-dioxa-4-azatricyclo [22.3.1.0$^{4,9}$]octacos-18-ene-2,3,10,16-tetraone To a solution of 17-ethyl-1-hydroxy-12-[2'-(3'',4''-dihydroxycyclohexyl)-1'-methylvinyl]-23,25-dimethoxy-13,19,21,27-tetramethyl-11,28-dioxa-4-azatricyclo [22.3.1.0$^{4,9}$]octacos-18-ene-2,3,10,16-tetraone (3.01 g) in dry methyl ene chloride (70 ml) was added an excess of imidazole (809 mg) followed by tert-butyldimethylsilyl chloride (716 mg). After 3 days of stirring at room temperature, the mixture was diluted with ethyl acetate which in turn was washed with 1N HCl, saturated sodium bicarbonate and brine, dried over magnesium sulfate and purified by flash chromatography (ethyl acetae:hexane (1:3)) to give the title compound (941 mg). ¹H NMR consistent with the desired structure.

17-Ethyl-1-hydroxy-12-[2'-(4"-(tert-butyldimethyl -silyloxy)-3"-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone To a solution of 17-ethyl-1-hydroxy-12-[2'-(4"-hydroxy-3"-methoxycyclohexyl)-1'-methylvinyl]-23,25 -dimethoxy-13,19,21,-27-tetramethyl-11,28-dioxa-4-azatricyclo[22.3.1.0⁴,⁹]octacos-18-ene-2,3,10,16-tetraone (200 mg) in dry methylene chloride (3 ml) was added an excess of 2,6-lutidine (45 μl) and the mixture was stirred at room temperature. After 10 minutes, tert-butyldimethylsilyl trifluoromethane-sulfonate (64 μl) was added by syringe. After 15 minutes the reaction mixture was diluted with ethyl acetate, extracted from saturated bicarbonate, washed with brine and the organic phase dried over magnesium sulfate. Removal of solvent in vacuo and flash chromatography on silica gel (ethyl acetate: hexane (1:2) + 1% methanol) gave the title compound (235 mg).

(¹H NMR consistent with the desired structure).

17-Ethyl-1,20-dihydroxy-12-[2'-(4"-tert-butyldimethyl -silyloxy)-3"-methoxycyclohexyl)-4"1'-methylvinyl]-23,25 -dimethoxy-13,19,21,27-tetramethyl-11,28-dioxa-4-azatricyclo [22.3.1.0⁴,⁹]octacos-18-ene-2,3,10,16-tetraone To a stirred solution of 17-ethyl-1-hydroxy -12-[2'-(4"-(tert-butyldimethylsilyloxy)-3"-methoxy -cyclohexyl)-1'-methylvinyl]-23,25-dimethoxy-13,19,21, 27-tetramethyl-11,28-dioxa-4-azatricyclo[22.3.1.0⁴,⁹]octacos-18-ene-2,3,10,16-tetraone (235 mg) in 95% ethanol (2.2 ml) was added 53 μl of pyridine followed by selenium dioxide (58 mg). The flask was fitted with a water condenser and heated to 70° C. on a mantle. After 20 hours the mixture was cooled to room temperature filtered through diatomaceous earth and the filtrate poured into a saturated sodium bicarbonate solution. This was extracted with ethyl acetate, washed with brine and dried over magnesium sulfate. The solution was concentrated and purified by flash chromatography on silica gel (ethyl acetate: hexane (1:2) + 1% methanol) to give the title compound (89 mg). (¹H NMR consistent with the desired structure).

17-Ethyl-20-fluoro-1-hydroxy-12-[2'-(4"-(tert-butyl -dimethylsiloxy)-3"-methoxycyclohexyl)-1'-methyl-vinyl]-23,25-dimethoxy-13,19,21,27-tetramethyl-11,28-dioxa-4-azatricyclo[22.3.1.0⁴,⁹]octacos-18-ene-2,3,10.16-tetraone A solution of 17-ethyl-20-dihydroxy-12-[2'-(4"-(tert-butyldimethylsiloxy)-3"-methoxycyclohexyl) -1'-methylvinyl]-23,25-dimethoxy-13,19,21,27-tetra -methyl-11,28-dioxa-4-azatricyclo[22.3.1.0⁴,⁹]octacos -18-ene-2,3,10.16-tetraone (30.5 mg) in methylene chloride (0.5 ml) was cooled to −78° C. in a dry ice/isopropanol bath. To this stiff ed solution, diethylaminosulfur trifluoride (4.5 μl) was added. After 3 minutes saturated sodium bicarbonate (500 μl) was added followed by ethyl acetate (2 ml) and the mixture was warmed to room temperature. Extraction from ethyl acetate, drying over magnesium sulfate and purification by flash chromatography on silica gel (ethyl acetate: hexane (1:2) + 1% MeOH) gave the title compound (22 mg). (¹H NMR consistent with the desired structure).

17-Ethyl-1,20-dihydroxy-12-[2'-(4"-(hydroxy-3"-methoxycyclohexyl)-1'-methylvinyl]-23,25-dimethoxy -13,19,21,27-tetramethyl-11,28-dioxa-4-azatricyclo -[22.3.1.0⁴,⁹]octacos-18-ene-2,3,10.16-tetraone To a solution of 17-ethyl-1,20-dihydroxy -12-[2'-(4"-(tert-butyldimethylsiloxy)-3"-methoxy -cyclohexyl)-1'-methylvinyl]23,25-dimethoxy-13,19,21,27 -tetramethyl-11,28-dioxa-4-azatricyclo[22.3.1.0⁴,⁹]-octacos-18-ene-2,3,10.16-tetraone (7 mg) in acetonitrile (0.3 ml) was added a solution of 2% hydrogen fluoride in aqueous acetonitrile (100 μl), and the mixture stirred at room temperature. After 28 hours the solution was diluted with ethyl acetate, extracted with saturated sodium bicarbonate and the organic phase dried by passage through a magnesium sulfate column. Purification of the concentrate by flash chromatography on silica gel (ethyl acetate: hexane (2:1) + 1% methanol) gave the title compound.

17-Ethyl-20-fluoro-1-hydroxy-12-[2'-(4"-(hydroxy-3"-methoxycyclohexyl)-1'-methylvinyl]-23,25-dimethoxy -13,19,21,27-tetramethyl-11,28-dioxa-4-azatricyclo [22.3.1.0⁴,⁹]octacos-18-ene-2,3,10.16-tetraone To a solution of 17-ethyl-20-fluoro-1-hydroxy-12-[2'-(4"-(tert-butyldimethylsiloxy)-3"-methoxycyclohexyl)-1'-methylvinyl]23,25-dimethoxy -13,19,21,27-tetramethyl-11,28-dioxa-4-azatricyclo -[22.3.1.0⁴,⁹]octacos- 18-ene-2,3,10.16-tetraone (7 mg) in acetonitrile (0.3 ml) was added a solution of 2% hydrogen fluoride in aqueous acetonitrile (100 μl), and the mixture stirred at room temperature. After 2 hours the solution was diluted with ethyl acetate, extracted with saturated sodium bicarbonate and the organic phase dried by passage through a magnesium sulfate column. Purification of the concentrate by flash chromatography on silica gel (ethyl acetate: hexane (1:1) + 1% methanol) gave the title compound.

MASS: (FAB) 816 (M+Na).
partial ¹³C NMR δ: 211.5 (C-16); 196.1 (2) 169.3 (10); 165.0 (3); 138.1 (C-19); 135.8 (C-1');
121.0 (C-18'major); 84.1 (C-3"); 43.1 (C-15); 26.0 (C-21).

17-Ethyl-1,14,20-trihydroxy-12-[2'-(4"-hydroxy-3"-methoxycyclohexyl)-1'-methylvinyl]-23,25-dimethoxy -13,19,21,27-tetramethyl-11,28-dioxa-4-azatricyclo -[22.3.1.0⁴,⁹]octacos-18-ene-2,3,10,16-tetraone
ALTERNATE ROUTE To a solution of 17-ethyl-1,14-dihydroxy-12-[2'-(4"-hydroxy-3"-methoxycyclohexyl)-1'-methylvinyl]-23, 25-dimethoxy-13,19,21,27-tetramethyl-11,28-dioxa -4-azatricyclo[22.3.1.0⁴,⁹]octacos-18-ene-2,3,10,16-tetraone (5.15 gm, 0.065 mol) in glacial acetic acid (500 ml) at room temperature, was added a solution of selenium dioxide (9.27 gm, 0.083 mol) in H₂O (90 ml). The reaction mixture was stirred at room temperature for 41 hours whereupon, it was poured into a stirred mixture of H₂O (3L) and celite. After stir ring for 15 minutes, the mixture was filtered through a pad of celite and extracted with diethyl ether (1×2 L, 2×1 L). The organic fractions were washed with saturated sodium bicarbonate and brine, dried over magnesium sulfate, filtrated and evaporated in vacuo. The product was purified by chromatography (silica, acetone:hexanes 2:5) to give the title compound MASS and $^1$H NMR were consistent with the structure.

EXAMPLE 1

17-Ethyl-1,14-dihydroxy-12-[2'-(4"-(2-furanyl)methoxy -3"-methoxycyclohexyl)-1'-methylvinyl]-23,25-dimethoxy -13,19,21,27-tetramethyl-11,28-dioxa-4-azatricyclo -[22.3.1.0$^{4,9}$]octacos-18-ene-2,3,10,16-tetraone To a solution of 17-ethyl-1,14-dihydroxy-12-[2'-(4"-hydroxy-3"-methoxycyclohexyl)-1'-methylvinyl]-23,25-dimethoxy-13,19,21,27-tetramethyl-11,28-dioxa-4-azatricyclo [22.3.1.0$^{4,9}$]octacos-18-ene-2,3,10,16-tetraone (63 mg in 1.0 ml methylene chloride) furfuryl trichloroacetimidate (39 μl neat) was added and the reagents allowed to mix for 5 minutes. Camphorsulfonic acid (3.7mg) was added and the mixture stirred at room temperature. After 4.5 hours the reaction was quenched by the addition of saturated sodium bicarbonate and extracted with ethyl acetate (3×5 ml). The combined organics were washed with brine and dried over magnesium sulfate. Purification of the concentrate by flash chromatography on silica gel (ethyl acetate: hexane (1:2)+1% methanol) gave the title compound (20 mg). MAS: (FAB) 878 (M+Li). Partial $^1$H NMR δ: 7.38(brs, 1 H); 6.30(m, 3 H); 5.32 M, 5.19 m(brd J=3 Hz, 1 H); 4.83 m, 4.21 M(brs, 1H); 4.62(dd J=15 Hz, 2 H); 4.41(brd J=14 Hz, 1 H).

EXAMPLES 2 and 3

17-Ethyl-1,14-dihydroxy-12-[2'-(4"-(2-furanyl)methoxy -3"-hydroxycyclohexyl)-1'-methylvinyl]-23,25-dimethoxy -13,19,21,27-tetramethyl-11,28-dioxa-4-azatricyclo -[22.3.1.0$^{4,9}$]octacos-18-ene-2,3,10,16-tetraone and 17-Ethyl-1,14-dihydroxy-12-[2'-(4"-hydroxy-3"-(2-furanyl)methoxycyclohexyl)-1'-methylvinyl]-23,25-dimethoxy-13,19,21,27-tetramethyl-11,28-dioxa-4-azatricyclo [22.3.1.0$^{4,9}$]octacos-18-ene-2,3,10,16-tetraone To a solution of 17-ethyl-1,14-dihydroxy-12-[2'-(3",4"-dihydroxycyclohexyl)-1'-methylvinyl]-23,25-dimethoxy-13,19,21,27-tetramethyl-11,28-dioxa-4-azatricyclo [22.3.1.0$^{4,9}$]octacos-18-ene-2,3,10,16-tetraone (52 mg in 0.9 ml methylene chloride) furfuryl trichloroacetimidate (20 μl neat) was added and the reagents allowed to mix for 5 minutes. Camphorsulfonic acid (2mg) was added and the mixture stirred at room temperature. After 3.5 hours the reaction was quenched by the addition of saturated sodium bicarbonate and extracted with ethyl acetate (3×5 ml). The combined organics were washed with brine and dried over magnesium sulfate. Purification of the concentrate by flash chromatography on silica gel (ethyl acetate:hexane (1:1)+1% methanol) gave the title compounds (16 mg 4" ether; 13 mg 3" ether).

4" ether: MASS: (FAB) 864 (M+Li); Partial $^1$H NMR δ: 7.41(brs, 1 H); 6.30(m, 2 H); 5.32 M, 5.19 m(brd J=3 Hz, 1 H); 4.87 m, 4.19 M(brs, 1H); 4.41(brd J=14 Hz, 1 H).

3" ether: MASS: (FAB) 864 (M+Li); Partial $^1$H NMR δ: 7.44(brs, 1 H); 6.37(m, 2H); 5.32 M, 5.19 m(brd J=3 Hz, 1 H); 4.88 m, 4.27 M(brs, 1 H); 4.41(brd J=14 Hz, 1 H).

EXAMPLE 4

17-Ethyl-1,14-dihydroxy-12-[2'-(4"-(2-thiophene) -methoxy-3"-methoxycyclohexyl)-1'-methylvinyl]-23,25-dimethoxy-13,19,21,27-tetramethyl-11,28-dioxa-4-azatricyclo [22.3.1.0$^{4,9}$]octacos-18-ene-2,3,10,16-tetraone The title compound was prepared essentially as described in Example 1 using 2-thiophenylmethyl trichloroacetimidate as the alkylating agent. Partial $^1$H NMR δ: 7.27(m, 1 H); 6.96(m, 2 H); 5.31 M, 5.18 m(brd J=3 Hz, 1 H); 4.81 m, 4.22 M(brs, 1 H); 4.41(brd J=14 Hz, 1 H); 3.07(d J=4 Hz, 1 H).

EXAMPLES 5 and 6

17-Ethyl-1,14-dihydroxy-12-[2'-(4"-(2-thiophene) -methoxy-3"-hydroxycyclohexyl)-1'-methylvinyl]-23,25-dimethoxy-13,19,21,27-tetramethyl-11,28-dioxa-4-azatricyclo [22.3.1.0$^{4,9}$]octacos-18-ene-2,3,10,16-tetraone and 17-Ethyl-1,14-dihydroxy-12-[2'-(4"-hydroxy-3"-(2-thiophene)methoxycyclohexyl)-1'-methylvinyl]-23,25-dimethoxy-13,19,21,27-tetramethyl-11,28-dioxa-4-azatricyclo [22.3.1.0$^{4,9}$]octacos-18-ene-2,3,10,16-tetraone The title compounds were prepared essentially as described in Examples 2 and 3 using 2-thiophenylmethyl trichloroacetimidate as the alkylating agent.

4" ether: MASS: (FAB) 896 (M+Na); Partial $^1$H NMR δ: 7.29(m, 1 H); 6.97(m, 2 H); 5.31 M, 5.19 m(brd J=3 Hz, 1 H); 4.41(brd J=14 Hz, 1 H); 3.04(d J=4 Hz, 1 H); 2.63 M, 2,61 m(s, 1 H); 3" ether: MASS: (FAB) 880 (M+Li); Partial $^1$H NMR δ: 7.28 (m, 1 H); 6.97 (m, 2 H); 5.31 M, 5.19 m (brd J=3 Hz, 1 H); 4.41 (brd J=14 Hz, 1 H); 3.08 (d J=3 Hz, 1 H); 2.69 (s, 1 H).

EXAMPLES 7 and 8

17-Ethyl-1,14-dihydroxy-12-[2'-(4"-(3-thiophene) -methoxy-3"-hydroxycyclohexyl)-1'-methylvinyl]-23,25-dimethoxy-13,19,21,27-tetramethyl-11,28-dioxa-4-azatricyclo [22.3.1.0$^{4,9}$]octacos-18-ene-2,3,10,16-tetraone and 17-Ethyl-1,14-dihydroxy -12-[2'-(4"-hydroxy-3"-(3-thiophene)methoxycyclohexyl) -1'-methylvinyl]-23,25-dimethoxy-13,19,21,27-tetra -methyl-11,28-dioxa-4-azatricyclo[22.3.1.0$^{4,9}$]octacos -18-ene-2,3,10,16-tetraone The title compounds were prepared essentially as described in Examples 2 and 3 using 3-thiophenylmethyl trichloroacetimidate as the alkylating agent.

4" ether: MASS: (FAB) 880 (M+Li); Partial $^1$H NMR δ: 7.30 (m, 1 H); 7.04 (m, 2 H); 5.31 M, 5.19 m (brd J=3 Hz, 1 H); 4.89 m, 4.19 M (s, 1 H); 4.41 (brd J=14 Hz, 1 H); 3.04 (d J=4 Hz, 1 H); 3" MASS: (FAB) 880 (M+Li); Partial $^1$H NMR δ: 7.28 (m, 2 H); 7.05 (dd, J=5, 2 Hz, 1 H); 5.31 M, 519 m (brd J=3 Hz, 1 H); 4.83 m, 4.25 M (brs, 1 H); 4.41 (brd J=14 Hz, 1 H); 3.06 (d J=3 Hz, 1 H); 2.69 (s, 1 H).

EXAMPLE 9

17-Ethyl-1,14-dihydroxy-12-[2'-(4''-(benzothien-2-yl)oxy-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetrone To a stirred solution of tri(benzothien-2-yl)bismuthine (100 mg., 0.164 mmol.) in CH$_2$Cl$_2$ (2 mL.) was added peracetic acid (0.050 mL., 0.224 mmol., 32% in acetic acid) followed in 10 minutes by 17-ethyl-1, 14-dihydroxy-12-[2'-(4''-hydroxy-3''-methoxycyclo-hexyl)-1'-methytvinyl]-23,25-dimethoxy-13,19,21,27-tetrameth yl-11,28-dioxa-4-azatricyclo[22.3.1.0$^{4,9}$]octacos-18-ene -2,3,10,16-tetraone (100 mg., 0.126 mmol.) and Cu(OAc)$_2$ (15 mg., 0.083 mmol.). The reaction mixture was stirred for 16 hours at room temperature. The reaction was then quenched with saturated aqueous NaHCO$_3$ and the mixture extracted 3× with CH$_2$Cl$_2$. The extracts were combined, dried with Na$_2$SO$_4$, filtered, and concentrated in vacuo. The product was isolated and purified by preparative TLC 3× on silica gel (3:1, hexane/acetone) to give 23 mg of 17-ethyl-1,14-dihydroxy-12-[2'-(4''-(benzothien -2-yl)oxy-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone.

EXAMPLE 10

17-Ethyl-1,14-dihydroxy-12-[2'-(4''-(thien-2-yl)oxy-3''-methoxycyclohexyl)-1'-methylvinyl]-23,25-dimethoxy-13,19,21,27-tetramethyl-11,28-dioxa-4-azatricyclo-[22.3.1.0$^{4,9}$]octacos-18-ene-2,3,10,16-tetraone To a stirred solution of tri(thien-2-yl)bismuthine (80 mg., 0.175 mmol.) in CH$_2$Cl$_2$(2 mL.) was added peracetic acid (0.060 mL., 0.253 mmol., 32% in acetic acid) followed in 15 minutes by 17-ethyl -1,14-dihydroxy-12-[2'-(4Δ-hydroxy-3Δ-methoxycyclo -hexyl)-1'-methylvinyl]-23,25-dimethoxy-13,19,21,27-tetramethyl-11,28-dioxa-4-azatricyclo[22.3.1.0$^{4,9}$]-octacos-18-ene-2,3,10,16-tetraone (100 mg., 0.126 mmol.) and Cu-(OAc)$_2$ (10 mg., 0.055 mmol.). The reaction mixture was allowed to stir at room temperature for 3 days. The reaction was quenched with saturated aqueous NaHCO$_3$, and the mixture extracted with CH$_2$Cl$_2$. The extracts were combined, dried with Na$_2$SO$_4$, filtered and concentrated in vacuo. The product was isolated and purified by preparative TLC 2× on silica gel (2:1, hexane/acetone) to give 36 mg of 17-ethyl-1,14-dihydroxy-12-[2'-(4''-(thien-2-yl)oxy-3''-methoxycyclo -hexyl)-1'-methylvinyl]-23,25-dimethoxy-13,19,21,27-tetramethyl-11,28-dioxa-4-azatricyclo[22.3.1.0$^{4,9}$]-octacos-18-ene-2,3,10,16-tetraone.

EXAMPLE 11

17-Ethyl-1,14-dihydroxy-12-[2'-(4''-5-indolylamino-carbonylmethoxy-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone

STEP 11A

17-Ethyl-1-hydroxy-14-(tert-butyldimethylsiloxy)-12-[2'-(4''-(tert-butyldimethylsiloxy)-3''-methoxycyclo-hexyl)-1'-methylvinyl]-23,25-dimethoxy-13,19,21,27-tetramethyl-11,28-dioxa-4-azatricyclo[22.3.1.0$^{4,9}$]-octacos-18-ene-2,3,10,16-tetraone To a solution of 17-ethyl-1,14-dihydroxy -12-[2'-(4''-hydroxy-3''-methoxycyclohexyl)-1'-methylvinyl]-23,25-dimethoxy-13,19,21,27-tetramethyl-11,28-dioxa-azatricyclo[22.3.1.0$^{4,9}$]octacos-18-ene-2,3,10,16-tetraone (2.0 g) in dry methylene chloride (25 ml) was added an excess of 2,6-lutidine (1.2 ml) and the mixture was stirred at room temperature. After 10 minutes, tert-butyldimethylsilyl trifluoromethanesulfonate (1.8 ml) was added via syringe. After 1 hour the reaction mixture was diluted with ethyl acetate, washed with 1N HCl, water, saturated sodium bicarbonate and brine. The organic phase was dried over magnesium sulfate. Removal of the solvent in vacuo and flash chromatography on silica gel (ethyl acetate: hexane (1:6)+1% methanol) gave the title compound (2.37 g). $^1$H NMR consistent with the desired structure.

STEP 11B

17-Ethyl-1-hydroxy-14-(tert-butyldimethylsiloxy)-12-[2'-(4''-hydroxy-3''-methoxycyclohexyl)-1'-methylvinyl]-23,25-dimethoxy-13,19,21,27-tetramethyl-11,28-dioxa-4-azatricyclo [22.3.1.0$^{4,9}$]octacos-18-ene-2,3,10,16-tetraone To a solution of 17-ethyl-1-hydroxy-14-(tert -butyldimethylsiloxy)-12-[2'-(4''-(tert-butyldimethyl -siloxy)-3''-methoxycyclohexyl)-1'-methylvinyl]-23,25-dimethoxy-13,19,21,27-tetramethyl-11,28-dioxa-4-azatricyclo [22.3.1.04,9]octacos-18-ene-2,3,10,16-tetraone (2.37 g) (STEP 11A) in dry methylene chloride (25 ml) was added a solution of 10% p-toluenesulfonic acid in methanol (25 ml), and the mixture was stirred at room temperature. After 10 minutes, the mixture was cooled to 0° C. and quenched with saturated sodium bicarbonate. The mixture was diluted with ethyl acetate and the layers were separated. The organic layer was washed with saturated sodium bicarbonate and brine and dried over magnesium sulfate. Purification of the concentrate by flash chromatography on silica gel (ethyl acetate: hexane (1:2)+1% methanol) gave the title compound (2.1 g). $^1$H NMR consistent with the desired structure.

STEP 11C

17-Ethyl-1-hydroxy-14-(tert-butyldimethylsiloxy)-1 2-[2'-(4''-allyloxy-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a solution of 17-ethyl-1-hydroxy-14-(tert -butyldimethylsiloxy)-12-[2'-(4''-hydroxy-3''-methoxy -cyclohexyl)-1'-methylvinyl]-23,25-dimethoxy-13,19,21,27-tetramethyl-11,28-dioxa-4-azatricyclo[22.3.1.04,9]-octacos-18-ene-2,3,10,16-tetraone (2.1 g) (STEP 11B) in 24 ml 33% methylene chloride in cyclohexane, was added allyl trichloroacetimidate (938 mg neat) and the reaction mixture was allowed to mix for 5 minutes. Trifluoromethanesulfonic acid (41 μl neat) was added slowly via syringe and the mixture stirred at room temperature. After 24 hours, the reaction mixture was diluted with ethyl acetate and washed with saturated sodium bicarbonate, water and brine. The organic layer was dried over magnesium sulfate. Purification of the concentrate by flash chromatography on silica gel (ethyl acetate: hexane (1:5))+1% methanol) gave the title compound (1.03 g). $^1$H NMR consistent with the desired structure.

STEP 11D

17-Ethyl-1hydroxy-14-(tert-butyldimethylsiloxy)-12-[2'-(4''-(2,3-dioxy-1-propoxy)-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a solution of 17-ethyl-1-hydroxy-14-(tert -butyldimethylsiloxy)-12-[2'-(4''-allyloxy-3''-methoxy -cyclohexyl)-1'-methylvinyl]-23,25-dimethoxy-13,19,21,27-tetramethyl-11,28-dioxa-4-azatricyclo[22.3.1.04,9]-octacos-18-ene-2,3,10,16-tetraone (STEP 11C) (1.03 g) in 22 ml tetrahydrofuran was added N-methylmorpholine N-oxide (883 mg) followed by 0.25 M osmium tetraoxide solution in THF (871 µl), and the mixture was stirred at room temperature. After 3 hours, the reaction was quenched by the addition of 20% sodium bisulfite (20 ml), and the precipitate w-as filtered through Celite and rinsed with ethyl acetate. The combined filtrate was washed with 20% sodium bisulfite (2×), saturated sodium bicarbonate and brine and dried over magnesium sulfate. The concentrate was purified by flash chromatography on silica gel (ethyl acetate:hexane (2:1)+1% methanol) to give the title compound (705 mg). 1 H NMR consistent with the desired structure.

STEP 11E

17-Ethyl-1-hydroxy-14-(tert-butyldimethylsiloxy)-12-[2'-(4''-ethanaloxy-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a solution of 17-ethyl-1-hydroxy-14-(tert -butyldimethylsiloxy)-12-[2'-(4''-(2,3-dioxy-1-propoxy) -3''-methoxycyclohexyl)-1'-methylvinyl]-23,25-dimethoxy-3,19,21,27-tetramethyl-11,28-dioxa-4-azatricyclo[22.3.1.04,9]octacos-18-ene-2,3,10,16-tetraone (1.56 g) (STEP 11D) in 20% aqueous tetrahydrofuran (20 ml) was added sodium metaperiodate (510 mg) and the mixture stirred vigorously for 30 minutes. At this time an additional 170 mg of sodium metaperiodate were added. After 30 minutes the mixture was diluted with ethyl acetate, filtered through Celite and the residue rinsed with ethyl acetate. The organic portion was washed with saturated sodium bicarbonate and brine, dried over magnesium sulfate and purified by flash chromatography on silica gel (ethyl acetate:hexane (1:2)+1% methanol) to give the title compound (1.45 g). $^1$H NMR consistent with the desired structure.

STEP 11F

17-Ethyl-1-hydroxy-14-(tert-butyldimethylsiloxy)-12-[2'-(4''-carboxymethoxy-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a solution of 17-ethyl-1-hydroxy-14-(tert -butyldimethylsiloxy)-12-[2'-(4''-ethanaloxy-3''-methoxy -cyclohexyl)-1'-methylvinyl]-23,25-dimethoxy-13,19,21,27-tetramethyl-11,28-dioxa-4-azatricyclo[22.3.1.04,9]-octacos-18-ene-2,3,10,16-tetraone (311 mg) (STEP 11E) in tert-butanol (6.6 ml) and 2-methyl-2-butene (1.65 ml) was added sodium chlorite (273 mg) and sodium dihydrogen phosphate (272 mg) in water (2.7 ml) slowly. After 2 hours, the solvent was removed in vacuo, and the resulting residue was dissolved in water and acidified to pH 3 with 1N HCl. The aqueous portion was extracted with ethyl acetate (3×10 ml) and the combined organic portion was washed with brine. This was dried over magenesium sulfate and purified by flash chromatography on silica gel (2% methanol in methylene chloride followed by 2% methanol in methylene chloride+0.5% acetic acid) to give the title compound (255 mg). $^1$H NMR consistent with the desired structure.

STEP 11G

17-Ethyl-1-hydroxy-14-(tert-butyldimethylsiloxy)-12-[2'-(4''-5-indolylamino-carbonylmethoxy-3''-methoxy -cyclohexyl)-1'-methylvinyl]-23,25-dimethoxy-13,19,21,27-tetramethyl-11,28-dioxa-4-azatricyclo[22.3.1.0$^{4,9}$]-octacos-18-ene-2,3,10.16-tetraone To a solution of 17-ethyl-1-hydroxy-14-(tert -butyldimethylsiloxy)-12-[2'-(4''-carboxymethoxy-3''-methoxycyclohexyl)-1'''-methylvinyl]-23,25-dimethoxy -13,19,21,27-tetramethyl-11,28-dioxa-4-azatricyclo -[22.3.1.04,9]octacos-18-ene-2,3,10,16-tetraone (150 mg) (STEP 11F) in methylene chloride (1.6 ml) was added benzotriazol-1-yloxy-tris(dimethylamino)-phosphonium hexafluorophosphate (103 mg) followed by triethylamine (43 µl). After 10 minutes, 5-aminoindole (43 mg) was added to the reaction mixture and stirred for 1 hour. The mixture was diluted with ethyl acetate and washed with 1N HCl, water, saturated sodium bicarbonate and brine, respectively. The organic portion was dried over magnesium sulfate and purified by flash chromatography on silica gel (ethyl acetate:hexane (1:2)+1% methanol) to give the title compound (138 mg). $^1$H NMR consistent with the desired structure.

STEP 11H

17-Ethyl-1,14-dihydroxy-12-[2'-(4''-5-indolylamino -carbonylmethoxy-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a solution of 17-ethyl-1-hydroxy-14-(tert -butyldimethylsiloxy)-12-[2'-(4''-5-indolylaminocarbonyl methoxy-3''-methoxycyclohexyl)-1'-methylvinyl]-23,25-di methoxy-13,19,21,27-tetramethyl-11,28-dioxa-4-azatricy clo[22.3.1.04,9]octacos-18-ene-2,3,10,16-tetraone (138 mg in 1 ml tetrahydrofuran contained in a polypropylene vial) was added 200 µl of a solution of hydrogen fluoride-pyridine complex (40% in (2:1) tetrahydrofuran:pyridine), and the mixture was stirred at room temperature. After 2 days, the reaction was quenched by the careful addition of saturated sodium bicarbonate and extracted with ethyl acetate. The combined organic portion was washed with brine, dried over magnesium sulfate, concentrated in vacuo and purified by flash chromatography (ethyl acetate:hexane (1:1)+1% methanol) to give the title compound. MASS (FAB) 971 (M+Li); partial $^1$H NMR δ: 9.52 (brs, 1 H); 8.15 (brs, 1 H); 7.91 (s, 1 H); 7.30 (s, 2 H); 7.16 (dd, J=3,3 Hz, 1 H); 6.49 (dd, J=,3 Hz, 1 H); 4.41 (brd, J=14 Hz, 1 H).

EXAMPLE 12

17-Ethyl-1-hydroxy-12-[2'-(4''-(methyl-N-tryptophanyl -carbonylmethoxy)-3''-methoxycyclohexyl) -1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone

STEP 12A

17-Ethyl-1-hydroxy-12-[2'-(4''-allyloxy-3''-methoxy -cyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a solution of 17-ethyl-1-hydroxy-12-[2'-(4''-hydroxy-3''-methoxycyclohexyl)-1'-methylvinyl]-23,25-dimethoxy-13,19,21,27-tetramethyl-11,28-dioxa-4-azatricyclo[22.3.1.04,9]octacos-18-ene-2,3,10,16-tetraone (510 mg) in 6.6 ml 33% methylene chloride in cyclohexane, was added allyl trichloroacetimidate (266 mg neat) and the reaction mixture was allowed to mix for 5 minutes. Trifluoromethanesulfonic acid (12 μl neat) was added slowly via syringe and the mixture stirred at room temperature. After 24 hours the reaction mixture was diluted with ethyl acetate and washed with saturated sodium carbonate, water and brine. The organic layer was dried over magnesium sulfate. Purification of the concentrate by flash chromatography on silica gel (ethyl acetate: hexane (1:9))+1% methanol) gave the title compound (434 mg). $^1$H NMR consistent with the desired structure.

STEP 12B

17-Ethyl-1-hydroxy-12-[2'-(4''-(2,3-dioxy-1-propoxy) -3''-methoxycyclohexyl)-1'-methylvinyl]-23,25-dimethoxy -13,19,21,27-tetramethyl-11,28-dioxa-4-azatricyclo -[22.3,1,0$^{4,9}$]octacos-18-ene-2,3,10,16-tetraone To a solution of 17-ethyl-1-hydroxy-12-[2'-(4''-allyloxy-3''-methoxycyclohexyl)-1'-methylvinyl]-23,25-dimethoxy-13,19,21,27-tetramethyl-11,28-dioxa-4-azatricyclo[22.3.1.04,9]octacos-18-ene-2,3,10,16-tetraone (434 mg)(STEP 12A) in 15 ml tetrahydrofuran, was added N-methylmorpholine N-oxide (431 mg) followed by 0.25 M osmium tetraoxide solution in THF (425 μl), and the mixture was stirred at room temperature. After 4.5 hours, the reaction was quenched by the addition of 20% sodium bisulfite, and the precipitate was filtered through Celite and rinsed with ethyl acetate. The combined filtrate was washed with 20% sodium bisulfite (2×), saturated sodium bicarbonate and brine and dried over magnesium sulfate. The concentrate was purified by flash chromatography on silica gel (ethyl acetate:-hexane (3:1)+1% methanol) to give the title compound (177 mg). $^1$H NMR consistent with the desired structure.

STEP 12C

17-Ethyl-1-hydroxy-12-[2'-(4''-ethanaloxy-3''-methoxy -cyclohexyl)-1'-methylvinyl]-23,25-dimethoxy-13,19,21,27-tetramethyl-11,28-dioxa-4-azatricyclo[22.3.1.0$^{4,9}$]octacos-18-ene-2.3.10.16-tetraone To a solution of 17-ethyl-1-hydroxy-12-[2'-(4''-(2,3-dioxy-1-propoxy)-3''-methoxycyclohexyl)-1'-methylvinyl]-23,25-dimethoxy-13,19,21,27-tetramethyl-11,28-dioxa-4-azatricyclo[22.3.1.04,9]octacos-18-ene-2,3,10,16-tetraone (177 mg) (STEP 12B) in 20% aqueous tetrahydrofuran (2 ml) was added sodium metaperiodate (67 mg) and the mixture stirred vigorously for 30 minutes. At this time an additional 20 mg of sodium metaperiodate were added. After 30 minutes the mixture was diluted with ethyl acetate, filtered through Celite and the residue rinsed with ethyl acetate. The organic portion was washed with saturated sodium bicarbonate and brine, dried over magnesium sulfate and purified by flash chromatography on silica gel (ethyl acetate:hexane (2:3)+1% methanol) to give the title compound (157 mg). $^1$H NMR consistent with the desired structure.

STEP 12D

17-Ethyl-1-hydroxy-12-[2'-(4''-carboxymethoxy-3''- methoxycyclohexyl)-1'-methylvinyl]-23,25-dimethoxy -13,19,21,27-tetramethyl-11,28-dioxa-4-azatricyclo -[22.3.1.0$^{4,9}$]octacos-18-ene-2,3,10,16-tetraone To a solution of 17-ethyl-1-hydroxy-12-[2'-(4''-ethanaloxy-3''-methoxycyclohexyl)-1'-methylvinyl]-23,25-dimethoxy-13,19,21,27-tetramethyl-11,28-dioxa-4-azatricyclo[22.3.1.04,9]octacos-18-ene-2,3,10,16-tetraone (157 mg) (STEP 12C) in tert-butanol (4 ml) and 2-methyl-2-butene (1 ml) was added sodium chlorite (159 mg) and sodium dihydrogen phosphate (159 mg) in water (1.6 ml) slowly. After 1 hour, the solvent was removed in vacuo, and the resulting residue was dissolved in water and acidified to pH 3 with 1 N HCl. The aqueous portion was with ethyl acetate (3×10 ml), and the combined organic portion was washed with brine. It was dried over magenesium sulfate and purified by f lash chromatography on silica gel (2% methanol in methylene chloride followed by 2% methanol in methylene chloride+0.5% acetic acid) to give the title compound (114 mg). $^1$H NMR consistent with the desired structure.

STEP 12E

17-Ethyl-1-hydroxy-12-[2'-(4''-methoxy-N-tryptophanyl -carbonylmethoxy-3''-methoxycyclohexyl)-1'-methylvinyl]-23,25-dimethoxy-13,19,21,27-tetramethyl-11,28- dioxa-4-azatricyclo[22.3.1.0$^{4,9}$]octacos-18-ene- 2,3,10,16-tetraone To a solution of 17-ethyl-1-hydroxy-12-[2' -(4''-carboxymethoxy-3''-methoxycyclohexyl)-1'- methylvinyl]-23,25-dimethoxy-13,19,21,27-tetramethyl-11,28-dioxa-4-azatricyclo[22.3.1.04,9]octacos-18-ene-2,3,10,16-tetraone (39 mg) (STEP 12D) in methylene chloride (0.5 ml) was added benzotriazol-1-yloxy-tris(-dimethylamino)phosphonium hexafluorophosphate (31 mg) followed by triethylamine (14 μl). After 10 minutes, tryptophan methyl ester hydrochloride (24 mg) was added to the reaction mixture and stirred for 1 hour. The mixture was diluted with ethyl acetate and washed with 1N HCl, water, saturated sodium bicarbonate and brine, respectively. The organic portion was dried over magnesium sulfate and purified by flash chromatography on silica gel (ethyl acetate:hexane (1:1)+1% methanol) to give the title compound (28 mg). MASS (FAB) 1041 (M+Li); Partial $^1$H NMR δ: 8.21 (brs, 1 H); 8.04 (brd, J=8 Hz, 1 H); 7.56 (d, J=8 Hz, 1 H); 7.33 (d, J=8 Hz, 1 H); 7.11(m, 3 H); 4.41 (brd, J=14 Hz, 1 H); 3.64 (s, 3 H).

EXAMPLE 13

7-Ethyl-1-hydroxy-12-[2'-(4"-3-indolylethylamino -carbonylmethoxy-3"-methoxycyclohexyl)-1'-methyl-vinyl]-23,25-dimethoxy-13,19,21,27-tetramethyl-11,28-dioxa-4-azatricyclo[22.3.1.0$^{4,9}$]octacos-18-ene-2,3,10,16-tetraone To a solution of 17-ethyl-1-hydroxy-12-[2'-(4"-carboxymethyloxy-3"-methoxycyclohexyl)-1'-methylvinyl]-23,25-dimethoxy-13,19,21,27-tetramethyl-11,28-dioxa-4-azatricyclo[22.3.1.04,9]octacos-18-ene-2,3,10,16 -tetraone (13 mg) (STEP 12D) in methylene chloride (150 μl) was added benzotriazol-1-yloxy-tris-(dimethylamino)phosphonium hexafluorophosphate (10.3 mg) followed by triethylamine (4.3 μl). After 10 minutes, tryptamine (5 mg) was added to the reaction mixture and stirred for 1 hour. The mixture was diluted with ethyl acetate and washed with 1 N HCl, water, saturated sodium bicarbonate and brine, respectively. The organic portion was dried over magnesium sulfate and purified by flash chromatography on silica gel (ethyl acetate:hexane (1:1)+1% methanol) to give the title compound (7.5 mg). MASS (FAB) 983 (M+Li); partial $^1$H NMR δ: 8.32 (brs, 1 H); 7.89 (m, 1 H); 7.58 (d, J=8 Hz 1 H); 7.31 (m, 1 H); 7.10 (m, 3 H); 4.51 (brd, J=3 Hz, 1 H); 4.41 (brd, J=14 Hz, 1 H).

EXAMPLE 14

17-Ethyl-1,14-dihydroxy-12-[2'-(4"-(1-N-methyl-5-indolyl)oxy-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone

STEP 14A

1-Methyl-5-bromoindole

A mixture of sodium hydroxide (0.4 g.,10 mmol.) in DMSO (20 mL.) was heated to 80°-85° C. for 6 hours to dissolve most of the solids then allowed to cool to room temperature. To the stirred mixture was added 5-bromoindole (2.0 g., 10 mmol.) followed in 1 hour by methyliodide (0.62 mL., 10 mmol.). After stirring for an additional 3 hours the reaction was shown by TLC analysis to be complete. The reaction mixture was diluted with water then extracted with ether. The extracts were washed 2× with water, dried with Na$_2$SO$_4$, and concentrated in vacuo to give 2.08 g. of 1-methyl-5-bromoindole as a yellow oil which crystallized on standing.

STEP 14B

Tri(1-methyl-indol-5-yl)bismuthine

To a solution of 1-methyl-5-bromoindole (5.0 g.,23.8 mmol.) in ether (100 mL.) at −78° C. was added a 1.7 M solution of t-butyllithium in pentane (28 mL. 47.6 mmol.). The mixture was stirred at −78° C. for 1 hour. To this mixture was then added a solution of bismuth trichloride (2.36 g., 7.5 mmol.) in THF (25 mL.) via syringe. The cooling bath was maintained for 2 hours then allowed to warm to room temperature overnight. In the morning the mixture was quenched with ice water and the product extracted 2× with toluene. The extracts were combined, washed with water, dried with Na$_2$SO$_4$, and concentrated in vacuo to a volume of about 30mL.. After chilling in the refrigerator for several hours the solid product was filtered, washed with cold toluene and vacuum dried to give tri(1-methyl-indol-5-yl)bismuthine (1.7 g.) as a mustard color solid.

STEP 14C

17-Ethyl-1,14-dihydroxy-12-[2'-(4"-(1-N-methyl-5-indolyl)oxy-3"-methoxycyclohexyl)-1'-methylvinyl]-23, 25-dimethoxy-13,19,21,27-tetramethyl-11,28-dioxa-4azatricyclo[22.3.1.0$^{4,9}$]octacos-18-ene-2,3,10,16-tetraone To a stirred solution of tri(1-methylindol -5-yl)bismuthine (450 mg., 0.75 mmol.)(STEP 14B) in CH$_2$Cl$_2$ (10 mL.) was added peracetic acid (0.158 mL.,0.75 mmol. 32% in acetic acid) followed in 15 minutes by 17-ethyl-1,14-dihydroxy-12-[2'-(4"-hydroxy -3"-methoxycyclohexyl)-1'-methylvinyl]-23,25-dimethoxy -13,19,21,27-tetramethyl-11,28-dioxa-4-azatricyclo-[22.3.1.0$^{4,9}$]octacos-18-ene-2,3,10,16-tetraone (350 mg., 0.442 mmol.) and Cu(OAc)$_2$. The mixture was stirred at room temperature for 2 days. The reaction was quenched with saturated aqueous NaHCO$_3$ and the product extracted 3× with CH$_2$Cl$_2$. The extracts were combined, dried over anhydrous Na$_2$SO$_4$, filtered, and concentrated in vacuo. The product was isolated and purified 2× by preparative TLC to give 203 mg. of the title compound as a colorless solid. MASS (FAB), m+Li 927. Partial $^1$H NMR (CDCl$_3$, 200 MHz) δ: 7.19 (bs, 1 H); 7.17 (d, J=10 Hz, 1 H); 6.98 (d, J=4 Hz, 1 H); 6.91 (dd, J=3 Hz and 10 Hz, 1 H); 6.34 (d, J=4 Hz, 1 H); 3.72 (s, 3 H); 3.51 (s, 3 H).

EXAMPLE 15

17-Ethyl-1,14,20-trihydroxy-12-[2'-(4"-(1-N-methyl -indol-5-yl)oxy-3"-methoxycyclohexyl)-1'-methyl-vinyl]-23,25-dimethoxy-13,19,21,27-tetramethyl-11,28-dioxa-4-azatricyclo[22.3.1.0$^{4,9}$]octacos-18-ene-2,3,10,16-tetraone To a stirred solution of tri(1-methylindol -5-yl)bismuthine (350 mg., 0.584 mmol.) in CH$_2$Cl$_2$ (6 mL.) was added peracetic acid (0.15 mL., 0.74 mmol., 1.32% in acetic acid) followed in 15 minutes by 17-ethyl-1,14,20-trihydroxy-12-[2'-(4"-hydroxy-3"-methoxycyclohexyl)-1'-methylvinyl]-23,25-dimethoxy -13,19,21,27-tetramethyl-11,28-dioxa-4-azatricyclo-[22.3.1.0$^{4,9}$]octacos-18-ene-2,3,10,16-tetraone (250 mg., 0.32 mmol.) and Cu(OAc)$_2$ (35 mg., 0.138 mmol.). The reaction mixture was stirred for 2 days at room temperature. The reaction was quenched with saturated aqueous NaHCO$_3$ and the mixture extracted 2× with CH$_2$Cl$_2$. The extracts were combined, dried with Na$_2$SO$_4$, filtered and concentrated in vacuo. The product was isolated by flash column chromatography on silica gel (3:1 hexane/acetone) followed by preparative TLC (3% CH$_3$OH in CH$_2$Cl$_2$) to give 111 mg of the title compound. MASS (FAB), M+Li 943. Partial $^1$H NMR (CDCl$_3$, 200 MHz) δ: 7.21 (bs, 1 H); 7.18 (d, J=7.5 Hz, 1 H); 6.98 (d, J=3 Hz, 1 H); 6.94 (dd, J=2.5 Hz and 7.5 Hz, 1 H); 6.37 (d, J=3 Hz, 1 H); 3.75 (s, 3 H); 3.59 (s, 3 H).

EXAMPLE 16

17-Ethyl-1-hydroxy-12-[2'-(4''-(1-N-methylindol-5-yl)oxy-3''-methoxycyclohexyl)-1'-methylvinyl]-23,25-dime-thoxy-13,19,21,27-tetramethyl-11,28-dioxa-4-azatricyclo [22.3.1.0$^{4,9}$]octacos-18-ene-2,3,10,16-tetraone To a stirred solution of tri(1-methylindol-5yl)bismuthine (35 mg.,0.058. mmol.) in CH$_2$Cl$_2$ (0.7 mL) was added peracetic acid (0.015 mL., 0.074 mmol., 32% in acetic acid) followed in 15 minutes by 17-ethyl-1-hydroxy-12-[2'-(4''-hydroxy-3''-methoxycyclo -hexyl)-1'-methylvinyl]-23,25-dimethoxy-13,19,21,27-tetramethyl-11,28-dioxa-4-azatricyclo[22.3.1.0$^{4,9}$]-octacos-18-ene-2,3,10,16-tetraone (25 mg., 0.032 mmol.) and Cu(OAc)$_2$ (5 mg., 0.03 mmol.). The reaction mixture was stirred for 3 days at room temperature. The reaction was quenched with saturated aqueous NaHCO$_3$ and extracted 2× with CH$_2$Cl$_2$. The extracts were combined, dried with Na$_2$SO$_4$, filtered and concentrated in vacuo. The product was isolated and purified by preparative TLC on silica gel (2:1 hexane/acetone then 5% CH$_3$OH in CH$_2$Cl$_2$) to give 10.2 mg of the title compound. Partial $^1$H NMR (CDCl$_3$, 200 MHz) δ: 7.18 (bs, 1 H); 7.16 (d, J=7.5 Hz, 1 H); 6.98 (d, J=3 Hz, 1 H); 6.92 (dd, J=2.5 Hz and 7.5 Hz, 1 H); 6.33 (d, J=3 Hz, 1 H); 3.64 (s, 3 H); 3.51 (s, 3 H).

EXAMPLES 17 AND 18

17-Ethyl-1,14-dihydroxy-12-[2'-(3''-hydroxy-4''-(1-N-methylindol-5-yl)oxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone and
17-Ethyl-1,14-dihydroxy-12-[2'-(4''-hydroxy-3'-(1-N-methylindol-5-yl)oxycyclohexyl)-1'-methylvinyl]-23,25-dimethoxy-13,19,21,27-tetramethyl-11,28-dioxa-4-azatricyclo[22.3.1.0$^{4,9}$]-octacos-18-ene-2,3,10,16-tetraone To a stirred solution of tri(1-methylindol-5-yl)bismuthine (150 mg., 0.25 mmol.) in CH$_2$Cl$_2$ (2 mL.) was added peracetic acid (0.05 mL., 0.23 mmol.,32% in acetic acid) followed in 10 minutes by 17-ethyl-1,14-dihydroxy-12-[2'-(3'', 4''-dihydroxycyclohexyl)-1'-methylvinyl]-23,25-dimethoxy-13,19,21,27-tetra methyl-11,28-dioxa-4-azatricyclo[22.3.1.0$^{4,9}$]octacos-18-ene-2,3,10,16-tetraone (100 mg, 0.129 mmol) and Cu(OAc)$_2$ (20 mg.,0.11 mmol.). The reaction mixture was stirred for 2 days at room temperature. The reaction was quenched with saturated aqueous NaHCO$_3$ and the mixture extracted 2× with CH$_2$Cl$_2$. The extracts were combined, dried with Na$_2$SO$_4$, filtered and concentrated in vacuo. The products were separated and purified 2× by preparative TLC (2:1 hexane/acetone then 5% CH$_3$OH in CH$_2$Cl$_2$) to give 19 mg of 17-ethyl-1,14-dihydroxy-12-[2'-(3''-hydroxy-4''-(1-methylindol-5-yl)-oxycyclohexyl)-1'-methylvinyl]-23,25-dimethoxy-13,19,—21,27-tetramethyl-11,28-dioxa -4-azatricyclo[22.3.1.—0$^{4,9}$]octacos-18-ene-2,3,10,16-tetraone, Partial $^1$H NMR (CDCl$_3$, 200 MHz) δ: 7.19 (d, J=10 Hz, 1 H); 7.17 (d, J=2.5 Hz, 1 H); 7.00 (d, J=3 Hz, 1 H); 6.88 (dd, J=2.5 Hz and 10 Hz, 1 H); 6.3 5 (d, J=3 Hz, 1 H); 3.73 (s, 3 H) and 33 mg of 17 -ethyl-1,14-dihydroxy-12-[2'-(4''-hydroxy-3''-(1-methylindol-5-yl)oxycyclo -hexyl)-1'-methylvinyl]-23,25-dimethoxy-13,19,21,27-tetramethyl-11,28-dioxa-4-azatricyclo[22.3.1.0$^{4,9}$]-octacos-18-ene-2,3,10,16-tetraone. Partial $^1$H NMR (CDCl$_3$, 200 MHz) δ: 7.18 (d, J=8 Hz, 1 H); 7.16 (d, J=2.5 Hz, 1 H); 6.98 (d, J=3 Hz, 1 H); 6.88 (dd, J=2.5 Hz and 8 Hz, 1 H); 6.33 (d, J=3 Hz, 1 H); 3.73 (s, 3 H).

EXAMPLE 19

Tri(indol-5-yl)bismuthine

A solution of 5-bromoindole (5.0 g., 25.5 mmol.) in ether (50 mL.) was slowly added, at 0° C., to a slurry of KH (2.8 g., 25 mmol., 35% in oil; washed 3× with hexanes) in ether (40 mL.). The reaction mixture was stirred for 20 minutes then chilled to −78° C. A precooled solution of t-butyllithium (29.7 mL., 50.5 mmol., 1.7 M in pentane) was added dropwise via syringe to the mixture followed in 40 minutes by a solution of BiCl$_3$ (1.89 g., 6.0 mmol.) in THF (25 mL.). The cooling bath was maintained for 2 hours then allowed to warm to room temperature overnight. The reaction was quenched with ice water and extracted 3× with toluene. The extracts were combined, dried with Na$_2$SO$_4$, filtered and concentrated in vacuo. The residue was diluted with 75 mL. of toluene then stored at 4° C. overnight. The solids were filtered and air dried to give 1.53 g of tri(indol-5-yl)bismuthine.

STEP 19B

17-Ethyl-1,14-dihydroxy-12-[2'-(4''-(indol-5-yl)oxy-3''-methoxycyclohexyl)-1'-methylvinyl]-23,25-dimethoxy -13,19,21,27-tetramethyl-11,28-dioxa-4-azatricyclo-[22.3.1.0$^{4,9}$]octacos-18-ene-2,3,10,16-tetraone To a stirred solution of tri(indol-5-yl)bismuthine (1.3 g.,2.33 mmol.), prepared by procedures outlined in STEP 14B in CH$_2$Cl$_2$ (30 mL.) was added peracetic acid (0.50 mL., 2.31 mmol., 32% in acetic acid) followed in 10 minutes by 17-ethyl-1,14-dihydroxy-12-[2'-(4''-hydroxy-3''-methoxycyclohexyl)-1'-methylvinyl]-23,25-dimethoxy-13,19,21,27-tetramethyl -11,28-dioxa-4-azatricyclo[22.3.1.0$^{4,9}$]octacos-18-ene-2,3,10,16-tetraone (1.0 g., 1.26 mmol.) and Cu(OAc)$_2$ (100 mg.,0.55 mmol.). The reaction mixture was allowed to stir at room temperature for 3 days. The reaction was quenched with saturated aqueous NaHCO$_3$ and the mixture extracted 2× with CH$_2$Cl$_2$. The extracts were combined, dried with Na$_2$SO$_4$, filtered and concentrated in vacuo. The product was isolated and purified by preparative TLC 2× with 2:1 hexane/acetone and once with 2:1 hexane/EtOAc to give 208 mg of the title compound. MASS (FAB), M+906. Partial $^1$H NMR (CDCl$_3$, 200 MHz) δ: 8.12 (bs, 1 H); 7.26 (d, J=10 Hz, 1 H); 7.22 (d, J=2.5 Hz, 1 H); 7.18 (m, 1 H); 6.9 (dd, J=2.5 Hz and 10 Hz, 1 H); 6.44 (m, 1 H); 3.53 (s, 3 H).

EXAMPLE 20

17-Allyl-1,14-dihydroxy-12-[2'-(4''-(indol-5-yl)oxy-3''-methoxycyclohexyl)-1'-methylvinyl]-23,25-dimethoxy -13,19,21,27-tetramethyl-11,28-dioxa-4-azatricyclo-[22.3,1,0$^{4,9}$]octacos-18-ene-2,3,10,16-tetraone To a stirred solution of tri(indol-5-yl)bismuthine (150 mg., 0.27 mmol.) in CH$_2$Cl$_2$ (3 mL.) was added peracetic acid (0.05 mL., 0.23 mmol., 32% in acetic acid) followed in 15 minutes by 17-allyl-1,14-dihydroxy-12-[2'-(4''-hydroxy-3''-methoxy -cyclohexyl)-1'-methylvinyl]-23,25-dimethoxy-13,19,21,27-tetramethyl-11,28-dioxa-4-azatricyclo-[22.3.1.0$^{4,9}$]octacos-18-ene-2,3,10,16-tetraone (100 mg., 0.124 mmol.) and Cu(OAc)$_2$ (20 mg., 0.11 mmol.). The reaction mixture was allowed to stir at room temperature for 2 days. The reaction was quenched with saturated aqueous NaHCO$_3$ and the mixture extracted with $CH_2Cl_2$. The extracts were combined, dried with $Na_2SO_4$, filtered and concentrated in vacuo. The product was isolated and purified by preparative TLC 2× (2:1 hexane/acetone then 5% $CH_3OH$ in $CH_2Cl_2$) to give 11 mg of the title compound. MASS (FAB), M+Li 925. Partial $^1H$ NMR ($CDCl_3$, 200 MHz) δ: 8.12 (bs, 1 H); 7.24 (d, J=10 Hz, 1 H); 7.22 (d, J=2.5 Hz, 1 H); 7.17 (t, J=3 Hz, 1 H); 6.9 (dd, J=3 Hz and 10 Hz, 1 H); 6.44 (bs, 1 H); 5.70 (m, 1 H); 3.53 (s, 3 H).

EXAMPLE 21

17-Ethyl-1,14-dihydroxy-12-[2'-(4"-(1-ethylindol-5-yl)oxy-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a stirred solution of tri(1-ethylindol-5-yl)bismuthine (150 mg., 0.23 mmol.), prepared by procedures outlined in STEP 13B, in $CH_2Cl_2$ (3 ml) was added peracetic acid (0.063 mL., 0.3 mmol., 32% in acetic acid) followed in 15 minutes by 17-ethyl-1,14-dihydroxy-12-[2'-(4"-hydroxy-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (100 mg., 0.126 mmol.) and Cu(OAc)$_2$ (20 mg., 0.11 mmol.). The reaction mixture was allowed to stir at room temperature for 3 days. The reaction was then quenched with saturated aqueous $NaHCO_3$ and the mixture extracted 2× with $CH_2Cl_2$. The extracts were combined, dried with $Na_2SO_4$, filtered, and concentrated in vacuo to a brown oil. The product was isolated and purified by preparative TLC on silica gel (first with 2:1 hexane/acetone followed by 3% $CH_3OH$ in $CH_2Cl_2$) to give 60 mg of the title compound. MASS (FAB) M+Na 957. Partial $^1H$ NMR ($CDCl_3$, 200 MHz) δ:7.19 (d, J=10 Hz, 1H>; 7.18 (d, J=3 Hz, 1H); 7.05 (d, J=4 Hz, 1H); 6.90 (dd, J=3 Hz, 10 Hz, 1H); 6.35 (d, J=4 Hz, 1H); 4.09 (q, J=6.7 Hz, 2H); 3.5 (s, 3H); 1.4 (t, J=6.7 Hz, 3H).

EXAMPLE 22

17-Ethyl-1,14-dihydroxy-12-[2'-(4"-(1-ethylindol-5-yl)oxy-3"-hydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a solution of tri(1-ethylindol-5-yl)bismuthine (0.2 gm) prepared by procedures outlined in Step 13B in $CH_2Cl_2$ (2 ml) at room temperature was added peracetic acid (37 μL, 0.2 mmol). After stirring for 15 minutes at room temperature, was added 17-ethyl-1,14-dihydroxy-12-[2'-(4",3"-dihydroxycyclohexyl)-1'-methylvinyl]-23,25-dimethoxy-13,19,21,28-tetramethyl-11,28-dioxa-4-azatricyclo[22.3.1.0$^{4,9}$]octacos-18-ene-2,3,10,16-tetraone (0.2 gm, 0.25 mmol) followed by Cu(OAc)$_2$ (0.2 gm) and the reaction mixture was stirred for 2 days. To the reaction mixture was then added saturated $NaHCO_3$ (approximately 20 ml) and the mixture was extracted twice with $CH_2Cl_2$. The combined organic extracts were dried over $Na_2SO_4$, filtered and concentrated in vacuo. The mixture of 17-ethyl-1,14-dihydroxy-12-[2'-(4"-(1-ethylindol-5-yl)oxy-3"-hydroxycyclohexyl)-1'-methylvinyl]-23,25-dimethyoxy-13,19,21,27-tetramethyl-11,28-dioxa-4-azatricyclo[22.3.1.0$^{4,9}$]octacos-18-ene-2,3,10,16-tetraone and 17-ethyl-1,14-dihydroxy-12-[2'-(4"-hydroxy-3"-(1-ethylindol-5-yl)oxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone were separated by chromatography (silica, 3:1, hexanes:ethyl acetate) to give the title compound (0.035 gm). TLC (silica, 3:1, hexanes:ethyl acetate) R$_f$=0.55. Partial $^1H$ NMR ($CDCl_3$, 200 MHz) δ:7.21 (d, J=10 Hz, 1H); 7.14 (d, J=3 Hz, 1H); 7.08 (d, J=4 Hz, 1H); 6.85 (dd, J=3 Hz and 10 Hz, 1H); 6.36 (d, J=4 Hz, 1H), 4.10 (q, J=6.7 Hz, 2H); 1.42 (t, J=6.7 Hz, 3H).

EXAMPLE 23

17-Ethyl-1,14-dihydroxy-12-[2'-(4"-(1-propylindol-5-yl)oxy-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a stirred solution of tri(1-propylindol-5-yl)bismuthine (200 mg., 0.29 mmol.), prepared by procedures analogous to STEP 14A and B, in $CH_2Cl_2$ (3 mL.) was added peracetic acid ( 0.075 mL., 0.36 mmol., 32% in acetic acid) followed in 10 minutes by 17-ethyl-1,1-4-dihydroxy-12-[2'-(4"-hydroxy-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (150 mg., 0.19 mmol.) and Cu(OAc)$_2$ (30 mg., 0.17 mmol.). The reaction mixture was stirred for 20 hours at room temperature. The reaction was then quenched with saturated aqueous $NaHCO_3$ and the mixture extracted with $CH_2Cl_2$. The extracts were combined, dried with $Na_2SO_4$, filtered and concentrated in vacuo. The product was isolated and purified by preparative TLC 3× on silica gel (2:1, hexane/acetone; 3% $CH_{30}H$ in $CH_2Cl_2$; 2:1, hexane/acetone) to give 70 mg of the title compound. MASS (FAB) M+Na 971. Partial $^1H$ NMR ($CDCl_3$, 200 MHz) δ:7.17 (d, J=10 Hz, 1H); 7.02 (d, J=4 Hz, 1H); 6.88 (dd, J=3 Hz and 10 Hz, 1H); 6.32 (d, J=4 Hz, 1H); 3.97 (t, J=7 Hz, 2H), 3.50 (s, 1.80 (m, 2H).

EXAMPLE 24

17-Ethyl-1,14-dihydroxy-12-[2'-(4"-(1-propylindol-5-yl)oxy-3"-hydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a stirred solution of tri(1-propylindol-5-yl)bismuthine (200 mg., 0.29 mmol.), prepared by procedures analogous to Step 14A and B, in $CH_2Cl_2$ (3 mL.) is added peracetic acid ( 0.075 mL., 0.36 mmol.,32% in acetic acid) followed in 10 minutes by 17-ethyl-1,14-dihydroxy-12-[2'-(3",4"-dihydroxy-3"-cyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (150 mg., 0.19 mmol.) and Cu(OAc)$_2$ (30 mg., 0.17 mmol.). The reaction mixture is stirred for 20 hours at room temperature. The reaction is then quenched with saturated aqueous $NaHCO_3$ and the mixture extracted with $CH_2Cl_2$. The extracts are combined, dried with $Na_2SO_4$, filtered and concentrated in vacuo. The product is isolated and purified from the C-3" ether by preparative TLC on silica gel to give the title compound.

EXAMPLE 25

17-Ethyl-1,14-dihydroxy-12-[2'-(4''-(1-hydroxyethylindol-5-yl)oxy-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone

STEP 25A 1-(2-Hydroxyethyl)-5-bromoindole

A mixture of NaOH (4.4 gm, 0.011 mol) in DMSO (175 ml) was stirred at 100° C. for 5 hours at which time it was cooled to 20° C. To this mixture was added 5-bromoindole (20 gm, 0.102 mol) and the reaction was stirred for 8 hours at room temperature. A solution of ethylene oxide (5.1 gm, 0.125 mol) in DMSO (20 ml) was prepared by bubbling the gas into DMSO. To the bromoindole reaction mixture was slowly added the ethylene oxide solution and stirring was continued for another 2.5 hours. The reaction mixture was then poured into ice water and extracted twice with diethyl ether. The combined ether extracts were concentrated in vacuo whereupon crystallization took place. The crude product was recrystallized from diethyl ether:hexanes (3:2) to afford the title compound (6.25 gm).

STEP 25B 1-(2-t-Butyldimethylsilyloxyethyl)-5-bromoindole

A solution of 1(2-hydroxyethyl)-5-bromoindole (6 gm, 0.025 mol), t-butyldimethylsilyl chloride (4.5 gm, 0.03 mol) and triethylamine (4.2 ml, 0.03 mol) in $CH_2Cl_2$ (60 ml) was stirred for 12 hours at room temperature. The reaction mixture was then washed twice with $H_2O$, dried over $Na_2SO_4$, filtered and concentrated in vacuo to provide the title compound as a yellow oil. $^1H$ NMR was consistent with the desired structure.

STEP 25C

Tri[1-(2-t-butyldimethylsilyloxyethyl)-indol-5-yl]bismuthine

To a solution of 1(2-t-butyldimethylsilyloxyethyl)-5-bromoindole (1.4 gm, 0.004 mol) in diethyl ether (14 ml) at −78° C. was added t-butyl lithium (4.7 ml of a 1.7M solution in pentaries, 0.008 mol). After stirring for 1.5 hours, a solution of bismuth trichloride (0.4 gm, 0.013 mol) in THF (4 mL) was added. The reaction was stirred at −78° C. for 2 hours and then allowed to warm slowly to room temperature and stirring was continued a further 8 hours. The reaction mixture was then poured into $H_2O$ and extracted with toluene. The combined organic extracts were dried over $Na_2SO_4$, filtered and the filtrate was concentred in vacuo. Purification by chromatography (silica, 4:1, hexanes:ethyl acetate) provided the title compound (1.03 gm) as a semisolid. $^1H$ NMR was consistent with desired structure.

STEP 25D

17-Ethyl-1,14-dihydroxy-12-[2'-(4''-(1-t-butyldimethylsilyloxyethylindol-5-yl)oxy-3,,-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a solution of tri[1-(2-t-butyldimethylsilyloxyethyl)-indol-5-yl]bismuthine (1.03 gm, 0.001 mol) in $CH_2Cl_2$ (10 ml) at room temperature was added peracetic acid (150 μL). After stirring for 15 minutes, 17-ethyl-1,14-dihydroxy-12-[2'-(4''-hydroxy-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (1 gm) was added to the reaction mixture followed by Cu-(OAc)$_2$ (0.0 4 gm) and the reaction mixture was stirred for 20 hours. To the react ion mixture was then added saturated NaHCO$_3$ and it was then extracted with $CH_2Cl_2$. The organic extracts were dried over $Na_2SO_4$, filtered and the filtrate was concentrated in The crude product was purified by chromatography (silica, 3:1, hexanes:ethyl acetate) to provide the title compound (0.38 gm). $^1H$ NMR was consistent with desired structure.

17-Ethyl-1,14-dihydroxy-12-[2'-(4''-(1-hyd roxyethylindol-5-yl)oxy-3''-methoxycyclohexyl)-1,-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a solution of 17-ethyl-1,14-dihydroxy-12--[2'-(4''-(1-t-butyldimethylsilyloxyethylindol-5-yl)oxy-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (0.38 gm) in $CH_2Cl_2$ (10 ml) at room temperature was added a solution of para-toluene sulfonic acid (0.05 gm) in $CH_3OH$. The reaction mixture was stirred for 3 hours until TLC (silica, 2:1, hexanes:ethyl acetate) verified that reaction was complete. The reaction mixture was poured into saturated NaHCO$_3$ and extracted twice with $CH_2Cl_2$. The combined organic extracts were dried over $Na_2SO_4$, filtered and concentrated in vacuo. The crude product was purified by chromatography (silica, 2:1 hexanes:ethyl acetate) to provide the title compound 0.245 gm. MASS (FAB) M+Li 957. Partial $^1H$ NMR (CDCl$_3$, 200 MHz) δ:7.18 (d, J=10 Hz, 1H); 7.16 (bs, 1H); 7.06 (d, J=4 Hz, 1H); 6.86 (dd, J=3Hz and 10 Hz, 1H); 6.33 (d, J=4 Hz, 1H); 4.13 (t, J=6.7 Hz, 2H); 3.83 (t, J=6.7 Hz, 2H); 3.43 (s, 3H).

EXAMPLE 26

17-Ethyl-1,14-dihydroxy-12-[2'-(4''-(1'-allylindol-5'-yl)oxy-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone

STEP 26A

1-Allyl-5-bromoindole

To a stirred mixture of NaOH (204 mg., 5.1 mmol., 1 eq.) in DMSO (10 mL.) was added 5-bromoindole (1.0 g., 5.1 mmol., 1 eq.). The solution was stirred for three hours upon complete dissolution of the NaOH (approximately 1 h.). To this solution was added allyl iodide (0.466 mL., 5.1 mmol., 1 eq.) via syringe. After 2 h. the mixture was diluted with water and extracted 2× with diethyl o ether. The organic extracts were combined, dried over anhydrous MgSO$_4$, filtered and concentrated in vacuo. The product was purified by flash column chromatography on silica gel (4:1 hexanes/acetone) affording 730 mg 1-allyl-5-bromoindole.

STEP 26B

Tri(1-allylindol-5-yl)bismuthine

To a stirred solution of 1-allyl-5-bromoindole (730 mg., 3.09 mmol., 1 eq.) in diethyl ether (15 mL) at −78° C. under N$_2$ was added t-butyllithium (1.8 mL., 3.09 mmol., 1 eq., 1.7M solution in pentane). The mixture was stirred at −78° C. under N₂ for 1 h.. To this mixture was added a solution of bismuth trichloride (292 mg., 0.93 mmol., 0.3 eq.) in dry THF (3 mL.) dropwise via syringe. The ice bath was packed with dry ice and the flask covered. The mixture was allowed to warm slowly to room temperature overnight. The reaction mixture was then diluted with toluene and washed with brine. The layers were separated and the aqueous layer extracted 3× with toluene. The organic extracts were combined, dried over anhydrous Na₂SO₄, filtered and concentrated in vacuo. The residue was dissolved in ether and filtered through a 0.4 micron pTFE membrane. The product started to crystallize. Cooled solution in freezer. Collected crystals giving 200 mg. of tris-1-allylindol-5-yl)bismuthine.

STEP 26C

17-Ethyl-1,14-dihydroxy-12-[2'-(4"-(1'-allylindol-5'-yl)oxy-3"-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone To a stirred solution of tri(1-allylindol-5-yl)bismuthine (186 mg., 0.275 mmol., 1.2 eq.) in CH₂Cl₂ (3 mL.) was added peracetic acid (0.064 mL., 0.303 mmol., 1.32 eq., 32% solution in dilute acetic acid). To this solution was added THF (1 mL.), 17-ethyl-1,14-dihydroxy-12-[2'-(4"-hydroxy-3"-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone (181 mg., 0.229 mmol., 1 eq.) and copper(II)acetate (10 mg., 0.055 mmol., 0.24 eq.). The mixture was capped and stirred overnight. The reaction was diluted with saturated aqueous NaHCO₃ and extracted 4× with CH₂Cl₂. The organic extracts were combined, dried over anhydrous Na₂SO₄, filtered and concentrated in vacuo. The product was isolated and purified by flash column chromatography on silica gel (2:1 hexanes/acetone) followed by preparative TLC (3.5% methanol/CH₂Cl₂) affording 56 mg pure title compound. MASS (FAB) M+Li 953. Partial ¹H NMR (CDCl₃, 200 MHz) δ:7.17 (bs, 1H); 7.15 (d, J=10 Hz, 1H); 7.02 (d, J=3 Hz, 1H); 6.88 (dd, J=2 Hz and 10 Hz, 1H); 6.36 (d, J=3 Hz, 1H); 5.95 (m, 1H); 4.63 (bd, J=14 Hz, 1H); 3.50 (s, 3H).

EXAMPLE 26

17-Ethyl-1,14-dihydroxy-12-[2'-(4"-(1'-allylindol-5'yl)oxy-3"-hydroxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone To a stirred solution of tri(1-allylindol-5-yl)bismuthine (1.0 g, 1.48 mmol, 1.2 eq) in CH₂Cl₂ (9 mL) and THF (3 mL) was added peracetic acid (0.315 mL, 1.62 mmol, 1.32 eq, 32% solution in diluted acetic acid). To this solution was added 17-ethyl-1,14-dihydroxy-12-[2,-4(4",3"-dihydroxycyclohexyl)-1'-methylvinyl]-23,25-dimethoxyo-13,19,21,27-tetramethyl-11,28-dioxa-4-azatricyclo[22.3.1.0⁴,⁹]octacos-18-ene-2,3,10,16-tetraone (956 mg, 1.23 mmol, 1 eq) and copper (II)acetate (22 mg, 0.123 mmol, 0.1 eq). The mixture was capped and stirred for four days. The reaction was diluted wit saturated aqueous NaHCO₃ and extracted 4× with CH₂Cl₂. The organic extracts were combined, dried over anhydrous NaSO₄, filtered and concentrated in vacuo. The product was isolated and purified by flash column chromatography on silica gel (3:1 hexanes/acetone) followed by preparative TLC (3.5% methanol/CH₂Cl₂ affording 163 mg pure 17-ethyl-1,14-dihydroxy-12-[2'-(4"-1'-allylindol-5'yl)oxy-3"-hydroxy cyclohexyl]-1'-methylvinyl]-23,25-dimethoxy-13,19,21, 27-tetramethyl-11,28-dioxa-4-azatricyclo[22.3.1.0⁴,⁹] octacos-18-ene-2,3,10,16-tetraone. MASS (FAB), M+Li 953. Partial ¹H NMR (CDCL₃, 200 MHz) δ: 7.17 (d, J=10 Hz, 1H); 7.15 (brs, 1H); 7.05 (d, J=3 Hz, 1H); 6.86 (dd, J=10 Hz, J=2.5 Hz, 1H); 6.39 (d, J=3 Hz, 1H); 6.05–5.85 (m, 1HO; 4.66 (brd, J=8.5 Hz, 2H); 4.57 (brd, J=5 Hz, 1H); 4.38 (brd, J=13 Hz, 1H).

EXAMPLE 28

17-Ethyl-1,14-dihydroxy-12-[2'-(4"-(9'-methylcarbazol-3'-yl)oxy-3"-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone

STEP 28A

Tri(9-methylcarbazol-3-yl)bismuthine

To a stirred mixture of 3-bromo-9-methylcarbazole (646 mg., 2.48 mmol., 1 eq.) in diethyl ether (12 mL) at −78° C. (not all carbazole in solution) under N₂ was added t-butyllithium (3.0 mL., 4.96 mmol., 2 eq., 1.7M solution in pentane). The mixture was warmed quickly to room temperature and then quickly cooled to −78° C. and stirred under N₂ for 40 minutes. To this mixture was added a solution of bismuth trichloride (235 mg., 0.744 mmol., 0.3 eq.) in dry THF (2.5 mL.) dropwise via syringe. The ice bath was packed with dry ice and the flask covered. The mixture was allowed to warm slowly to room temperature overnight. The reaction mixture was poured into a separatory funnel containing brine and etracted 4× with CH₂Cl₂. The organic extracts were combined, dried over anhydrous Na₂SO₄, filtered and concentrated in vacuo. The solid residue was triurated with ether and ether/methanol. The solids were collected giving 200 mg. of tri(9-methylcarbazol-3-yl)bismuthine. The supernatant was saved for further purification.

STEP 28B

17-Ethyl-1,14-dihydroxy-12-[2'-(4"-(9'-methylcarbazol-3'-yl)oxy-3"-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone To a stirred mixture of tri(9-methylcarbazol-3-yl)bismuthine (200 mg., 0.267 mmol., 1.2 eq.) in CH₂Cl₂ (3 mL.) and THF (1 mL.) was added peracetic acid (0.062 mL., .295 mmol., 1.32 eq., 32% solution in dilute acetic acid). To this solution was added 17-ethyl-1,14-dihydroxy-12-[2'-(4"-hydroxy-3"-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone (175 mg., 0.222mmol., 1 eq.) and copper(II)acetate (10 mg., 0.055 mmol., 0.24 eq.). The mixture was capped and stirred for 48 hours. The reaction was diluted with saturated aqueous NaHCO₃ and extracted 4× with CH₂Cl₂. The organic extracts were combined, dried over anhydrous Na₂SO₄, filtered and concentrated in vacuo. The product was isolated and purified by flash column chromatography on silica gel (3:1 hexanes/acetone) followed by preparative TLC (3.5% methanol/CH₂Cl₂) affording 100 mg of the title compound. MASS (FAB) M+Li 977. Partial ¹H NMR (CDCl$_3$, 200 MHz) δ:7.68 (d, J=2 Hz, 1H); 7.48–7.10 (m, 6H); 4.58 (bd, J=4.8 Hz, 1H); 4.39 (bd, J=14 Hz, 1H); 3.80 (s, 3H); 3.53 (s, 2H).

EXAMPLE 29

17-Ethyl-1,14-dihydroxy-12-[2'-(4"-(1'-benzylindol-5-yl)oxy-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone

STEP 29A

1-Benzyl-5-bromoindole

To a stirred mixture of Na$_0$H (204 mg., 5.1 mmol., 1 eq.) in DMSO (10 mL.) was added 5-bromoindole (1.0 g., 5.1 mmol., 1 eq.). The solution was stirred for 20 hours upon complete dissolution of the NaOH (approximately 1 h.). To this solution was added benzyl bromide (0.606 mL., 5.1 mmol., 1 eq.) via syringe. After 7 h. the mixture was diluted with water and extracted 4× with diethyl ether. The organic extracts were combined, dried over anhydrous MgSO$_4$, filtered and concentrated in vacuo. The product was purified by crystallization (ether/hexanes) affording 888 mg of 1-benzyl-5-bromoindole.

STEP 29B

Tri(1-benzylindol-5-yl)bismuthine

To a stirred mixture of 1-benzyl-5-bromoindole-3 (888 mg., 3.105 mmol., 1 eq.) in diethyl ether (15 mL) at −78° C. (not all indole was in solution) under N$_2$ was added t-butyllithium (3.65 mL., 6.21 mmol., 2 eq., 1.7M solution in pentane). The mixture was stirred at −78° C. under N$_2$ for 1 hour. To this mixture was added a solution of bismuth trichloride (294 mg., 0.932 mmol., 0.3 eq.) in dry THF (3 mL.) dropwise via syringe. The ice bath was packed with dry ice and the flask covered. The mixture was allowed to warm slowly to room temperature overnight. The reaction mixture was poured into a separatory funnel containing brine and extracted 4× with CH$_2$Cl$_2$. The organic extracts were combined, dried over anhydrous Na$_2$SO$_4$, filtered and concentrated in vacuo. The solid residue was triurated with ether. The solids were collected giving 200 mg. of tri(9-methylcarbazol-3-yl)bismuthine. The supernatant was saved for further purification.

STEP 29C

17-Ethyl-1,14-dihydroxy-12-[2'-(4"-(1'-benzylindol-5-yl)oxy-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a stirred mixture of tri(1-benzylindol-5-yl)-bismuthine (200 mg., 0.242 mmol., 1.2 eq.) in CH$_2$Cl$_2$ (3 mL.) and THF (1 mL.) was added peracetic acid (0.060 mL., .285 mmol., 1.4 eq., 32% solution in dilute acetic acid). To this solution was added 17-ethyl-1,14-dihydroxy-12-[2'-(4"-hydroxy-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (159 mg., 0.202 mmol., 1 eq.) and copper(II)acetate (10 mg., 0.055 mmol., 0.24 eq.). The mixture was capped and stirred overnight. The reaction was diluted with saturated aqueous NaHCO$_3$ and extracted 4× with CH$_2$Cl$_2$. The organic extracts were combined, dried over anhydrous Na$_2$SO$_4$, filtered and concentrated in vacuo. The product was isolated and purified by flash column chromatography on silica gel (3:1 hexanes/acetone) followed by preparative TLC (3.5% methanol/CH$_2$Cl$_2$) affording 100 mg of the title compound. MASS (FAB) M+Li 1003. Partial $^1$H NMR (CDCl$_3$, 200 MHz) δ:7.3–7.0 (m, 8H); 6.84 (dd, J=9 Hz, 1H); 6.40 (d, 3 Hz, 1H); 5.23 (bs, 2H); 4.6 (bd, J=6 Hz, 1H); 4.38 (bd, J=14 Hz, 1H); 3.50 (s, 3H).

EXAMPLE 31

17-Ethyl-l-hydroxy-12-[2'-(4"-(l-N-methyl-5-indolyl)-oxy-3"-allyloxycyclohexyl)-1'-methylvinyl]-23,25-dimethoxy-13,19,21,27-tetramethyl-11,28-dioxa-4-azatricyclo [22.3.1.0$^{4,9}$]octacos-18-ene-2,3,10,16-tetraone

STEP 31A

17-Ethyl-l-hydroxy-12-[2'-(4"-(tert-butyldimethylsiloxy)-3"-allyloxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a solution of 17-ethyl-l-hydroxy-12-[2'-(4"-(tert-butyldimethylsiloxy)-3"-hydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (300 mg) in 9 ml 33% methylene chloride in cyclohexane was added allyl trichloroacetimidate (138 mg neat) and the reaction mixture was allowed to mix for 5 minutes. Trifluoromethanesulfonic acid (18 μl neat) was added slowly via syringe and the mixture stirred at room temperature. After 3 days the reaction was diluted with ethyl acetate and quenched with saturated sodium bicarbonate. The layers were separated, and the organic layer was washed with brine then dried over magnesium sulfate. Purification of the concentrate by flash chromatography on silica gel (ethyl acetate: hexane (1:4)+1% methanol) gave the title compound (230 mg; trichloroacatamide present). $^1$H NMR consistent with the desired structure.

STEP 31B

17-Ethyl-l-hydroxy-12-[2'-(4"-hydroxy-3"-allyloxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a solution of 17-ethyl-l-hydroxy-12-[2'-(4"-(tert-butyldimethylsiloxy)-3"-allyloxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (115 mg) (STEP 31A) in acetonitrile (2.5 ml) was added a solution of 2% HF in aqueous acetonitrile (40 μl), and the mixture was stirred at room temperature. After 4 hours, the solution was diluted with ethyl acetate and quenched with saturated sodium bicarbonate. The layers were separated, and the organic layer was washed with brine and dried over magnesium sulfate. Purification of the concentrate-by flash chromatography on silica gel (ethyl acetate:hexane (1:2)) gave the title compound (42 mg). $^1$H NMR consistent with the desired structure.

STEP 31C

17-Ethyl-1-hydroxy-12-[2'-(4"-(1-N-methyl-5-indolyl)oxy-3"-allyloxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2.3.10.16-tetraone To a solution of tri(1-methylindol-5-yl)bismuthine (53 mg) in methylene chloride (700 µl) was added peracetic acid (17 µl), and the mixture was stirred at room temperature for 15 minutes. 17-ethyl-1-hydroxy-12-[2'-(4"-hydroxy-3"-allyloxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (42 mg) was dissolved in methylene chloride (270 µl) and added to the reaction mixture. After 18 hours the mixture was diluted with ethyl acetate and washed with saturated sodium bicarbonate and brine then dried over magnesium sulfate. Purification of the concentrate by flash chromatography on silica gel (ethyl acetate:-hexane (1:3) +1% methanol) gave the title compound (25 mg). MASS (FAB) 938 (M+Li); Partial $^1$H NMR δ: 7.19 (s, 1H); 7.18 (d, J=9 Hz, 1H); 6.98 (d, J=3 Hz, 1H); 6.92 (dd, J=9,3 Hz, 1H); 6.34 (d, J=3 Hz, 1H); 5.89 (m,1H); 4.56 (brd, J=4 Hz, 1H); 3.72 (s, 3H).

EXAMPLE 32

17-Ethyl-1-hydroxy-12-[2'-(4"-(1-N-methyl-5-indolyl)oxy-3"-n-propyloxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a solution of 17-ethyl-1-hydroxy-12-[2'-(4"-(1-N-methyl-5-indolyl)oxy-3"-allyloxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (20 mg)(EXAMPLE 31) in ethyl acetate (500 µl) was added rhodium on carbon (5 mg). The flask was filled with hydrogen, and the mixture was stirred at room temperature. After 1.5 hours the mixture was filtered through Celite then the solvent was removed in vacuo to give the title compound (20 mg). MASS (FAB) 940 (M+Li); Partial $^1$H NMR δ: 7.18 (s,1H); 7.16 (d, J=9 Hz, 1H); 6.96 (d, J=3Hz, 1H); 6.92 (dd, J=9,3Hz, 1H); 6.34 (d, J=3 Hz, 1H); 4.55 (brd, J=4 Hz, 1H); 3.72 (s, 3H).

EXAMPLE 33

17-Ethyl-1,14-dihydroxy-12-[2'-(4"-(1-N-methyl-5-indolyl)oxy-3"-i-propyloxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone

STEP 33A

17-Ethyl-1,14-dihydroxy-12-[2'-(4"-hydroxy-3"-i-propyloxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a solution of 17-ethyl-1,14-dihydroxy-12-[2'-(3",4"-dihydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (300 mg in 4.5 ml 33% methylene chloride in cyclohexane) isopropyl trichloroacetimidate (142 mg neat) was added and the reagents allowed to mix for 5 minutes. Trifluoromethanesulfonic acid (13.4 µl neat) was added slowly via syringe and the mixture stirred at room temperature. After 5 days the reaction was diluted with ethyl acetate and quenched with saturated sodium bicarbonate. The layers were separated, and the organic layer was washed with brine then dried over magnesium sulfate. Purification of the concentrate by preparative TLC on silica gel (ethyl acetate : hexane (1:1)+1% methanol) gave the title compound (42 mg). $^1$H NMR consistent with the desired structure.

STEP 33B

17-Ethyl-1,14-dihydroxy-12-[2'-(4"-(1-N-methyl-5-indolyl)oxy-3"-i-propyloxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a solution of tri(1-methylindol-5-yl)bismuthine (52 mg) in methylene chloride (700 µl) was added peracetic acid (17 µl), and the mixture was stirred at room temperature for 15 minutes. 17-ethyl-1,14-dihydroxy-12-[2'-(4"-hydroxy-3"-ipropyloxycyclohexyl)-1'-methylvinyl]-23,25-dimethoxy-13,19,21,27- tetramethyl-11,28-dioxa-4-azatricyclo[22.3.1.0$^{4,9}$]octacos-18-ene-2,3,10,16-tetraone (42 mg) was dissolved in methylene chloride (450 µl) and added to the reaction mixture. After 18 hours the mixture was diluted with ethyl acetate and washed with saturated sodium bicarbonate and brine then dried over magnesium sulfate. Purification of the concentrate by preparative TLC on silica gel (ethyl acetate:hexane (1:1+1% methanol) gave the title compound (9 mg). MASS (FAB) 956 (M+Li) Partial $^1$H NMR δ: 7.19 (s, 1H); 7.16 (d, J=9 Hz, 1H); 6.97 (d, J=3 Hz, 1H); 6.92 (dd, J=9, 3 Hz, 1H); 6.34 (d, J=3 Hz, 1H); 4.41 (brd, J=14 Hz, 1H); 2.72 (s, 3H).

EXAMPLE 34

17-Ethyl-1,14-dihydroxy-12-[2'-(4"-(1-N-methyl-5-indolyl)oxy-3"-allyloxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone

STEP 34A

17-Ethyl-1,14-dihydroxy-12-[2'-(4"-(tert-butyldimethylsiloxy)-3"-hydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a solution of 17-ethyl-1,14-dihydroxy-12-[2'-(3",4"-dihydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (1.0 g) in dry methylene chloride (14 ml) was added 2,6-lutidine (240 µl) and the mixture was stirred at room temperature. After 10 minutes, tert-butyldimethylsilyl trifluoromethanesulfonate (295 µl) was added via syringe. After 15 minutes the reaction mixture was diluted with ethyl acetate, washed with 1N HCl, water, saturated sodium bicarbonate and brine. The organic phase was dried over magnesium sulfate. Removal of the solvent in vacuo and flash chromatography on silica Eel (ethyl acetate: hexane (1:3)+1% methanol) gave the title compound (293 mg). $^1$H NMR consistent with the desired structure.

STEP 34B

17-Ethyl-1,14-dihydroxy-12-[2'-(4''-(tert-butyldimethylsiloxy)-3''-allyloxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a solution of 17-ethyl-1,14-dihydroxy-12-[2'-(4''-(tert-butyldimethylsiloxy)-3''-hydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (290 mg in 3.9 ml 33% methylene chloride in cyclohexane) allyl trichloroacetimidate (131 mg neat) was added and the reagents allowed to mix for 5 minutes. Trifluoromethanesulfonic acid (6 µl neat) was added slowly via syringe and the mixture stirred at room temperature. After 5 days the reaction was diluted with ethyl acetate and quenched with saturated sodium bicarbonate. The layers were separated, and the organic layer was washed with brine then dried over magnesium sulfate. Purification of the concentrate by preparative TLC on silica gel (ethyl acetate:hexane (1:5) + 1% methanol) gave the title compound (150 mg). $^1$H NMR consistent with the desired structure.

STEP 34C

17-Ethyl-1,14-dihydroxy-12-[2'-(4''-hydroxy-3''-allyloxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a solution of 17-ethyl-1,14-dihydroxy-12-[2'-(4''-(tert-butyldimethylsiloxy)-3''-allyloxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (150 mg) in acetonitrile (3 ml) was added a solution of 2% HF in aqueous acetonitrile (80 µl), and the mixture was stirred at room temperature. After 2 hours, the solution was diluted with ethyl acetate and quenched with saturated sodium bicarbonate. The layers were separated, and the organic layer was washed with brine and dried over magnesium sulfate. Purification of the concentrate by flash chromatography on silica gel (ethyl acetate:hexane (1:1) + 1% methanol) gave the title compound (63 mg). $^1$H NMR consistent with the desired structure.

STEP 34D

17-Ethyl-1,14-dihydroxy-12-[2'-(4''-(1-N-methyl-5-indolyl)oxy-3''-allyloxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a solution of tri(1-methylindol-5-yl)bismuthine (60 mg) in methylene chloride (1.0 ml) was added peracetic acid (23 µl), and the mixture was stirred at room temperature for 15 minutes. 17-ethyl-1,14-dihydroxy-12-[2'-(4''-hydroxy-3''-allyloxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (60 mg) was dissolved in methylene chloride (500 µl) and added to the reaction mixture. After 20 hours the mixture was diluted with ethyl acetate and washed with saturated sodium bicarbonate and brine then dried over magnesium sulfate. Purification of the concentrate by preparative TLC on silica gel (ethyl acetate:hexane (1:2) + 1% methanol) gave the title compound (26 mg). Partial $^1$H NMR δ: 7.18 (s, 1H); 7.16 (d, J = 9 Hz, 1H); 6.97 (d, J = 3 Hz, 1H); 6.91 (dd, J = 9,3 Hz, 1H); 6.34 (d, J = 3 Hz, 1H); 5.89 (m, 1H); 4.57 (brd, J = 4 Hz, 1H); 4.41 (brd, J = 14 Hz, 1H); 3.70 (s, 3H).

EXAMPLE 35

17-Ethyl-1,14-dihydroxy-12-[2'-(4''-(1-N-methyl-5-indolyl)oxy-3''-n-propyloxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a solution of 17-ethyl-1,14-dihydroxy-12-[2'-(4''-(1-N-methyl-5-indolyl)oxy-3''-allyloxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (14 mg) in ethyl acetate (400 µl) was added rhodium on carbon (4 mg). The flask was filled with hydrogen, and the mixture was stirred at room temperature. After 1.5 hours the mixture was filtered through Celite then the solvent was removed in vacuo Purification by flash chromatography (ethyl acetate:hexane (1:1) + 1% methanol) gave the title compound (10 mg). Partial $^1$H NMR δ: 7.17 (s, 1H); 7.15 (d, J = 9 Hz, 1H); 6.97 (d, J = 3 Hz, 1H); 6.92 (dd, J = 9,3 Hz, 1H); 6.34 (d, J = 3 Hz, 1H); 4.56 (brd, J = 4 Hz, 1H); 4.40 (brd, J = 14 Hz, 1H); 3.71 (s, 3H).

EXAMPLE 36

17-Ethyl-1,14-dihydroxy-12-[2'-(4''-(1-(3-t-butyldimethylsilyloxypropyl)indol-5-yl)oxy-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a solution of tri[1-(3-t-butyldimethylsilyloxypropyl)-indol-5-yl]-bismuthine (0.43 gm, 0.4 mmol.) in CH$_2$Cl$_2$ (4 mL.) at room temperature was added peracetic acid (0.075 mL., 32% in acetic acid) followed in 15 minutes by 17-ethyl-1,14-dihydroxy-12-[2'-(4''-hydroxy-3''-methoxycyclohexyl)-1'-methylvinyl] -23,25-dimethoxy-13,19,21,27-tetramethyl-11,28-dioxa-4-azatricyclo[22.3.1.0$^{4,9}$]octacos-18-ene-2,3,10,16-tetraone (350 mg., 0.44 mmol.) and Cu(OAc)$_2$ (30 mg.). The reaction mixture was stirred for 2 days. The reaction was then quenched with saturated NaHCO$_3$ and the mixture extracted with CH$_2$Cl$_2$. The organic extracts were combined, dried over Na$_2$SO$_4$, filtered, and concentrated in vacuo The product was isolated and purified by preparative TLC on silica gel (3:1, hexane/acetone) to give 144 mg. of the title compound.

EXAMPLE 37

17-Ethyl-1,14-dihydroxy-12-[2'-(4''-(1-(3-hydroxypropyl)indol-5-yl)oxy-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a solution of 17-ethyl-1,14-dihydroxy-12-[2'-(4''-(1-(3-t-butyldimethylsilyloxy-propyl)indol-5-yl)oxy-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (144mg) in CH$_2$Cl$_2$ (4 mL.) at rt was added a solution of p-toluene sulfonic acid (20 mg.) in CH$_3$OH (4 mL.). The reaction mixture was stirred for 3 hr., quenched with saturated NaHCO$_3$, then extracted with CH$_2$Cl$_2$. The extracts were combined, dried over Na₂SO₄, filtered and concentrated in vacuo. The product was purified by preparative TLC on silica gel (2:1, hexane/acetone) to give 81 mg of the title compound. Partial $^1$H NMR (CDCl₃, 200 MHz) d: 7.22 (d, J=9 Hz, 1H); 7.18 (d, J=3 Hz, 1H); 7.07 (d, J=3 Hz, 1H); 6.89 (dd, J=3 Hz and J=9 Hz, 1H); 6.34 (d, J=3 Hz, 1H); 4.20 (t, J=6.5 Hz, 2H); 2.00 (m, 2H).

EXAMPLE 38

17-Ethyl-1,14-dihydroxy-1-2-[2'-(3''-hydroxy-4''-(1-t-butyldimethylsilyloxyethylindol-5-yl)oxycyclohexyl)1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a solution of tri[1-(2-t-butyldimethylsilyloxyethyl)-indol-5-yl]bismuthine (250 mg., 0.24 mmol.) in CH₂Cl₂ (2 mL.) at rt was added peracetic acid ( 0.05 mL., 32% in acetic acid) followed in 15 minutes by 17-ethyl-1,14-dihydroxy-12-[2'-(3'',4''-dihydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (200mg, 0.25 mmol) and Cu(OAc)₂ (20 mg.). The reaction mixture was stirred for 2 days. The reaction was then quenched with saturated NaHCO₃ and extracted with CH₂Cl₂. The organic extracts were combined, dried with Na₂SO₄, filtered and concentrated in vacuo. The product was isolated and purified by preparative TLC (3:1, hexane/acetone) to afford 74 mg. of the title compound.

EXAMPLE 39

17-Ethyl-1,14-dihydroxy-12-[2'-(3''-hydroxy-4''-(1-hydroxyethylindol-5-yl)oxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a solution of 17-ethyl-1,14-dihydroxy-12-[2'-(3''-hydroxy-4''-(1-t-butyl-dimethylsilyloxyethylindol-5-yl)oxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (74mg) in CH₂Cl₂ (2 mL.) at rt was added a solution of p-toluene sulfonic acid (10 mg.) in CH₃OH (2 mL.). The reaction mixture was stirred for 3 hr., quenched with saturated NaHCO₃, then extracted with CH₂Cl₂. The extracts were combined, dried over Na₂SO₄, filtered and concentrated in vacuo. The product was purified by preparative TLC on silica gel (2:1, hexane/acetone) to give 44.8 mg of the title compound. Partial $^1$H NMR (CDCl, 200 MHz) d: 7.24 (d, J=9 Hz, 1H); 7.15 (d, J=3 Hz, 1H); 7.12 (d, J=3.5 Hz, 1H); 6.86 (dd, J=3 and J=9 Hz, 1H); 6.39 (d, J=3.5, 1H); 4.20 (t, J=5, 2H).

EXAMPLE 40

Tri[1-2(t-butyldimethylsilyloxyethyl)-indol-6-yl]-bismuthine

Step A: 6-Bromoindole

To a solution of 4-bromo-2-nitrotoluene (4.3 g., 20 mmol.) in DMF (40 mL.) was added DMF dimethylacetal (7.15 g., 60 mmol.) and pyrrolidine (1.4 g., 20 mmol.). The solution was heated to 110° C. for 4 hr. then cooled to rt. and diluted with ethyl ether. The mixture was washed 3× with water, dried with Na₂SO₄, filtered and the solvent evaporated. The residue was dissolved in 80% aqueous acetic acid (125 mL.) and heated to 75° C. Zinc dust (9.75 g., 150 mmol.) was added gradually over 20 min. The reaction mixture was heated to 85° C. for 2 hr. then cooled to ~35° C. and filtered to remove unreacted zinc. The filtrate was diluted with ethyl ether, washed 3× with water then with saturated aqueous NaHCO₃. The solution was dried with Na₂SO₄, filtered and concentrated in vacuo to ~30 mL. then diluted with hexanes and filtered. The filtrate was concentrated to an off-white solid which was dissolved in hexane, filtered, and concentrated to give 1.65 g. of the title compound as a light green solid.

Step B: 1-(2-t-Butyldimethylsilyloxyethyl)-6-bromoindole

To a slurry of NaH (192 mg., 4.8 mmol., 60% oil dispersion) in DMF (4 mL.) was added, dropwise, a solution of 6-bromoindole (0.85 g., 4.34 mmol.) in DMF (4 mL.). After stirring for 10 min. at ft., 2-t-butyldimethylsiloxyethyl bromide ((1.15 g., 4.8 mmol., neat) was added and the mixture stirred for 1.5 hr. The reaction mixture was partitioned between ice water and hexane. The organics were washed 2× with water, dried with Na₂SO₄, filtered and concentrated in vacuo to a dark oil. The product was isolated by flash column chromatography (silica, 4:1 hexanes/acetone) to give 1.04 g. of the title compound as an oil.

Step C: Tri[1-(2-t-butyldimethylsilyloxyethyl)indole-6-yl]-bismuthine

To a solution of 1-(2-t-butyldimethylsilyloxyethyl)-6-bromoindole (1.0 g., 2.81 mmol.) in ethyl ether (10 mL.) at −78° C. was added t-butyllithium (3.4 mL., 5.8 mmol., 1.7M in pentane). After stirring for 10 min. a solution of BiCl₃ (285 mg., 0.9 mmol.) in THF (3 mL.) was added. The reaction mixture was stirred for an additional 10 min. at −78° C. then allowed to warm to rt overnight. The reaction mixture was partitioned between ice water and CH₂Cl₂. The organic layer was washed with water, dried with Na₂SO₄ and concentrated to a dark oil. Flash column chromatography (silica, 4:1 hexane/acetone) afforded 630 mg. of the title compound as an dark oil (~60% pure) which was used without further purification in Example 41/the next step.

EXAMPLE 41

17-Ethyl-1,14-dihydroxy-12--[2'-(4''-(1-t-butyldimethylsilyloxyethylindol-6-yl)oxy-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a solution of tri[1-(2-t-butyldimethyl-silyloxyethyl)-indol-6-yl]bismuthine (0.60 g., 0.58 mmol.) in CH₂Cl₂ (5 mL.) at room temperature was added peracetic acid (0.080 mL., 32% in acetic acid) followed in 15 minutes by 17-ethyl-1,14-dihydroxy-12-[2'-(4''-hydroxy-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (350 mg., 0.44 mmol.) and Cu(OAc)₂ (30 mg.). The reaction mixture was stirred for 20 hr. The reaction was then quenched with saturated NaHCO₃ and the mixture extracted with CH₂Cl₂. The organic o extracts were combined, dried over Na₂SO₄, filtered, and concentrated in vacuo. The product was isolated and purified by preparative TLC on silica gel (3:1, hexane/acetone) to give 150 mg. of the title compound.

EXAMPLE 42

17-Ethyl-1,14-dihydroxy-12-[2'-(4''-(1-hydroxyethylindol-6-yl)oxy-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a solution of 17-ethyl-1,14-dihydroxy-12-[2'-(4''-(1-t-butyldimethylsilyloxyethylindol-6-yl)oxy-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone. (150 mg) in CH$_2$Cl$_2$ (4 mL.) at rt was added a solution of p-toluene sulfonic acid (20 mg.) in CH$_3$OH (4 mL.). The reaction mixture was stirred for 2 hr., quenched with saturated NaHCO$_3$, then extracted with CH$_2$Cl$_2$. The extracts were combined, dried over Na$_2$SO$_4$, filtered and concentrated in vacuo. The product was purified by preparative TLC on silica gel (2:1, hexane/acetone) to give 55 mg of the title compound.

Partial $^1$H NMR (CDCl, 200 MHz) d: 7.47 (d, J=6 Hz, 1H); 7.03 (d, J=3 Hz, 1H); 6.94 (bs, 1H); 6.82 (dd, J=1.5 Hz and J=6 Hz, 1H); 6.41 (d,J=3 Hz, 1H); 6.41 (d, J=3 Hz, 1H); 4.20 (t, J=5 Hz, 2H); 3.93 (t, J=5 Hz, 2H); 3.50 (s, 3H).

EXAMPLE 43

Tri(1-methylindol-6-yl)bismuthine

To a solution of 1-methyl-6-bromoindole (760 mg., 3.6 mmol.) in ethyl ether (15 mL.) at −78° C. was added t-butyllithium (4.4 mL., 7.5 mmol., 1.7M in pentane). After 10 min. a solution of BiCl$_3$ (375 mg., 1.2 mmol.) in THF (4 mL.) was added and the cooling bath removed. The reaction mixture stirred for 4 hr then poured into ice water and extracted with CH$_2$Cl$_2$. The extracts were combined, backwashed with water, dried with Na$_2$SO$_4$, filtered, and concentrated in vacuo to a dark oil. The product was crystallized from methanol to afford 290 mg. of the title compound as a tan solid.

EXAMPLE 44

17-Ethyl-1,14-dihydroxy-12-[2'-(4''-(1-methylindol-6-yl)oxy-3''-methoxycyclohexyl)-1'-methylvinyl]-23,25-dimethoxy-13,19,21,27-tetramethyl-11,28-dioxa-4-azatricyclo-22.3.1.0$^{4,9}$]octacos-18-ene-2,3,10,16-tetraone To a solution of tri[1-methylindol-6-yl]bismuthine (200 mg., 0.33 mmol.) in CH$_2$Cl$_2$ (2 mL.) at room temperature was added peracetic acid (0.070 mL., 32% in acetic acid) followed in 15 minutes by 17-ethyl-1,1-4-dihydroxy-12-[2'-(4''-hydroxy-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (150 mg., 0.19 mmol.) and Cu(OAc)$_2$ (30 mg.). The reaction mixture was stirred for 4 days. The reaction was then quenched with saturated NaHCO$_3$ and the mixture extracted with CH$_2$Cl$_2$. The organic extracts were combined, dried over Na$_2$SO$_4$, filtered, and concentrated in vacuo The product was isolated and purified by preparative TLC on silica gel (2:1, hexane/acetone) to give 76 mg. of the title compound. Partial $^1$H NMR (CDCl, 400 MHz) d: 7.44 (d, J=7 Hz, 1H); 6.91 (d, J=3 Hz, 1H) 6.88 (d, J=2 Hz, 1H); 6.81 (m, 1H); 6.37 (d, J=3, 1H); 3.68 (s, 3H); 3.51 (s, 3H).

EXAMPLE 45

17-Ethyl-1,14-dihydroxy-12-[2'-(4''-(1-dibenzyphosphonoxy-ethylindol-5-yl)oxy-3''-methoxycyclohexyl)-1'-methylvinyl]-23,25-dimethoxy-13,19,21,27-tetra-methyl-11,28-dioxa-4-azatricyclo[22.3.1.0$^{4,9}$]octacos-18-ene-2,3,10,16-tetraone To a solution of 17-ethyl-1,14-dihydroxy-12-[2'-(4''-(1-hydroxyethylindol-5-yl)oxy-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (202 mg, azeotroped with toluene) in dry THF was added dibenzyl phosphate (88.6 mg) followed by triphenylphosphine (83.5 mg). The reaction mixture was cooled down to 0° C., then added diethyl azodicarboxylate (50 mL). The reaction mixture was stirred at 0° C. for 5 minutes, removed the ice bath, and stirred at room temperature for 2h. The crude reaction mixture was loaded directly onto the silica gel column and purified (ethyl acetate:hexane (2:3)+1% MeOH) to give the title compound (197 mg). Partial $^1$H NMR (CDCl$_3$)d: 7.29 (m, 6H); 7.18 (m, 5H); 7.12 (d, J=9 Hz, 1H); 7.0 (d, J=4 Hz, 1H); 6.89 (dd, J=9, 2 Hz, 1H); 6.36 (d, J=4 Hz, 1H); 4.82 (m, 4H); 4.40 (brd, J=14 Hz, 1H); 4.20 (m, 4H).

EXAMPLE 46

Monopotassium salt of 17-Ethyl-1,14-dihydroxy-12-[2'-(4''-(1-phosphonoxy-ethylindol-5-yl)oxy-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a solution of 17-ethyl-1,14-dihydroxy-12-[2'-(4''-(1-dibenzylphosphate-ethylindol-5-yl)oxy-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (197 mg) in methanol (3.2 mL) was added potassium bicarbonate (16.3 mg) dissolved in water (200 mL). Added palladium hydroxide over carbon, then charged the reaction mixture with hydrogen via balloon. After the reaction was complete (10 min. by TLC analysis), it was filtered over Celite and rinsed with methanol and small amount of water. The solvent was removed in vacuo, and the crude material was purified on HP-20 column to give the title compound (69 mg).

Partial $^1$H NMR (CD$_3$OD) d: 7.34 (d, J=9 Hz, 1H); 7.27 (d, J=4 Hz, 1H); 7.12 (d, J=2 Hz, 1H); 6.85 (dd, J=9, 2 Hz, 1H); 6.31 (d, J=4 Hz, 1H); 5.23 (m, 2H); 4.35 (m, 2H); 4.13 (m, 2H).

EXAMPLE 47

17-Ethyl-1,14-dihydroxy-12-[2'-(4''-(1-(N,N-dimethylglycyloxy)ethylindol-5-yl)oxy-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a solution of 17-ethyl-1,14-dihydroxy-12-[2'-(4''-(1-hydroxyethylindol-5-yl)oxy-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (26.6 mg) in dry methylene chloride (0.3 mL) was added hydrochloride salt of N,N-dimethylglycine (5.8 mg), DMAP (3.4 mg) and EDC (8 mg), respectively at room temperature. The reaction mixture was stirred for 4 h, then diluted with ethyl acetate and washed with saturated sodium bicarbonate and brine. The organic layer was dried over magnesium sulfate, and the solvent was removed in vacuo. The crude material was purified by flash chromatography (1:2/acetone:hexane) to give 23 mg of the title compound.

Partial $^1$H NMR (CDCl$_3$) d: 7.21 (m, 2H); 7.04 (d, J=4 Hz, 1H); 6.91 (dd, J=9, 2 Hz, 1H); 6.49 (d, J=4 Hz, 1H); 4.41 (m, 2H); 4.32 (m, 2H); 3.07 (s, 3H); 2.26 (s, 3H).

EXAMPLE 48

7-Ethyl-1,14-dihydroxy-12-[2'-(4''-(1-succinyloxyethylindol-5-yl)oxy-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a solution of 17-ethyl--1,14-dihydroxy-2-[2'-(4''-(1-hydroxyethylindol-5-yl)oxy-3''-methoxycyclohexyl)-1'-methylvinyl]-23,25-dimethoxy-3,19,21,27-tetramethyl-11,28-dioxa-4-azatricyclo[22.3.1.0$^{4,9}$]octacos-18-ene-2,3,10,16-tetraone (109 mg) in dry methylene chloride was added succinic anyhydride (11.5 mg) and triethylamine (19 ml). Added DMAP (7 mg) to the reaction mixture and followed the reaction by TLC. After 1.5 h, the reaction mixture was diluted with ethyl acetate and adjusted to pH 4 with 1N HCl. It was poured into the separatory funnel and the layers were separated. The aqueous layer was extracted with ethyl acetate, and the combined organic layer was washed with brine. It was dried over magnesium sulfate, and the crude material was purified by flash chromatography (3% methanol/CH$_2$Cl$_2$) to give 66 mg of the title compound. Partial $^1$H NMR (CDCl$_3$) d: 7.19 (m, 2H); 7.04 (d, J=4 Hz, 1H); 6.91 (dd, J =9, 2 Hz, 1H); 6.39 (d, J=4 Hz, 1H); 4.32 (m, 4H); 2.49 (brs, 4H).

EXAMPLE 49

17-Ethyl-1,14-dihydroxy-12-[2'-(4''-(1-methyl-3-phenylindol-5-yl)oxy-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone

Step A: 5-Bromo-3-phenylisatin

To a stirred mixture of 5-bromoisatin (5 g., 22.1 mmol., 1 eq.) in dry THF (150 mL.) was added phenylmagnesium bromide (14.7 mL., 44.2 mmol., 2 eq., 3M solution in diethyl ether)(The addition of Grignard reagent was initiated at −78° C. The reaction mixture became too viscous to stir after addition of approximately 5 mL. of the Grignard reagent. The cooling bath was removed and the remainder of the Grignard reagent was added by quick dropwise addition.). The reaction mixture was stirred overnight. Analysis by TLC showed a small amount of unreacted starting material. An additional 1.5 mL. of the Grignard reagent was added and the reaction mixture was stirred an additional 6 hours. The reaction mixture was poured into a separatory funnel containing saturated aqueous ammonium chloride and was extracted 4× with diethyl ether. The organic extracts were combined, dried over anhydrous MgSO$_4$, filtered and concentrated in vacuo. The product was carried on without further purification.

Step B: 5-Bromo-3-phenylindole

To a stirred solution of 5-bromo-3phenylisatin (6.39 g., 21 mmol., 1 eq.) in dry THF (50 ml.) at 0° C. was added lithium aluminum hydride (2.0 g., 52.5 mmol., 2.5 eq.) portionwise over 1.5 hours. The cooling bath was removed and the reaction was allowed to stir overnight. The mixture was cooled to 0° C. and carefully quenched with 1N aqueous HCl. The mixture was filtered through Celite ™ and the Celite ™ was washed with THF. The filtrate was concentrated in vacuo, dissolved in EtOAc and washed with water. The organic layer was dried over anhydrous MgSO$_4$, filtered and concentrated in vacuo.

Step C: 5-bromo-1-methyl-3-phenylindole

To a stirred solution of 5-bromo-3-phenylindole (2.4 g., 8.78 mmol., 1 eq.) in dimethylformamide (20 mL.) was added NaH (422 mg. of a 60% dispersion in oil, 10.54 mmol., 1.2 eq.). The mixture was stirred 15 minutes. Methyl iodide (0.6 ml, 9.66 mmol, 1.1 eq) was added via syringe and the reaction mixture was stirred 3 hours. The reaction was quenched with water and extracted 4× with EtOAc. The organic extracts were combined, dried over anhydrous MgSO$_4$, filtered and concentrated in vacuo The product was purified by flash column chromatography (2:1 hexanes/acetone) giving 1.63 g. 5-bromo-1-methyl-3-phenylindole.

Step D: Tri(1-methyl-3-phenylindole-5-yl)bismuthine

To a stirred solution of 5-bromo-1-methyl-3-phenylindole (1.63 g., 5.7 mmol., 1 eq.) in Et$_2$O (35 mL.) at −78° C. under N$_2$ atmosphere was added t-buLi (6.7 mL. of a 1.7M solution in hexanes, 11.4 mmol., 2 eq.) dropwise via syringe. The reaction was stirred 10 minutes at −78° C. To this mixture was added a solution of BiCl$_3$ (540 mg., 1.71 mmol., 0.3 eq.) in THF (7 mL.) dropwise quickly. The reaction was stirred 10 minutes at −78° C. and the cooling bath was removed and the mixture allowed to warm to room temperature. After 3 hours the mixture was poured into a separatory funnel containing water and extracted 4× with CH$_2$Cl$_2$. The organic extracts were combined, dried over anhydrous Na$_2$SO$_4$, filtered and concentrated in vacuo. The residue was triturated with Et$_2$O and the solids collected and washed with Et$_2$O giving 710 mg of Tri(1-methyl-3-phenylindol-5-yl)bismuthine.

Step E: 17-Ethyl-1,14-dihydroxy-12-[2'-(4''-(1-methyl-3-phenylindol-5-yl)oxy-3''-methoxycyclohexyl)-1'-methylvinyl]-23,25-dimethoxy-1 3,19,21,27-tetramethyl-11,28-dioxa-4-azatricyclo[22.3.1.0$^{4,9}$]octacos-18-ene-2,3,10,16-tetraone To a stir red solution of tri(1-methyl-3-phenylindol-5-yl)b ismuthine (645 mg., 0.78 mmol., 1.2 eq.) in CH$_2$Cl$_2$ (10 mL.) and THF (3 mL.) was added peracetic acid (0.514 mL. of a 32% solution in dilute acetic acid, 0.858 mmol., 1.3 eq.). The mixture was stirred 5 minutes and 17-ethyl-1,14-dihydroxy-12-[2'-(4''-hydroxy-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (514 mg., 0.65 mmol., 1 eq.) was added. Cu(OAc)$_2$ (12 mg., 0.065 mmol., 0.1 eq) was added. The flask was capped and the mixture stirred. After 48 hours the reaction was quenched with saturated aqueous NaHCO₃ and extracted 4× with CH₂Cl₂. The organic extracts were combined, dried over anhydrous Na₂SO₄, filtered and concentrated in vacuo. The product was purified by flash column chromatography on silica gel (2:1 hexanes-/acetone) and again (3.5% CH₃OH/CH₂Cl₂) giving 78 mg 17-ethyl-1,14-dihydroxy-12-[2'-(4''-(1-methyl-3-phenylindol-5-yl)oxy-3''-methoxycyclohexyl)-1'-methylvinyl]-23,25-dimethoxy 13,19,21,27-tetramethyl-11,28-dioxa-4-azatricyclo-[22.3.1.0$^{4,9}$]octacos-18-ene-2,3,10,16-tetraone. Mass (FAB) 1003 (M⁺+Li); 996 (M⁺). Partial ¹H NMR (CDCl₃, 400 MHz) d: 7.59 (d, J=7 Hz, 2 H); 7.50 (m, 1 H); 7.41 (t, J=7 Hz, 2 H); 7.25-7.15 (m, 3 H); 6.99 (dd. J=9 Hz, J=2 Hz, 1 H); 4.57 (d, J=6 Hz, 1 H); 4.39 (bd, J=13 Hz, 1 H); 3.78 (s, 3 H).

EXAMPLE 50

17-Ethyl-1,14-dihydroxy-12-[2'-(4''-(1-methyl-3-(2-hydroxyethyl)indol-5-yl)oxy-3''-methoxycyclohexyl)-1'methylvinyl]-23,25-dimethoxy-13,19,21,27-tetramethyl-11,28-dioxa-4-azatricyclo[22.3.1.0$^{4,9}$]octacos-18-ene-2,3,10,16-tetraone

Step A: 5-Bromo-3-hydroxyethylindole

To a stirred solution of 5-bromoindole-3-acetic acid (1.9 g., 7.48 mmol., 1 eq.) in dry THF (17 mL.) at 0° C. was added lithium aluminum hydride (570 mg. 14.96 mmol., 2 eq.) portionwise over 30 minutes. The reaction mixture coagulated. THF (20 mL.) was added and the cooling bath was removed. The mixture was stirred vigorously. Let stir overnight. The reaction mixture was carefully quenched with 1N aqueous HCl and then acidified with 2N aqueous HCl. The mixture was filtered through Celite ™ and the Celite ™ was washed with THF. The filtrate was concentrated in vacuo, dissolved in EtOAc, and washed with water. The organic layer was dried over anhydrous MgSO₄, filtered and concentrated in vacuo. TLC analysis of the residue showed unreacted starting material. The residue was dissolved in Et₂O and extracted with 0.25N aqueous NaOH. The organic layer was dried over anhydrous MgSO₄, filtered and concentrated in vacuo giving 1.16 g 5-bromo-3-hydroxyethylindole.

Step B: 5-Bromo-3-(2-t-butyldimethylsilyloxy)ethylindole

To a stirred solution of 5-bromo-3hydroxyethylindole (1.16 g., 4.83 mmol., 1 eq.) in CH₂Cl₂ (12mL.) was added triethylamine (1.0 mL., 7.25 mmol., 1.5 eq.) followed by addition of t-butyldimethylchlorosilane (875 mg., 1.2 mmol., 1.2 eq.) and dimethylaminopyridine(catalytic). The mixture was stirred overnight, poured into a separatory funnel containing water and extracted 4× with CH₂Cl₂. The organic extracts were combined, dried over anhydrous Na₂SO₄, filtered and concentrated in vacuo giving 1.66g. 5-bromo-3-(2-t-butyldimethylsilyloxy)ethylindole.

Step C: 5-Bromo-1-methyl-3-(2-t-butyldimethylsilyloxy)ethylindole

To a stirred solution of 5-bromo-3-(2-t-butyldimethylsilyloxy)ethylindole (1.66 g., 4.66mmol., 1 eq.) in DMF (15mL.) was added NaH (225 mg. of a 60% dispersion in oil, 5.6 mmol., 1.2 eq.). After 15 minutes iodomethane (0.320 mL., 5.13 mmol., 1.1 eq.) was added. The mixture was stirred 4 hours and then poured into a separatory funnel containing water and extracted 2× with EtOAc. The organic extracts were combined, dried over anhydrous MgSO₄, filtered and concentrated in vacuo giving 1.49 g. 5-bromo-1-methyl-3-(2-t-butyldimethylsilyloxy)ethylindole.

Step D: Tri(1-methyl-3-(2-t-butyldimethylsilyloxy)-ethylindol-5-yl)bismuthine To a stirred solution of 5-bromo-1-methyl-3-(2-t-butyldimethylsilyloxy)ethylindole (1.49 g., 4.03 mmol., 1 eq.) in Et₂O (15 mL.) at −78° C. under nitrogen atmosphere was added t-butyllithium (4.8 mL. of a 1.7 M solution in pentanes, 8.06 mmol., 2 eq.) dropwise via syringe. The mixture was stirred 10 minutes at −78° C. and then a solution of BiCl₃ (381 mg., 1.21 mmol., 0.3 eq.) in THF (5mL.) was added quickly dropwise via syringe. The mixture was stirred for 7 minutes at −78° C. under nitrogen. The cooling bath was removed and the mixture was allowed to warm to room temperature. After 1 hour the mixture was poured into a separatory funnel containing water and extracted 4× with CH₂Cl₂. The organic extracts were combined, dried over anhydrous Na₂SO₄, filtered and concentrated in vacuo giving 554 mg. crude product. ¹H NMR analysis of the residue indicates mixture of approximately 2:1 of the desired bismuthine to reduced indole. Used the mixture crude in subsequent reaction.

Step E: 17-Ethyl-1,14-dihydroxy-12-[2'-(4''-(1-methyl-3-(2-t-butyldimethylsilyloxyethyl)-indol-5-yl)oxy-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a stirred solution of tri(1-methyl-3-(2-t-butyldimethylsilyloxy)ethylindol-5-yl)bismuthine (554 mg. crude ) in CH₂Cl₂ (10 mL.) and THF (3 mL.) was added peracetic acid (0.120mL. of a 32% solution in dilute acetic acid, 0.571 mmol.). To this mixture was added 17-ethyl-1,14-dihydroxy-12-[2'-(4''-hydroxy-3''-methoxycyclohexyl)-1'-methylvinyl]-23,25-dimethoxy-13,19,21,27-tetramethyl-11,28-dioxa-4-azatricyclo-[22.3.1.0$^{4,9}$]octacos-18-ene-2,3,10,16-tetraone (347 mg., 0.439 mmol.) followed by addition of Cu(OAc)₂ (24 mg., 0.13 mmol.). The reaction mixture was allowed to stir overnight. The mixture was poured into a separatory funnel containing saturated aqueous NaHCO₃ and extracted 4× with CH₂Cl₂. The organic extracts were combined, dried over anhydrous Na₂SO₄, filtered and concentrated in vacuo. The product was purified by flash column chromatography on silica gel (2:1 hexanes-/acetone) giving 200 mg. 17-ethyl-1,14-dihydroxy-12-[2'-(4''-(1-methyl-3-(2-t-butyldimethyl -silyloxyethyl)indol-5-yl)oxy-3''-methoxycyclohexyl)-1 '-methylvinyl]-23,25-dimethoxy-13,19,21;27-tetramethyl -11,28-dioxa-4-azatricyclo[22.3.1.0$^{4,9}$]octacos-18-ene -2,3,10,16-tetraone as a brown oil.

Step F: 17-Ethyl-1,14-dihydroxy-12-[2'-(4'-'-(1-methyl-3-(2-hydroxyethyl)indol-5-yl)oxy-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene -2.3.10.16-tetraone To a stirred solution of 17-ethyl-1,14-dihydroxy-12-[2⇌-(4''-(1-methyl-3-(2-t-butyldimethyl -silyloxyethyl)indol-5-yl)oxy-3''-methoxycyclohexyl)-1 '-methylvinyl]-23,25-dimethoxy-13,19,21,27-tetramethyl -11,28-dioxa-4-azatricyclo[22.3.1.0$^{4,9}$]octacos-18-ene -2,3,10,16-tetraone (200 mg.) in CH$_2$Cl$_2$ (6 mL.) and CH$_3$OH (6mL.) was added p-toluenesulfonic acid monohydrate (30mg.). The reaction mixture was allowed to stir 3 hours. The reaction was quenched with saturated aqueous NaHCO$_3$ and extracted 4× with CH$_2$Cl$_2$. The organic extracts were combined, dried over anhydrous Na$_2$SO$_4$, filtered and concentrated in vacuo. The product was purified by preparative TLC on silica gel (1:1 hexanes/acetone) and again (7% CH$_3$OH/CH$_2$Cl$_2$) giving 75 mg. 17-ethyl-1, 14-dihydroxy -12-[2'-(4Δ-(1-methyl-3-(2-hydroxyethyl)indol-5-yl)oxy -3''-methoxy-cyclohexyl)-1 '-methylvinyl]-23,25-dimethoxy-13,19,21,27-tetramethyl-11,28-dioxa-4-azatricyclo-[22.3.1.0$^{4,9}$]octacos-18-ene-2,3,10,16-tetraone.

Mass (FAB) 972 (M++Li).

Partial $^1$H NMR (CDCl$_3$, 400 NMR) d: 7.17-7.13 (m, 2H); 6.94 (dd, J=9 Hz, J=2 Hz, 1 H); 6.88 (s, 1 H); 4.58

(d, J-6 Hz, 1 H); 4.39 (bd, J=13 Hz, 1 H); 3.84 (t, J=6 Hz, 2 H); 3.70 (s, 3 H); 2.94 (t, J=7 Hz, 2 H).

EXAMPLE 51

17-Ethyl-1,14-dihydroxy-12-[2-'-(4''-(1,3-dimethylindol -5-yl)oxy-3''-methoxycyclohexyl)-1'-methvinyl]-23,25-dimethoxy-13,19,21,27-tetramethyl-11,28-dioxa-4-azatricyclo[22.3.1.0$^{4,9}$]octacos-18-ene-2,3,10,16-tetraone

Step A: 5-Bromo-3-methylindole

To a stirred mixture of 5-bromoisatin (5 g., 22.1 mmol., 1 eq.) in dry THF (150 mL.) was added methylmagnesium bromide (32 mL. of a 1.4M solution in toluene, 44.2 mmol., 2 eq.) dropwise via syringe. After 45 minutes TLC analysis showed small amount of unreacted bromoisatin. Added 3.2 mL. of methylmagnesium bromide solution. Let stir 1 hour. Cooled reaction mixture to 0° C. Added lithium aluminum hydride (1.26 g., 33.15 mmol., 1.5 eq.) portionwise. Let stir 30 minutes at 0° C. Removed cooling bath and let stir overnight. Cooled mixture to 0° C. and carefully quenched reaction with 1N aqueous HCl. Acidified with 2N aqueous HCl. Removed cooling bath. Let stir for 3 hours. Filtered mixture through Celite™. Washed Celite™ with THF. Concentrated filtrate in vacuo. Diluted residue with water and extracted 4× with CH$_2$Cl$_2$. The organic extracts were combined, dried over anhydrous Na$_2$SO$_4$, filtered and concentrated in vacuo. Loaded residue onto a silica gel plug in a fritted filter and eluted with 4:1 hexanes/acetone. Collected fractions containing the desired product and concentrated in vacuo giving 2.85 g. 5-bromo-3-methylindole.

Step B: 5-Bromo-1,3-dimethylindole

To a stirred solution of 5-bromo-3-methylindole (2.85 g., 13.6 mmol., 1eq.) in DMF (35 mL.) was added NaH (651 mg. of a 60% dispersion in oil, 16.28 mmol., 1.2 eq.). The mixture was stirred 15 minutes. To this mixture was added iodomethane (0.930 mL., 14.93 mmol., 1.1 eq.). The mixture was stirred for 2 hours. The DMF was removed in vacuo. The residue was diluted with water and extracted 4× with Et$_2$O. The organic extracts were combined, dried over anhydrous MgSO$_4$, filtered and concentrated in vacuo giving 3.04 g. 5-bromo-1,3-dimethylindole as a reddish liquid.

Step C: Tri(1,3-dimethylindol-5-yl)bismuthine

To a stirred solution of 5-bromo-1,3-dimethylindole (3.04 g., 13.57 mmol., 1 eq.) in Et$_2$O (50 mL.) at −78° C. under nitrogen atmosphere was added t-butyllithium (16 mL. of a 1.7M solution in hexanes, 27.2 mmol., 2 eq.) dropwise via syringe. The mixture was stirred for 10 minutes at −78° C. To the reaction was added a solution of BiCl$_3$ (1.28 g., 4.07 mmol., 0.3 eq.) in THF (17 mL.) quickly dropwise via syringe. The mixture was stirred 5 minutes at −78° C. The cooling bath was removed and the reaction was allowed to warm to room temperature. The reaction mixture was poured into a separatory funnel containing ice water and extracted 4× with CH$_2$Cl$_2$. The organic extracts were combined, dried over anhydrous Na$_2$SO$_4$, filtered and concentrated in vacuo. The residue was triturated with Et$_2$O. The solids were filtered off. The filtrate was concentrated in vacuo. giving 1.28 g. brown oil. $^1$H NMR analysis of the residue indicates material is a mixture of approximately 1:2 desired tri(1,3-dimethylindol-5-yl)bismuthine: dimethylindole. Material was used crude in subsequent Step D.

Step D: 17-Ethyl-1,14-dihydroxy-12-[2'-(4''-(1,3-di -methylindol-5-yl)oxy-3''-methoxycyclohexyl) 1'-methylvinyl]-23,25-dimethoxy-13,19,21,27-tet-ramethyl-11,28-dioxa-4-azatricyclo -[22.3.1.0$^{4,9}$]octacos-18-ene-2,3,10,16-tetraone To a stirred solution of tri(1,3-dimethyl -indol-5-yl)bismuthine (approximately 420 mg.[based on 1.28 g. of material containing one third bismuthine, 0.7 mmol., 1.2 eq.) in CH$_2$Cl$_2$ (12 mL.) and THF (4 mL.) was added peracetic acid (0.1 93 mL. of a 32% solution in acetic acid, 0.916 mmol., 1.3 eq.). To this mixture was added 17-ethyl-1,14-dihydroxy-12-[2'-(4''-hydroxy-3''-m-ethoxycyclohexyl)-1'-methylvinyl]-23,25-dimethoxy-13,19,21,27-tetramethyl-11,28-dioxa-4-azatricy-clo[22.3.1.0$^{4,9}$]octacos-18-ene-2,3,10,16-tetraone (464 mg., 0.59 mmol., 1 eq.) followed by addition of Cu-(OAc)$_2$ (30 mg., 0.176 mmol., 0.3 eq.). The mixture was stirred 4 days. The reaction was quenched with saturated aqueous NaHCO$_3$ and extracted 4× with CH$_2$Cl$_2$. The organic extracts were combined, dried over anhydrous Na$_2$SO$_4$, filtered and concentrated in vacuo. The product was purified by flash column chromatography (2:1 hexanes/acetone) and again (3.5% CH$_3$0OH/CH$_2$Cl$_2$) followed by preparative TLC (eluted 6× with 4:1 hexanes/acetone) giving 117 mg. of 17-ethyl-1,14-dihydroxy-12-[2'-(4''-(1,3-dimethyl -indol-5-yl)oxy-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone.

Mass (FAB) 934 (M+).

Partial $^1$H NMR (CDCl$_3$, 400 MHz) d: 7.14–7.10 (m, 2 H);

6.91 (dd, J=9 Hz, J=2 Hz, 1 H); 6.76 (s, 1 H); 4.57 (d, J=6 Hz, 1 H); 4.39 (bd, J=13 Hz, 1 H); 3.66 (s, 3 H); 2.24

(s, 3 H).

EXAMPLE 52

17-Ethyl-1,14-dihydroxy-12-[2'-(4''- (1-benzylindol-5-yl)oxy-3''-hydroxycyclohexyl)-1'-methylvinyl]-23,25-di methoxy-13,19,21,27-tetramethyl-11, 28-dioxa-4-azatricyclo [22.3.1.0$^{4,9}$]octacos-18-ene-2,3,10,16-tetraone To a stirred solution of tri(1-benzylindol -5-yl)bismuthine (1.28 g., 1.54 mmol., 1.2 eq.) in CH$_2$Cl$_2$ (9 mL.) and THF (3 mL.) was added peracetic acid (0.357 mL. of a 32% solution in dilute acetic acid, 1.69 mmol., 1.3 eq.). To this mixture was added 17-ethyl-1,14-dihydroxy-12-[2'-(3", 4"-dihydroxy -cyclohexyl)-1'-methylvinyl]-23,25-dimethoxy -13,19,21,27-tetramethyl-11,28-dioxa-4-azatricyclo-[22.3.1.0$^{4,9}$]octacos-18-ene-2,3,10,16-tetraone (1 g., 1.28 mmol., 1 eq.) followed by addition of Cu(OAc)$_2$ (23 mg.). The mixture was stirred 2 days. The reaction was quenched with saturated aqueous NaHCO$_3$ and extracted 4× with CH$_2$Cl$_2$. The organic extracts were combined, dried over anhydrous Na$_2$SO$_4$, filtered and concentrated in vacuo. The product was purified by flash column chromatography on silica gel (2:1 hexanes/acetone) and again (3.5% CH$_3$OH/CH$_2$Cl$_2$ ) and again (2:1 hexanes/acetone) giving 253 mg. 17-ethyl-1,14-dihydroxy-12-[2'-(4"-(1-benzylindol-5-yl)oxy-3"-hydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone.

Mass (FAB) 990(M++Li)..

Partial $^1$H NMR (CDCl$_3$, 400 MHz): 7.30–7.05 (m, 8 H);

6.82 (dd, J=2 Hz, J=8 Hz, 1 H); 6.43 (d, J=3 Hz, 1 H);

5.27 (s, 2 H); 4.58 (d, J=6 Hz, 1 H); 4.40 (bd, J=13 Hz,

1 H).

EXAMPLE 53

17-Ethyl-1,14-dihydroxy-12-[2'-(4"-(1-(3-hydroxy -propyl)indol-6-yl)oxy-3"-methoxycyclohexyl)-1'-methylvinyl]-23,25-dimethoxy-13,19,21,27-tetramethyl -11,28-dioxa-4-azatricyclo[22.3.1.0$^{4,9}$]octacos-18-ene 2,3,10,16-tetraone Step A: 2-t-Butyldimethylsilyloxyethyl bromide To a solution of 2-bromoethanol (50 g, 0.40 mol) in CH$_2$Cl$_2$ (50 mL) was added t-butyldimethyl-chlorosilane (63.4 g, 0.42 mol), triethylamine (45.4 g, 0.45 mol) and dimethylaminopyridine (0.5 g). After stirring overnight the reaction mixture was washed 3× with water. The organic fraction was dried with Na$_2$SO$_4$, filtered, and concentrated in vacuo to provide 85 g of the title compound as a light yellow oil.

$^1$H NMR (CDCl$_3$) δ:3.85 (t, 2 H); 3.36 (t, 2 H); 0.86 (s, 9 H); 0.05 (s, 6 H).

Step B:
1-(2-Butyldimethylsilyloxyethyl)-5-bromoindole

To a slurry of sodium hydride (12 g, 0.3 mol, 60% dispersion in oil) in DMF (200 mL) was added dropwise a solution of 5-bromoindole (50 g, 0.255 mol) in DMF (300 mL). After stirring for 15 minutes 2-t-butyldimethylsilyloxyethyl bromide (60 g, 0.255 mol, neat) was added dropwise and the reaction mixture stirred for 1 hour. The reaction mixture was partitioned between ice water and ethyl ether. The organic fraction was washed with water, dried over Na$_2$SO$_4$, filtered and concentrated in vacuo. The product was purified by column chromatography (silica, 3:1 hexane/acetone) to give 68.6 g of the title compound as a light yellow oil. $^1$H NMR (CDCl$_3$) δ:7.72 (s, 1 H); 7.1–7.3 (m, 3 H); 6.4 (d, 1 H); 4.18 (t, 2 H); 3.86 (t, 2 H); 0.8 (s, 9 H); −0.18 (s, 6 H).

Step C: 17-Ethyl-1,14-dihydroxy-12-[2'-(4"-(1-(3-t -butyldimethylsilyloxypropyl)indol-6-yl)oxy -3"-methoxycyclohexyl)-1'-methylvinyl]-23, 25-dimethoxy-13,19,21,27-tetramethyl-11,28-dioxa-4-azatricyclo[22.3.1.0$^{4,9}$]octacos-18-ene-2.3.10.16-tetraone To a solution of tri[1-(3-t-butyldimethyl -silyloxypropyl)-indol-6-yl]bismuthine (0.917 gm, crude) in CH$_2$Cl$_2$ (7 mL) at room temperature was added peracetic acid (0.10 mL, 32% in acetic acid) followed in 15 minutes by 17-Ethyl-1,14-dihydroxy-12-[2' -(4'''-hydroxy-3"-methoxycyclohexyl)-1'methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (500 mg,. 0.63 mmol) and Cu(OAc)$_2$ (50 mg). The reaction mixture was stirred for 2 days. The reaction was then quenched with saturated NaHCO$_3$ and the mixture extracted with CH$_2$Cl$_2$. The organic extracts were combined, dried over Na$_2$SO$_4$, filtered, and concentrated in vacuo. The product was isolated and purified by preparative TLC on silica gel (3:1,hexane/acetone) to give 318 mg of the title compound.

Step D:
17-Ethyl-1,14-dihydroxy-12-[2'-(4"-(1-(3-hydroxypropyl)indol-6-yl)oxy-3"-methoxycyclohexyl)-1'-methylvinyl]-23,
25-dimethoxy-13,19,21,27-tetramethyl-11,
28-dioxa-4-azatricyclo[22.3.1.0$^{4,9}$]octacos
-18-ene-2,3,10,16-tetraone To a solution of 17-Ethyl-1,14-dihydroxy -12-[2'-(4"-(1-(3-t-butyldimethylsilyloxypropyl)indol -6-yl)oxy-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetra -one (318 mg) in CH$_2$Cl$_2$ (5 mL) at rt was added a solution of p-toluene sulfonic acid (25 mg) in CH$_3$OH (5 mL). The reaction mixture was stirred for 3 hours quenched with saturated NaHCO$_3$, then extracted with CH$_2$Cl$_2$. The extracts were combined, dried over Na$_2$SO$_4$, filtered and concentrated in vacuo. The product was purified by preparative TLC on silica gel (2:1,hexane/acetone) to give 190 mg of the title compound.

Partial 1 H NMR (CDCl$_3$, 200 MHz) δ:7.43 (d, J=9 Hz, 1 H); 7.02 (d, J=2 Hz, 1 H); 6.98 (d, J=3 Hz, 1 H); 6.78 (dd, J=2 Hz and J=9 Hz, 1 H); 6.38 (d, J=3 Hz, 1 H); 4.20 (t, J=6.5 Hz, 2 H); 2.00 (m, 2 H).

EXAMPLE 54

17-Ethyl-1,14-dihydroxy-12-[2'-(4"-((2''''-(3'''''-diethylaminopropionyloxy)ethyl)indol-5'''-yl)oxy-3"-methoxycyclohexyl)-1'-methylvinyl]-23,25-dimethoxy -13,19,21,27-tetramethyl-11,28-dioxa-4-azatricyclo-[22.3.1.0$^{4,9}$]octacos-18-ene-2,3,10,16-tetraone To a stirred solution of 17-Ethyl-1,14-dihydroxy-12-[2'-( 4"-( 1'''-(2'''''-hydroxyethyl)indol -5'''-yl)oxy-3"-methoxycyclohexyl)-1'-methylvinyl]-23,25-dimethoxy-13,19,21,27-tetramethyl-11,28-dioxa-4-azatricyclo-[22.3.1.0$^{4,9}$]octacos-18-ene-2,3,10,16 -tetraone (200 mg., 0.210 mmol., 1 eq.) in CH$_2$Cl$_2$ (2 mL.) under nitrogen was added 3-N,N-diethylaminopropionic acid hydrochloride (57 mg., 0.315 mmol., 1.5 eq.), dimethylaminopyridine (26 mg., 0.210 mmol., 1 eq.) and EDC (60 mg., 0.315 mmol., 1.5 eq.). The reaction was stirred for 1 hour. The mixture was diluted with ethyl acetate, washed with 1N aq. HCl, saturated aqueous NaHCO3 and then brine. The organic layer was dried over anhydrous MgSO4, filtered and concentrated in vacuo. The product was purified by flash column chromatography (3:2 hexanes/acetone) to give 194 mg. 17-Ethyl-1,14-dihydroxy-12-[2'-(4''-((2''''-(3'''''-diethylaminopropionyloxy)ethyl)indol -5'''-yl)oxy-3''-methoxycyclohexyl)-1'-methylvinyl]-23, 25-dimethoxy-13,19,21,27-tetramethyl-11,28-dioxa-4-azatricyclo[22.3.1.0$^{4,9}$]octacos-18-ene-2,3,10,16-tetraone. Mass (FAB) 1079 (M+ +1).

EXAMPLE 55

17-Ethyl-1,14-dihydroxy-12-[2'-(4''-((2''''-(3'''''-dimethylaminopropionyloxy)ethyl)indol-5'''-yl)oxy-3''-methoxycyclohexyl)-1'-methylvinyl]-23,25-dimethoxy-13,19,21,27-tetramethyl-11,28-dioxa-4-azatricyclo-[22.3.1.0$^{4,9}$]octacos-18-ene-2,3,10,16-tetraone The title compound is prepared in the manner of Example 54 employing 3-N,N-dimethylamino-propionic acid.

EXAMPLE 56

17-Ethyl-1,14-dihydroxy-12-[2'-(4''-((2''''-(3'''''-aminopropionyloxy)ethyl)indol-5'''-yl)oxy-3''-methoxycyclohexyl)-1'-methylvinyl]-23,25-dimethoxy-13,19,21,27-tetramethyl-11,28-dioxa-4-azatricyclo-[22.3.1.0$^{4,9}$]octacos-18-ene-2,3,10,16-tetraone The title compound is prepared in the manner of Example 54 employing 3-aminopropionic acid in suitably protected form followed by deprotection of the amino group.

EXAMPLE 57

17-Ethyl-1,14-dihydroxy-12-[2°-(4''-((2''''-(3'''''-benzyloxycarbonyl-2''''''-benzyloxycarbonylamino propionyloxy)ethyl)indol-5'''-yl)oxy-3''-methoxycyclo-hexyl)-1'-methylvinyl]-23,25-dimethoxy-13,19,21,27-tetramethyl-11,28-dioxa-4-azatricyclo[22.3.1.0$^{4,9}$]-octacos-18-ene-2,3,10,16-tetraone To a stirred solution of 17-Ethyl-1,14-dihydroxy-12-[2'-(4''-(1'''-(2''''-hydroxyethyl)indol -5'''-yl)oxy-3''-methoxycyclohexyl)-1'-methylvinyl]-23, 25-dimethoxy-13,19,21,27-tetramethyl-11,28-dioxa-4-azatricyclo-[22.3.1.0$^{4,9}$]octacos-18-ene-2,3,10,16-tetraone (500 mg., 0.526 mmol., 1 eq.) in CH2Cl2 (5 mL.) under nitrogen was added N-Cbz-aspartic acid -β-benzyl ester (225 mg., 0.631 mmol., 1.2 eq.), dimethyl-aminopyridine (64 mg., 0.526 mmol., 1 eq.) and EDC (120 mg., 0.631 mmol., 1.2 eq.). The reaction was stirred for 2 hours. TLC analysis indicated reaction complete. The mixture was diluted with ethyl acetate, washed with 1N aq. HCl, saturated aqueous NaHCO3 and then brine. The organic layer was dried over anhydrous MgSO4, filtered and concentrated in vacuo. The product was purified by flash column chromatography (70:30 hexanes-/acetone) to give 687 mg 17-Ethyl-1,14-dihydroxy-12-[2'-(4''-((2''''-(3'''''-benzyloxycarbonyl-2''''''-benzyloxycarbonylaminopropionyloxy) ethyl)indol-5'''-yl)oxy-3''-methoxy -cyclohexyl)-1'-methylvinyl]-23,25-dimethoxy-13,19,21,27-tetramethyl-11,28-dioxa-4-azatricyclo[22.3.1.0$^{4,9}$]-octacos-18-ene-2,3,10,16-tetraone.

EXAMPLE 58

17-Ethyl-1,14-dihydroxy-12-[2'-(4''-((2''''-(aspartyloxy) ethyl)indol-5''' -yl)oxy-3''-methoxycyclohexyl)-1'-methylvinyl]-23,25-dimethoxy-13,19,21,27-tetramethyl -11,28-dioxa-4-azatricyclo[22.3.1.0$^{4,9}$]octacos-18-ene -2.3.10.16-tetraone To a solution of 17-Ethyl-1,14-dihydroxy -12-[2'-(4''-((2''''-(3'''''-benzyloxycarbonyl-2''''''-benzyloxy-carbonylaminopropionyloxy)ethyl)indol-5'''-yl)oxy-3''-methoxycyclohexyl)-1'-methylvinyl]-23,25-dimethoxy-13,19,21,27-tetramethyl-11,28-dioxa-4-azatricyclo-[22.3.1.0$^{4,9}$]octacos-18-ene-2,3,10,16-tetraone (125 mg. 0.093 mmol., 1 eq.) in methanol (2 mL.) was added palladium hydroxide on carbon (25 mg.). The flask was charged with hydrogen and allowed to stir for 30 minutes. The reaction was filtered through a 0.45 μm PTFE membrane and concentrated in vacuo. The product was purified by flash column chromatography (100:10:5:0.5/CHCl3: MeOH: formic acid: H2O) to give 95 mg 17-Ethyl-1,14-dihydroxy-12-[2'-(4''-((2''''-(aspartyloxy)ethyl)indol-5'''-yl)oxy-3''-methoxycyclo -hexyl)-1'-methylvinyl]-23,25-dimethoxy-13,19,21,27-tetramethyl-11,28-dioxa-4-azatricyclo[22.3.1.0$^{4,9}$]-octacos-18-ene-2,3,10,16-tetraone. Mass (FAB) 1067 (M+).

EXAMPLE 59

17-Ethyl-1,14-dihydroxy-12-[2'-(4''-((2''''-(1'''''-imidazolylcarbonyloxy) ethyl)indol-5'''-yl)oxy-3''methoxycyclohexyl)-1'-methylvinyl]-23,25-dimethoxy -13,19,21,27-tetramethyl-11,28-dioxa-4-azatricyclo- [22.3.1.0$^{4,9}$]octacos-18-ene-2.3.10.16-tetraone To a stirred solution of 17-Ethyl-1,14-dihydroxy-12-[2'-(4''-(1'''-(2''''-hydroxyethyl)indol-5'''-yl)oxy-3''-methoxycyclohexyl)-1'-methylvinyl]-23,25-dimethoxy-13,19,21,27-tetramethyl-11,28-dioxa-4-azatricyclo-[22.3.1.0$^{4,9}$]octacos-18-ene-2,3,10,16-tetraone (1.5 g., 1.58 mmol., 1 eq.) in CH2Cl2 (15 mL.) under nitrogen was added carbonyl diimidazole (256 mg., 1.58 mmol., 1 eq.). After 45 minutes the reaction mixture was diluted with ethyl acetate, washed with 1N aq. HCl and then brine. The organic layer was dried over anhydrous MgSO4, filtered and concentrated in vacuo. The residue was used without further purification

EXAMPLE 60

17-Ethyl-1,14-dihydroxy-12-[2'-(4''-((2''''-(1'''''-piperazinocarbonyloxy)ethyl)indol-5'''-yl)oxy-3''-methoxycyclohexyl)-1'-methylvinyl]-23,25-dimethoxy -13,19,21,27-tetramethyl-11,28-dioxa-4-azatricyclo -[22.3.1.0$^{4,9}$]octacos-18-ene-2 3 10 16-tetraone To a stirred solution of 17-Ethyl-1,14-dihydroxy-12-[2'-(4''-((2''''-(1'''''-imidazolyl -carbonyloxy)ethyl)-indol-5'''-yl)oxy-3''-methoxycyclohexyl) -1'-methylvinyl]-23,25-dimethoxy-13,19,21,27-tetramethyl-11,28-dioxa-4-azatricyclo[22.3.1.0$^{4,9}$]-octacos-18-ene-2,3,10,16-tetraone (100 mg., 0.096 mmol., 1 eq.) in THF (1 mL.) at room temperature under nitrogen was added piperazine (82 mg., 0.956 mmol., 10 eq.). The mixture was stirred for 2 hours at room temperature, stored overnight in freezer then stirred for an additional 6 hours at room temperature. The reaction was diluted with ethyl acetate, washed with 1N HCl, saturated NaHCO3, and brine. The product was purified by flash column chromatography on silica gel (5% methanol/CH$_2$Cl$_2$ and then 5% methanol/CH$_2$Cl$_2$ plus 1% NH$_4$OH) to give 74 mg. Mass (FAB) 1064 (M++).

EXAMPLE 61

17-Ethyl-1,14-dihydroxy-12-[2'-(4''-(1'''-(2''''-(2'''''-hydroy)ethylaminocarbonyloxy)ethyl)indol-5'''-yl)oxy-3''-methoxycyclohexyl)-1'-methylvinyl]-23,25-dimethoxy-13,19,21,27-tetramethyl-11,28-dioxa-4-aza-tricyclo[22.3.1.0$^{4,9}$]octacos-18-ene-2,3,10,16-tetraone To a stirred solution of 17-Ethyl-1,14-dihydroxy-12-[2'-(4''-(1'''-(2''''-(1'''''-imidazolyl -carbonyloxy)-ethyl)indol-5 '''-yl)oxy-3''-methoxycyclo -hexyl)-1'-methylvinyl]-23, 25-dimethoxy-13,19,21,27-tetramethyl-11,28-dioxa-4- azatricyclo[22.3.1.0$^{4,9}$]-octacos-18-ene-2,3,10,16-tetraone (100 mg., 0.096 mmol., 1 eq.) in THF ( 1 mL.) at room temperature under nitrogen was added ethanolamine (29 µL., 0.478 mmol., 5 eq.). The reaction was stirred for 30 minutes at room temperature. The reaction was diluted with ethyl acetate, washed with 1N HCl, saturated NaHCO$_3$, and brine. The product was purified by flash column chromatography on silica gel (45/65 acetone/hexanes) to give 50 mg. 17-Ethyl-1,14dihydroxy-12-[2'-(4''-(1'''-(2''''-(2'''''-hydroy) -ethylaminocarbonyloxy)ethyl)indol-5'''-yl)oxy-3''-methoxycyclohexyl)-1'-methylvinyl]-23,25-dimethoxy -13,19,21,27-tetramethyl-11,28-dioxa-4-azatricyclo-[22.3.1.0$^{4,9}$]octacos-18-ene-2,3,10,16-tetraone. Mass (FAB) 1061 (M++Na); 1038 (M++1).

EXAMPLE 62

17-Ethyl-1,14-dihydroxy-12-[2'-(4''-(1'''-(2''''-(isopropylaminocarbonyloxy)ethyl)indol-5'''-yl)oxy-3''-methoxycyclohexyl)-1'-methylvinyl]-23,25-dimethoxy -13,19,21,27-tetramethyl-11,28-dioxa-4-azatricyclo-[22.3.1.0$^{4,9}$]octacos-18-ene-2.3.10.16-tetraone To a stirred solution of 17-Ethyl-1,14-dihydroxy-12-[2'-(4''-(1'''-(2''''-(1'''''-imidazolyl -carbonyloxy)ethyl)indol-5'''-yl)oxy-3''-methoxycyclo -hexyl)-1'methyl-vinyl]-23,25-dimethoxy-13,19,21,27-tetramethyl-11,28-dioxa-4-azatricyclo[22.3.1.0$^{4,9}$]-octacos-18-ene-2,3,10,16-tetraone (116 mg., 0.111 mmol., 1 eq.) in THF (1 mL.) at room temperature under nitrogen was added isopropylamine (48 µL., 0.555 mmol., 5 eq.). The reaction was stirred for overnight. The reaction was diluted with ethyl acetate, washed with 1N HCl and brine. The product was purified by flash column chromatography on silica gel (2:3 acetone/hexanes) to give 50 mg. 17-Ethyl -1,14-dihydroxy-12-[2'-(4''-(1'''-(2''''-(isopropyamino -carbonyloxy)ethyl)indol-5'''-yl)oxy-3''-methoxycyclohexyl) -1'-methylvinyl]-23,25-dimethoxy-13,19,21,27-tetramethyl-11,28-dioxa-4-azatricyclo[22.3.1.0$^{4,9}$]-octacos-18-ene-2,3,10,16-tetraone. Mass (FAB) 1043 (M++Li).

EXAMPLE 63

17-Ethyl-1,14-dihydroxy-12-[2'-(4''-(1'''-(2''''-(1'''''-piperidinocarbonyloxy)ethyl)indol-5''''-yl)oxy -3''-methorycyclohexyl)-1'-methylvinyl]-23,25-dimethoxy -13,19,21,27-tetramethyl-11,28-dioxa-4-azatricyclo-[22.3.1.0$^{4,9}$]octacos-18-ene-2.3.10.16-tetraone To a stirred solution of 17-Ethyl-1,14dihydroxy-12-[2'-(4''-(1'''-(2''''-(1'''''-imidazolyl -carbonyloxy)ethyl)indol-5'''-yl)oxy-3''-methoxycyclo -hexyl)-1'-methylvinyl]-23,25-dimethoxy-13,19,21,27-tetramethyl-11,28-dioxa-4-azatricyclo[22.3.1.0$^{4,9}$]-octacos-18-ene-2,3,10,16-tetraone (150 mg., 0.143 mmol., 1 eq.) in THF (1 mL.) at room temperature under nitrogen was added piperidine (42 µL., 0.717 mmol., 5 eq.). The reaction was stirred 1 hour. The reaction was diluted with ethyl acetate, washed with 1N HCl and brine. The product was purified by flash column chromatography on silica gel (4:1 hexanes/ acetone) to give 115 mg. 17-Ethyl-1,14-dihydroxy -12-[2'-(4''-(1'''-(2''''-(1'''''-piperidinocarbonyl -oxy)ethyl)indol-5'''-yl)oxy-3''-methoxycyclohexyl)-1'-methylvinyl]-23,25-dimethoxy-13,19,21,27-tetramethyl -11,28-dioxa-4-azatricyclo[22.3.1.0$^{4,9}$]octacos-18-ene -2,3,10,16-tetraone. Mass ( FAB) 1062 (M+).

EXAMPLE 64

17-Ethyl-1,14-dihydroxy-12-[2'-(4''-(1'''-(2''''-(1'''''-morphilinocarbonyloxy)ethyl)indol-5'''-yl)oxy -3''-methoxycyclohexyl)-1'-methylvinyl]-23,25-dimethoxy -13,19,21,27-tetramethyl-11,28-dioxa-4-azatricyclo-[22.3.1.0$^{4,9}$]octacos-18-ene-2.3.10.16-tetraone To a stirred solution of 17-Ethyl-1,14-dihydroxy-12-[2'-(4''-(1'''-(2''''-(1'''''-imidazolylcarbonyloxy)ethyl) indol-5'''-yl)oxy-3''-methoxycyclo -hexyl)-1'-methylvinyl]-23,25-dimethoxy-13,19,21,27-tetramethyl-11,28-dioxa-4-azatricyclo[22.3.1.0$^{4,9}$]-octacos-18-ene-2,3,10,16-tetraone (100 mg., 0.096 mmol., 1 eq.) in THF (1 mL.) at room temperature under nitrogen was added morphiline (42 µL., 0.478 mmol., 5 eq.). The reaction was stirred 4 hours. The reaction was diluted with ethyl acetate, washed with 1N HCl, saturated aqueous NaHCO$_3$ and brine. The product was purified by preparative TLC on silica gel (4% MeOH/CH$_2$Cl$_2$) to give 85 mg. product. The compound was further purified by preparative TLC on silica gel (4% MeOH/CH$_2$Cl$_2$) to give 67 mg. 17-Ethyl -1,14-dihydroxy-12-[2'-(4''-(1'''-(2''''(1'''''-morphilinocarbonyloxy)ethyl)indol-5'''-yl)oxy-3''-methoxycyclohexyl)-1'-methylvinyl]-23,25-dimethoxy-13, 19,21,27-tetramethyl-11,28-dioxa-4-azatricyclo-[22.3.1.0$^{4,9}$]octacos-18-ene-2,3,10,16-tetraone. Mass (FAB) 1064 (M+).

EXAMPLE 65

17-Ethyl-1,14-dihydroxy-12-[2'-(4''-(1'''-(2''''-diphenylaminocarbonyloxy)ethyl)indol-5'''-yl)oxy-3''-methoxycyclohexyl)-1'-methylvinyl]-23,25-dimethoxy -13,19,21,27-tetramethyl-11,28-dioxa-4-azatricyclo-[22.3.1.0$^{4,9}$]octacos-18-ene-2,3,10,16tetraone To a stirred solution of 17-Ethyl-1,14-dihydroxy-12-[2'-(4''-(1'''-(2''''-hydroryethyl)indol -5'''-yl)oxy-3''-methoxycyclohexyl )-1'-methylvinyl]-23, 25-dimethoxy-13,19,21,27-tetramethyl-11,28-dioxa-4azatricyclo[22.3.1.0$^{4,9}$]octacos-18-ene-2,3,10,16tetraone (100 mg., 0.105 mmol., 1 eq.) in CH$_2$Cl$_2$ (1 mL.) under nitrogen was added diphenylcarbamylchloride (29 mg., 0.13 mmol., 1.2 eq.), triethylamine (22µL., 0.16 mmol., 1.5 eq.) and dimethylaminopyridine (3mg., 0.021 mmol., 0.2 eq.). The reaction was stirred overnight. More diphenylcarbamylchloride (15 mg.) and triethylamine (11µL.) were added. After 3 hours the reaction mixture was diluted with ethyl acetate, washed with 1N aq. HCl, water and then brine. The organic layer was dried over anhydrous MgSO$_4$, filtered and concentrated in vacuo. The product was purified by preparative TLC (3% MeOH/ CH$_2$Cl$_2$) to give 50 mg. 17-Ethyl-1,14-dihydroxy-12-[2'-(4''-(1'''-(2''''-(diphenylaminocarbonyloxy)ethyl) -indol-5'''-yl)oxy-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10, 16-tetraone. Mass (FAB) 1046 (M+).

EXAMPLE 66

17-Ethyl-1,14-dihydroxy-12-[2'-(4"-(1'"-(2""-(diethylaminocarbonyloxy)ethyl)indol-5'"-yl)oxy-3"-methoxycyclohexyl)-1'-methylvinyl]-23,25-dimethoxy-13,19,21,27-tetramethyl-11,28-dioxa-4-azatricyclo-[22.3.1.0$^{4,9}$]octacos-18-ene-2,3,10,16-tetraone To a stirred solution of 17-Ethyl-1,14-dihydroxy-12-[2'-(4"-(1'"-(2""-hydroxyethyl)indol -5'"-yl)oxy-3"-methoxycyclohexyl)-1'-methylvinyl]-23, 25-dimethoxy-13,19,21,27-tetramethyl-11,28-dioxa-4-azatricyclo[22.3.1.0$^{4,9}$]octacos-18-ene-2,3,10,16tetraone (100 mg., 0.105 mmol. 1 eq.) in CH$_2$Cl$_2$ (1 mL.) under nitrogen was added diethylcarbamylchloride (16 µL., 0.13 mmol., 1.2 eq.), triethylamine (22 µL., 1.5 eq.), and dimethylaminopyridine (13 mg., 1.0 eq.). The reaction was stiff ed overnight. The mixture was heated and maintained at reflux for 4 days. The mixture was cooled, diluted with ethyl acetate, washed with 1N aq. HCl and then brine. The organic layer was dried over anhydrous MgSO$_4$, filtered and concentrated in vacuo. The product was purified by preparative TLC (3% MeOH CH$_2$Cl$_2$) to give 16 mg. 17-Ethyl-1,14-dihydroxy-12-[2'-(4"-(1'" -(2""-(diethylaminocarbonyloxy)ethyl)indol-5'"-yl) -oxy-3"-methoxycyclohexyl)-1'-methylvinyl]-23,25-dimethoxy-13,19,21,27-tetramethyl-11,28-dioxa-4azatricyclo[22.3.1.0$^{4,9}$]octacos-18-ene-2,3,10,16-tetraone. Mass (FAB) 1057 (M++Li).

EXAMPLE 67

17-Ethyl-1,14-dihydroxy-12-[2'-(4"-(1'"-(2""-methanesulfonyloxyethyl)indol-5'"-yl)oxy-3"-methoxy-cyclohexyl)-1'-methylvinyl]-23,25-dimethoxy-13,19,21,27-tetramethyl-11,28-dioxa-4-azatricyclo[22.3.1.0$^{4,9}$]-octacos-18-ene-2,3,10,16-tetraone To a stirred solution of 17-Ethyl-1,14-dihydroxy-12-[2'-(4"-(1'"-(2""-hydroxyethyl)indol -5'"-yl)oxy-3"-methoxycyclohexyl)-1'-methylvinyl]-23, 25-dimethoxy-13,19,21,27-tetramethyl-11,28-dioxa-4-azatricyclo[22.3.1.0$^{4,9}$]octacos-18-ene-2,3,10,16-tetra -one (500 mg., 0.526 mmol., 1 eq.) in CH$_2$Cl$_2$ (20 mL.) under nitrogen at 0° C. was added triethylamine (147 µL., 1.053 mmol., 2 eq.), followed by methanesulfonylchloride (54 µL., 0.579 mmol., 1.1 eq.). The reaction was stirred 10 minutes and the cooling bath was removed. The reaction was stirred at room temperature for three hours. The mixture was stored in the freezer overnight. The solvent was removed in vacuo. The product was used without purification

EXAMPLE 68

17-Ethyl-1,14-dihydroxy-12-[2'-(4"-(1'"-(2""-azido -ethyl)indol-5'"-yl)oxy-3"-methoxycyclohexyl)-1' -methylvinyl]-23,25-dimethoxy-13,19,21,27-tetramethyl -11,28-dioxa-4-azatricyclo[22.3.1.0$^{4,9}$]octacos-18-ene -2.3.10.16-tetraone To a stirred solution of 17-Ethyl-1,14-dihydroxy-12-[2'-(4"-(1'"-(2""-methanesulfonyloxy -ethyl)indol-5'"-yl)oxy-3"-methoxycyclohexyl)-1'methylvinyl]-23,25-dimethoxy-13,19,21,27-tetramethyl -11,28-dioxa-4-azatricyclo[22.3.1.0$^{4,9}$]octacos-18-ene-2, 3,10,16-tetraone (0.526 mmol., 1 eq.) in DMF (10 mL.) under nitrogen was added sodium azide (171 mg., 2.63 mmol., 5 eq.).,- The reaction was heated to 60° C. for 2 hours The solvent was removed in vacuo. The residue was diluted with ethyl acetate and washed with brine. The aqueous layer was extracted 3× with ethyl acetate. The organic extracts were dried over anhydrous MgSO$_4$, filtered and concentrated in vacuo. The product was purified by flash column chromatography on silica gel (2:1 hexanes/acetone) giving 310 mg. 17-Ethyl-1,14-dihydroxy-12-[2'-(4"-1'"-(2""-azidoethyl)indol-5'"-yl)oxy-3"-methoxy -cyclohexyl)-1'-methylvinyl]-23,25-dimethoxy-13,19,21, 27-tetramethyl-11,28-dioxa-4-azatricyclo[22.3.1.0$^{4,9}$]-octacos-18-ene-2,3,10,16-tetraone. Mass (FAB) 975 (M+).

EXAMPLE 69

17-Ethyl-1,14-dihydroxy-12-[2'-(4"-(1'"-(2""-amino -ethyl)indol-5'"-yl)oxy-3"-methoxycyclohexyl)-1'-methylvinyl]-23,25-dimethoxy-13,19,21,27-tetramethyl -11,28-dioxa-4-azatricyclo[22.3.1.0$^{4,9}$]octacos-18-ene -2,3,10,16-tetraone To a stirred solution of 17-Ethyl-1,14-dihydroxy-12-[2'-(4"-(1'"-(2""-azidoethyl)indol -5'"-yl)oxy-3"-methoxycyclohexyl)-1'-methylvinyl]-23, 25-dimethoxy-13,19,21,27-tetramethyl-11,28-dioxa-4azatricyclo[22.3.1.0$^{4,9}$]octacos-18-ene-2,3,10,16tetraone (260 mg., 0.27 mmol., 1 eq.) in THF (6 mL.) was added water (7 drops) followed by triphenylphosphine (87 mg., 0.33 mmol., 1.25 eq.). The reaction was stirred at room temperature for 16 hours The solvent was removed in vacuo. The product was purified by flash column chromatography on silica gel (10% MeOH/CH$_2$Cl$_2$) giving 227 mg. 17-Ethyl-1,14-dihydroxy-12-[2'-(4"-(1'"-(2""-aminoethyl)indol -5'"-yl)oxy-3"-methoxycyclohexyl)-1'-methylvinyl]-23, 25-dimethoxy-13,19,21,27-tetramethyl-11,28-dioxa-4-azatricyclo[22.3.1.0$^{4,9}$]octacos-18-ene-2,3,10,16-tetraone. Mass (FAB) 956( M++Li).

EXAMPLE 70

17-Ethyl-1,14-dihydroxy-12-[2'-(4"-(1'"-t-butyldi -methylsilyloxyethoxyethylindol-5'"-yl)oxy-3"-methoxy -cyclohexyl)-1'-methylvinyl]-23,25-dimethoxy-13,19,21, 27-tetramethyl-11,28-dioxa-4-azatricyclo[22.3.1.0$^{4,9}$]-octacos-18-ene-2.3.10.16-tetraone To a solution of tri[1-(2-t-butyldi -methylsilyloxyethoxyethyl)-indol-5-yl]bismuthine (360 mg., 0.31 mmol.) in CH$_2$Cl$_2$ (3 mL.) at rt was added peracetic acid (0.05 mL., 32% in acetic acid) followed in 10 minutes by 17-Ethyl-1,14-dihydroxy -12-[2'-(3", 4"-dihydroxycyclohexyl)-1'-methylvinyl]-23,25-dimethoxy-13,19,21,27-tetramethyl-11,28-dioxa-4 -azatricyclo-[22.3.1.0$^{4,9}$]-octacos-18-ene-2,3,10,16-tet -raone (200 mg, 0.25 mmol) and Cu(OAc)$_2$ (20 mg.). The reaction mixture was stirred for 18 hrs. The reaction was then quenched with saturated NaHCO$_3$ and extracted with CH$_2$Cl$_2$. The organic extracts were combined, dried with Na$_2$SO$_4$, filtered and concentrated in vacuo. The product was isolated and purified by preparative TLC (3:1, hexane/acetone) to afford 120 mg. of the title compound as a dark oil.

EXAMPLE 71

17-Ethyl-1,14-dihydroxy-12-[2'-( 4''-(1'''-hydroxy -ethoxyethylindol-5'''-yl)oxy-3''-methoxycyclohexyl)- 1'-methylvinyl]-23,25 -dimethoxy-13,19,21,27-tetramethyl -11,28-dioxa-4-azatricyclo[22.3.1.0$^{4,9}$]octacos-18-ene -2.3.10.16-tetraone To a solution of 17-Ethyl-1,14-dihydroxy -12-[2'-(4''- (1'''-t-butyldimethylsilyloxyethoxy-ethyl -indol-5'''- yl)oxy-3''-methoxycyclohexyl)-1'-methylvinyl]-23,25- dimethoxy-13,19,21,27-tetramethyl-11,28-dioxa-4-aza- tricyclo[22.3.1.0$^{4,9}$]octacos-18-ene -2,3,10,16-tetraone (120 mg) in CH$_2$Cl$_2$ (3 mL.) at rt was added a solution of p-toluene sulfonic acid (20 mg.) in CH$_3$OH (3 mL.). The reaction mixture was stirred for 3 hr., quenched with saturated NaHCO$_3$, then extracted with CH$_2$Cl$_2$. The extracts were combined, dried over Na$_2$SO$_4$, filtered and concentrated in vacuo. The product was purified by preparative TLC on silica gel (2:1, hexane/acetone) to give 51 mg of the title compound. Partial $^1$H NMR (CDCl$_3$, 200 MHz) δ:7.19 (d, J=9 Hz, 1 H); 7.17 (d, J=2 Hz, 1 H); 7.08 (d, J=3.5 Hz, 1 H); 6.89 (dd, J=2 and J=9 Hz, 1 H); 6.34 (d, J=3.5 Hz, 1 H); 4.22 (t, J=5 Hz, 2 H); 3.73 (t, J=5 Hz, 2 H); 3.57 (t, J=5 Hz, 2 H); 3.39 (t, J=5 Hz, 2 H)

EXAMPLE 72

17-Ethyl-1,14-dihydroxy-12-[2'-(3''-methoxy-4''-(1'''- (1''''-oxoprop-3''''-yl)indol-5'''-yl)oxycyclohexyl) -1'-methylvinyl]-23,25-dimethoxy-13,19,21,27-tetra -methyl-11,28-dioxa-4-azatricyclo[22.3.1.0$^{4,9}$]octacos -18-ene-2.3.10.16-tetraone To a solution of 17-Ethyl-1,14-dihydroxy -12-[2'-(4''- (1'''-(3''''-hydroxypropyl)indol-5'''-yl) -oxy-3''-methoxycyclohexyl)-1'-methylvinyl]-23,25-dimethoxy- 13,19,21,27-tetramethyl-11,28-dioxa-4azatricyclo[22.3.1.0$^{4,9}$]octacos-18-ene-2,3,10,16-tetraone (700 mg., 0.726 mmol.) in CH$_2$Cl$_2$ (25 mL) was added DMSO (2 mL.) and diisopropylethylamine ( 3.7 mL.) followed by pyridine sulfur trioxide (650 mg., 4.1 mmol.). The mixture was stirred for 20 min. then poured into saturated aqueous NaHCO$_3$. The product was extracted into CH$_2$Cl$_2$ which was then dried with Na$_2$SO$_4$, filtered, and concentrated in vacuo. The product was purified by column chromatography (silica gel, 4:1 hexane/acetone) to give 457 mg. of the title compound. Partial $^1$H NMR (CDCl$_3$, 200 MHz) δ:9.77 (s, 1 H); 7.19 (d, J=2 Hz, 1 H); 7.15 (d, J=9 Hz, 1 H); 7.04 (d, J=3.5 Hz, 1 H); 6.89 (dd, J=2 and J=9 Hz, 1 H); 6.33 (d, J=3.5 Hz, 1 H); 4.39 (t, J=5 Hz, 2 H); 2.94 (t, J=5 Hz, 2 H).

EXAMPLE 73

17-Ethyl-1,14-dihydroxy-12-[2'-(3''-methoxy-4''-(1'''- (1''''-carboxyeth-2''''-yl)indol-5'''-yl)oxycyclo -hexyl)-1'-methylvinyl]-23,25-dimethoxy-13,19,21,27- tetramethyl-11,28-dioxa-4-azatricyclo[22.3.1.0$^{4,9}$]- octacos-18-ene-2.3.10.16-tetraone To a stirred solution of 17-Ethyl-1,14-dihydroxy-12- [2'-(3 ''-methoxy-4''-(1'''-(1''''-oxoprop -3''''-yl)indol- 5'''-yl)oxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (100 mg.), 5-bromoindole (300 mg.) and 2-methyl-2-butene (0.80 mL.) in t-butanol (4mL.) was added a solution of sodium chlorite (15 mg.) and sodium dihydrogen phosphate (15 mg.) in water (0.15 mL.). The reaction mixture was stirred for 0.5 hr. then concentrated in vacuo. The residue was partioned between 10 ml. water containing 2 drops of 2N HCl and diethyl ether. The organic extract was dried with Na$_2$SO$_4$, filtered, and concentrated in vacuo. The product was purified by preparative TLC 2× first with 2:1 hexane/acetone then 7% CH$_3$OH in CH$_2$Cl$_2$ and finally flash column chromatography on C$_{18}$ column packing with 60% CH$_3$CN in water to give 11 mg. of the title compound. Mass (FAB) 1001 (M+Na).

EXAMPLE 74

17-Ethyl-1,14-dihydroxy-12-[2'-(4''-(2'''-(2-naphthyl)- 2'''-hydroxyethyloxy)-3''-methoxycyclohexyl) -1'- methylvinyl]-23,25-dimethoxy-13,19,21,27-tetra -methyl-11,28-dioxa-4-azatricyclo-[22.3.1.0$^{4,9}$]octacos -18-ene-2,3,10,16-tetraone Step A: 17-Ethyl-1-hydroxy-14-(tert-butyldimethyl -siloxy)-12-[2'-(4''-(2'''-(2-naphthyl) -2'''-hydroxyethyloxy)-3''-methoxycyclo -hexyl)-1'-methylvinyl]-23,25-dimethoxy-13, 19,21,27-tetramethyl-11,28-dioxa-4-azatri -cyclo-[22.3.1.0$^{4,9}$]octacos-18-ene-2,3,10, 16-tetraone To a stirred solution of 17-ethyl-1-hydroxy-14-( t- butyl-dimethyisilyloxy)-12-[2'-(4''-ethanaloxy-3''- methoxycyclohexyl)-1'-methylvinyl]-23, 25-dimethoxy- 13,19,21,27-tetramethyl-11,28-dioxa-4-azatricyclo[22.3.1.0$^{4,9}$]octacos-18-ene-2,3,10,16-tetraone (1.0 g) in THF (10 mL) at −50° C. was added a solution of 2-naphthyl magnesium bromide (0.5 M in THF). The solution was stirred for 0.5 hr. then quenched by addition of aqueous NH$_4$Cl solution and the product extracted 2× with CH$_2$Cl$_2$. The extracts were combined, dried with Na$_2$SO$_4$, filtered and concentrated in vacuo. Purification of the residue by column chromatography followed by preparative TLC afforded 332 mg of the title compound as a colorless solid.

Step B: 17-Ethyl-1,14-dihydroxy-12-[2'-(4''-(2'''– (2-naphthyl)-2'''-hydroxyethyloxy)-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone The product from Step A was deprotected with HF/pyridine as described in Step B from above to afford 190 mg of the title compound as a colorless solid ($^1$H NMR was consistent with the desired structure).

EXAMPLE 75

17-Ethyl-1,14-dihydroxy-12-[2'-(4''-(2'''-(2-thienyl) -2'''-hydroxyethyloxy)-3''-methoxycyclohexyl)-1'- methylvinyl]-23,23-dimethoxy-13,19,21,27-tetramethyl- 11, 28-dioxa-4-azatricyclo[22.3.1.0$^{4,9}$]octacos-18-ene-2,3, 10,16-tetraone The title compound was prepared essentially as described in Example 74 ($^1$H NMR was consistent with the desired structure).

EXAMPLE 76

17-Ethyl-1,14-dihydroxy-12-[2'-(4''-(2'''-(3-pyridyl)-2'''-hydroxyethyloxy)-3''-methoxycyclohexyl)-1'-methyl-vinyl]-23,25-dimethoxy-13,19,21,27-tetramethyl-11,28-dioxa-4-azatricyclo[22.3.1.0$^{4,9}$]-octacos-18-ene-2,3,10,16-tetraone The title compound was prepared essentially as described in Example 74 ($^1$H NMR was consistent with the desired structure).

Utilizing the general procedures described in Examples 1 to 76, the following compounds of Formula I (wherein R$^4$ is hydrogen, R$^5$ is methyl, ethyl, propyl or allyl; R$^{10}$ is hydrogen and n is 2) are prepared from the appropriately substituted starting materials and reagents.

| EXAMPLE NO. | R$^1$ | R$^2$ | R$^3$ | R$^5$ |
|---|---|---|---|---|
| 77 | 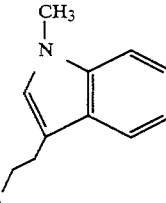 | H | OH | CH$_3$CH$_2$ |
| 78 | 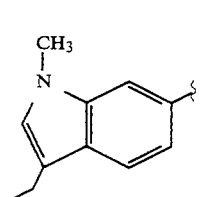 | CH$_3$ | OH | CH$_3$CH$_2$ |
| 79 | 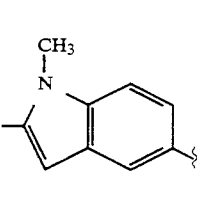 | CH$_3$ | OH | CH$_3$CH$_2$ |
| 80 | 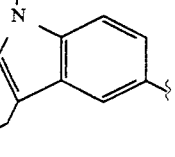 | CH$_3$ | OH | CH$_3$CH$_2$ |
| 81 | 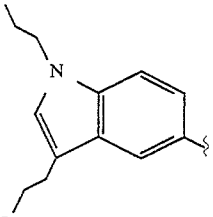 | CH$_3$ | OH | CH$_3$CH$_2$ |
| 82 | 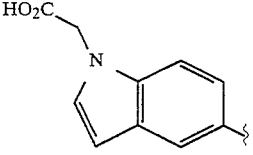 | CH$_3$ | OH | CH$_3$CH$_2$ |
| 83 | 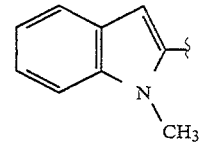 | CH$_3$ | OH | CH$_3$CH$_2$ |
| 84 | 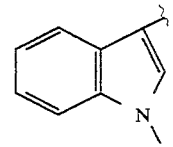 | CH$_3$ | OH | CH$_3$CH$_2$ |
| 85 |  | CH$_3$ | OH | CH$_3$CH$_2$ |

EXAMPLE 86

A lotion comprising the composition shown below may be prepared.

| Ingredient | (weight %) |
|---|---|
| 95% Ethanol | 80.0 |
| Compound of Formula I | 3.0 |
| Minoxidil | 2.0 |
| α-Tocopheral-acetate | 0.01 |
| Ethylene oxide (40 mole) adducts of hardened castor oil | 0.5 |
| Purified water | 14.0 |
| perfume and dye | q.s. |

Into 95% ethanol are added a compound of Formula I, minoxidil, α-tocopherol acetate, ethylene oxide (40 mole) adducts of hardened castor oil, perfume, and a dye, and the mixture is stirred and dissolved, followed by an addition of purified water, to obtain a liquid lotion.

EXAMPLE 87

A lotion comprising the composition shown below may be prepared.

| Ingredient | (weight %) |
|---|---|
| 95% Ethanol | 80.0 |
| Compound of Formula I | 0.005 |
| Cyclosporin A | 0.01 |
| Hinokitiol | 0.01 |
| Ethylene oxide (40 mole) adducts of hardened castor oil | 0.5 |

| Ingredient | (weight %) |
|---|---|
| Purified water | 19.0 |
| perfume and dye | q.s. |

Into 95% ethanol are added a compound of Formula I, cyclosporin A, hinokitiol, ethylene oxide (40 mole) adducts of hardened castor oil, perfume, and a dye, and the mixture is stirred and dissolved, followed by the addition of purified water, to obtain a liquid lotion.

EXAMPLE 88

An emulsion is prepared form an A phase and a B phase having the following compositions.

| | (weight %) |
|---|---|
| (A phase) | |
| Whale wax | 0.5 |
| Cetanol | 2.0 |
| Petrolatum | 5.0 |
| Squalane | 10.0 |
| Polyoxyethylene (10 mole) monostearate | 2.0 |
| Sorbitane monooleate | 1.0 |
| Compound of Formula I | 0.01 |
| Minoxidil | 0.5 |
| (B phase) | |
| Glycerine | 10.0 |
| Purified water | 68.5 |
| Perfume, dye, and preservative | q.s. |

The A phase and the B phase are respectively heated and melted and maintained at 80° C., both phases are mixed to be emulsified, and are cooled under stirring to normal temperature to obtain an emulsion.

EXAMPLE 89 a cream is prepared from A phase and B phase having the following compositions.

| | (weight %) |
|---|---|
| (A phase) | |
| Fluid paraffin | 5.0 |
| Cetostearyl alcohol | 5.5 |
| Petrolatum | 5.5 |
| Glycerine monostearate | 3.0 |
| Polyoxyethylene (20 mole) 2-octyldodecyl ether | 3.0 |
| Propylparaben | 0.3 |
| (B phase) | |
| Compound of Formula I | 0.8 |
| Minoxidil | 1.0 |
| Glycerine | 7.0 |
| Dipropylene glycol | 20.0 |
| Polyethylene glycol 4000 | 5.0 |
| Sodium Hexametaphosphate | 0.005 |
| Purified water | 43.895 |

The A phase is heated and melted, and maintained at 70° C., the B phase is added to the A phase followed by stirring, and the obtain emulsion is cooled to obtain a cream.

EXAMPLE 90

A hair liquid comprising the composition shown below may be prepared.

| Ingredient | (weight %) |
|---|---|
| Polyoxyethlene butyl ether | 20.0 |

| Ingredient | (weight %) |
|---|---|
| Ethanol | 50.0 |
| Compound of Formula I | 1.0 |
| Minoxidil | 1.0 |
| Propylene glycol | 5.0 |
| Polyoxyethylene hardened castor oil derivative (ethylene oxide 80 mole adducts) | 0.4 |
| Perfume | q.s. |
| Purified water | q.s. |

Into ethanol is added polyoxypropylene butyl ether, propylene glycol, polyoxyethylene hardened castor oil, a compound of Formula I, minoxidil, and perfume, which are mixed under stirring, and to the mixture is added purified water, to obtain a hair liquid.

EXAMPLE 91

A hair shampoo comprising the composition shown below may be prepared.

| Ingredient | (weight %) |
|---|---|
| Sodium laurylsulfate | 5.0 |
| Triethanolamine laurylsulfate | 5.0 |
| Betaine lauryldimethylaminoacetate | 6.0 |
| Ethylene glycol distearate | 2.0 |
| Propylene glycol | 5.0 |
| Compound of Formula I | 1.0 |
| Minoxidil | 2.0 |
| Ethanol | 2.0 |
| Perfume | 0.3 |
| Purified water | 71.7 |

Into 71.1 g of purified water is added 5.0 g of sodium laurylsulfate, 5.0 g of triethanolamine laurylsulfate, 6.0 g of betaine lauryldimethylamino-acetate, then a mixture obtained by adding 1.0 g of a compound of Formula I, 2.0 g of minoxidil, 5.0 g of polyethylene glycol, and 2.0 g of ethylene glycol distearate to 2.0 g of ethanol, followed by stirring, and 0.3 g of perfume, is successively added, and the mixture is heated then cooled to obtain a hair shampoo.

While the foregoing specification teaches the principles of the present invention, with examples provided for the purpose of illustration, it will be understood that the practice of the invention encompasses all of the casual variations, adaptations, modification, deletions, or additions of procedures and protocols described herein, as come within the scope of the following claims and its equivalents.

What is claimed is:

1. A compound selected from the group consisting of:
17-Ethyl-1,14-dihydroxy-12-[2'-(4"-(2'''-(3-pyridyl)-2'''-hydroxyethyloxy)-3"-methoxycyclohexyl)-1'-methylvinyl]-23,25-dimethoxy-13,19,21,27-tetramethyl-11,28-dioxa-4-azatricyclo[22.3.1.0$^{4,9}$]-octacos-18-ene-2,3, 10,16-tetraone;

17-Ethyl-1,14-dihydroxy-12-[2'-(4"-(2'''-(3-pyridyl)-2'''-oxoethyloxy)-3"-methoxycyclohexyl)-1'-methylvinyl]-23,25-dimethoxy-13,19,21,27-tetramethyl-11,28-dioxa-4-azatricyclo[22.3.1.0$^{4,9}$]-octacos-18-ene-2,3, 10,16-tetraone;

17-Ethyl-1,14-dihydroxy-12-[2'-(4"-(2'''-(2-thienyl)-2'''-hydroxyethyloxy)-3"-methoxycyclohexyl)-1'-methylvinyl]-23,23-dimethoxy-13,19,21,27-tetramethyl-11,28 -dioxa-4-azatricyclo[22.3.1.0$^{4,9}$]octacos-18-ene-2,3, 10,16-tetraone;

17-Ethyl-1,14-dihydroxy-12-[2'-(4"-(2'''-(3-thienyl)-2'''-hydroxyethyloxy)-3"-methoxycyclohexyl)-1'-methylvinyl]-23,23-dimethoxy-13,19,21,27-tetramethyl-11,28-dioxa-4-azatricyclo[22.3.1.0$^{4,9}$]octacos-18-ene-2,3, 10,16-tetraone;

17-Ethyl-1,14-dihydroxy-12-[2'-(4"-(2'''-(2-thienyl)-2'''-oxoethyloxy)-3"-methoxycyclohexyl)-1'-methylvinyl]-23,23-dimethoxy-13,19,21,27-tetramethyl-11,28 -dioxa-4-azatricyclo[22.3.1.0$^{4,9}$]octacos-18-ene-2,3, 10,16-tetraone;

-17-Ethyl-1,14-dihydroxy-12-[2'-(4"-(2'''-(3-thienyl)-2'''-oxoethyloxy)-3"-methoxycyclohexyl)-1'-methylvinyl]-23,23-dimethoxy-13,19,21,27-tetramethyl-11,28 -dioxa-4-azatricyclo[22.3.1.0$^{4,9}$]octacos-18-ene-2,3, 10,16-tetraone;

17-Ethyl-1,14-dihydroxy-12-[2'-(4"-(2'''-(benzothien-2-yl)-2'''-hydroxyethyloxy)-3"-methoxycyclohexyl)-1'-methylvinyl]-23,23-dimethoxy-13,19,21,27-tetramethyl -11,28-dioxa-4-azatricyclo[22.3.1.0$^{4,9}$]octacos-18-ene -2,3,10,16-tetraone;

-17Ethyl-1,14-dihydroxy-12-[2'-(4"-(2'''-(benzothien-3-yl)-2'''-hydroxyethyloxy)-3"-methoxycyclohexyl)-1'-methylvinyl]-23,23-dimethoxy-13,19,21,27-tetramethyl -11,28-dioxa-4-azatricyclo[22.3.1.0$^{4,9}$]octacos-18-ene -2,3,10,16-tetraone;

17-Ethyl-1,14-dihydroxy-12-[2'-(4"-(2'''-(benzothien-5-yl)-2'''-hydzoxyethyloxy)-3"-methoxycyclohexyl)-1'-methylvinyl]-23,23-dimethoxy-13,19,21,27-tetramethyl -11,28-dioxa-4-azatricyclo[22.3.1.0$^{4,9}$]octacos-18-ene -2,3,10,16-tetraone;

17-Ethyl-1,14-dihydroxy-12-[2'-(4"-(2'''-(benzothien-6-yl)-2'''-hydroxyethyloxy)-3"-methoxycyclohexyl)-1'methylvinyl]-23,23-dimethoxy-13,19,21,27-tetramethyl -11,28-dioxa-4-azatricyclo[22.3.1.0$^{4,9}$]octacos-18-ene -2,3,10,16-tetraone;

17-Ethyl-1,14-dihydroxy-12-[2'-(4"-(2'''-(benzothien-2-yl)-2'''-oxoethyloxy)-3"-methoxycyclohexyl)-1'-methylvinyl]-23,23-dimethoxy-13,19,21,27-tetramethyl -11,28-dioxa-4-azatricyclo[22.3.1.0$^{4,9}$]octacos-18-ene -2,3,10,16-tetraone;

17-Ethyl-1,14-dihydroxy-12-[2'-(4"-(2'''-(benzothien-3-yl)-2'''-oxoethyloxy)-3"-methoxycyclohexyl)-1'methylvinyl]-23,23-dimethoxy-13,19,21,27-tetramethyl -11,28-dioxa-4-azatricyclo[22.3.1.0$^{4,9}$]octacos-18-ene -2,3,10,16-tetraone;

17-Ethyl-1,14-dihydroxy-12-[2'-(4"-(2'''-(benzothien-5-yl)-2'''-oxoethyloxy)-3"-methoxycyclohexyl)-1'methylvinyl]-23,23-dimethoxy-13,19,21,27-tetramethyl -11,28-dioxa-4-azatricyclo[22.3.1.0$^{4,9}$]octacos-18-ene -2,3,10,16-tetraone;

17-Ethyl-1,14-dihydroxy-12-[2'-(4"-(2'''-(benzothien-6-yl)-2'''-oxoethyloxy)-3"-methoxycyclohexyl)-1'-methylvinyl]-23,23-dimethoxy-13,19,21,27-tetramethyl -11,28-dioxa-4-azatricyclo[22.3.1.0$^{4,9}$]octacos-18-ene -2,3,10,16-tetraone;

17-Ethyl-1,14-dihydroxy-12-[2'-(4"-(2'''-(benzofuran-2-yl)-2'''-hydroxyethyloxy)-3"-methoxycyclohexyl)-1'-methylvinyl]-23,23-dimethoxy-13,19,21,27-tetramethyl -11,28-dioxa-4-azatricyclo[22.3.1.0$^{4,9}$]octacos-18-ene -2,3,10,16-tetraone;

17-Ethyl-1,14-dihydroxy-12-[2'-(4"-(2'''-(benzofuran-3-yl)-2'''-hydroxyethyloxy)-3"-methoxycyclohexyl)-1'-methylvinyl]-23,23-dimethoxy-13,19,21,27-tetramethyl -11,28-dioxa-4-azatricyclo[22.3.1.0$^{4,9}$]octacos-18-ene -2,3,10,16-tetraone;

17-Ethyl-1,14-dihydroxy-12-[2'-( 4"-(2'''-(benzofuran-5-yl)-2'''-hydroxyethyloxy)-3"-methoxycyclohexyl)-1'-methylvinyl]-23,23-dimethoxy-13,19,21,27-tetramethyl -11,28-dioxa-4-azatricyclo[22.3.1.0$^{4,9}$]octacos-18-ene -2,3,10,16-tetraone;

17-Ethyl-1,14-dihydroxy-12-[2'-(4"-(2'''-(benzofuran-6-yl)-2'''-hydroxyethyloxy)-3"-methoxycyclohexyl)-1'-methylvinyl]-23,23-dimethoxy-13,19,21,27-tetramethyl -11,28-dioxa-4-azatricyclo[22.3.1.0$^{4,9}$]octacos-18-ene -2,3,10,16-tetraone;

17-Ethyl-1,14-dihydroxy-12-[2'-(4"-(2'''-(benzofuran-2-yl)-2'''-oxoethyloxy)-3"-methoxycyclohexyl)-1'-methylvinyl]-23,23-dimethoxy-13,19,21,27-tetramethyl -11,28-dioxa-4-azatricyclo[22.3.1.0$^{4,9}$]octacos-18-ene -2,3,10,16-tetraone;

17-Ethyl-1,14-dihydroxy-12-[2'-(4"-(2'''-(benzofuran-3-yl)-2'''-oxoethyloxy)-3"-methoxycyclohexyl)-1'-methylvinyl]-23,23-dimethoxy-13,19,21,27-tetramethyl -11,28-dioxa-4-azatricyclo[22.3.1.0$^{4,9}$]octacos-18-ene -2,3,10,16-tetraone;

17-Ethyl-1,14-dihydroxy-12-[2'-(4"-(2'''-(benzofuran-5-yl)-2'''-oxoethyloxy)-3"-methoxycyclohexyl)-1'-methylvinyl]-23,23-dimethoxy-13,19,21,27-tetramethyl -11,28-dioxa-4-azatricyclo[22.3.1.0$^{4,9}$]octacos-18-ene -2,3,10,16-tetraone;

17-Ethyl-1,14-dihydroxy-12-[2'-(4"-(2'''-(benzofuran-6-yl)-2'''-oxoethyloxy)-3"-methoxycyclohexyl)-1'-methylvinyl]-23,23-dimethoxy-13,19,21,27-tetramethyl -11,28-dioxa-4-azatricyclo[22.3.1.0$^{4,9}$]octacos-18-ene -2,3,10,16-tetraone;

or a pharmaceutically acceptable salt thereof.

* * * * *